United States Patent
Cha et al.

(10) Patent No.: US 10,421,721 B2
(45) Date of Patent: Sep. 24, 2019

(54) HETEROCYCLIC COMPOUND AND ORGANIC LIGHT EMITTING DEVICE COMPRISING SAME

(71) Applicant: LG Chem, Ltd., Seoul (KR)

(72) Inventors: Yongbum Cha, Daejeon (KR); Jin Joo Kim, Daejeon (KR); Sung Kil Hong, Daejeon (KR); Sang Duk Suh, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/554,594

(22) PCT Filed: Sep. 9, 2016

(86) PCT No.: PCT/KR2016/010160
§ 371 (c)(1),
(2) Date: Aug. 30, 2017

(87) PCT Pub. No.: WO2017/047992
PCT Pub. Date: Mar. 23, 2017

(65) Prior Publication Data
US 2018/0037547 A1    Feb. 8, 2018

(30) Foreign Application Priority Data

Sep. 14, 2015   (KR) .................. 10-2015-0129920
Aug. 18, 2016   (KR) .................. 10-2016-0104935

(51) Int. Cl.
*C07D 209/86*   (2006.01)
*C07D 401/04*   (2006.01)
(Continued)

(52) U.S. Cl.
CPC ......... *C07D 209/86* (2013.01); *C07D 401/04* (2013.01); *C07D 403/04* (2013.01);
(Continued)

(58) Field of Classification Search
CPC .. C07D 209/86; C07D 401/04; C07D 403/04; C07D 403/10; C07D 403/14;
(Continued)

(56) References Cited

U.S. PATENT DOCUMENTS

2004/0251816 A1   12/2004   Leo et al.
2012/0181922 A1   7/2012    Kawamura et al.

FOREIGN PATENT DOCUMENTS

JP   2011222831 A    11/2011
KR   20100108924 A   10/2010
(Continued)

OTHER PUBLICATIONS

Effect of Benzo-Annelation on Local Aromaticity in Heterocyclic Conjugated Compounds. Slavko Radenković, Jelena Kojić, Jelena Petronijević, and Marija Antić. The Journal of Physical Chemistry A 2014 118 (49), 11591-11601. DOI: 10.1021/jp507309m (Year: 2014).*

(Continued)

*Primary Examiner* — Daniel P Shook
(74) *Attorney, Agent, or Firm* — Lerner, David, Littenberg, Krumholz & Mentlik, LLP

(57) ABSTRACT

The present specification relates to a hetero-cyclic compound and an organic light emitting device including the same.

17 Claims, 1 Drawing Sheet

(51) Int. Cl.
| | |
|---|---|
| *C07D 403/04* | (2006.01) |
| *C07D 403/10* | (2006.01) |
| *C07D 403/14* | (2006.01) |
| *C07D 405/04* | (2006.01) |
| *C07D 405/10* | (2006.01) |
| *C07D 405/14* | (2006.01) |
| *C07D 409/04* | (2006.01) |
| *C07D 409/10* | (2006.01) |
| *C07D 409/14* | (2006.01) |
| *C09K 11/06* | (2006.01) |
| *H01L 51/00* | (2006.01) |
| *H01L 51/50* | (2006.01) |

(52) U.S. Cl.
CPC ......... *C07D 403/10* (2013.01); *C07D 403/14* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C09K 11/06* (2013.01); *H01L 51/0052* (2013.01); *H01L 51/0059* (2013.01); *H01L 51/0062* (2013.01); *H01L 51/0067* (2013.01); *H01L 51/0072* (2013.01); *C09K 2211/1029* (2013.01); *C09K 2211/1044* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .. C07D 405/04; C07D 405/10; C07D 405/14; C07D 409/04; C07D 409/10; C07D 409/14; H01L 51/0062; H01L 51/0067; H01L 51/0072; H01L 51/5012; H01L 51/5016; H01L 51/5056; H01L 51/5072; H01L 51/5088; H01L 51/5092; H01L 51/5096

See application file for complete search history.

(56) References Cited

FOREIGN PATENT DOCUMENTS

| KR | 20120021203 A | | 3/2012 |
|---|---|---|---|
| KR | 20150004099 A | | 1/2015 |
| KR | 20150010016 A | | 1/2015 |
| KR | 20150098062 A | | 8/2015 |
| KR | 1020150098062 | * | 8/2015 |
| KR | 1020160054855 A | * | 5/2016 |
| WO | 2003012890 A2 | | 2/2003 |
| WO | 2010114264 A2 | | 10/2010 |
| WO | WO2010114264 A2 | * | 10/2010 |
| WO | WO2015009076 A1 | * | 10/2010 |
| WO | 2013069939 A1 | | 5/2013 |
| WO | 2015009076 A1 | | 1/2015 |

OTHER PUBLICATIONS

Search report from International Application No. PCT/KR2016/010160, dated Dec. 16, 2016.

Extended European Search Report including Written Opinion for Application No. EP16846813.0 dated Apr. 10, 2019.

Stepan Vyskocil et al., "Copper (II)-Mediated Oxidative Coupling of 2-Aminonaphthalene Homologues. Competition between the Straight Dimerization and the Formation of Carbazoles", Journal of Organic Chemistry, Jan. 31, 2001, vol. 66, pp. 1359-1365.

* cited by examiner

[Figure 1]
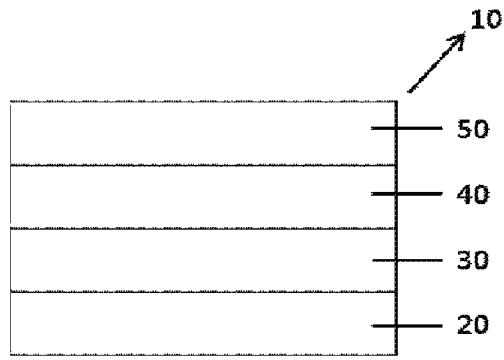
[Figure 2]
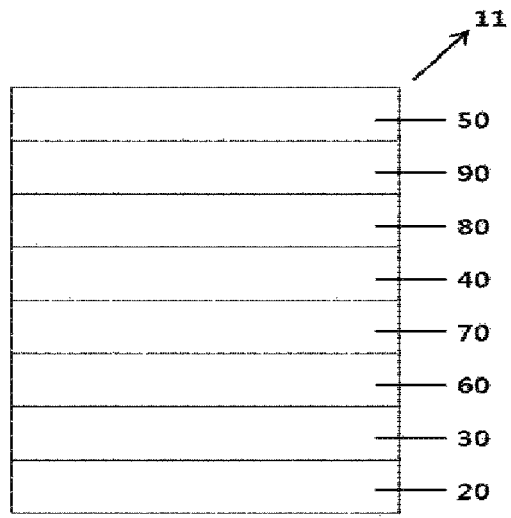

HETEROCYCLIC COMPOUND AND ORGANIC LIGHT EMITTING DEVICE COMPRISING SAME

CROSS-REFERENCE TO RELATED APPLICATIONS

The present application is a national phase entry under 35 U.S.C. § 371 of International Application No. PCT/KR2016/010160, filed Sep. 9, 2016, which claims priority to and the benefit of Korean Patent Application Nos. 10-2015-0129920 and 10-2016-0104935, filed in the Korean Intellectual Property Office on Sep. 14, 2015 and Aug. 18, 2016, respectively, the disclosures of which are incorporated herein by reference.

TECHNICAL FIELD

The present specification relates to a hetero-cyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. 2003-012890

DISCLOSURE

Technical Problem

The present specification provides a hetero-cyclic compound and an organic light emitting device including the same.

Technical Solution

An exemplary embodiment of the present application provides a hetero-cyclic compound represented by the following Chemical Formula 1.

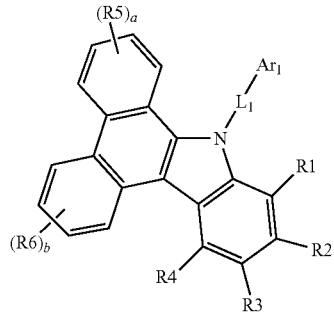

[Chemical Formula 1]

In Chemical Formula 1,

L1 is a direct bond; a substituted or unsubstituted arylene group; or a substituted or unsubstituted heteroarylene group, Ar1 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; a substituted or unsubstituted pyridyl group; a substituted or unsubstituted pyrimidyl group; a substituted or unsubstituted triazinyl group; a substituted or unsubstituted pyridazinyl group; a substituted or unsubstituted pyrazinyl group; or a substituted or unsubstituted polycyclic heteroaryl group, R1 and R2, R2 and R3, or R3 and R4 in R1 to R6 combine with each other to form a ring substituted with (R7)c, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, R7 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group;

a substituted or unsubstituted arylphosphine group; a substituted or unsubstituted phosphine oxide group; a substituted or unsubstituted aryl group; or substituted or unsubstituted heteroaryl group, a to c are each an integer of 1 to 4, when a to c are each 2 or more, two or more structures in the parenthesis are the same as or different from each other, and provided that when Ar1 is a substituted or unsubstituted pyrimidyl group, L1 is a substituted or unsubstituted arylene group; or a substituted or unsubstituted heteroarylene group.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the hetero-cyclic compound represented by Chemical Formula 1.

Advantageous Effects

An organic light emitting device including the hetero-cyclic compound according to an exemplary embodiment of the present specification has excellent thermal stability and may improve efficiency, achieve low driving voltage and/or improve lifetime characteristics.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the hetero-cyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

In the present specification, examples of the substituents will be described below, but the present specification is not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a binding portion.

In the present specification, the halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

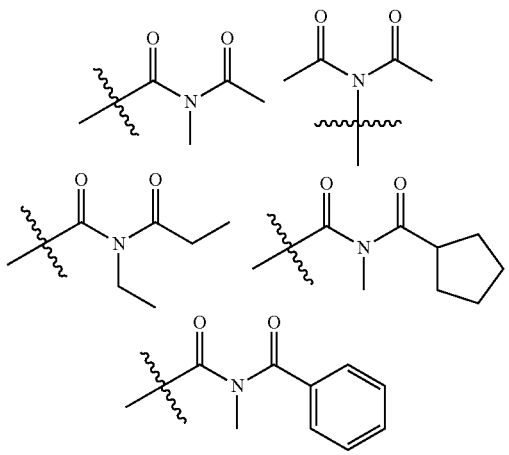

In the present specification, for the amide group, the nitrogen of the amide group may be substituted with hydrogen, a straight-chained, branch-chained, or cyclic alkyl group having 1 to 30 carbon atoms. Specifically, the amide group may be a compound having the following structural formulae, but is not limited thereto.

In the present specification, the number of carbon atoms of a carbonyl group is not particularly limited, but is preferably 1 to 30. Specifically, the carbonyl group may be a compound having the following structures, but is not limited thereto.

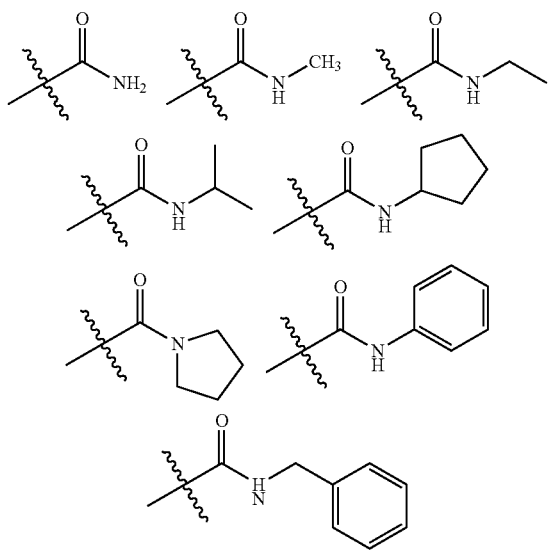

In the present specification, for the ester group, the oxygen of the ester group may be substituted with a straight-chained, branch-chained, or cyclic alkyl group having 1 to 25 carbon atoms, or an aryl group having 6 to 30 carbon atoms. Specifically, the ester group may be a compound having the following structural formulae, but is not limited thereto.

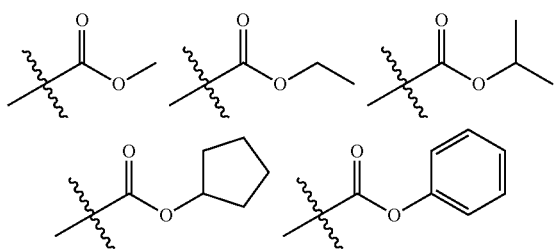

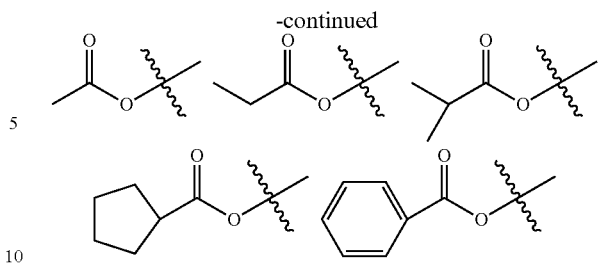

In the present specification, the alkyl group may be straight-chained or branch-chained, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylbutyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the cycloalkyl group is not particularly limited, but a cyclohexyl group having 3 to 30 carbon atoms is preferred, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the amine group may be selected from the group consisting of —NH2; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, the N-alkylarylamine group means an amine group in which an alkyl group and an aryl group are substituted with N of the amine group.

In the present specification, the N-arylheteroarylamine group means an amine group in which an aryl group and a heteroaryl group are substituted with N of the amine group.

In the present specification, the N-alkylheteroarylamine group means an amine group in which an alkyl group and a heteroarylamine group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, the alkenyl group may be straight-chained or branch-chained, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be $-BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branch-chained alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group include a diphenylphosphine oxide group, dinaphthylphosphine oxide, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

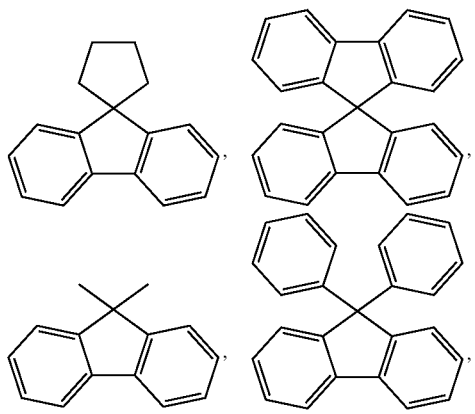

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, the heteroaryl group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic.

Examples of the hetero-cyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the N-arylheteroarylamine group and the N-alkylheteroarylamine group are the same as the above-described examples of the heteroaryl group.

In the present specification, the arylene group means that there are two bonding positions in an aryl group, that is, a divalent group. The above-described description on the aryl group may be applied, except that the arylene groups are each a divalent group.

In the present specification, the heteroarylene group means that there are two bonding positions in a heteroaryl group, that is, a divalent group. The above-described description on the heteroaryl group may be applied, except that these are each a divalent group.

In the present specification, in a substituted or unsubstituted ring formed by combining adjacent groups with each other, the "ring" means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, the hetero ring includes one or more of an atom other than carbon, that is, a heteroatom, and specifically, the heteroatom may include one or more atoms selected from the group consisting of O, N, Se, and S, and the like. The hetero ring may be monocyclic or polycyclic, may be an aromatic ring, an aliphatic ring, or a fused ring of the aromatic ring and the aliphatic ring, and may be selected from the examples of the heteroaryl group, except for the hetero ring which is not monovalent.

According to an exemplary embodiment of the present specification, in Chemical Formula 1, R1 and R2, R2 and R3, or R3 and R4 combine with each other to form a ring substituted with (R7)c.

According to an exemplary embodiment of the present specification, in Chemical Formula 1, R1 and R2, R2 and R3, or R3 and R4 combine with each other to form a hydrocarbon ring substituted with (R7)c.

According to an exemplary embodiment of the present specification, in Chemical Formula 1, R1 and R2, R2 and R3, or R3 and R4 combine with each other to form a benzene ring substituted with (R7)c.

According to an exemplary embodiment of the present specification, in Chemical Formula 1, R1 and R2 combine with each other to form a benzene ring substituted with (R7)c.

According to an exemplary embodiment of the present specification, in Chemical Formula 1, R2 and R3 combine with each other to form a benzene ring substituted with (R7)c.

According to an exemplary embodiment of the present specification, in Chemical Formula 1, R3 and R4 combine with each other to form a benzene ring substituted with (R7)c.

According to an exemplary embodiment of the present specification, in Chemical Formula 1, R7 is hydrogen.

According to an exemplary embodiment of the present specification, in Chemical Formula 1, R1 and R2 combine with each other to form a benzene ring.

According to an exemplary embodiment of the present specification, in Chemical Formula 1, R2 and R3 combine with each other to form a benzene ring.

According to an exemplary embodiment of the present specification, in Chemical Formula 1, R3 and R4 combine with each other to form a benzene ring.

According to an exemplary embodiment of the present specification, Chemical Formula 1 is represented by any one of the following Chemical Formulae 1-1 to 1-3.

[Chemical Formula 1-1]

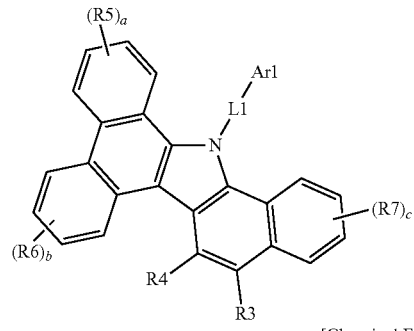

[Chemical Formula 1-2]

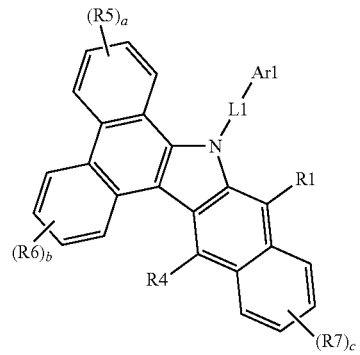

[Chemical Formula 1-3]

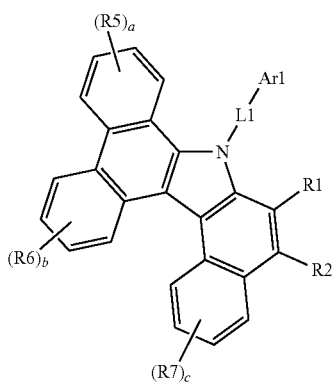

In Chemical Formulae 1-1 to 1-3, the definitions of L1, Ar1, and R1 to R7 are the same as those in Chemical Formula 1.

According to an exemplary embodiment of the present specification, in Chemical Formula 1, L1 is a direct bond; a substituted or unsubstituted monocyclic or polycyclic arylene group having 6 to 30 carbon atoms; or a substituted or unsubstituted monocyclic or polycyclic heteroarylene group having 2 to 30 carbon atoms.

According to an exemplary embodiment of the present specification, in Chemical Formula 1, L1 is a direct bond; a substituted or unsubstituted monocyclic or polycyclic arylene group having 6 to 20 carbon atoms; or a substituted or unsubstituted monocyclic or polycyclic heteroarylene group having 2 to 20 carbon atoms.

According to an exemplary embodiment of the present specification, in Chemical Formula 1, L1 is a direct bond; a substituted or unsubstituted phenylene group; a substituted or unsubstituted biphenylene group; a substituted or unsubstituted triazinylene group; a substituted or unsubstituted quinazolinylene group; or a substituted or unsubstituted carbazolylene group.

According to an exemplary embodiment of the present specification, in Chemical Formula 1, L1 is a direct bond; a phenylene group; a biphenylene group; a triazinylene group; a quinazolinylene group; or a carbazolylene group.

According to an exemplary embodiment of the present specification, in Chemical Formula 1, Ar1 is selected from the group consisting of a substituted or unsubstituted diarylamine group; a substituted or unsubstituted diheteroaryl amine group; a substituted or unsubstituted silyl group; a substituted or unsubstituted phosphine oxide group; a substituted or unsubstituted monocyclic or polycyclic aryl group having 6 to 30 carbon atoms; and a substituted or unsubstituted monocyclic or polycyclic heteroaryl group having 2 to 30 carbon atoms.

According to an exemplary embodiment of the present specification, Ar1 is selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quarterphenylfluorenylamine group; a substituted or unsubstituted N-terphenylfluorenylamine group; a substituted or unsubstituted N-biphenyl terphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenyl terphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; substituted or unsubstituted

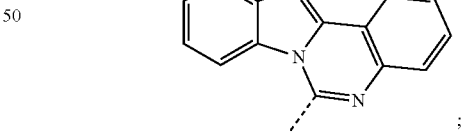

substituted or unsubstituted

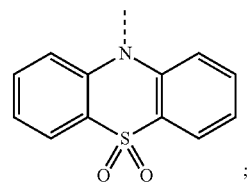

and a structure represented by the following Chemical Formula a,

---- means a moiety bonded to Chemical Formula 1 via L1.

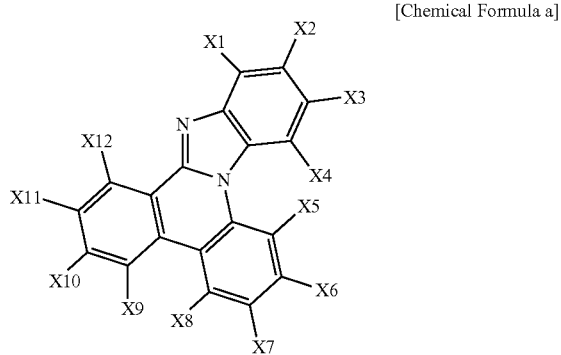

[Chemical Formula a]

In Chemical Formula a, at least one of X1 to X12 is a moiety bonded to Chemical Formula 1 via L1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

According to an exemplary embodiment of the present specification, in Chemical Formula a, one of X1 to X12 is a moiety bonded to Chemical Formula 1 via L1, and the others are hydrogen.

According to an exemplary embodiment of the present specification, in Chemical Formula a, X11 and X12 are linked to each other to form a substituted or unsubstituted monocyclic or polycyclic hydrocarbon ring having 6 to 20 carbon atoms.

According to an exemplary embodiment of the present specification, in Chemical Formula a, X11 and X12 are linked to each other to form a substituted or unsubstituted monocyclic or polycyclic hydrocarbon ring having 6 to 10 carbon atoms.

According to an exemplary embodiment of the present specification, in Chemical Formula a, X11 and X12 are linked to each other to form a substituted or unsubstituted benzene ring.

According to an exemplary embodiment of the present specification, in Chemical Formula a, X11 and X12 are linked to each other to form a benzene ring.

According to an exemplary embodiment of the present specification, Ar1 is selected from the group consisting of a phenyl group; a biphenyl group; a phenanthrenyl group; a naphthyl group; a terphenyl group; a fluorenyl group; an anthracenyl group; a chrysenyl group; a quarterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; benzonaphthofuranyl group; a benzonaphthothiophene group; a dimethylphosphine oxide group; diphenylphosphine oxide group; dinaphthylphosphine oxide group; a benzoxazolyl group; a benzothiazolyl group; a benzimidazolyl group; a triphenylsilyl group; a phenothiazinyl group; a phenoxazinyl group; a thiophene group; a diphenylamine group; an N-phenylnaphthylamine group; an N-phenylbiphenylamine group; an N-phenylphenanthrenylamine group; an N-biphenylnaphthylamine group; a dibiphenylamine group; an N-biphenylphenanthrenylamine group; a dinaphthylamine group; an N-quarterphenylfluorenylamine group; an N-terphenylfluorenylamine group; an N-biphenyl terphenylamine group; an N-biphenylfluorenylamine group; a substituted or unsubstituted N-phenylfluorenylamine group; an N-naphthylfluorenylamine group; an N-phenanthrenylfluorenylamine group; a difluorenylamine group; an N-phenyl terphenylamine group; an N-phenylcarbazolylamine group; an N-biphenylcarbazolylamine group; an N-phenylbenzocarbazolylamine group; an N-biphenylbenzocarbazolylamine group; an N-fluorenylcarbazolylamine group; a benzocarbazolyl group; a dibenzocarbazolyl group; a carbazolyl group;

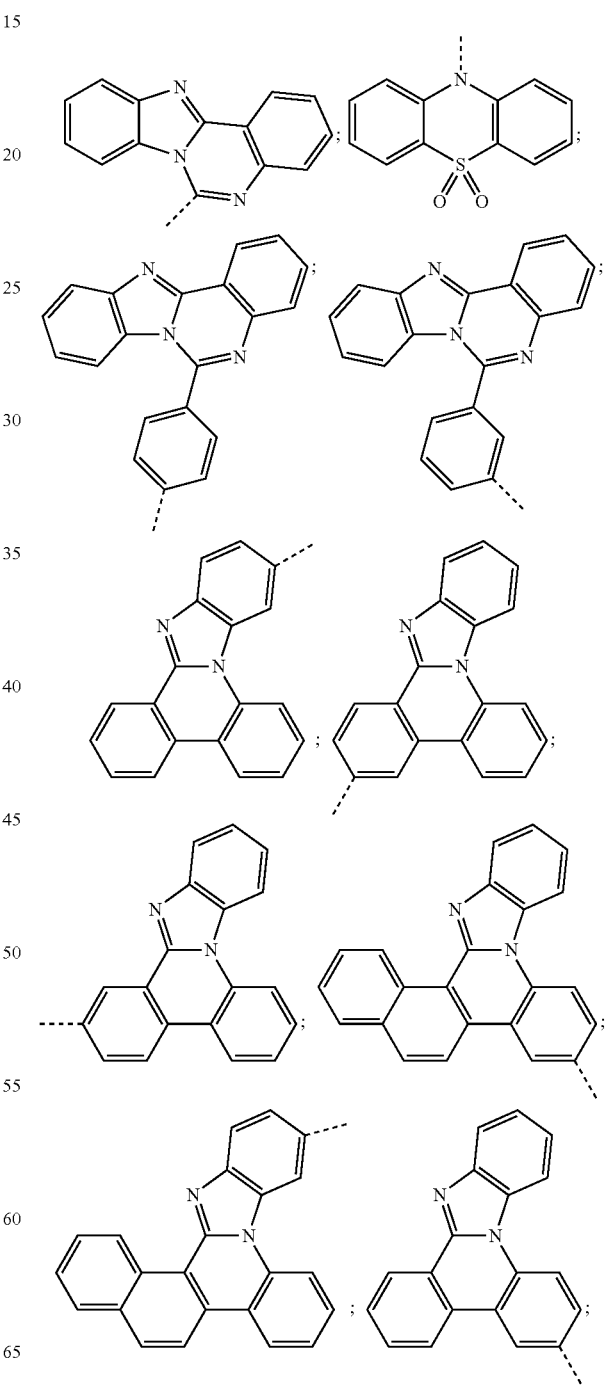

-continued

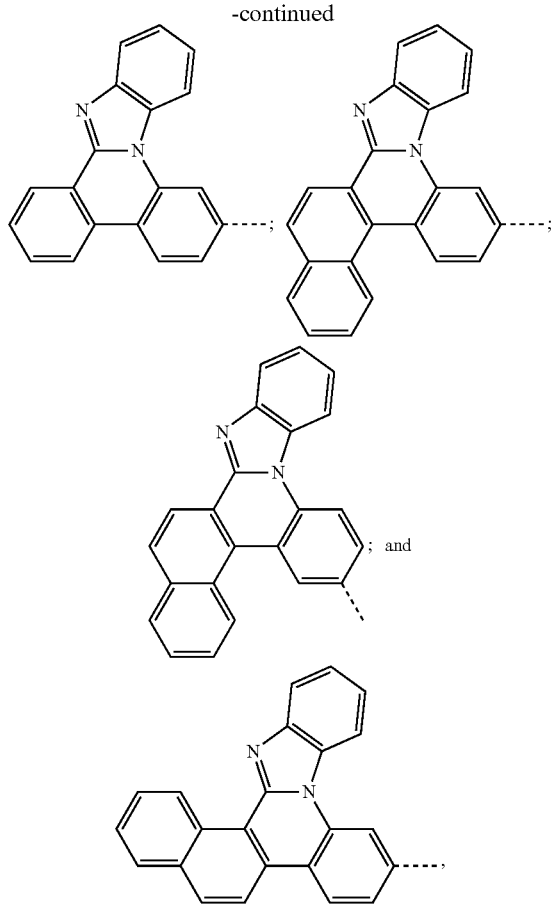

and

Ar1 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; a diphenylamine group; a dibiphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group; and

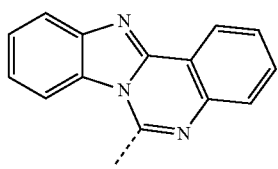

---- means a moiety bonded to Chemical Formula 1 via L1.

According to an exemplary embodiment of the present specification, in Chemical Formula 1, Ar1 is represented by any one of the following Structural Formulae [A-1] to [A-5].

[A-1]

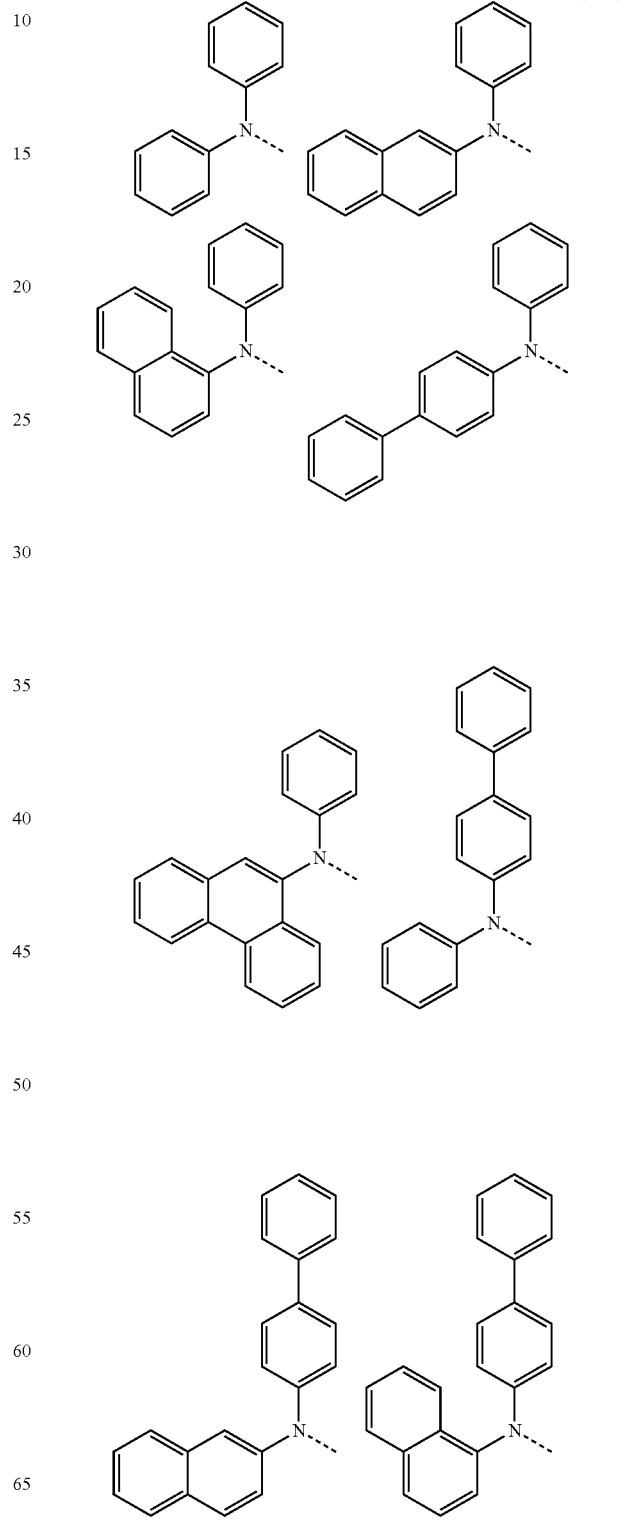

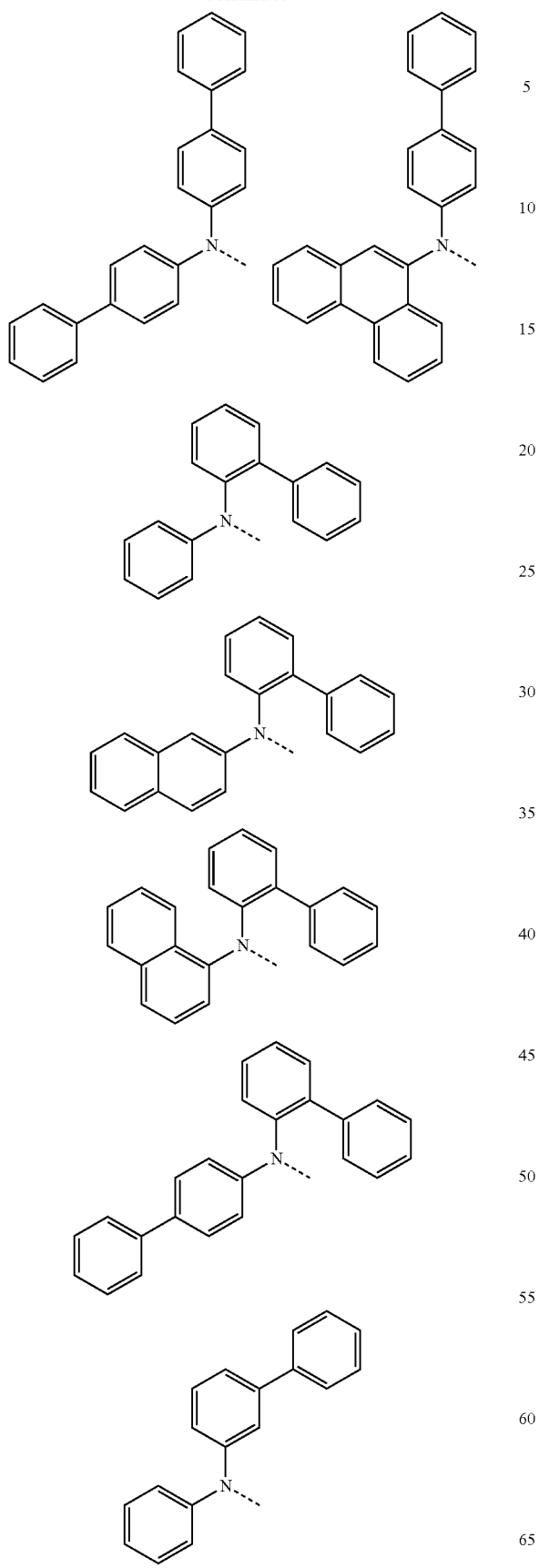
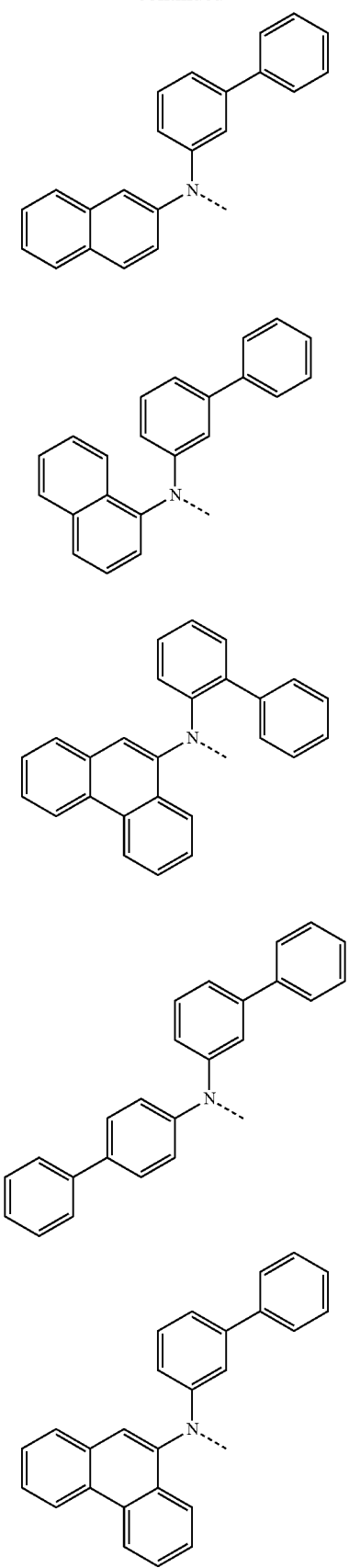

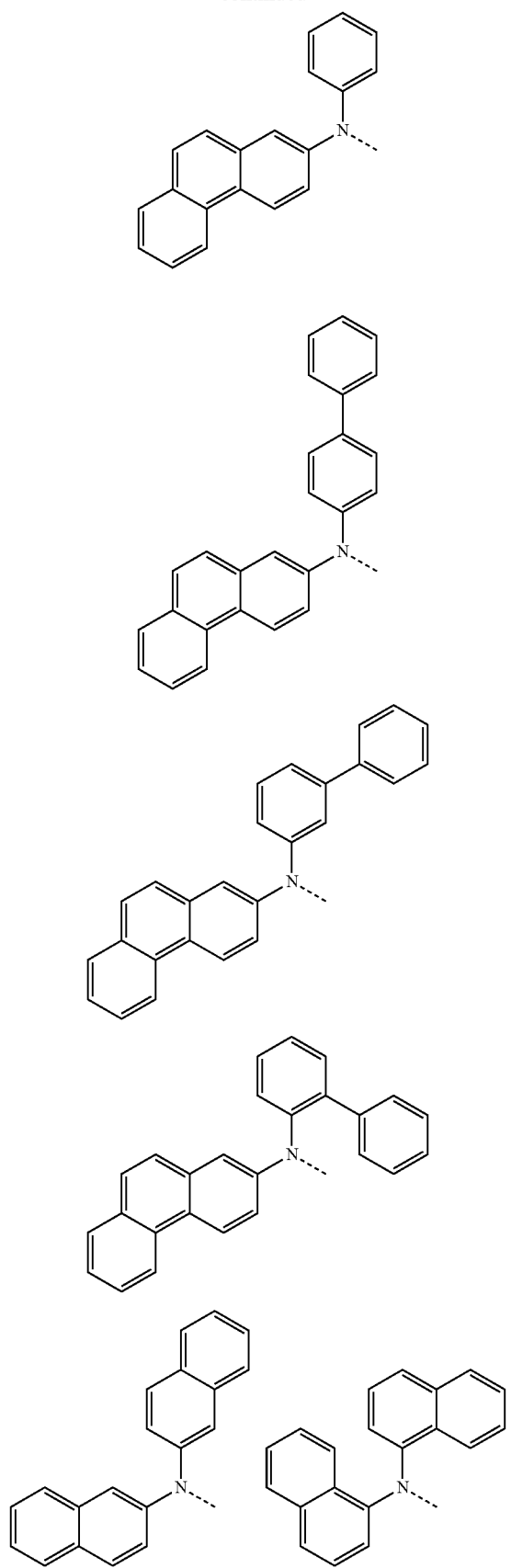
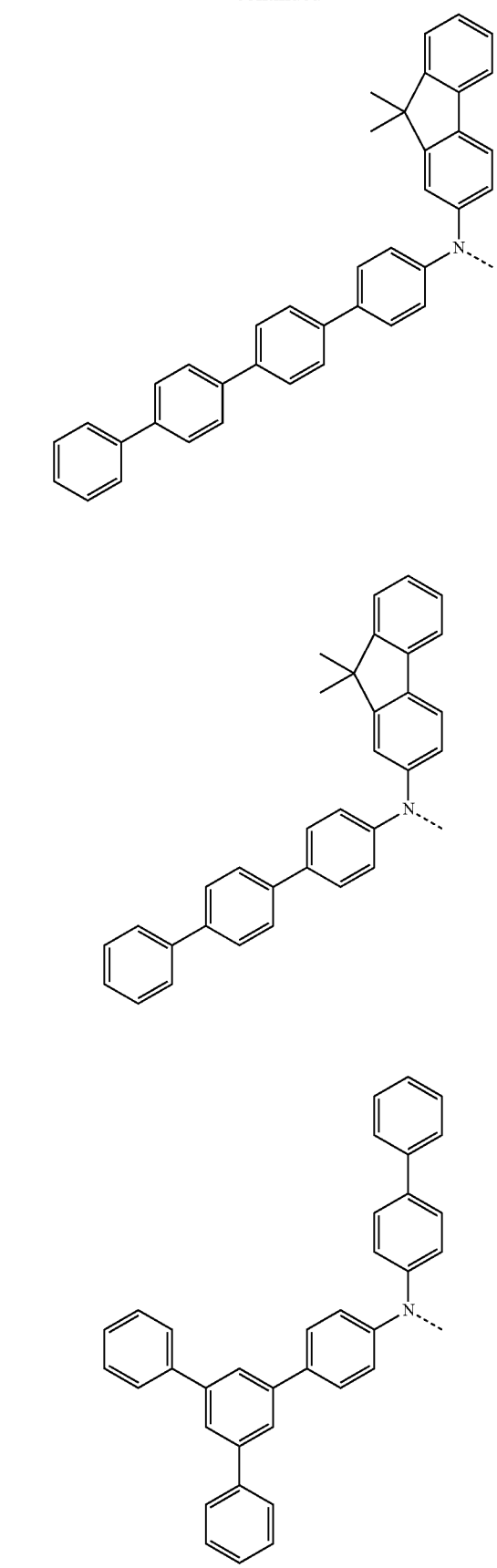

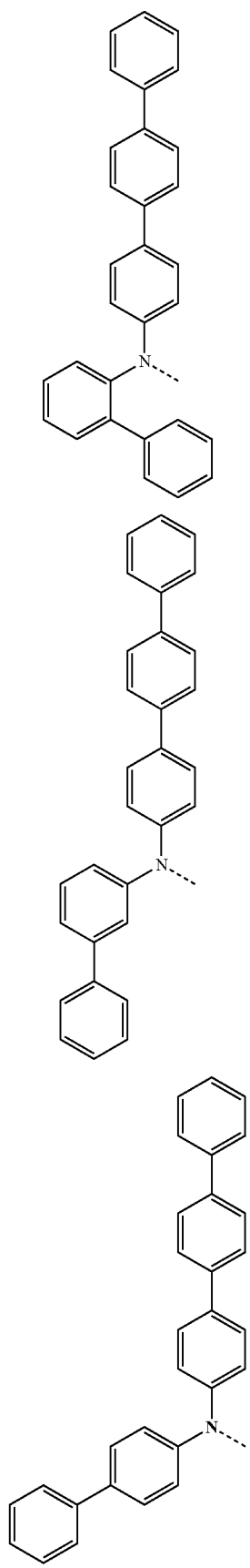
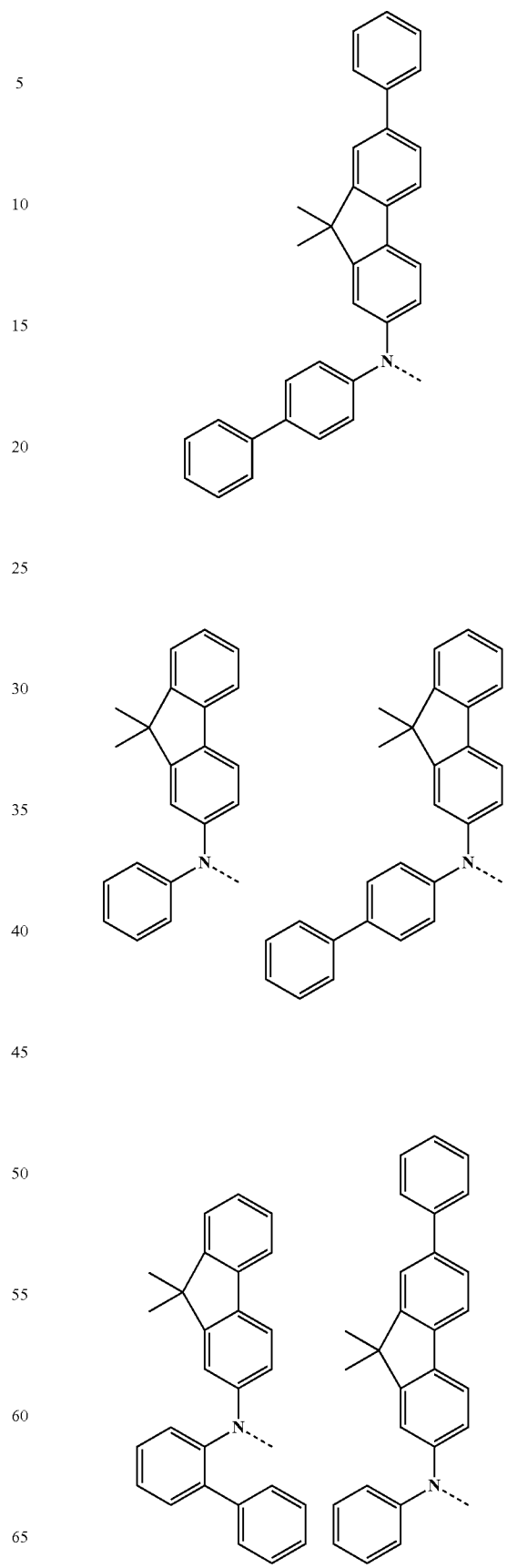

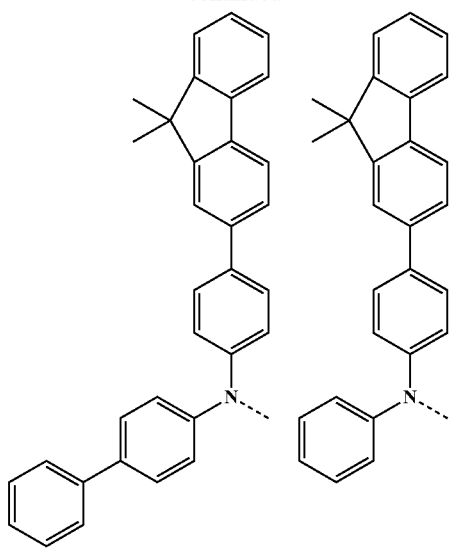
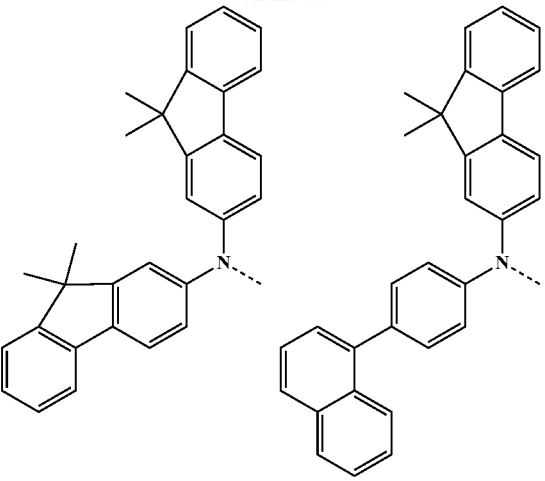
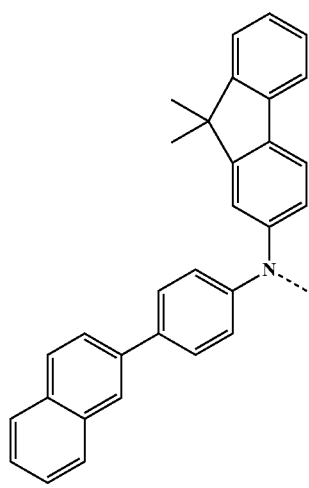
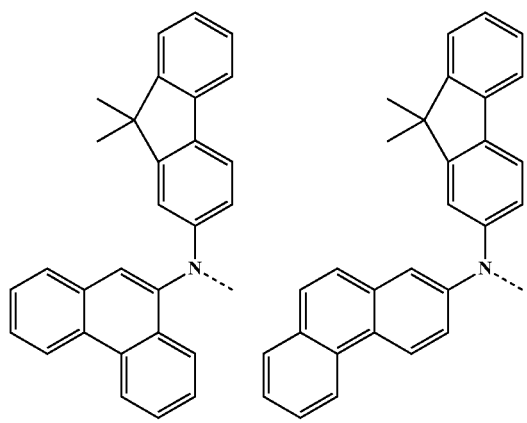
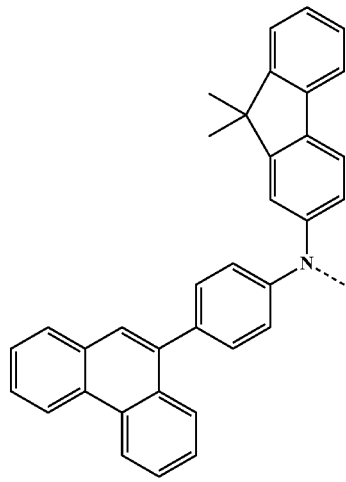

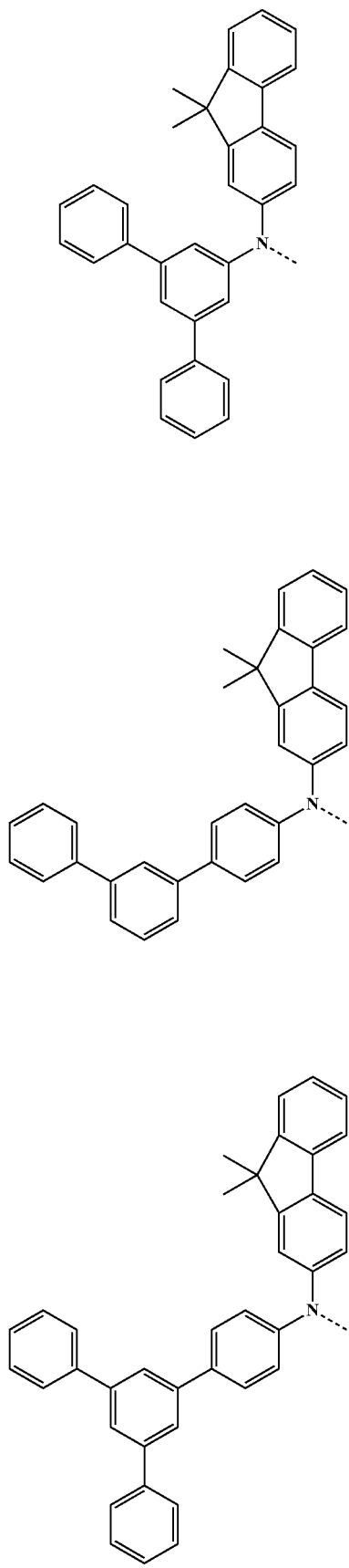
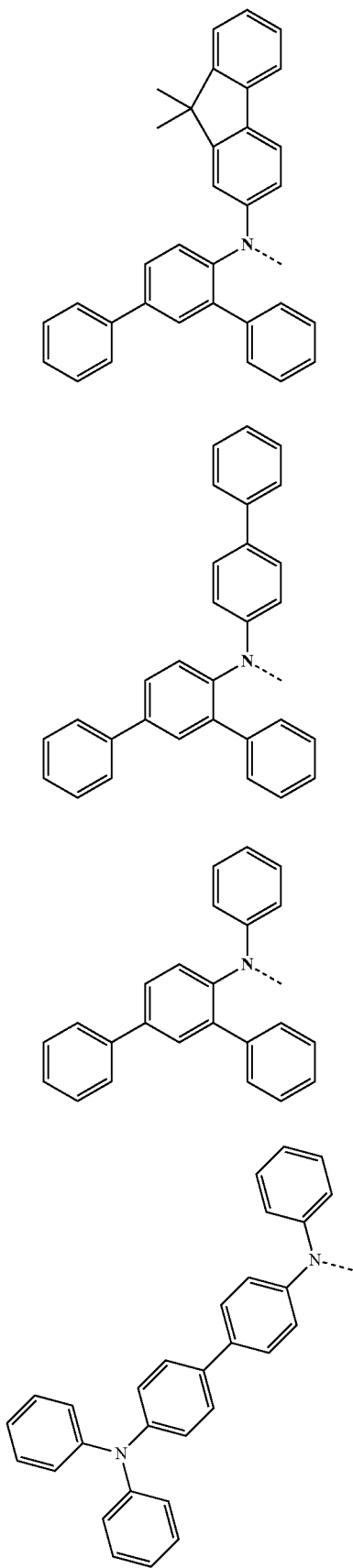

-continued
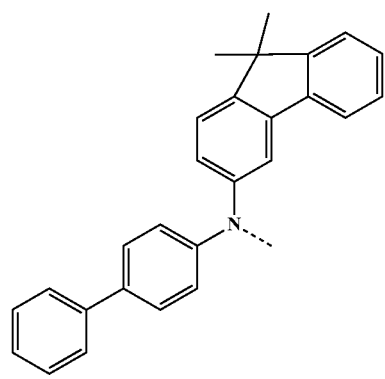
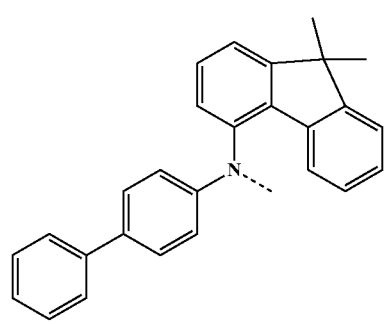
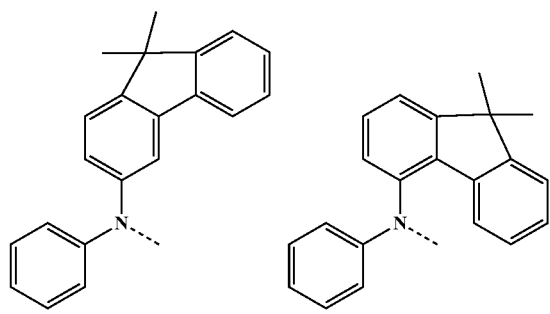
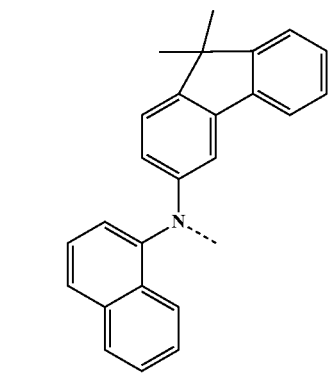
-continued
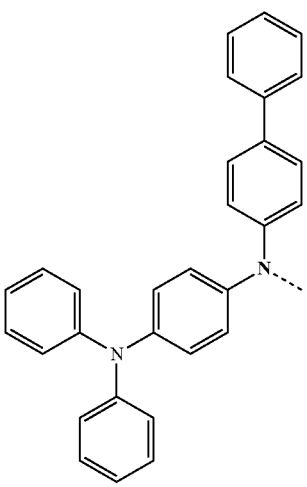
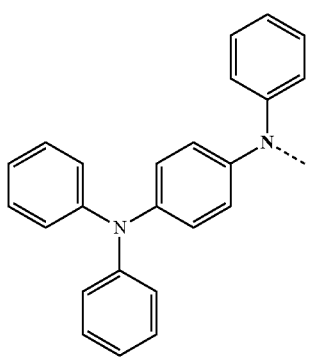
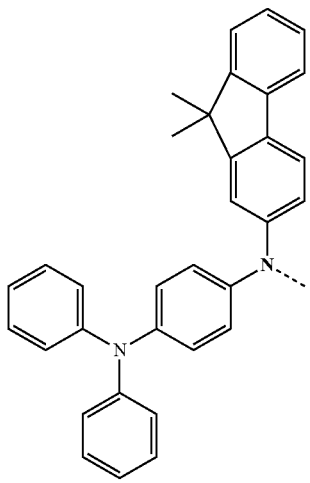
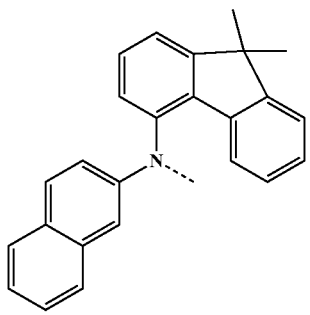

-continued
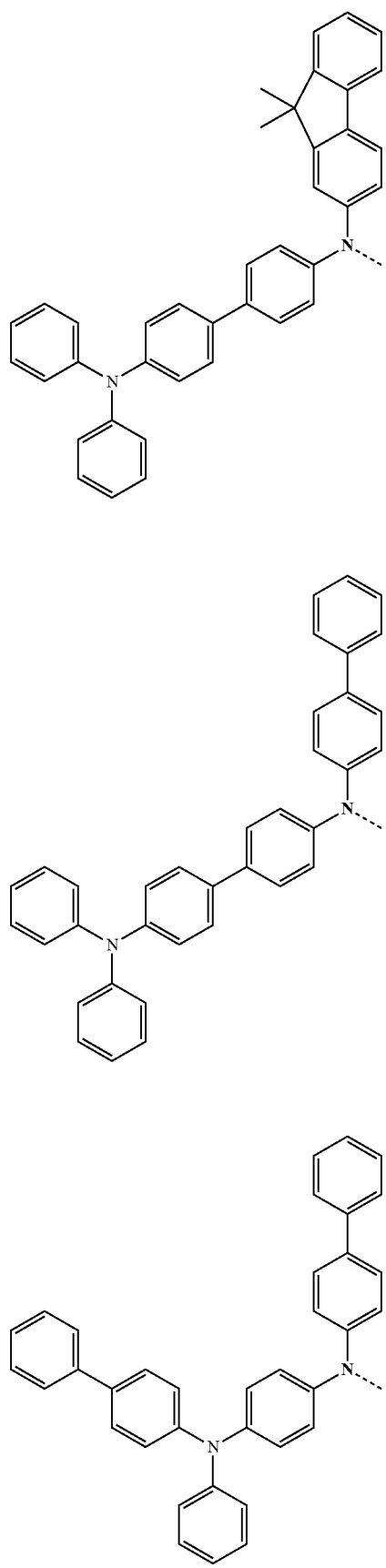
-continued
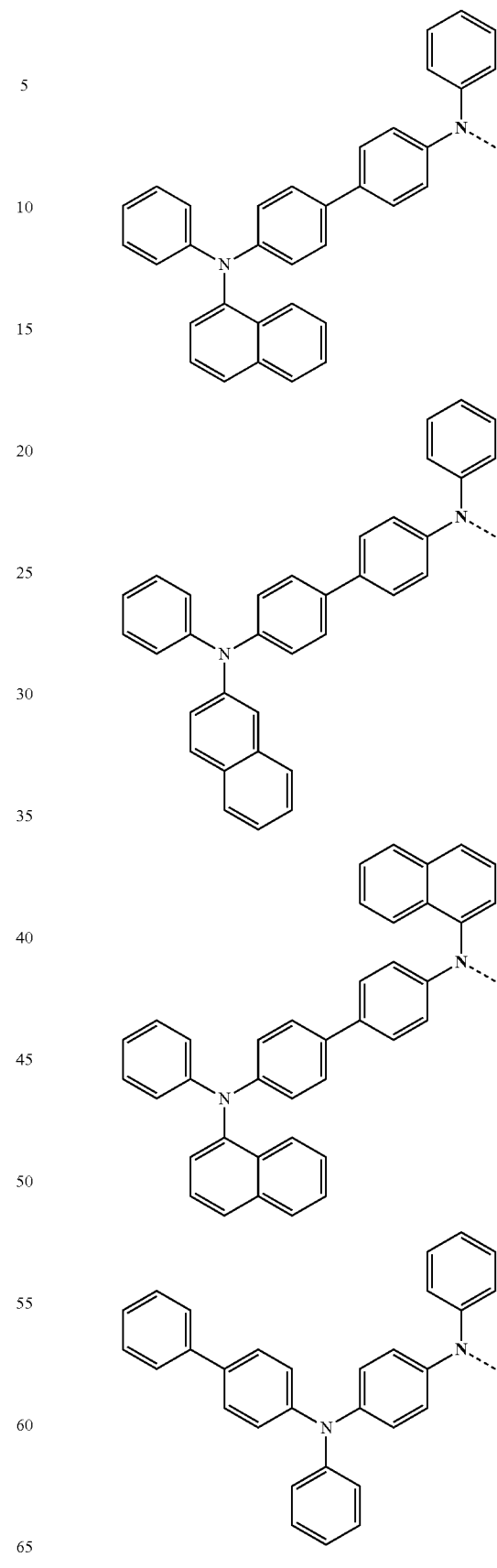

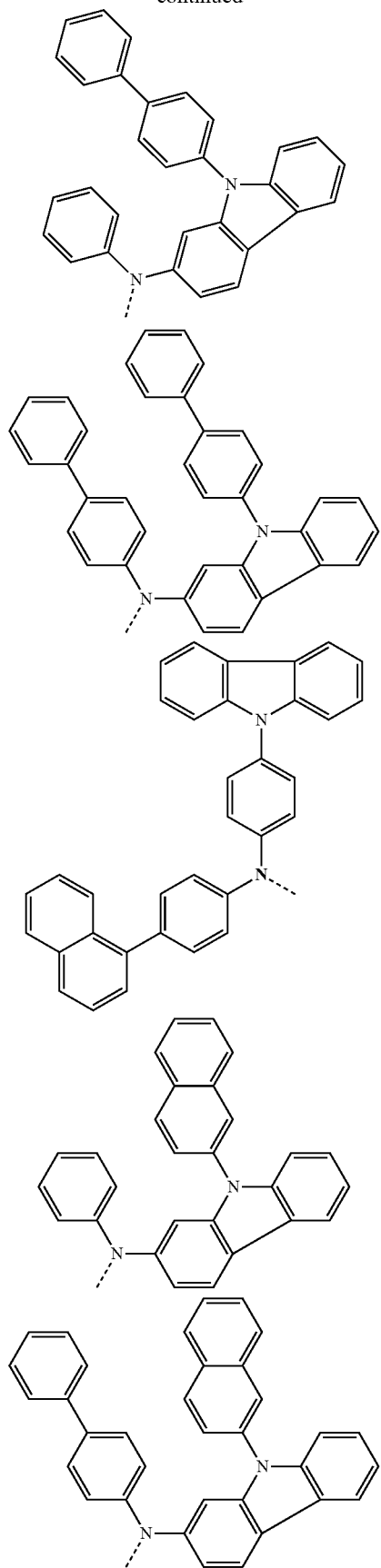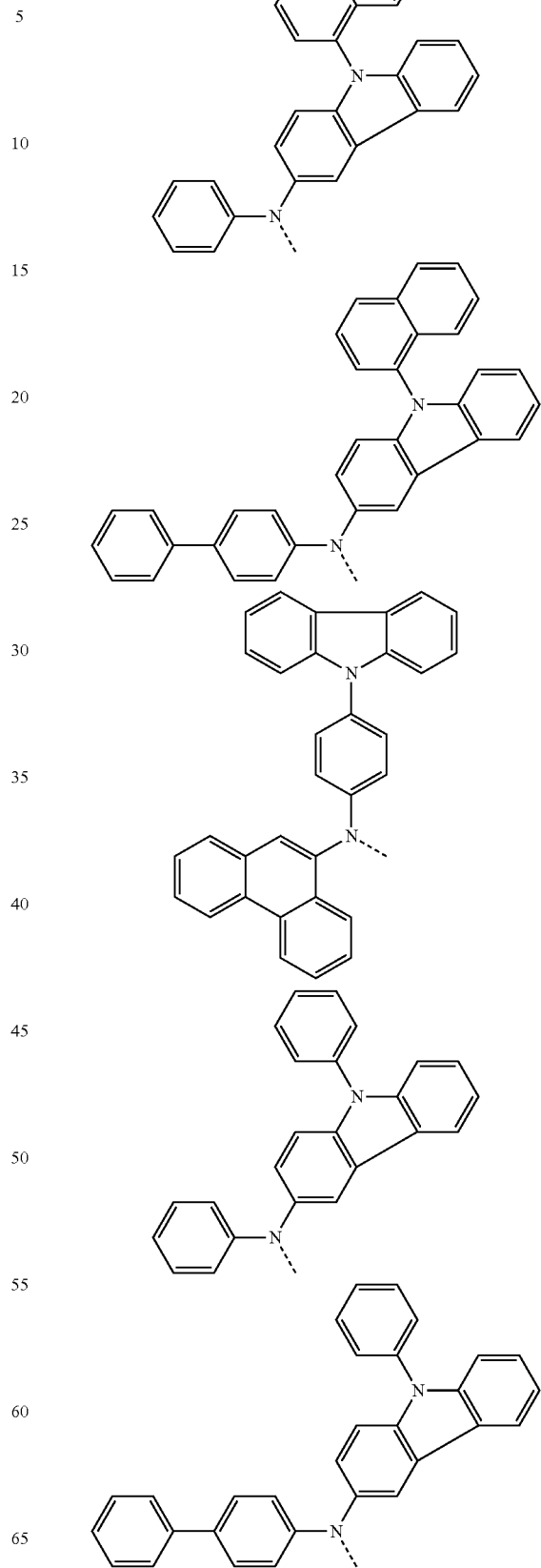

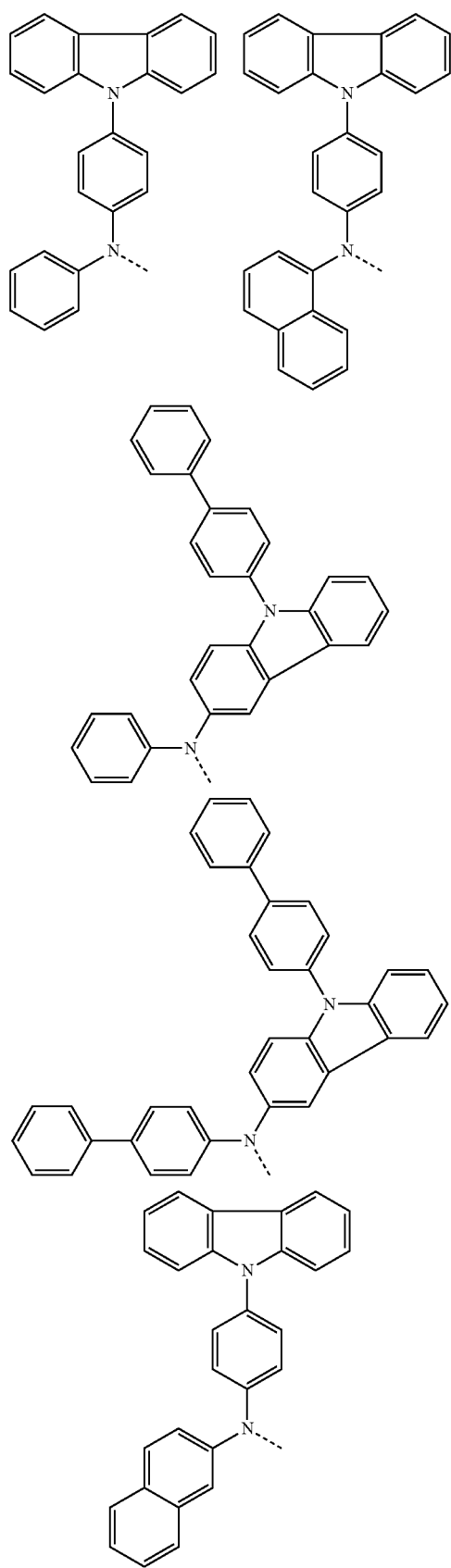
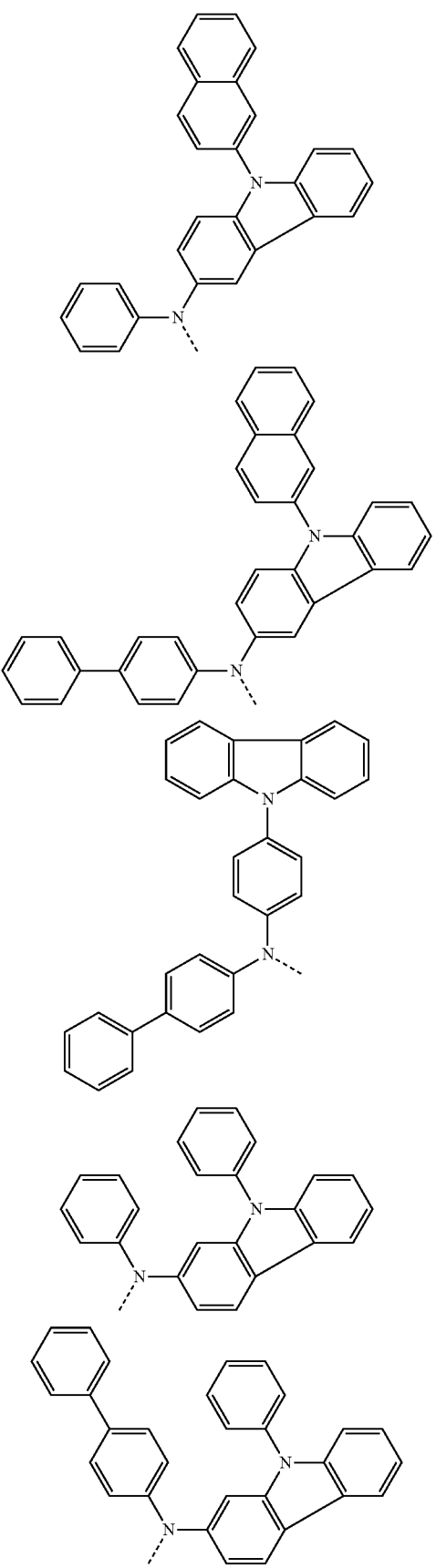

35
-continued
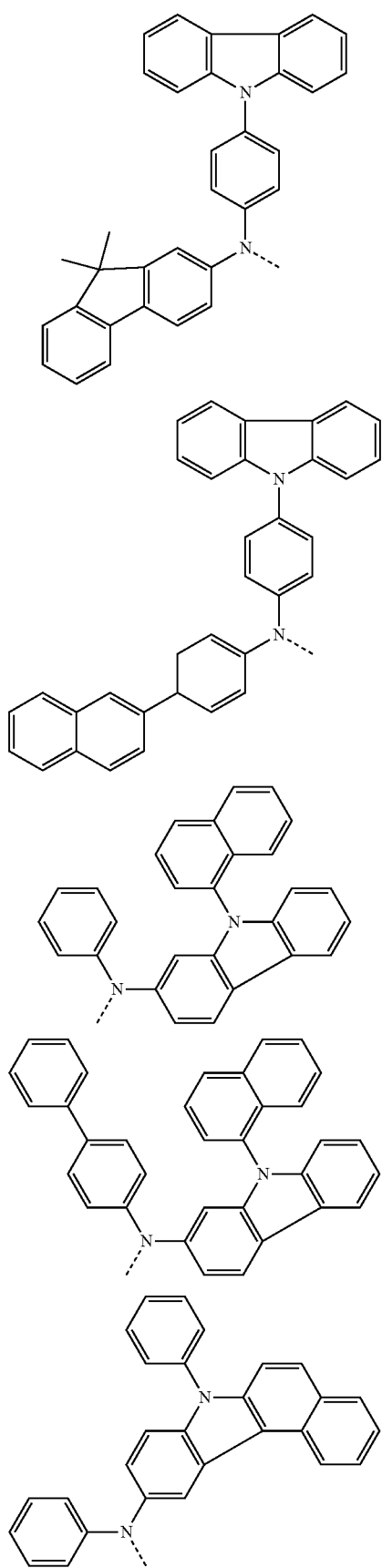
36
-continued
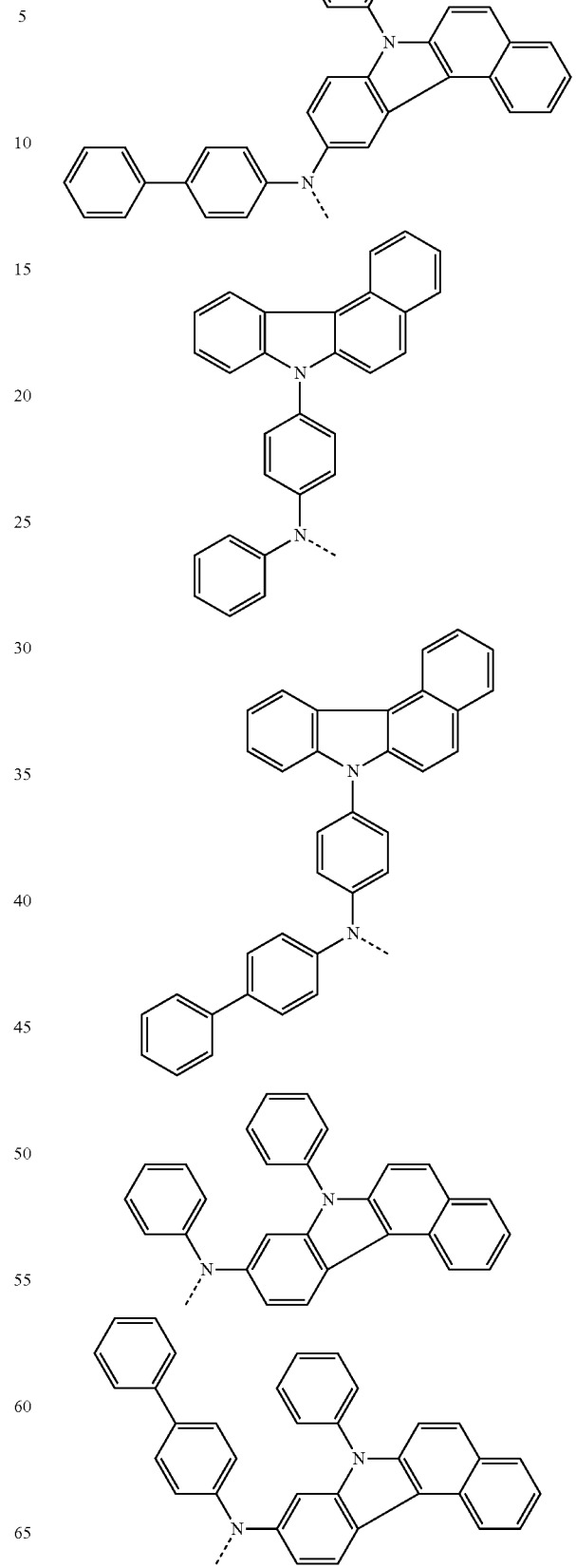

-continued
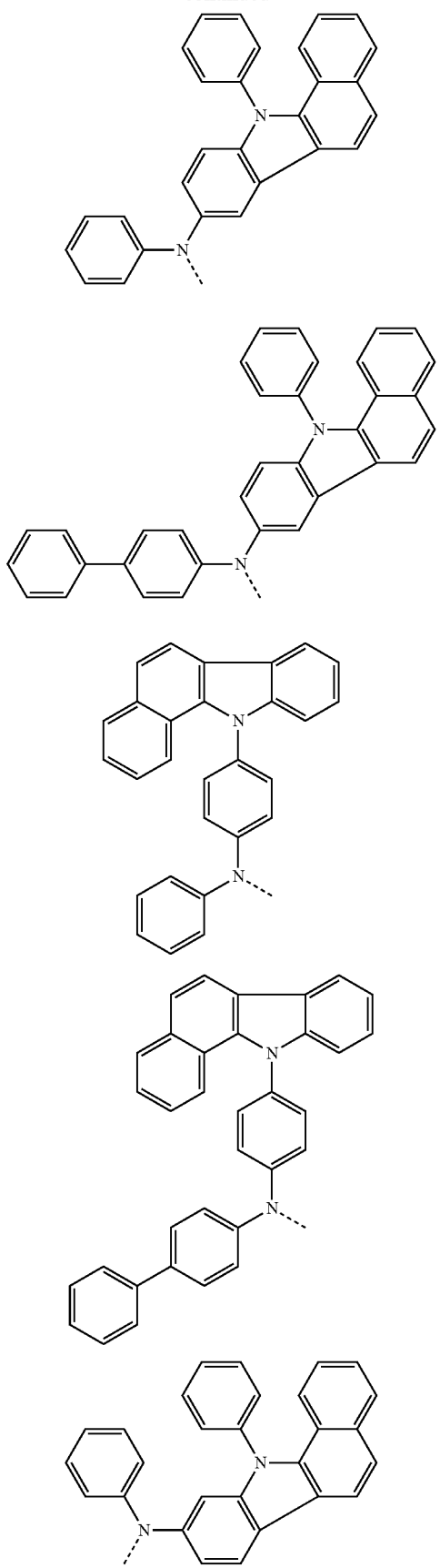
-continued
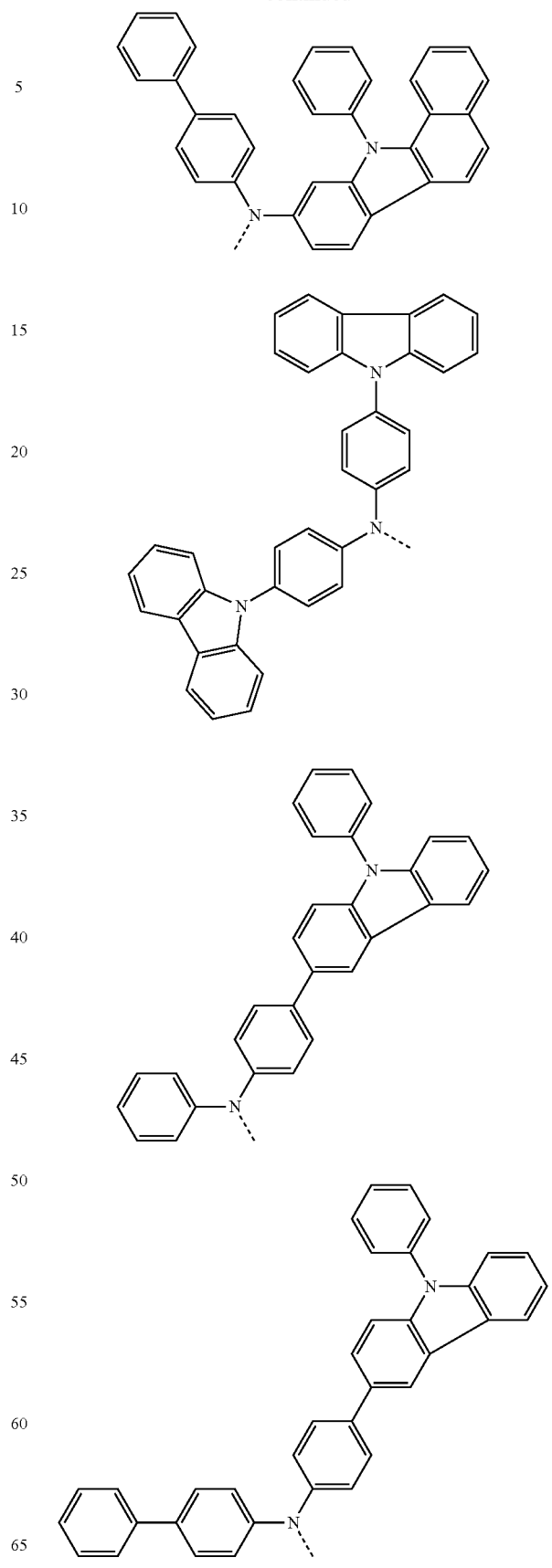

39
-continued
40
-continued
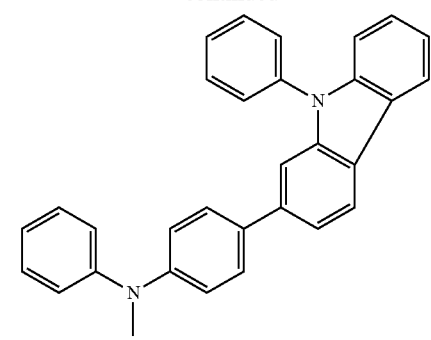
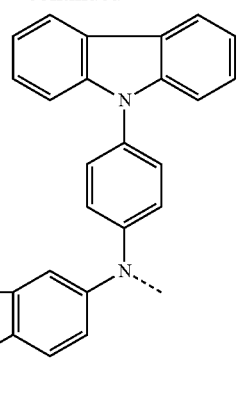
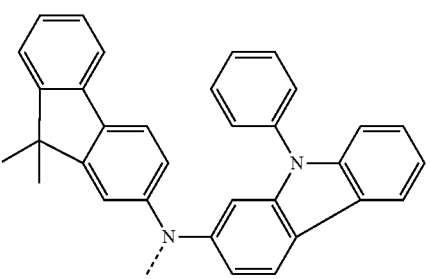
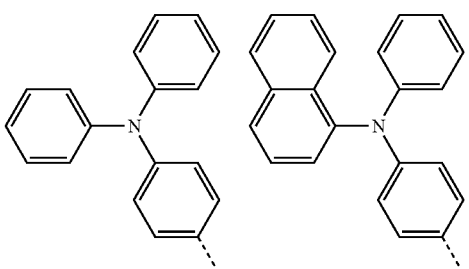
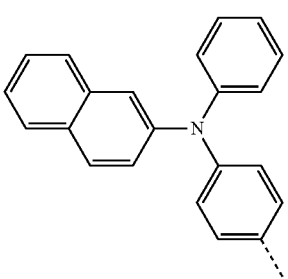
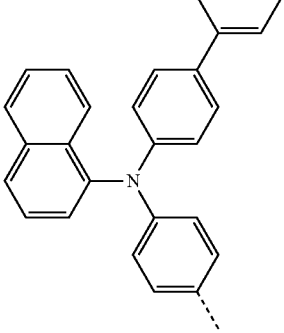

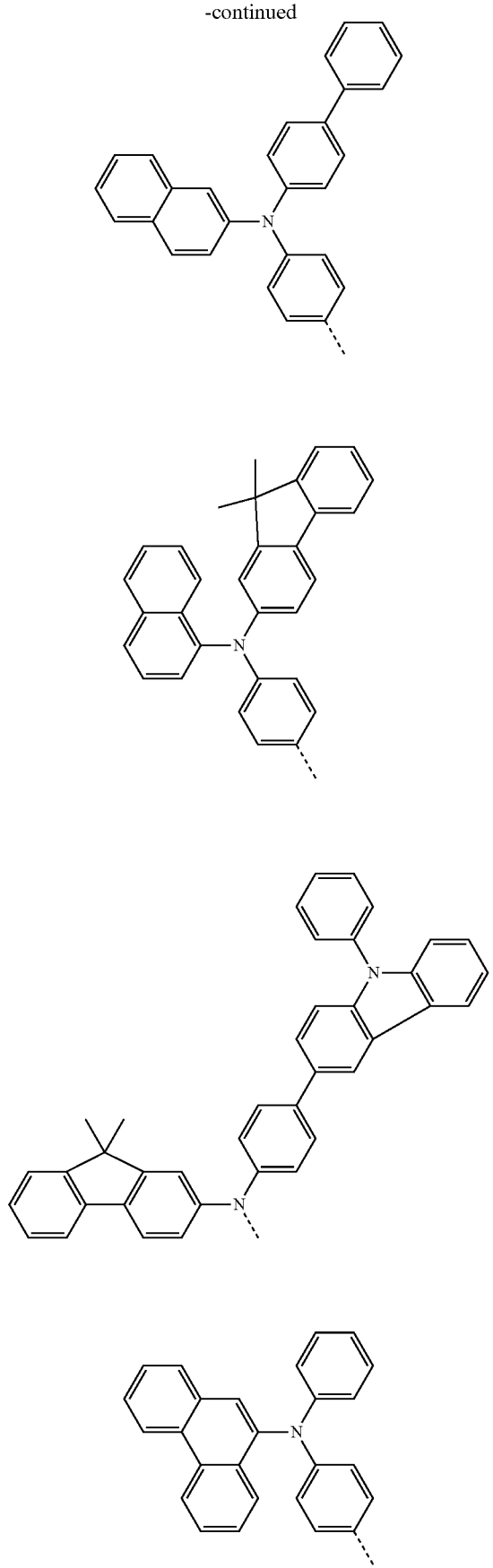

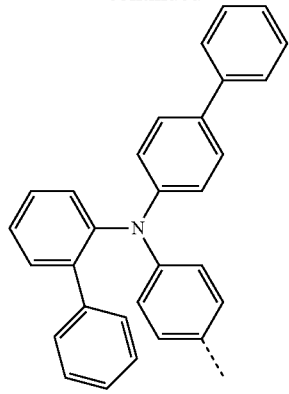
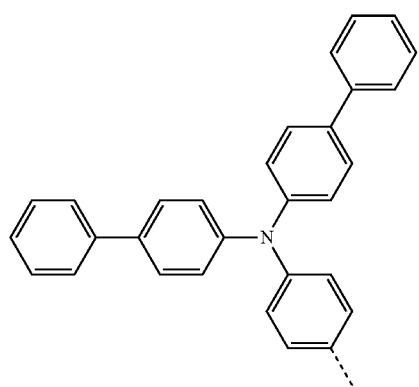
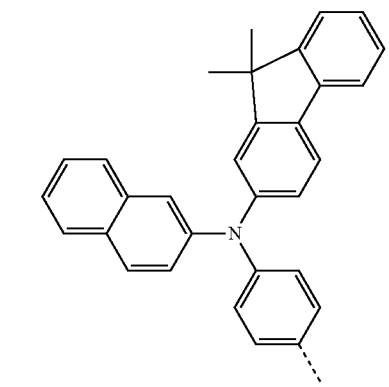
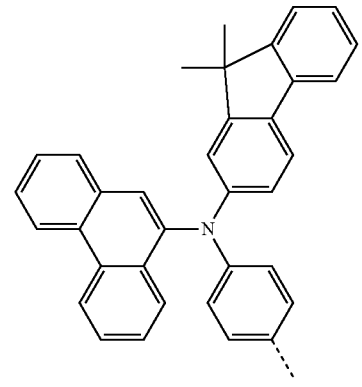
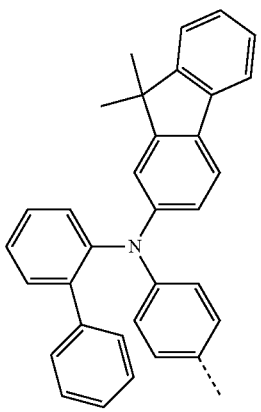
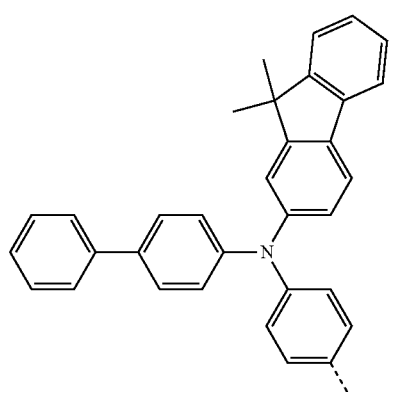
[A-2]
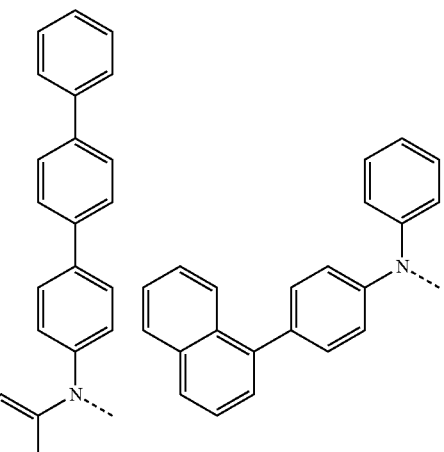
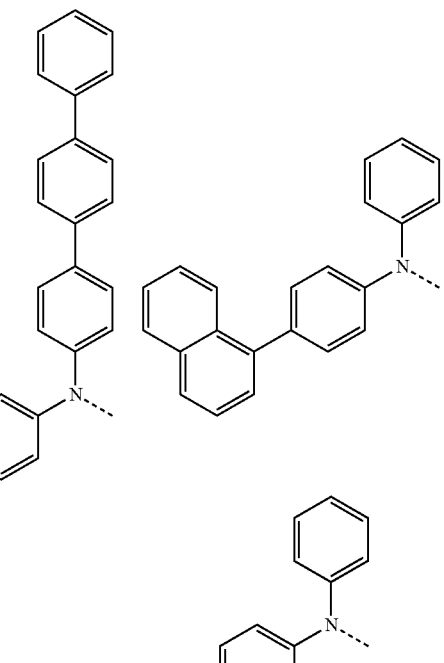

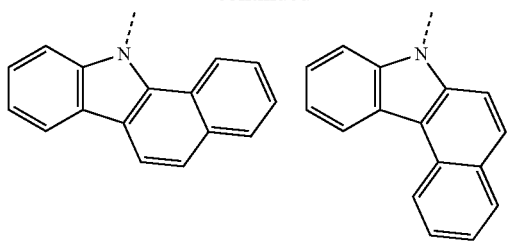
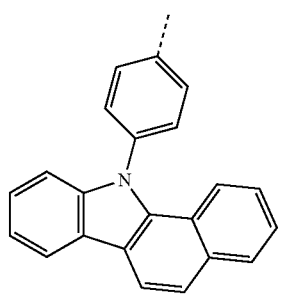
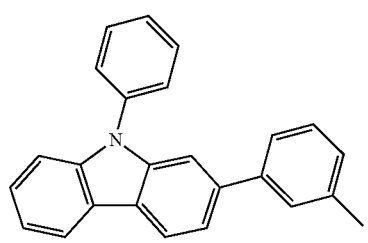
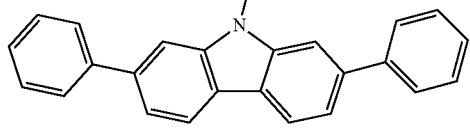
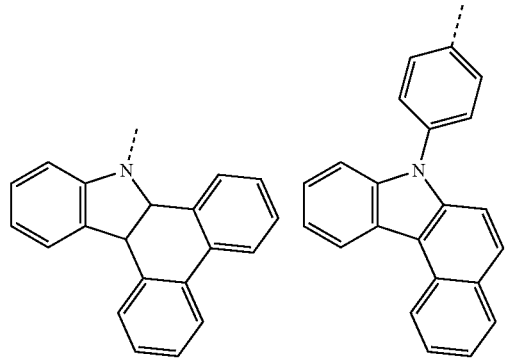
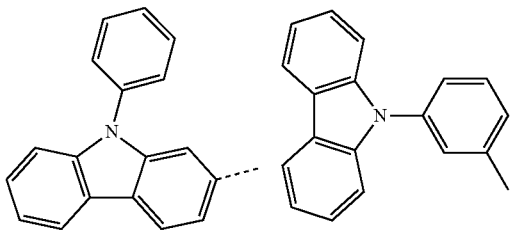
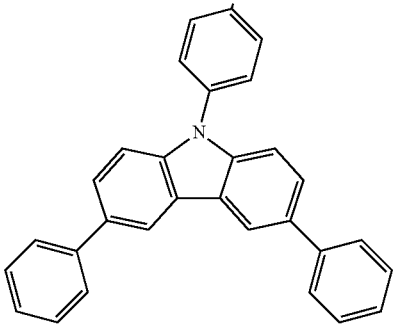
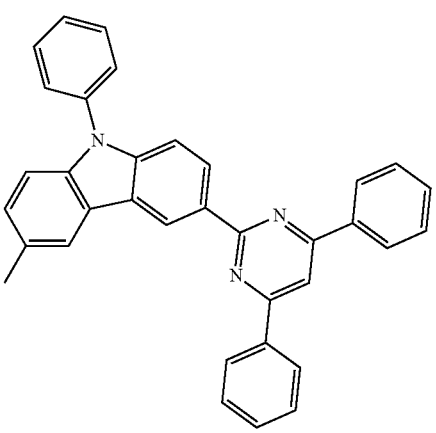
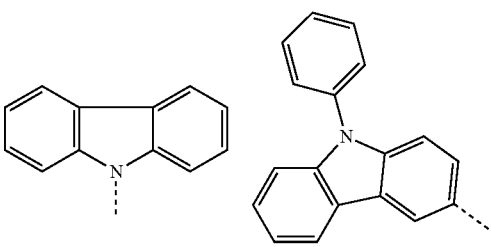

-continued
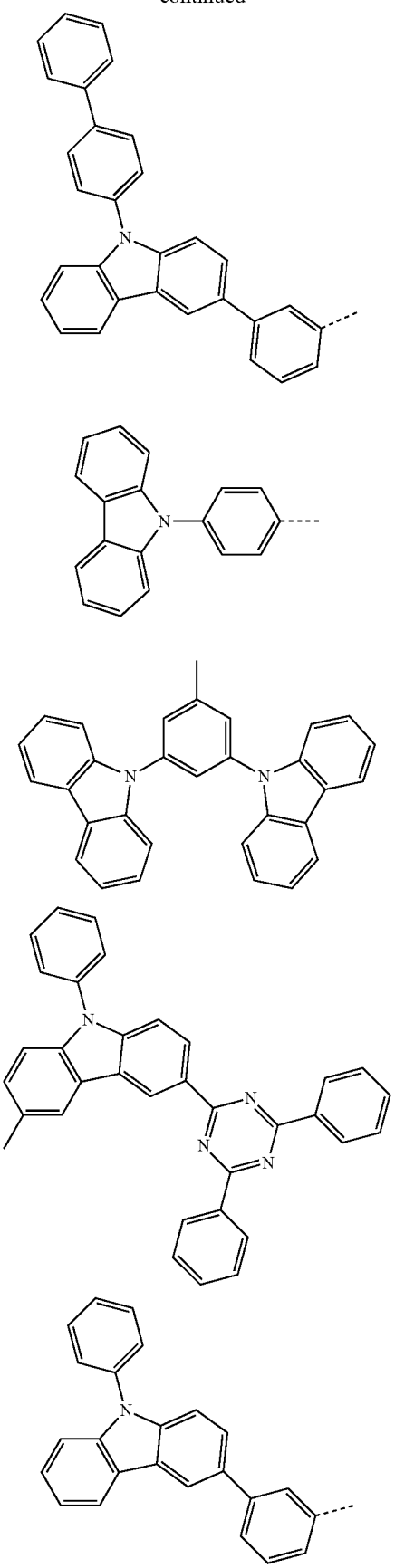
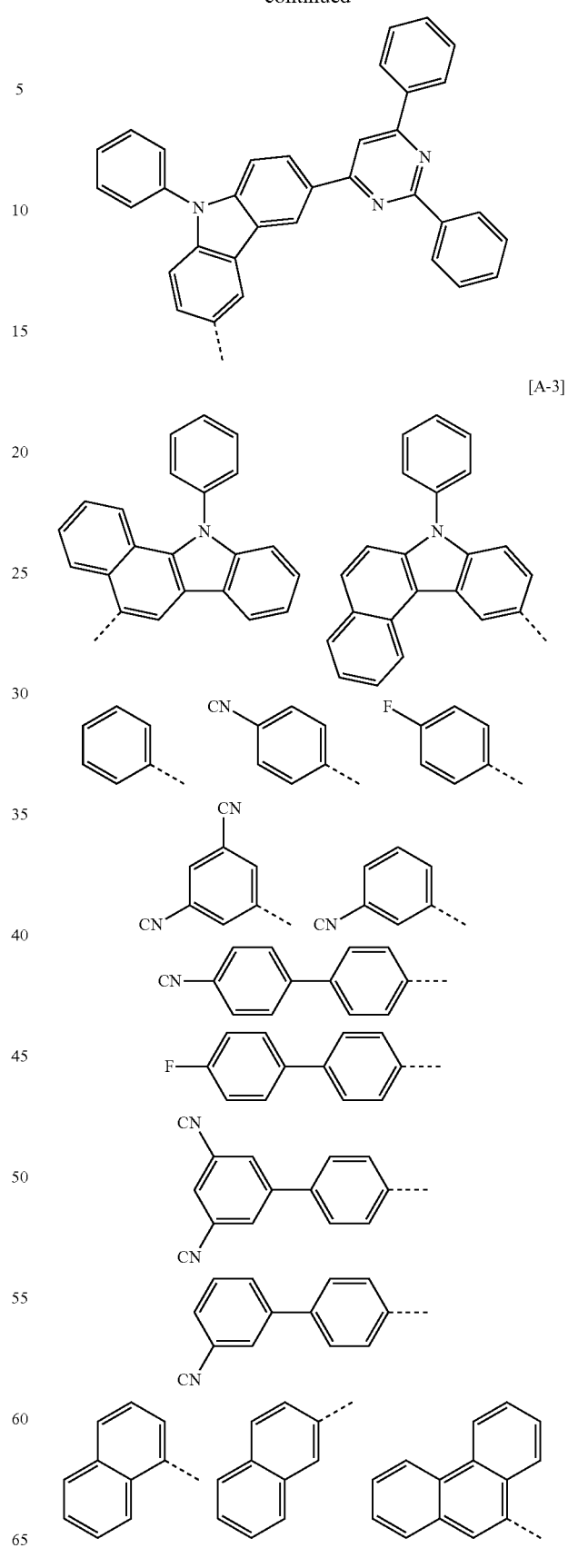
[A-3]

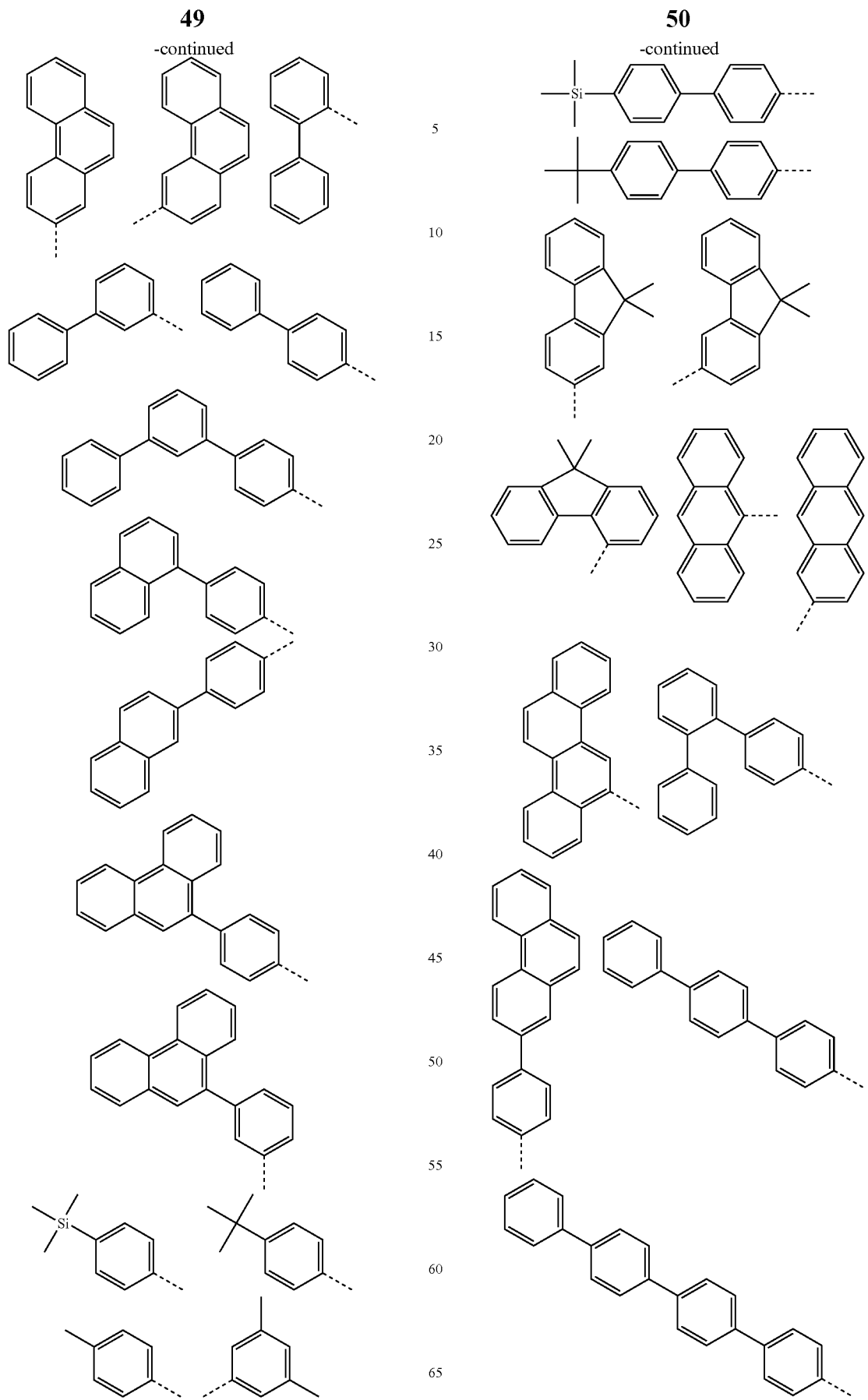

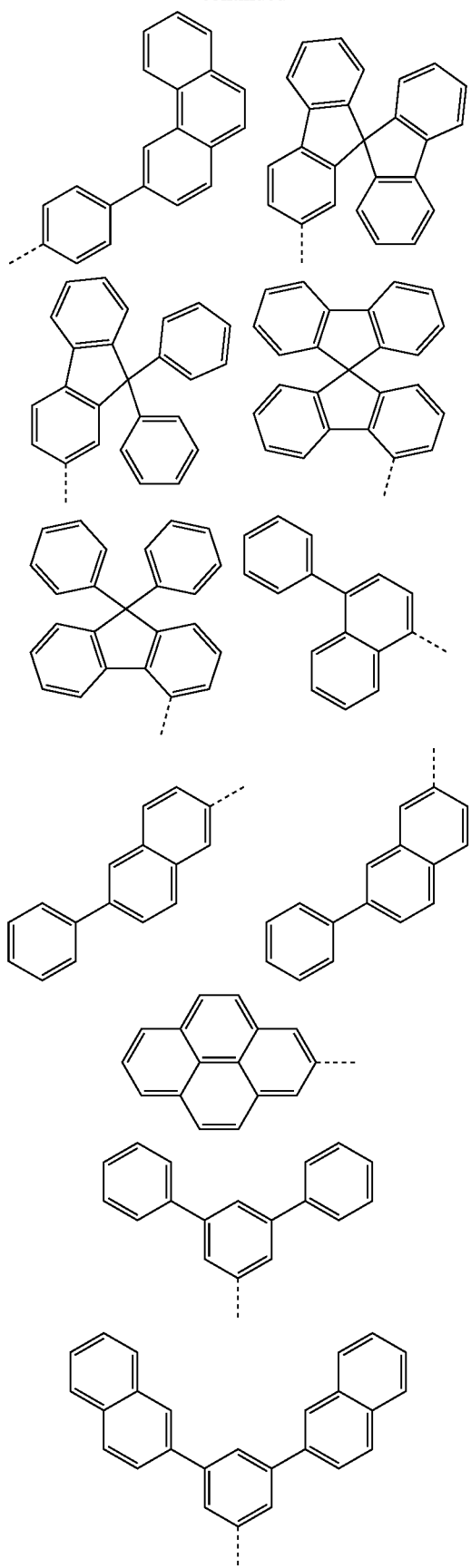
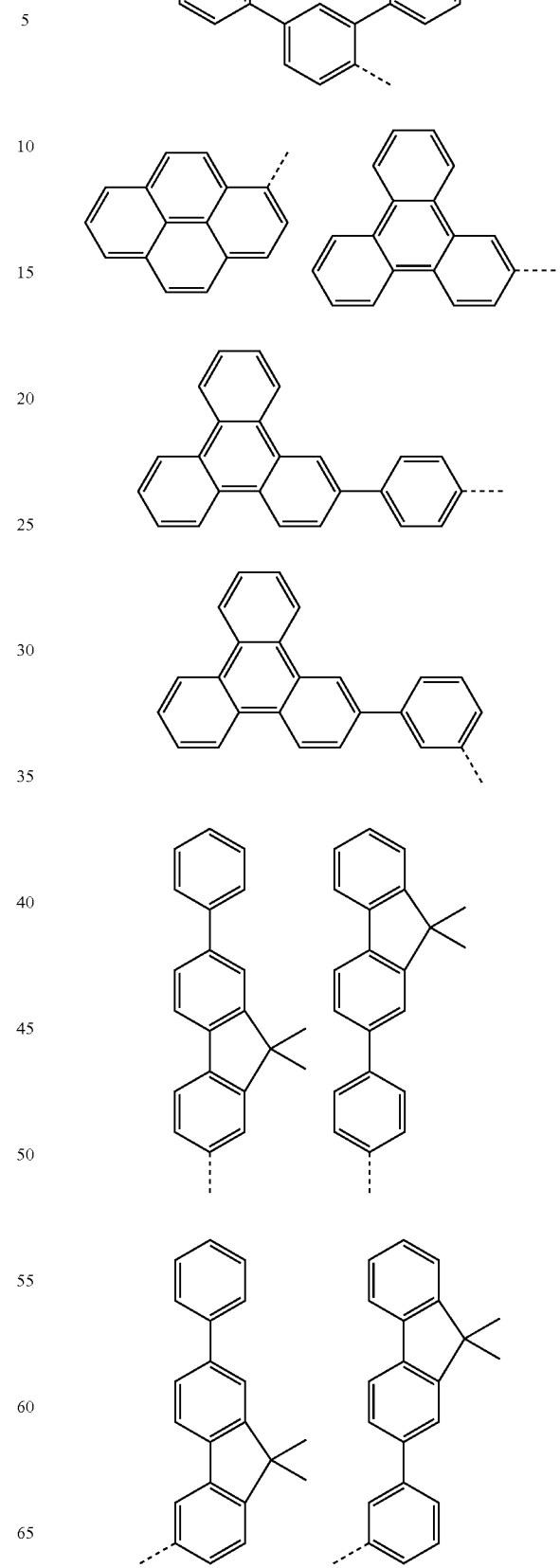

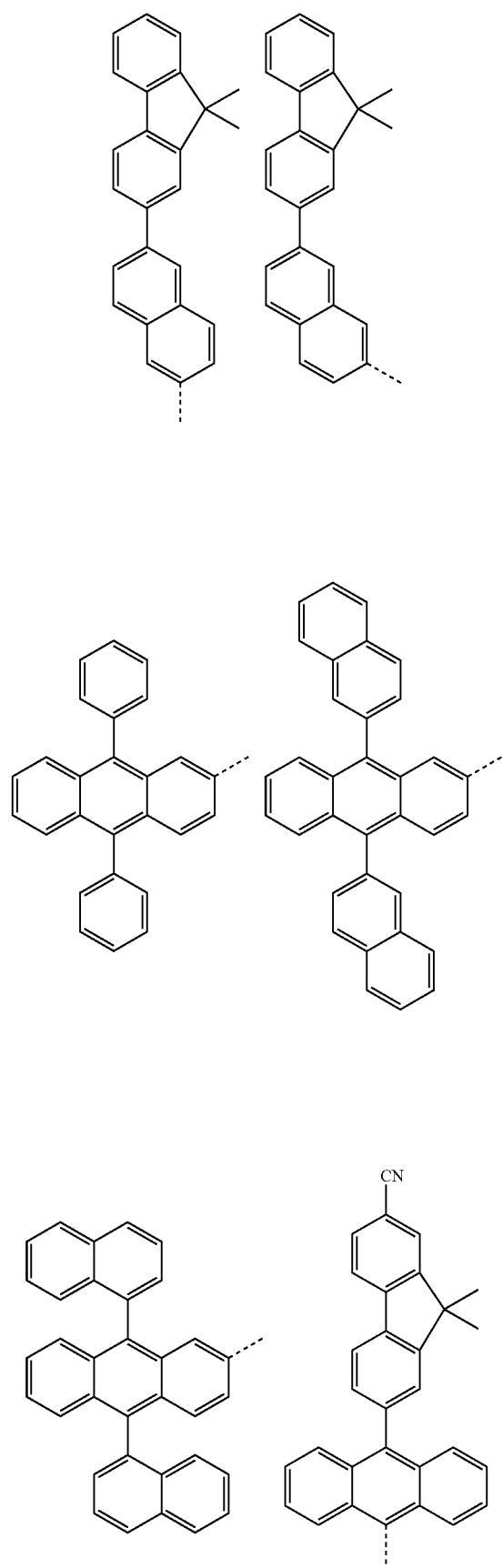
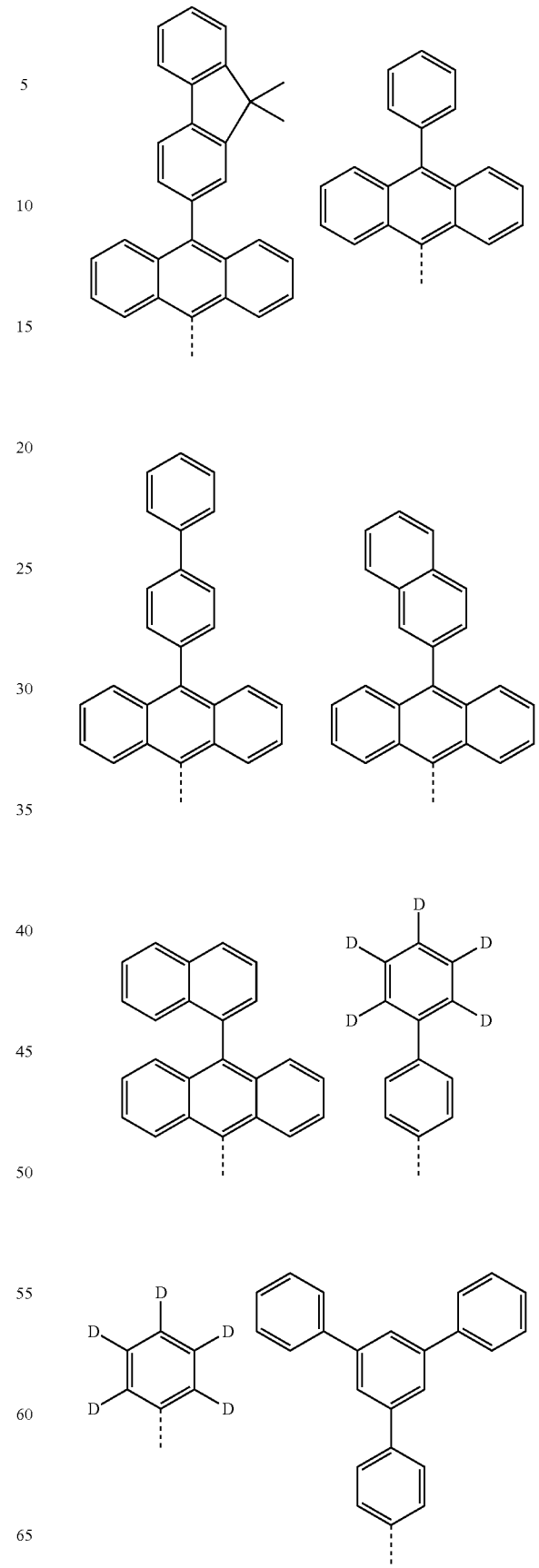

-continued
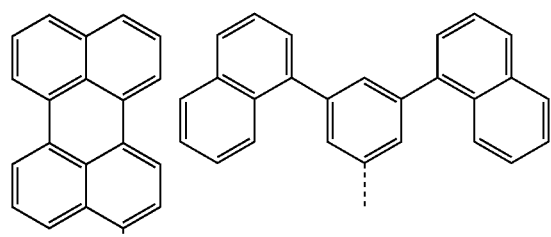
[A-4]
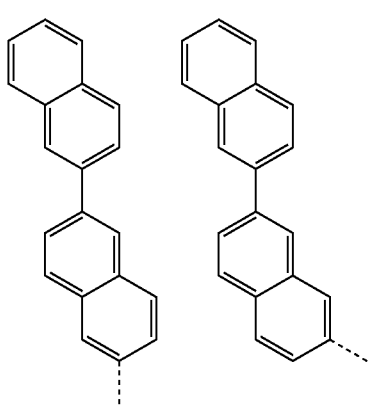
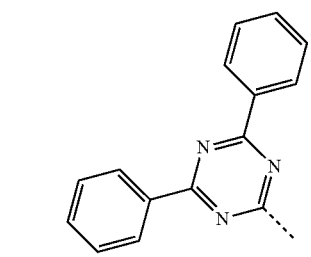
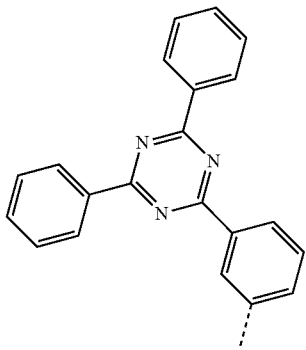
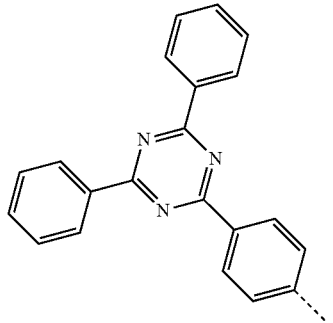
-continued
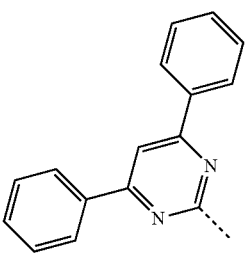
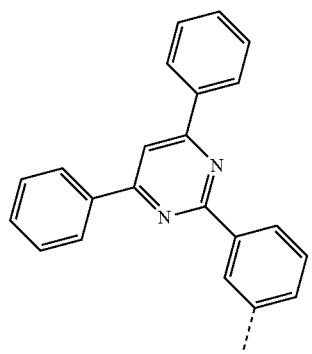
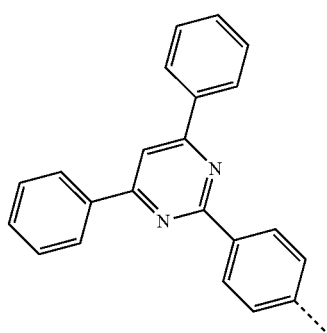
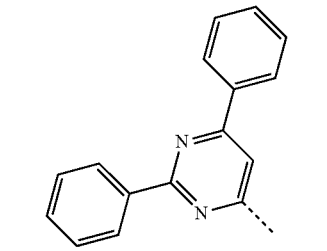
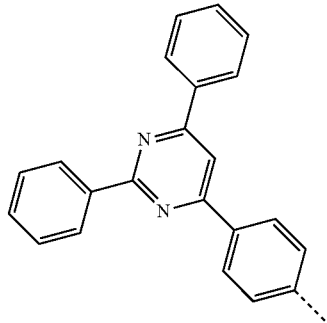

-continued
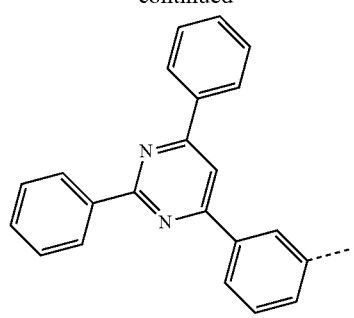
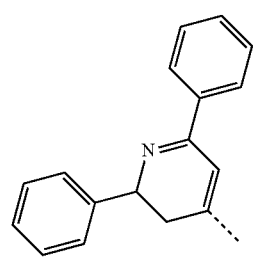
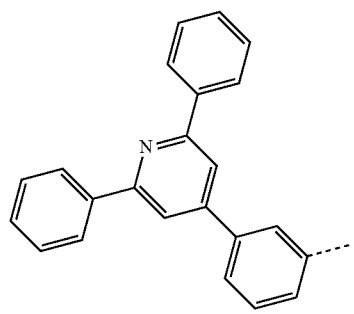
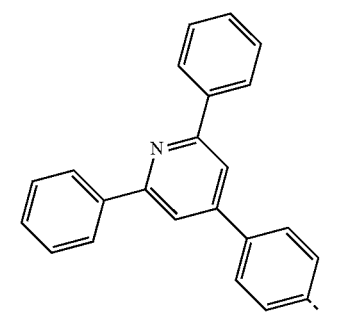
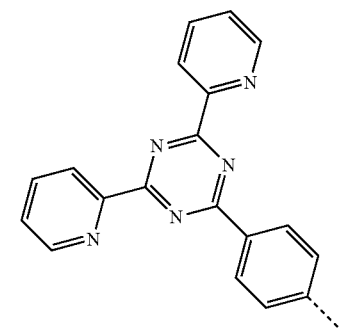
-continued
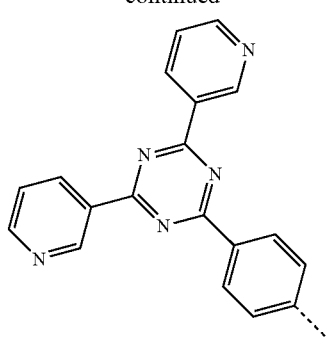
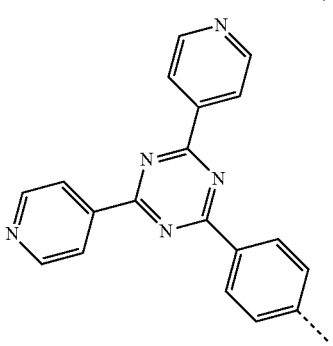
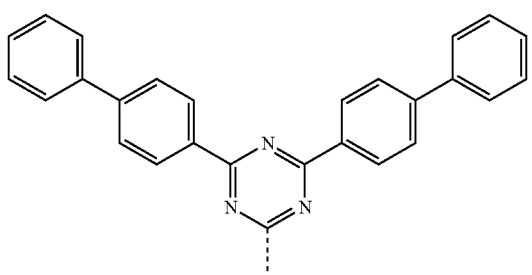
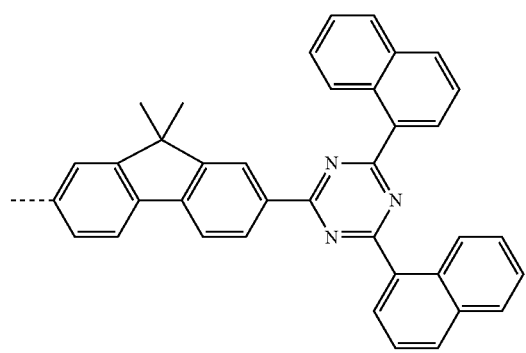
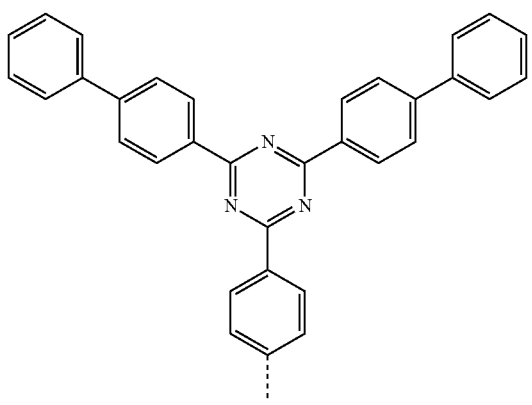

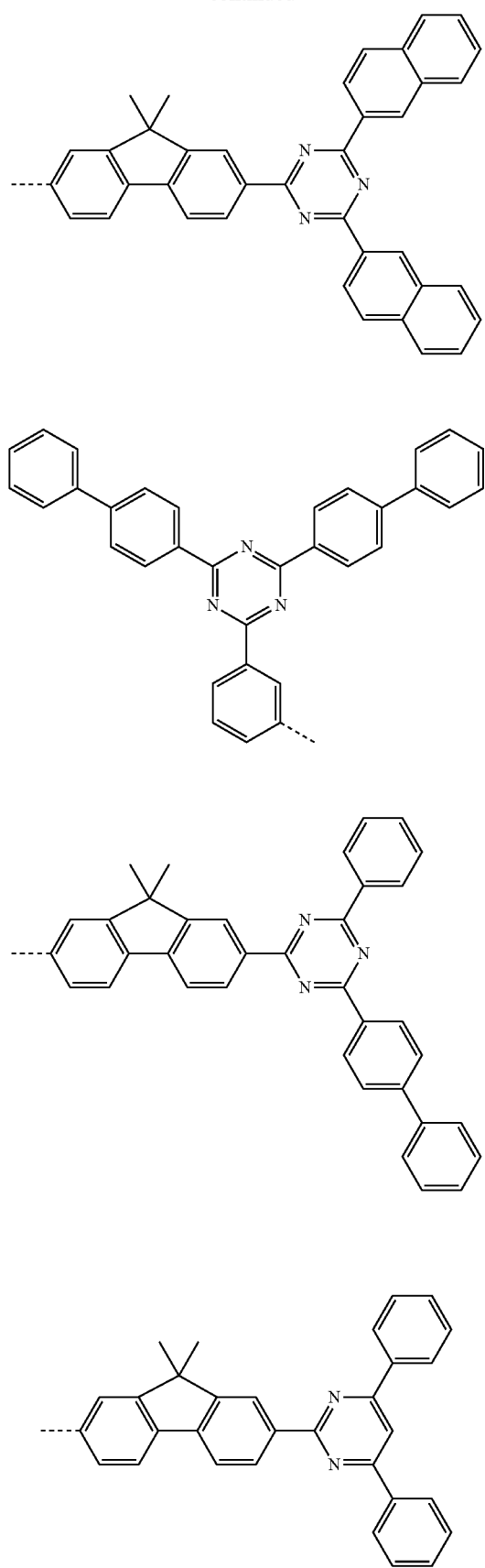
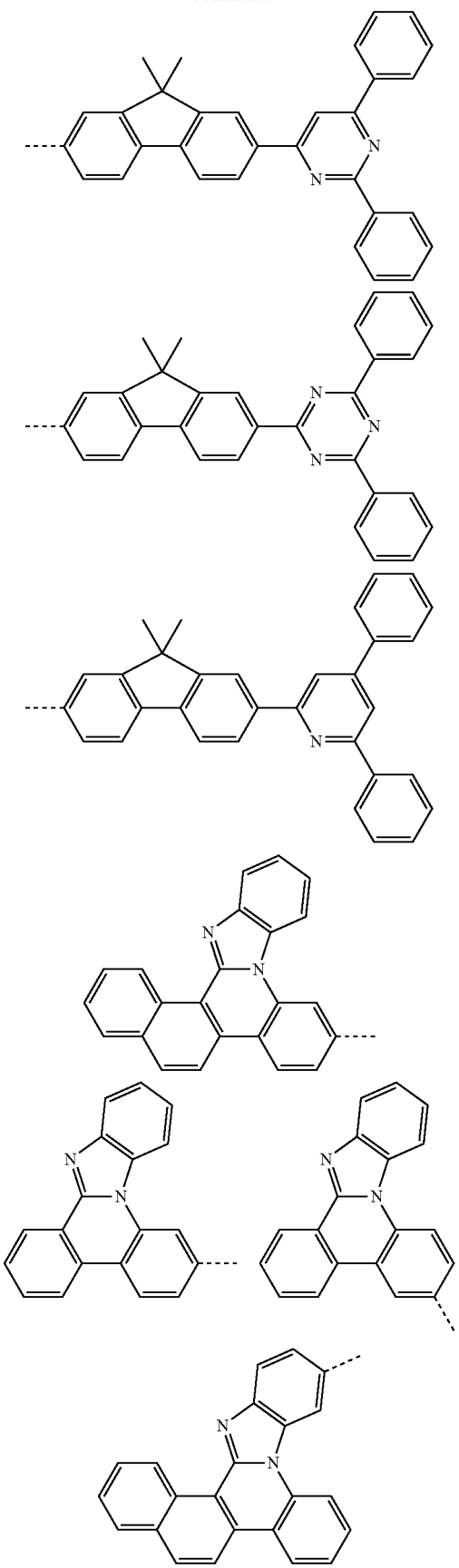

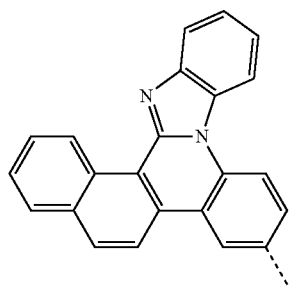
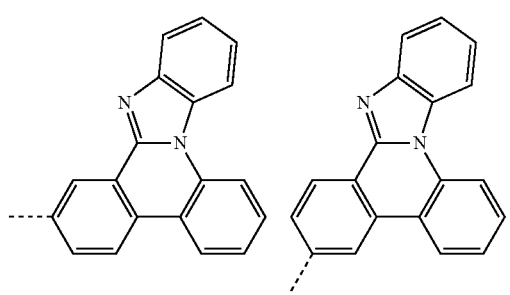
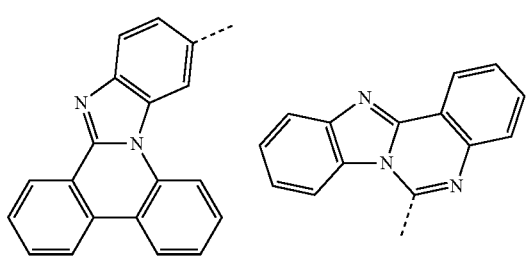
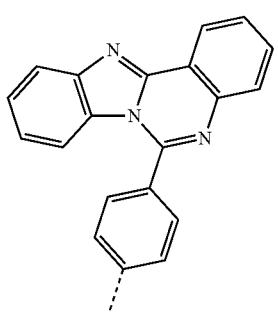
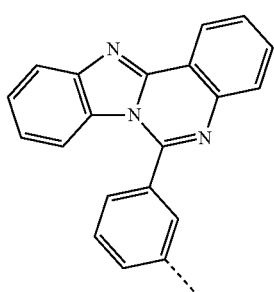
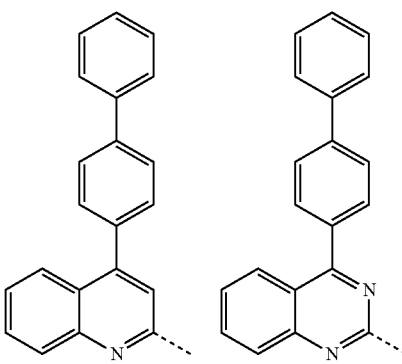
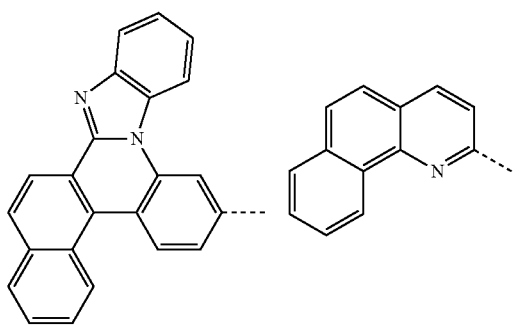
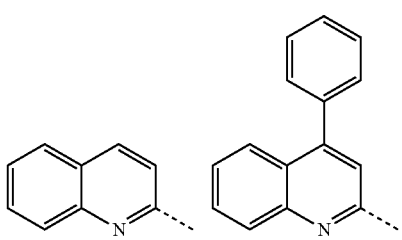
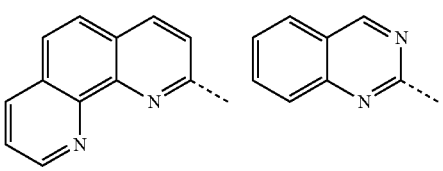
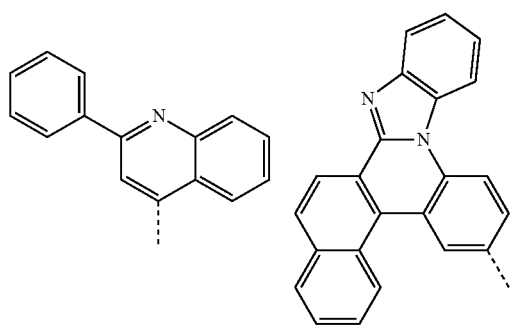
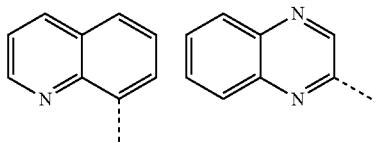

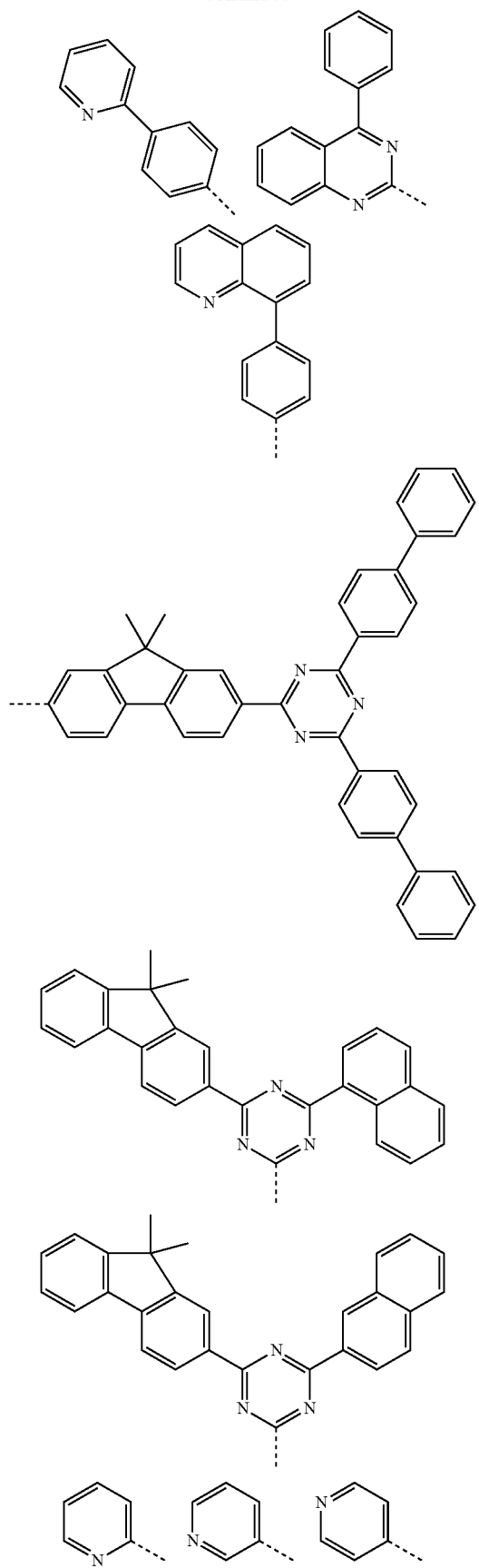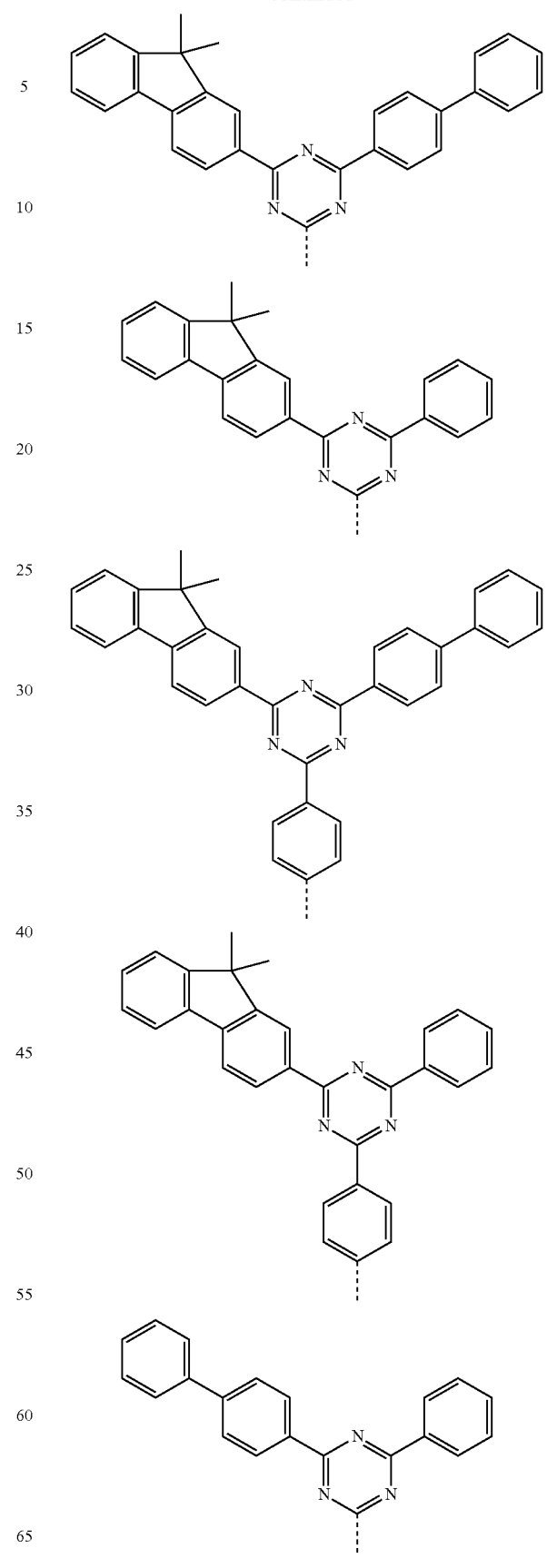

[A-5]
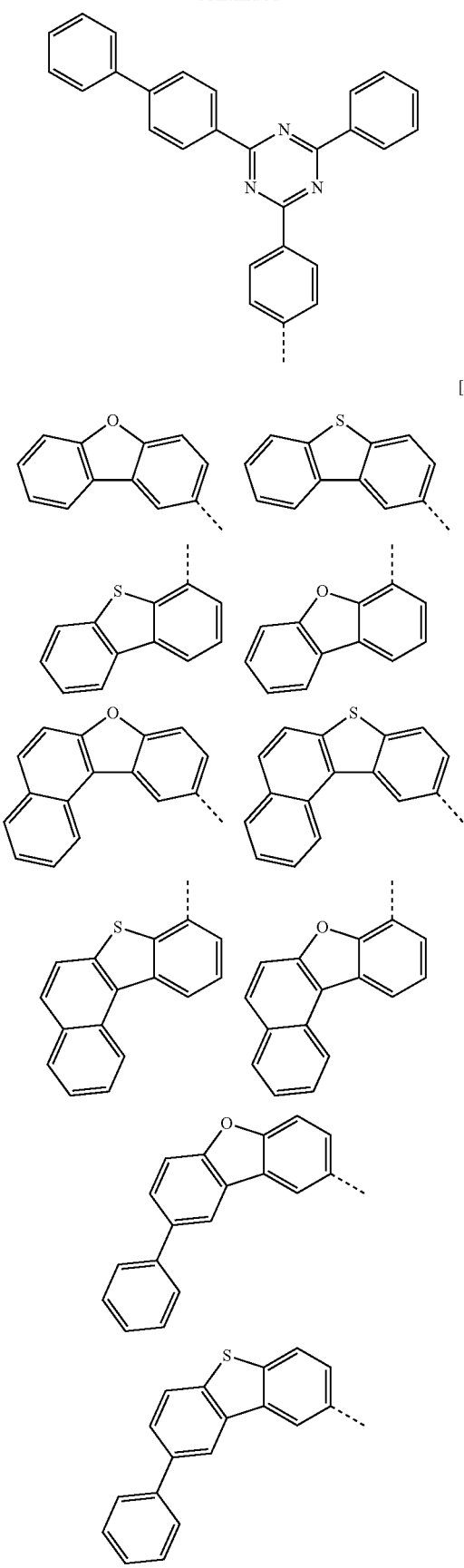
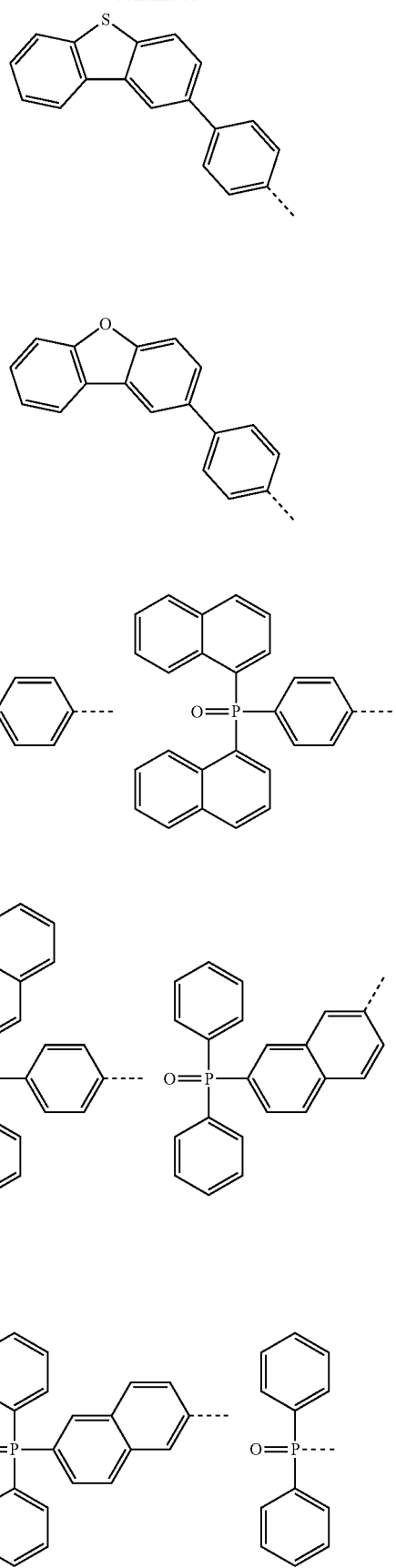

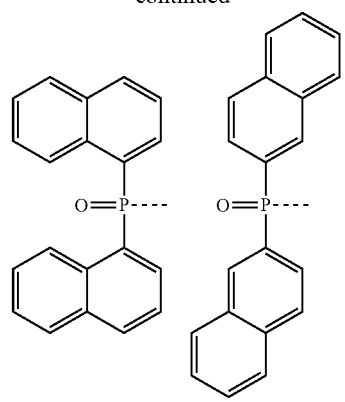
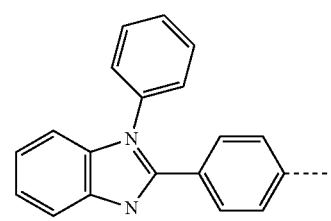
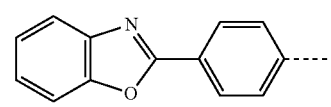
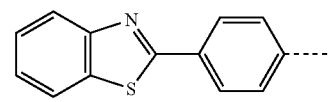
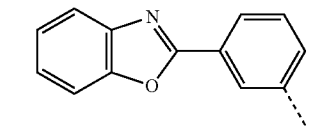
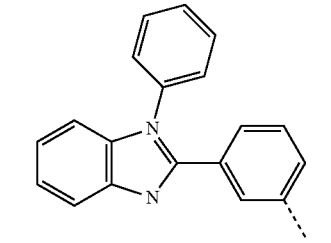
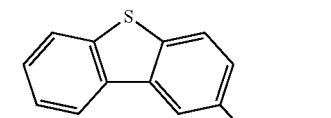
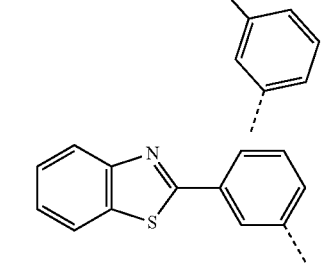
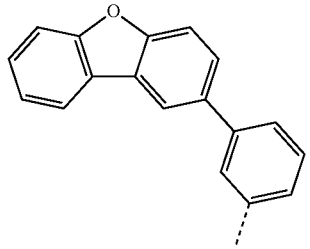
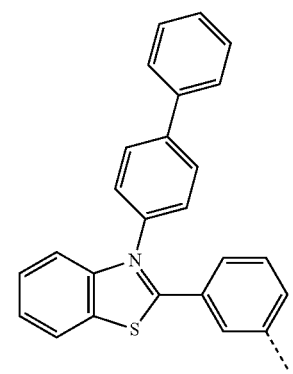
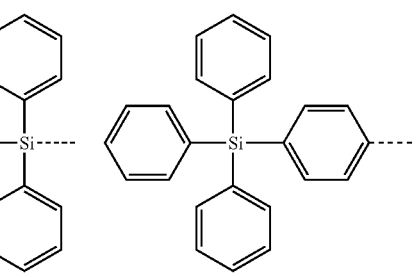
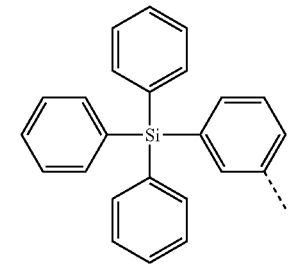
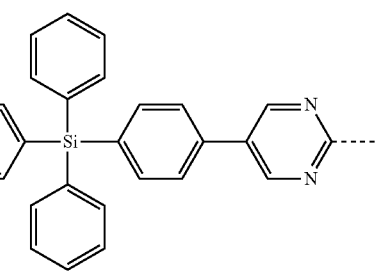

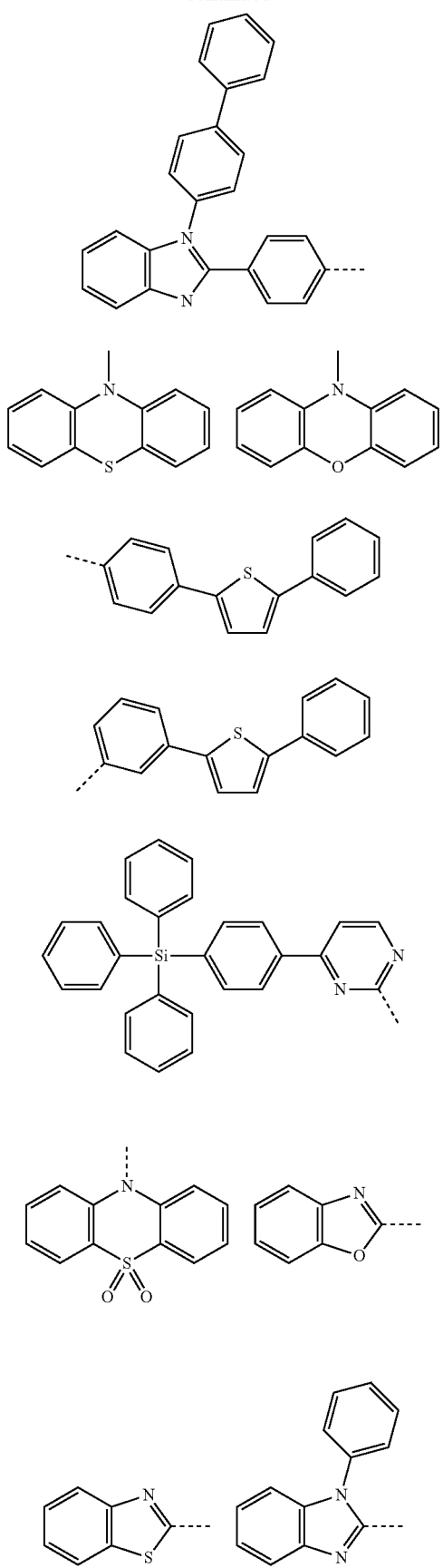
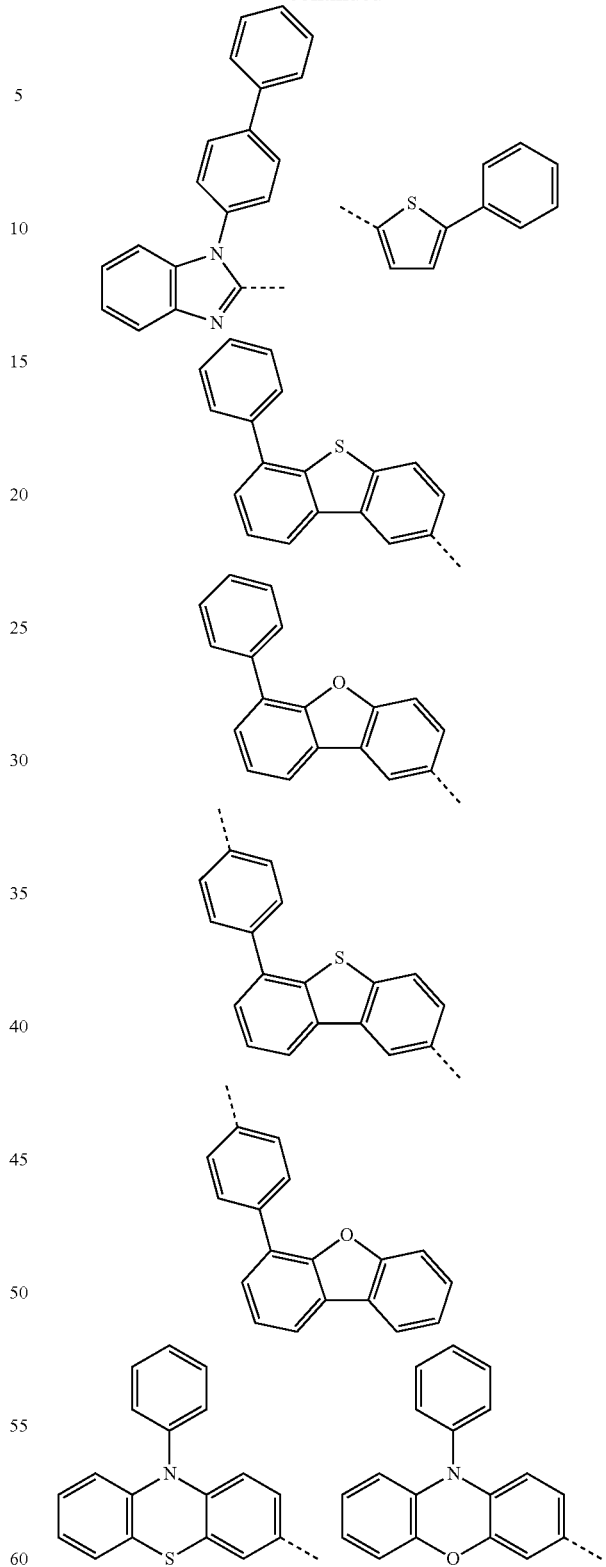
In the structural formulae, ---- means a moiety bonded to Chemical Formula 1 via L1.
According to an exemplary embodiment of the present specification, Chemical Formula 1 is represented by any one of the following compounds.

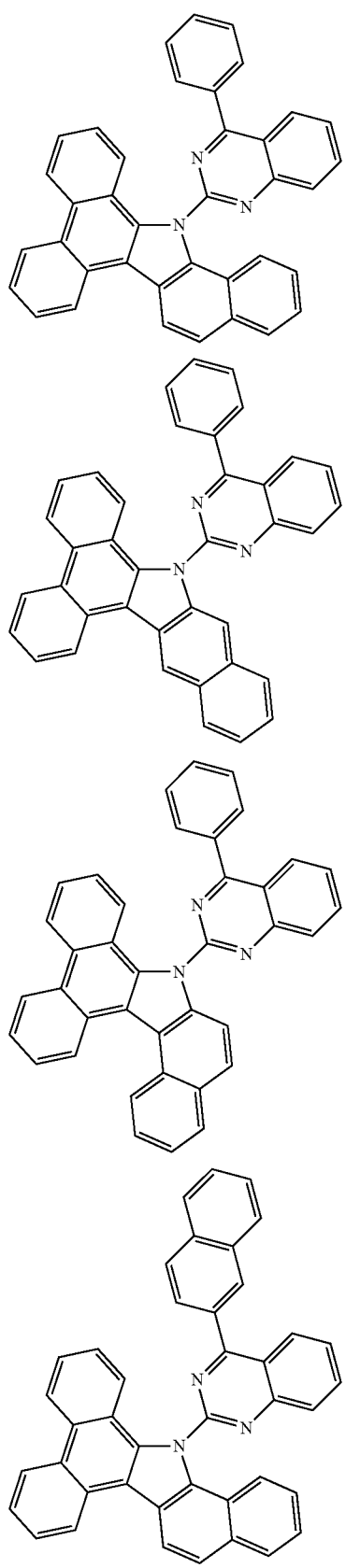
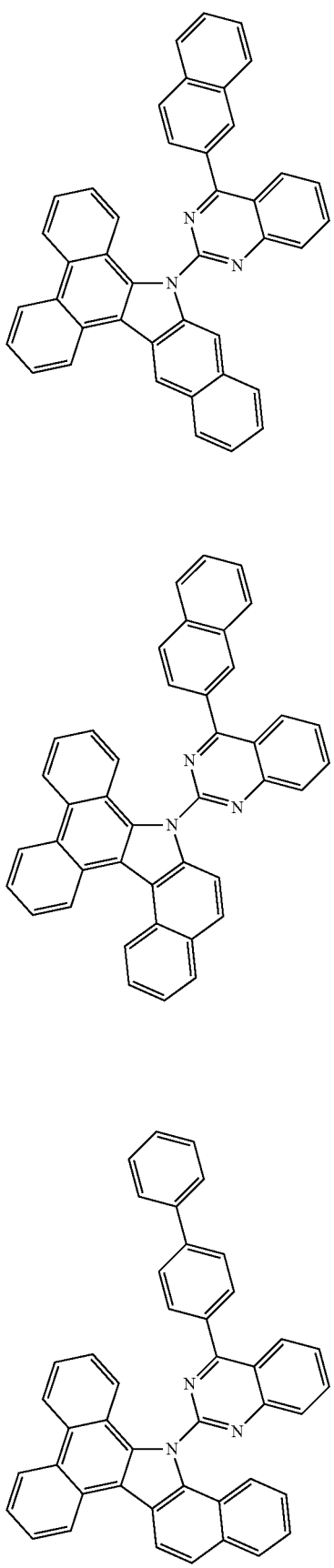

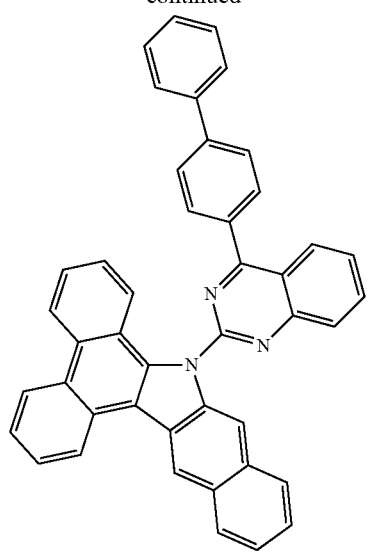
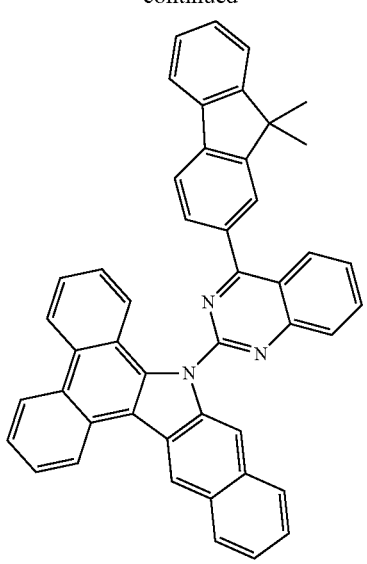
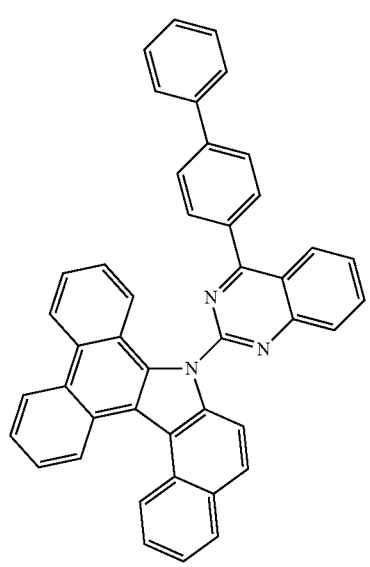
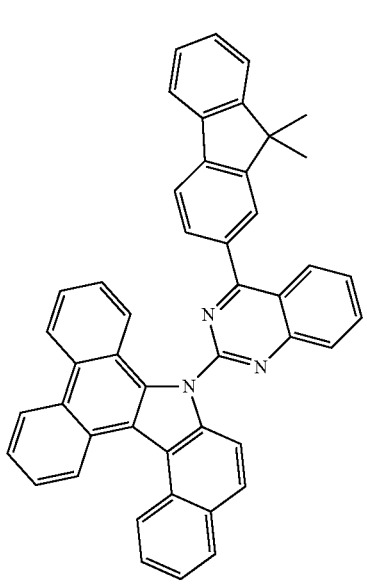
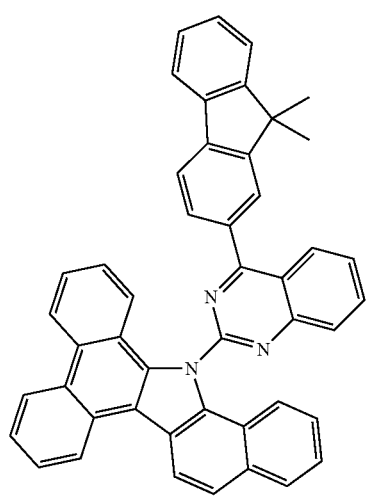
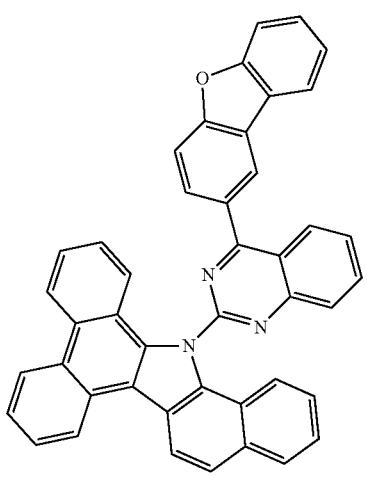

75
-continued
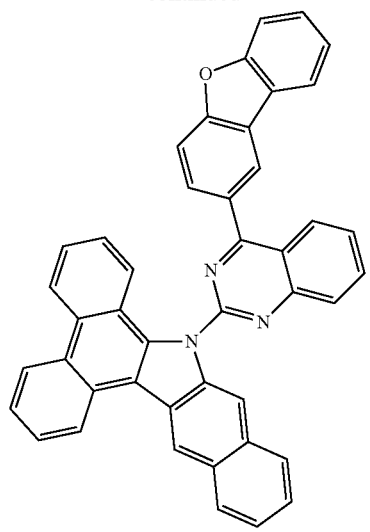
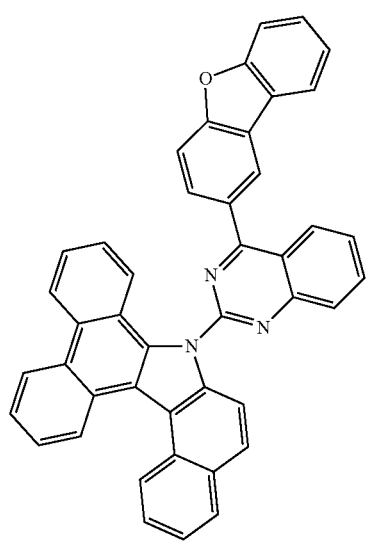
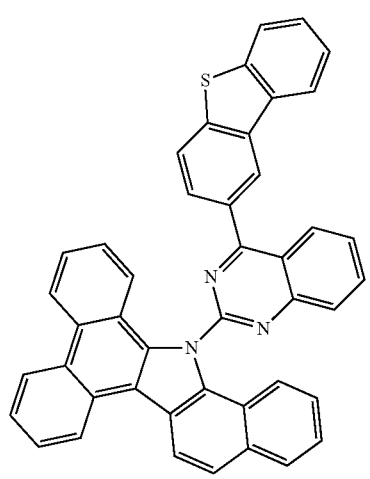
76
-continued
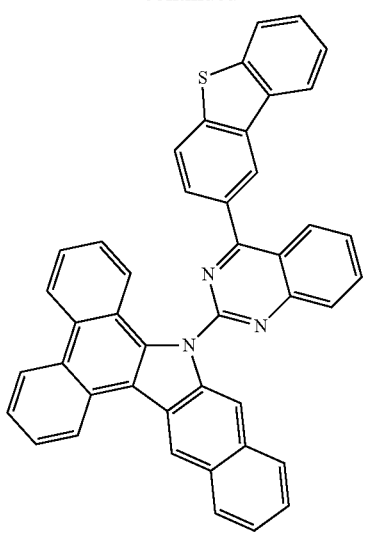
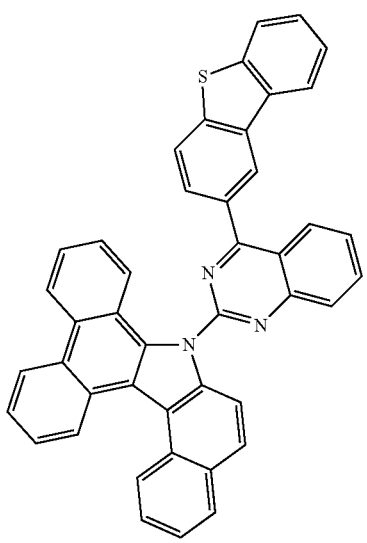
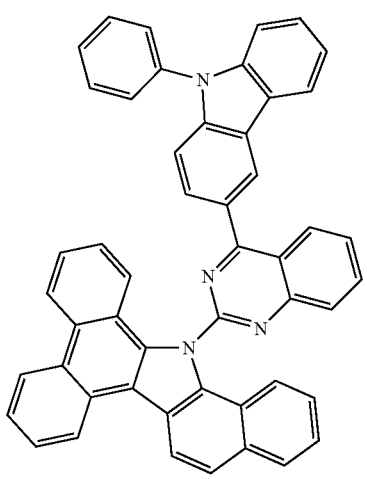

77
-continued
78
-continued
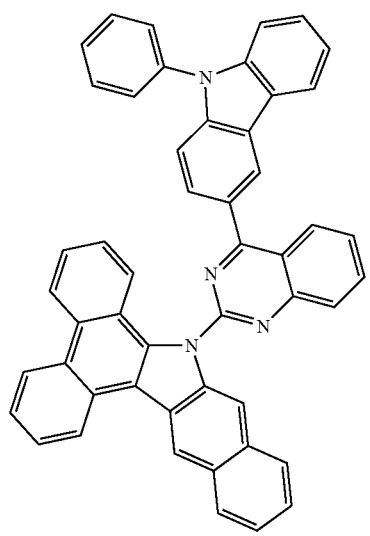
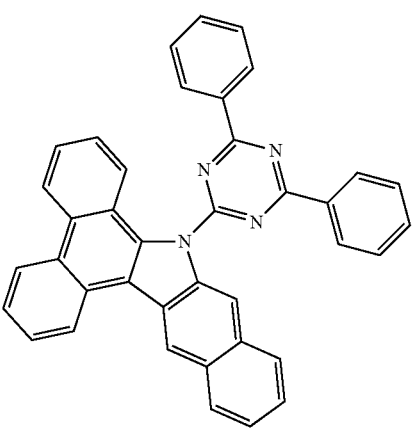
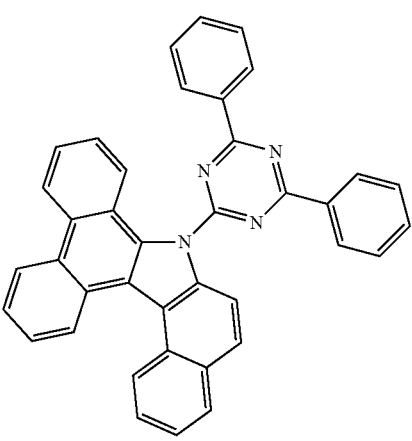
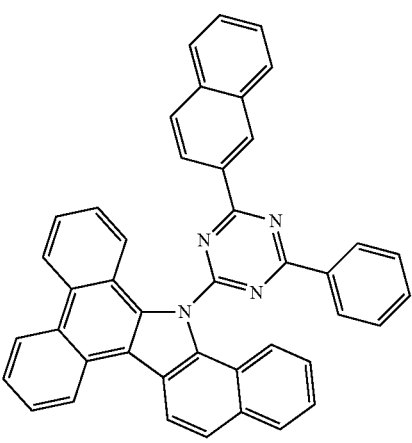

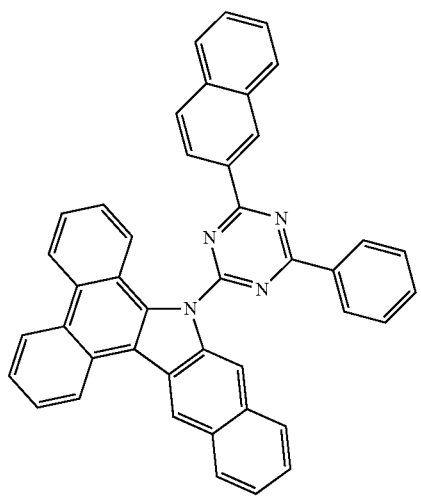
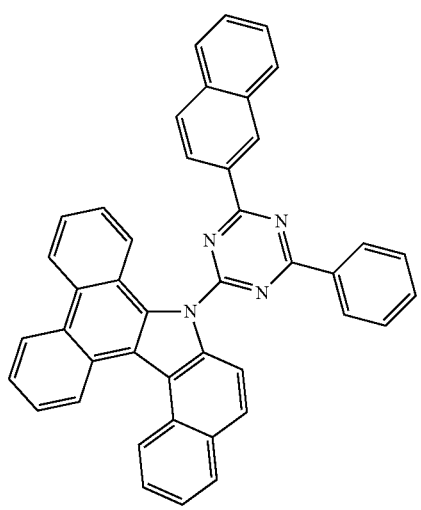
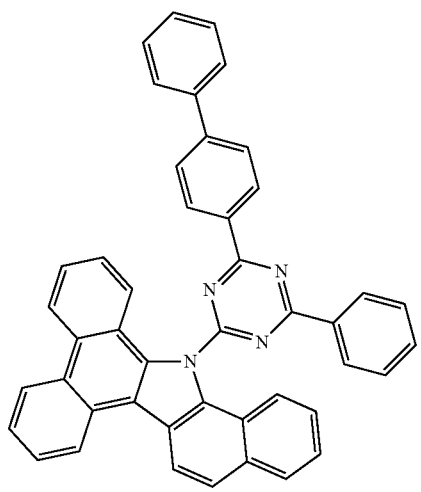
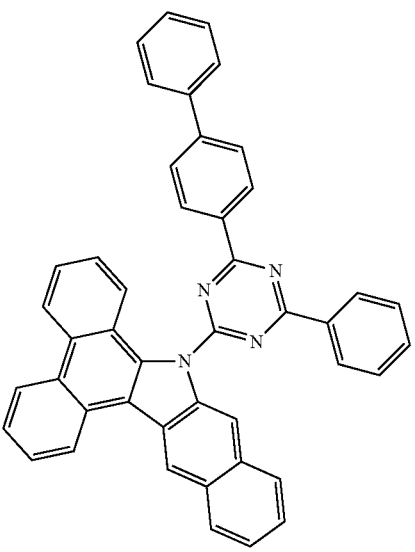
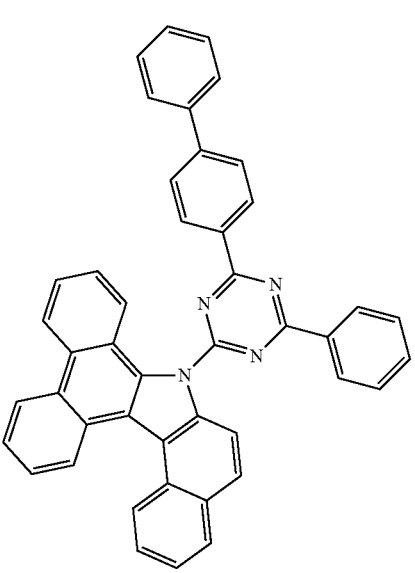
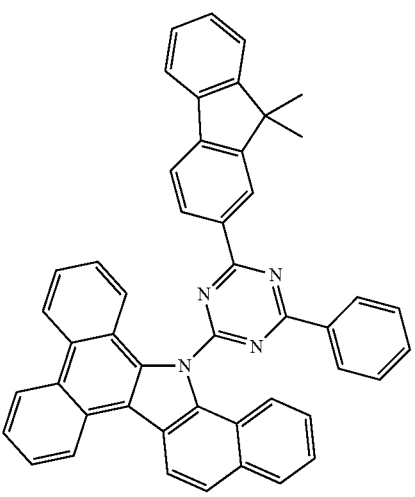

81
-continued
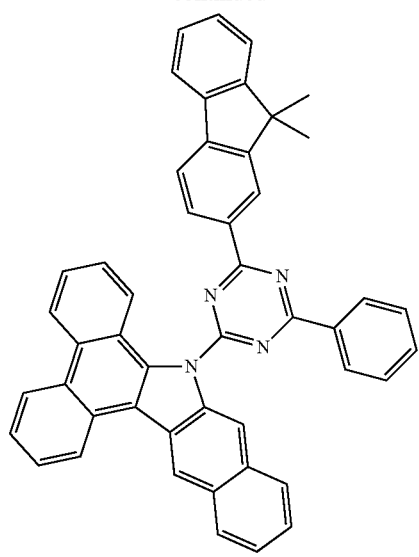
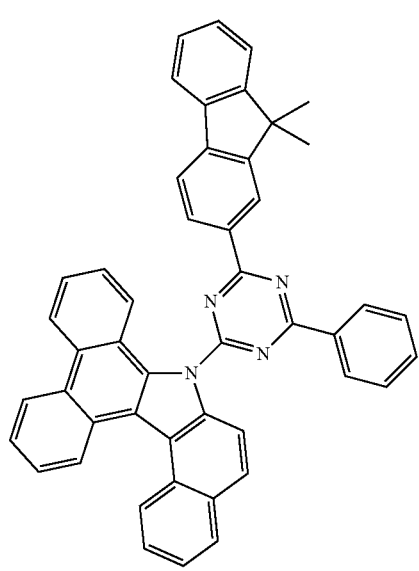
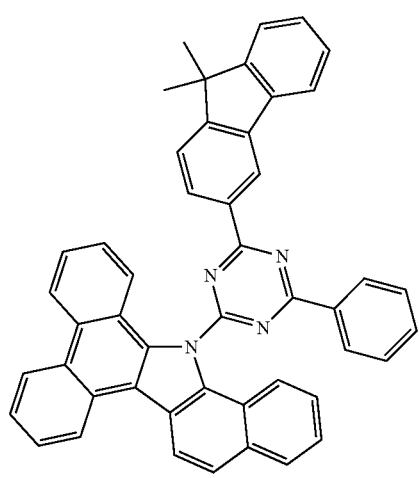
82
-continued
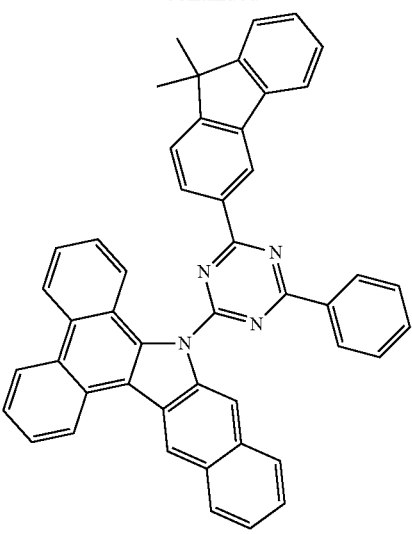
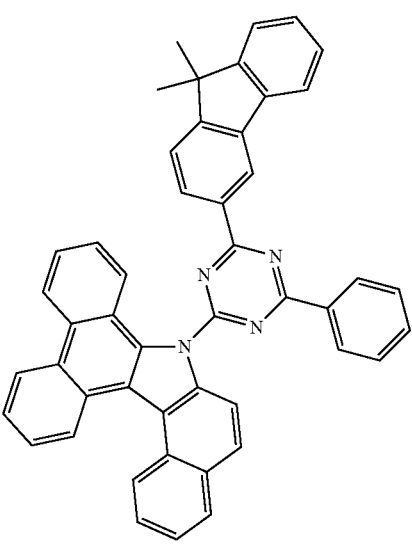
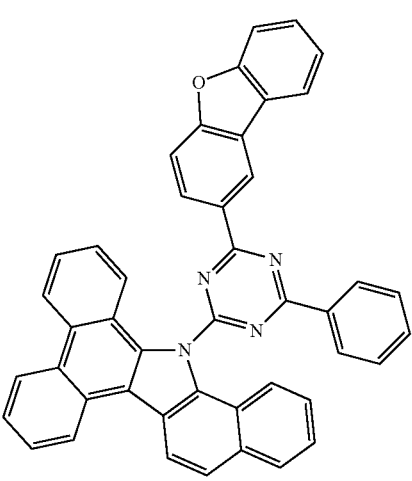

83
-continued
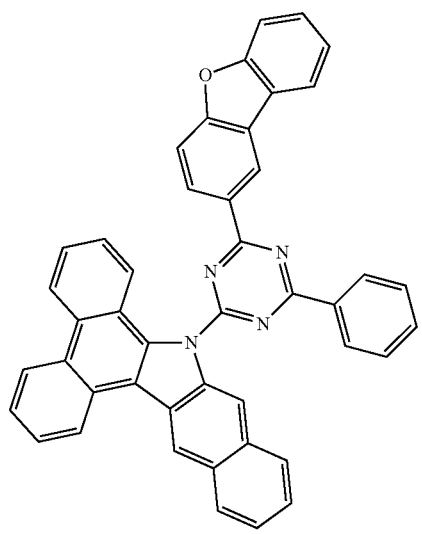
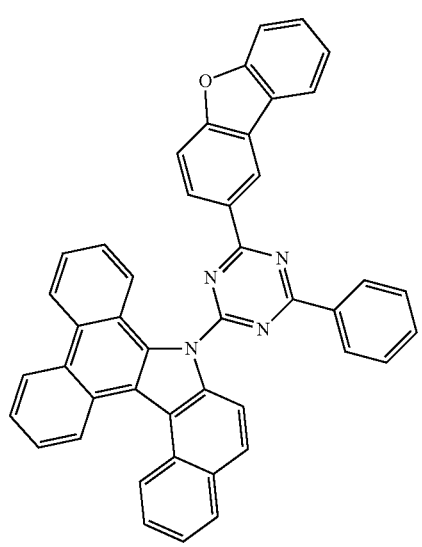
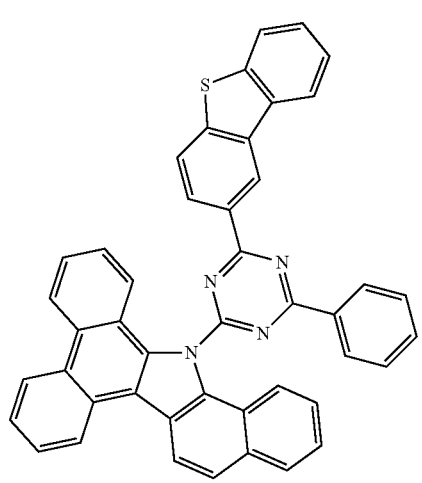
84
-continued
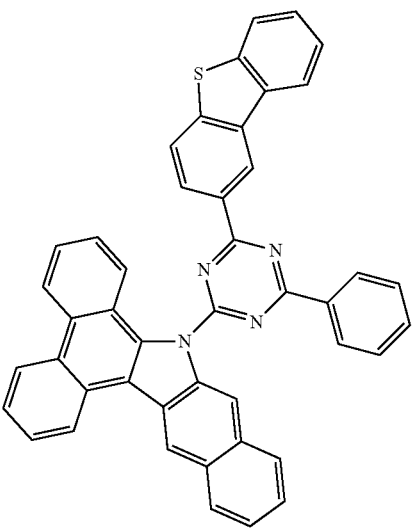
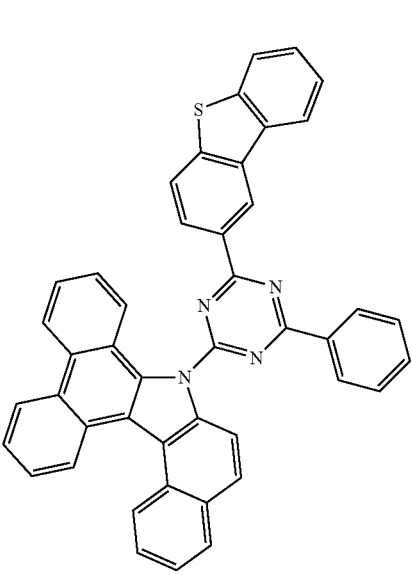
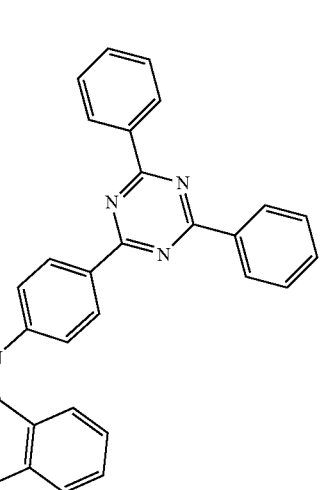

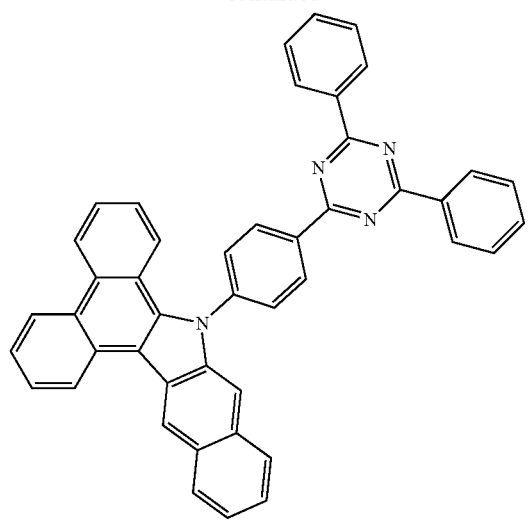
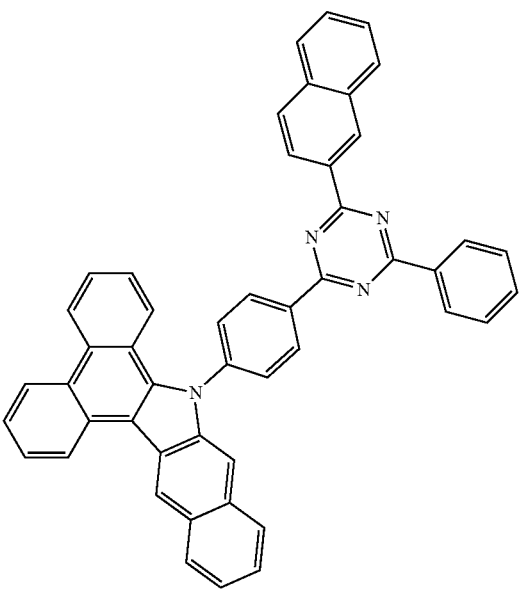

87
-continued
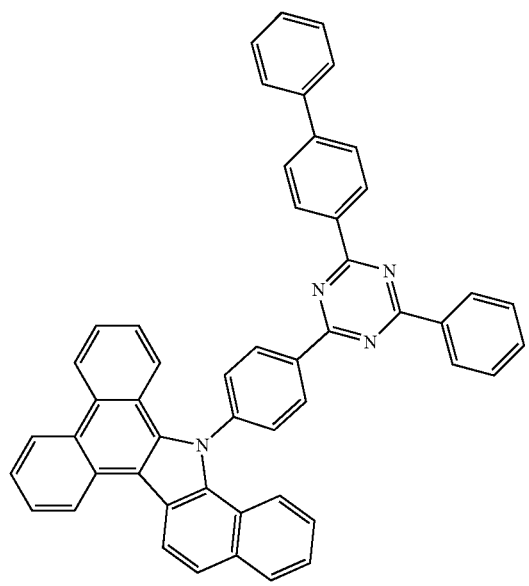
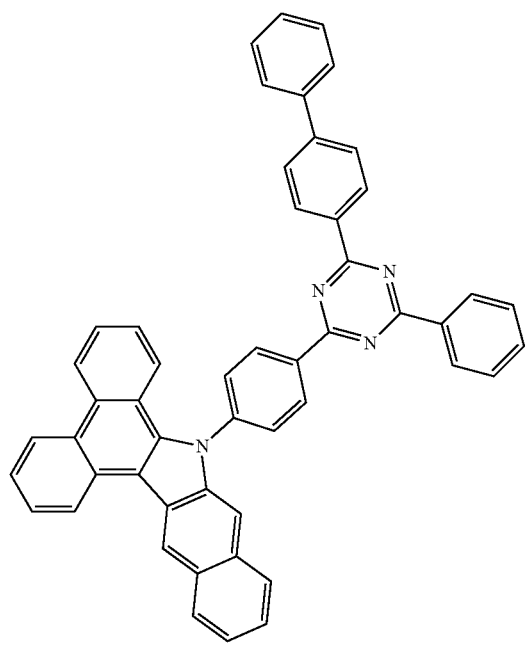
88
-continued
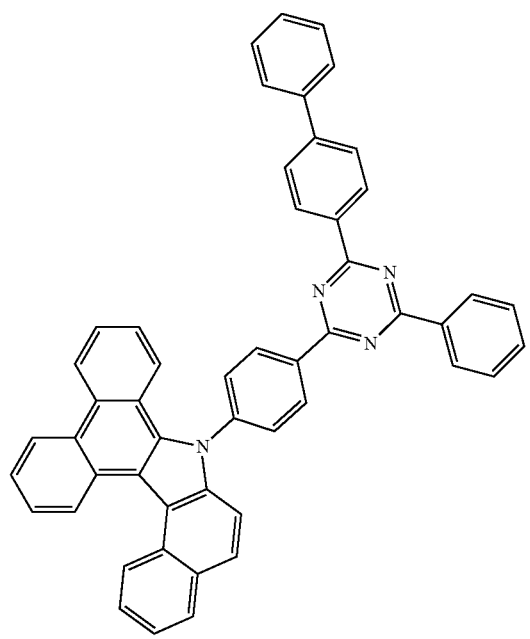
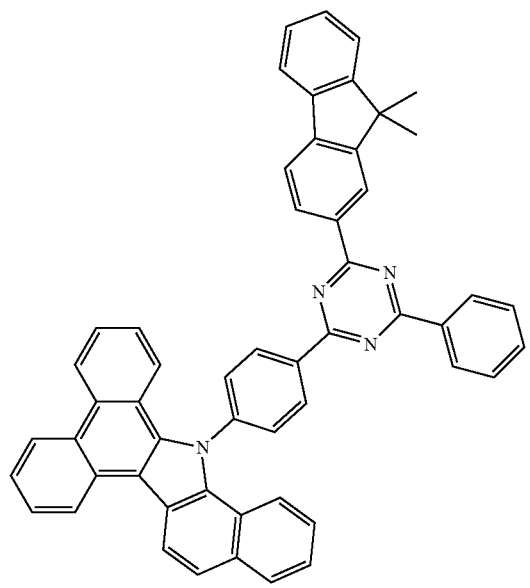

89
-continued
90
-continued
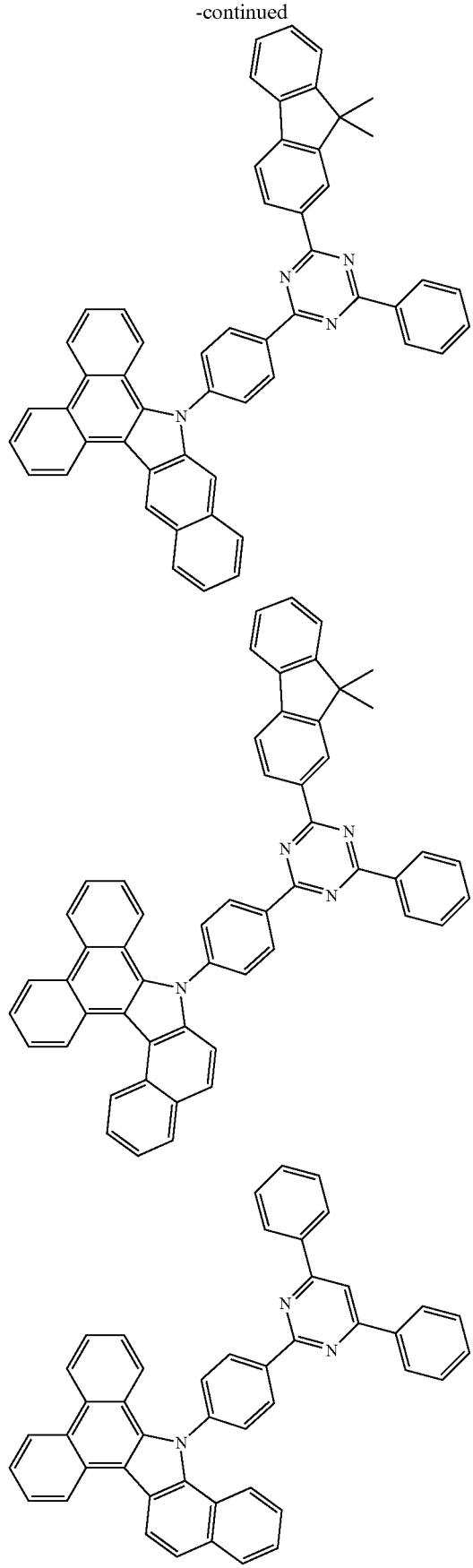
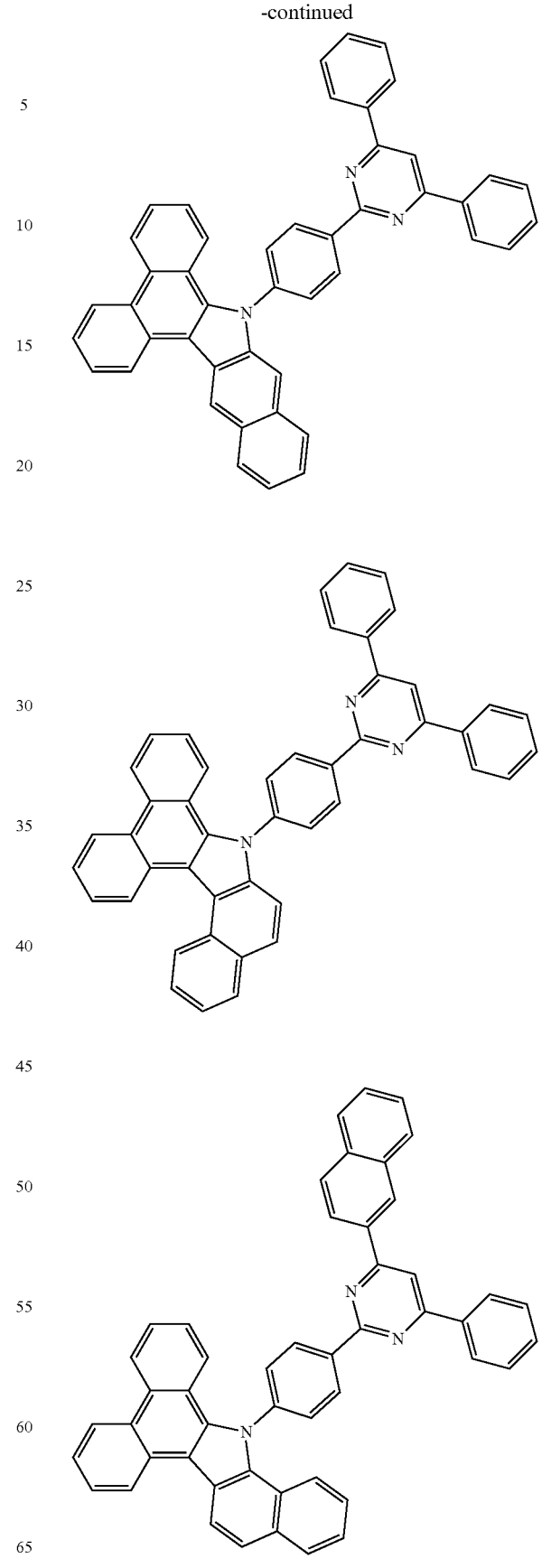

91
-continued
92
-continued
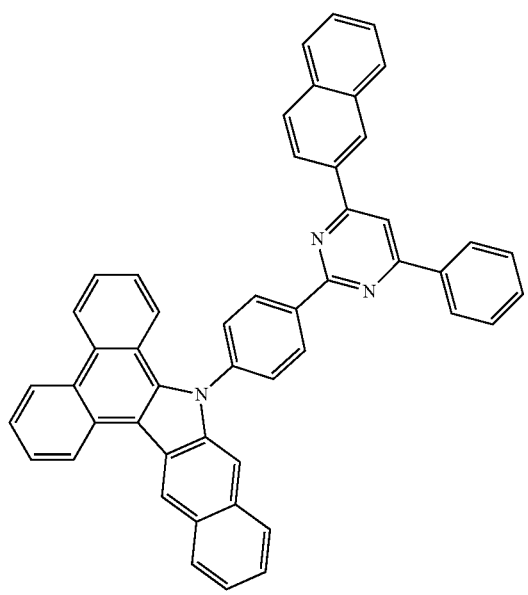
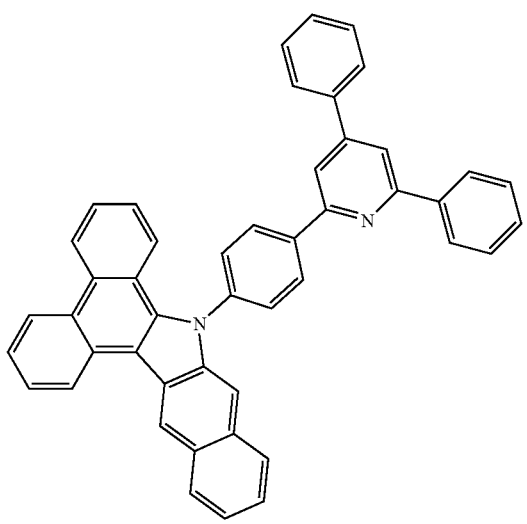
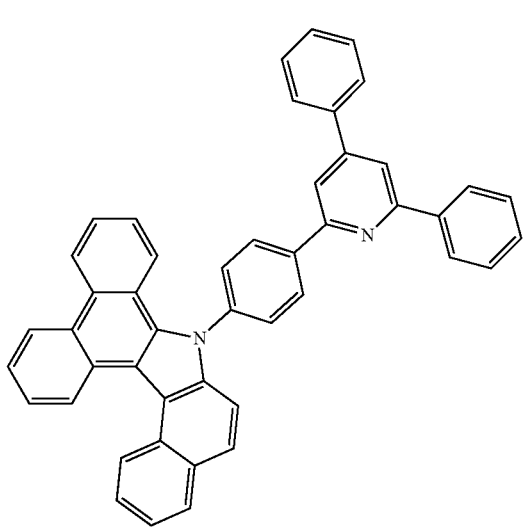
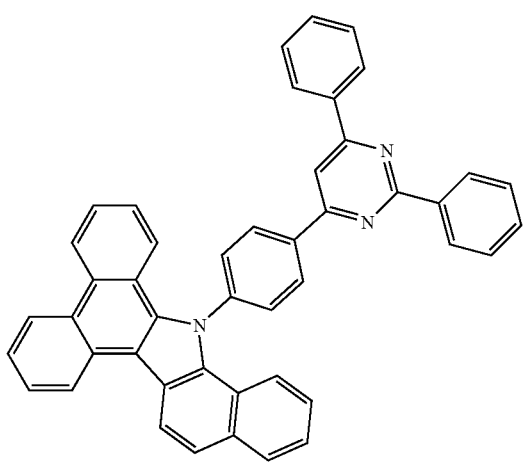

93
-continued
94
-continued
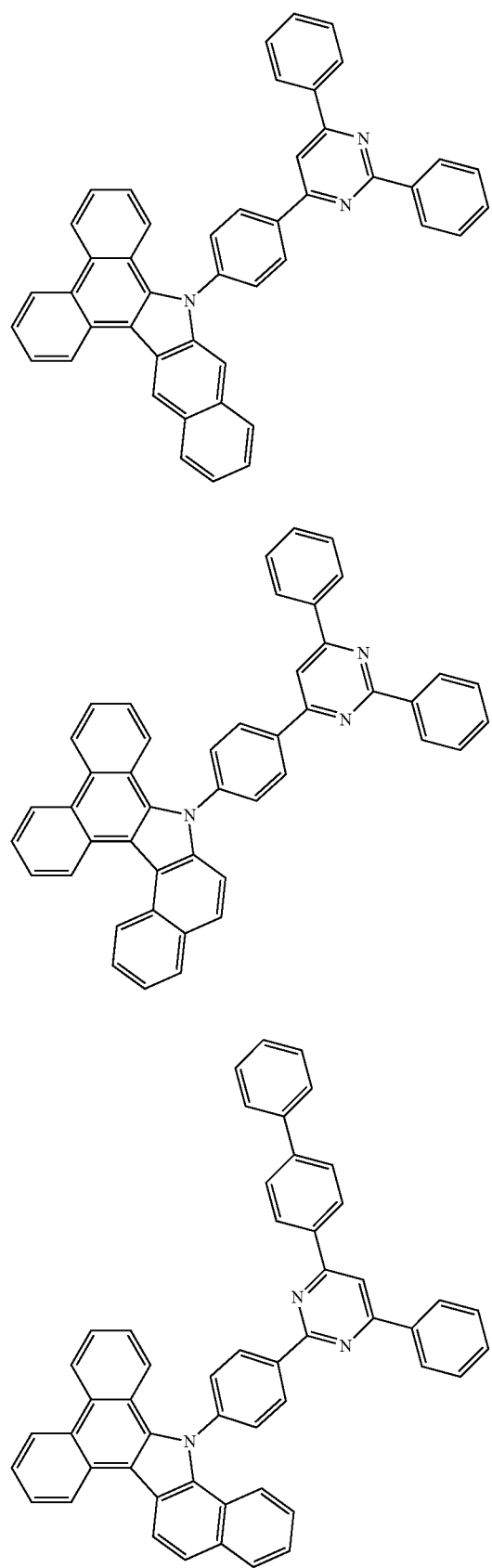
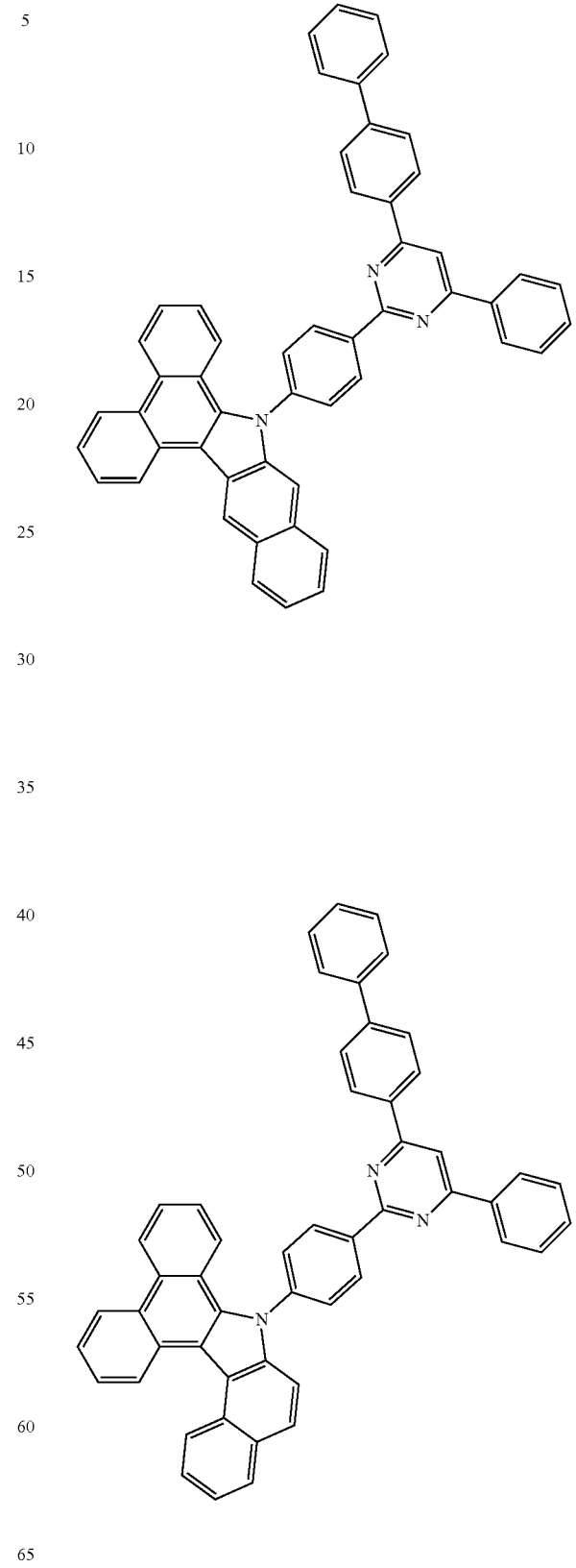

95
-continued
96
-continued
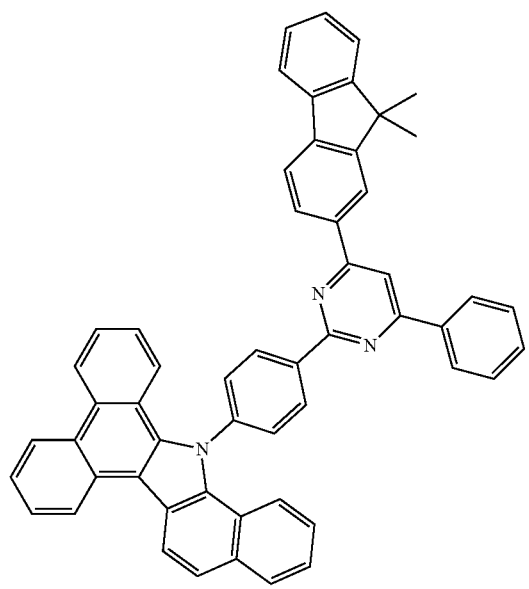
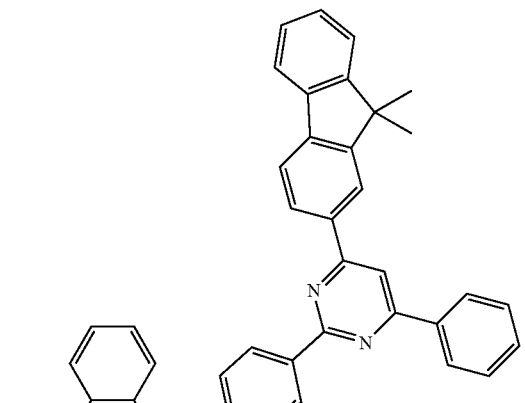
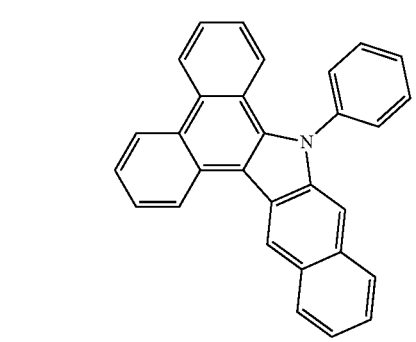
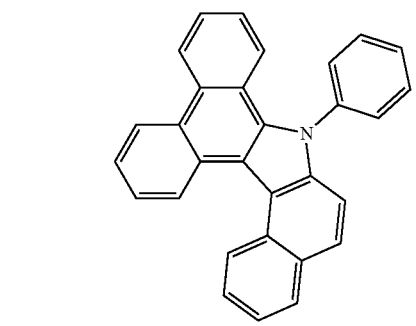

97
-continued
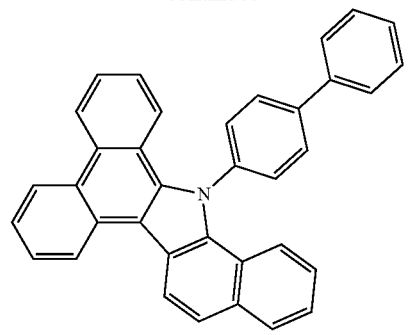
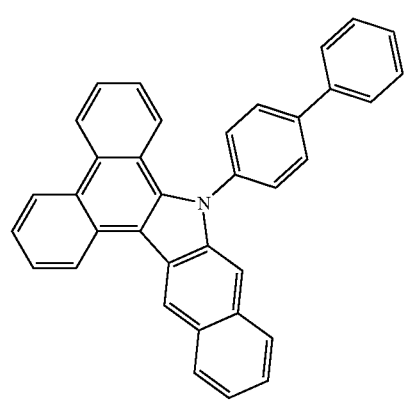
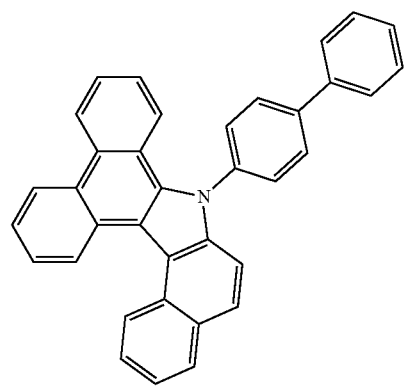
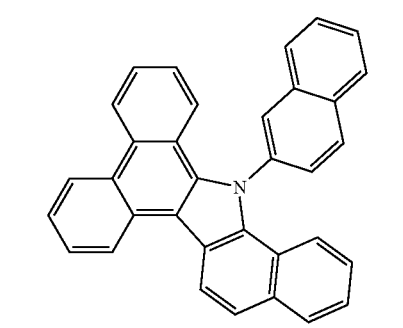
98
-continued
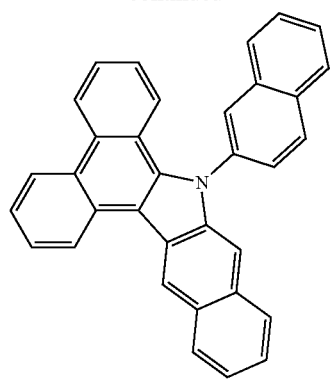
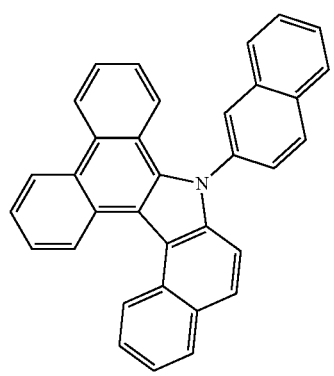
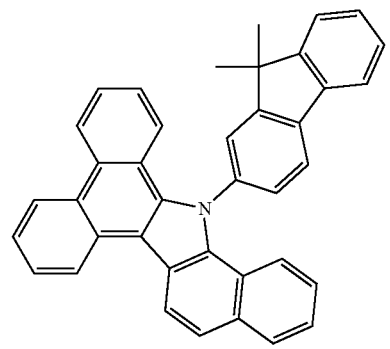
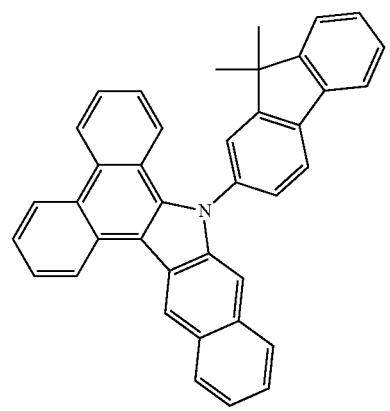

-continued
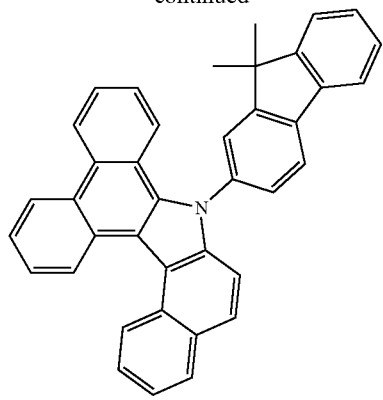
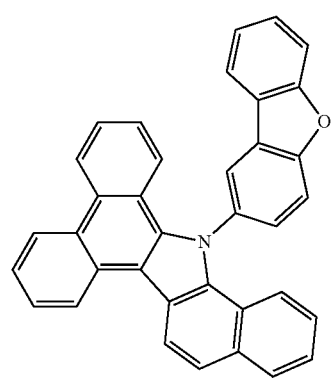
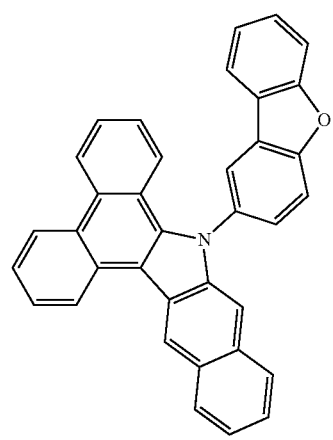
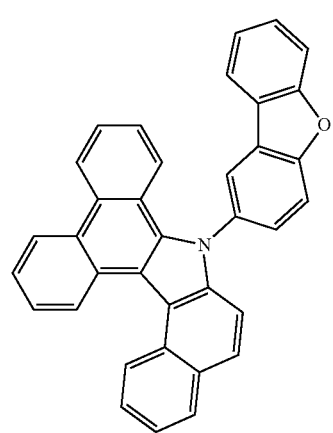
-continued
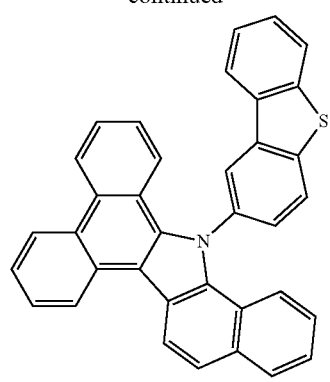
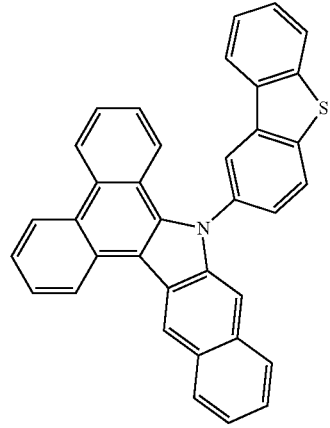
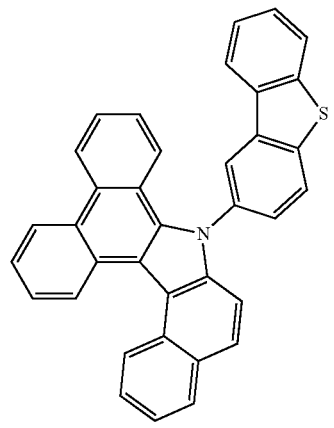
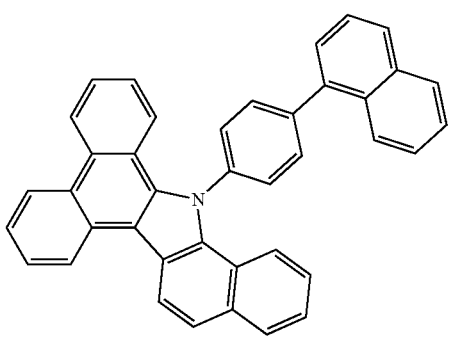

101
-continued
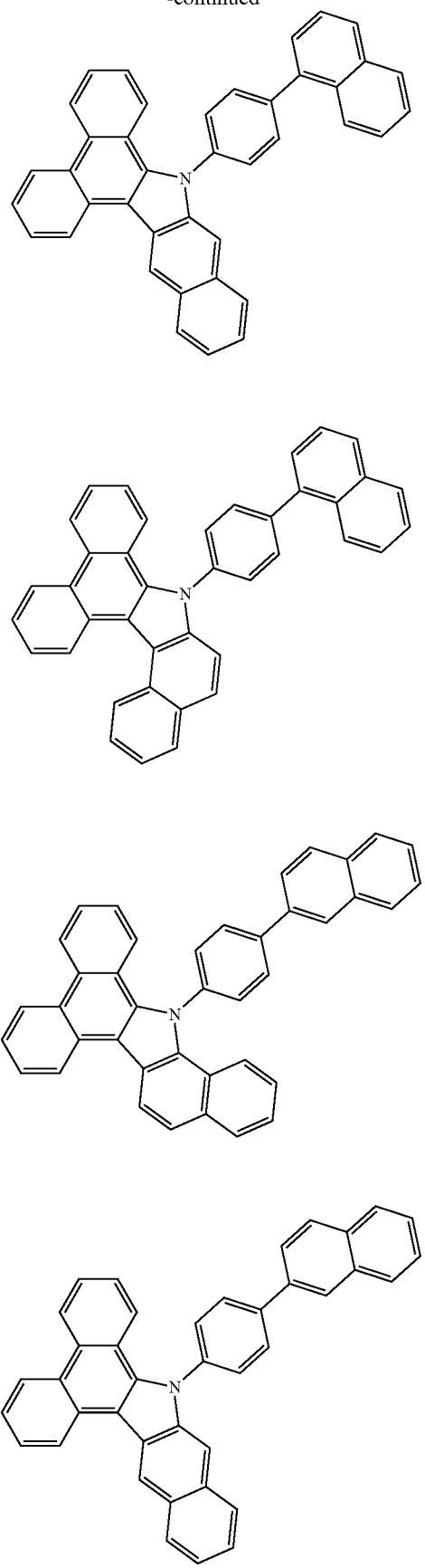
102
-continued
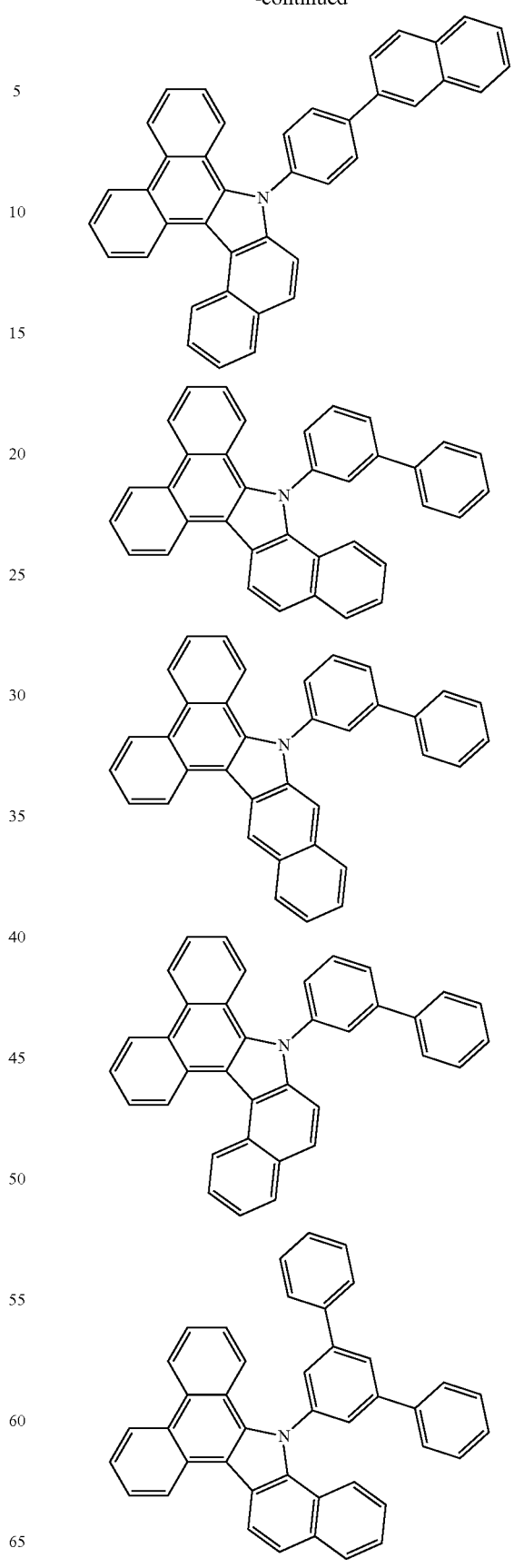

-continued
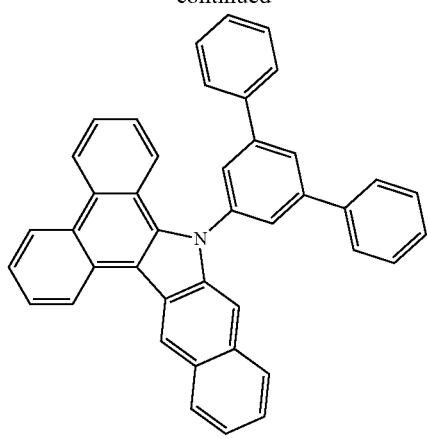
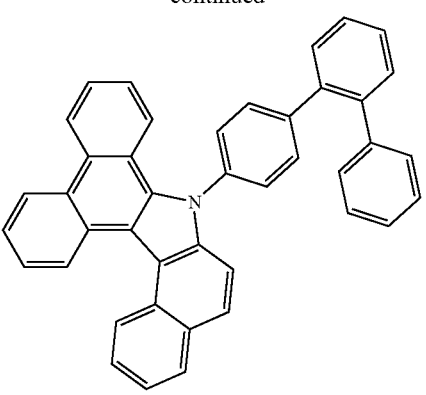
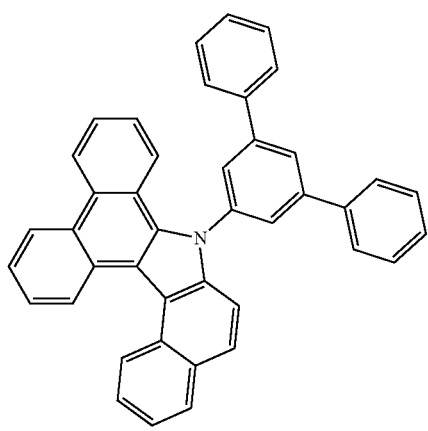
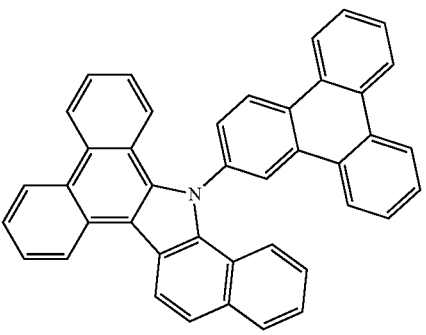
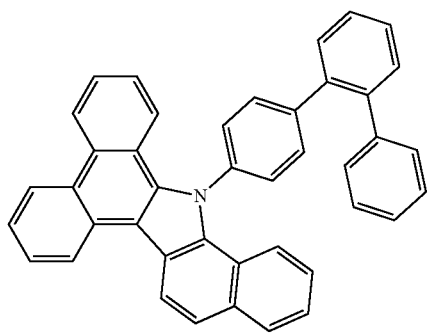
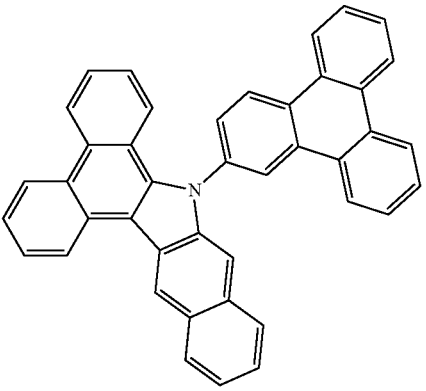
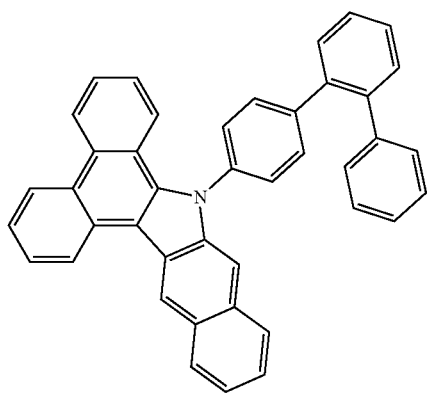
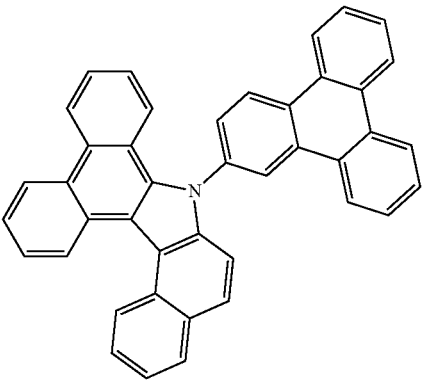

105
-continued
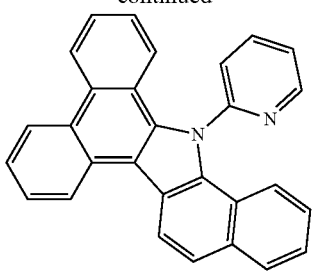
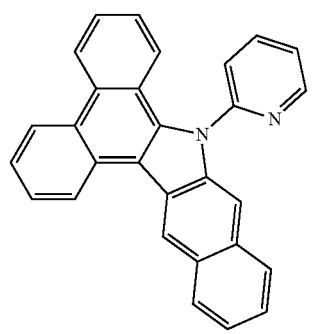
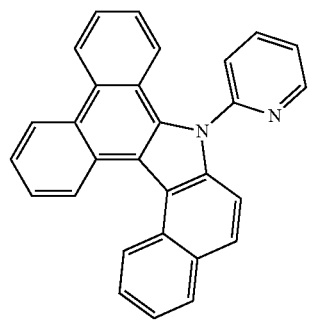
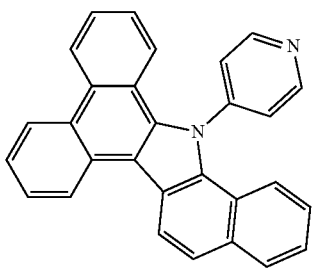
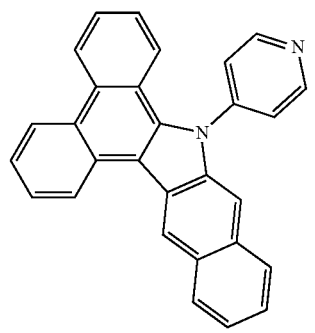
106
-continued
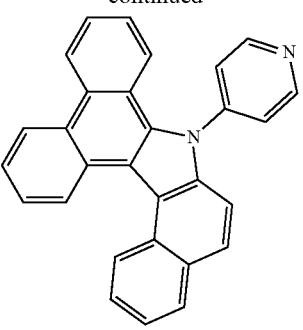
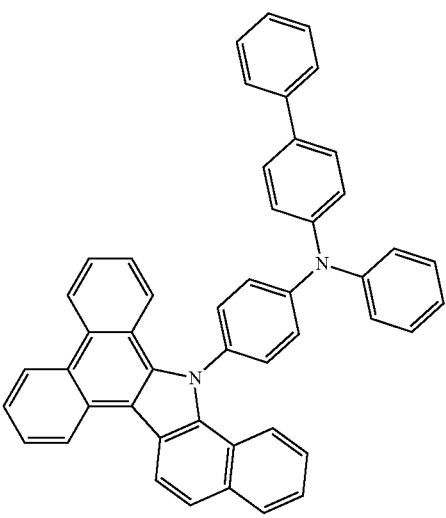
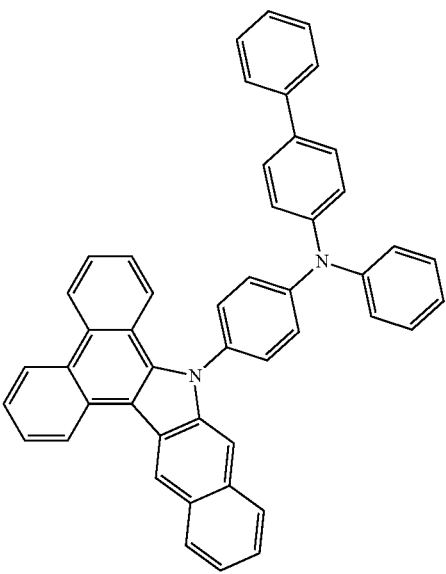

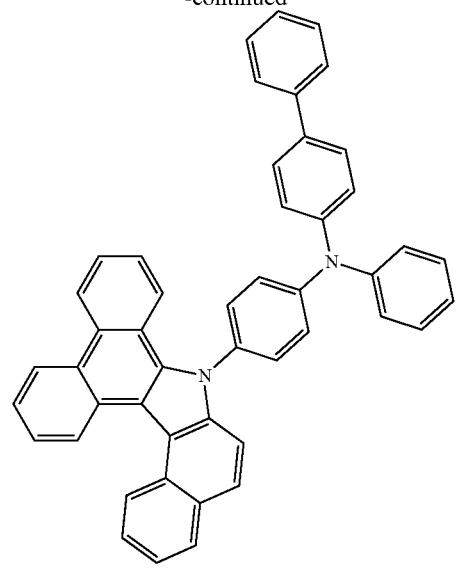
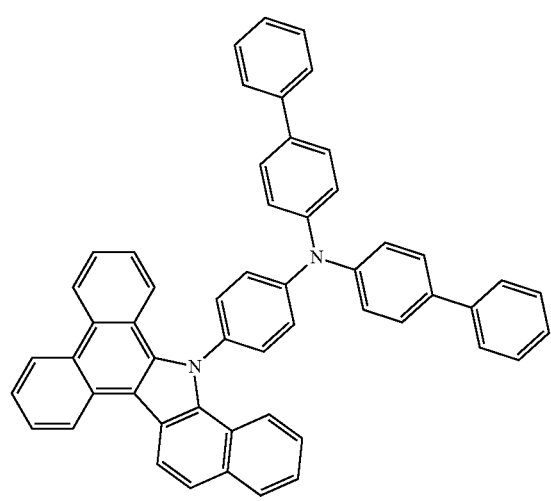
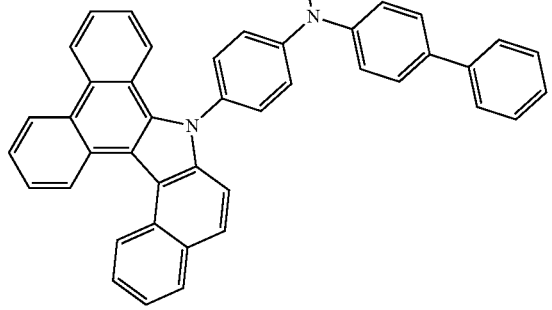
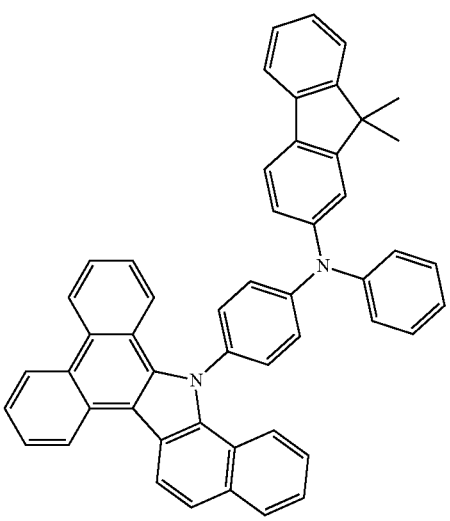
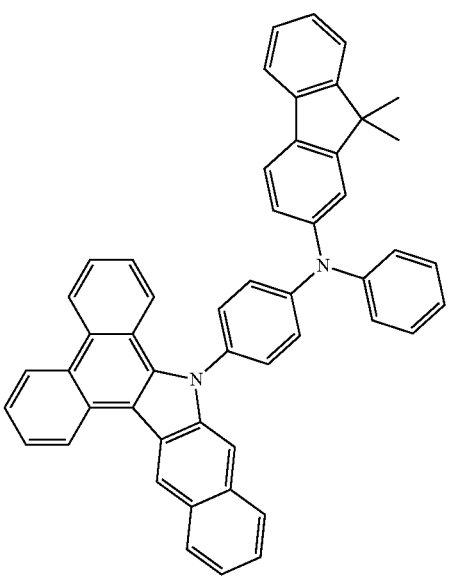

109
-continued
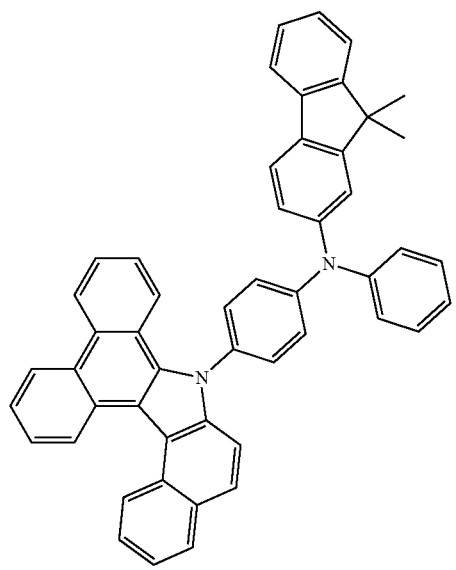
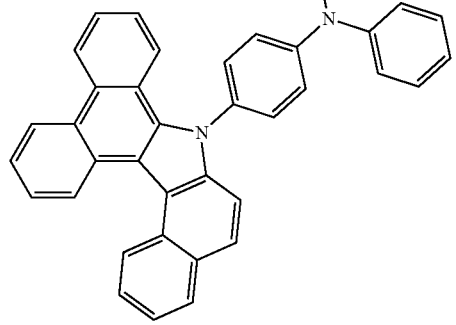
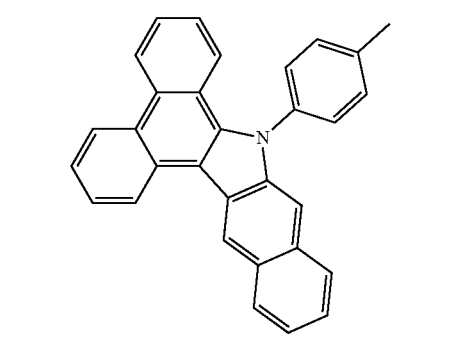
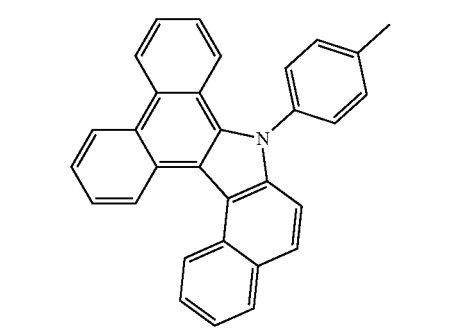
110
-continued
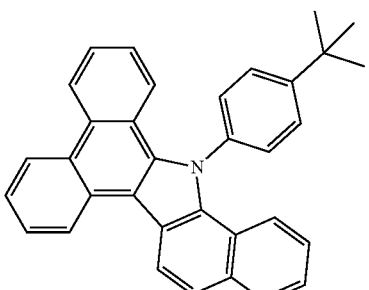
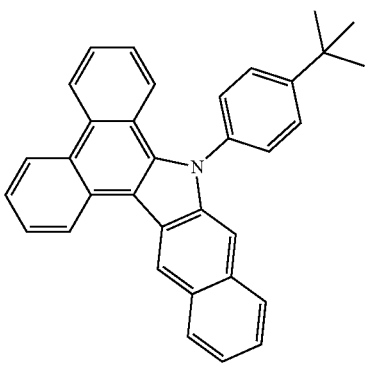
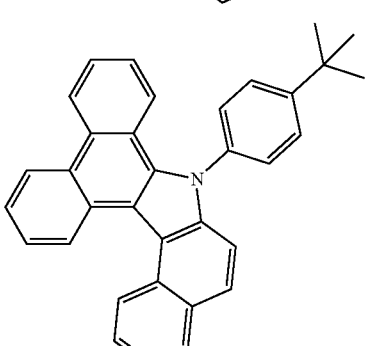
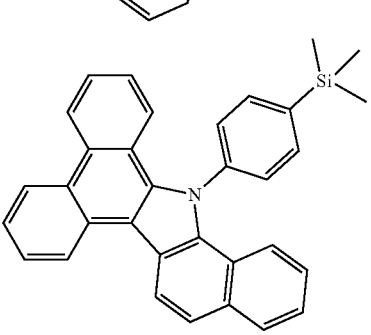
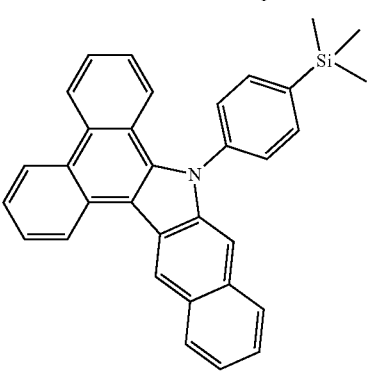

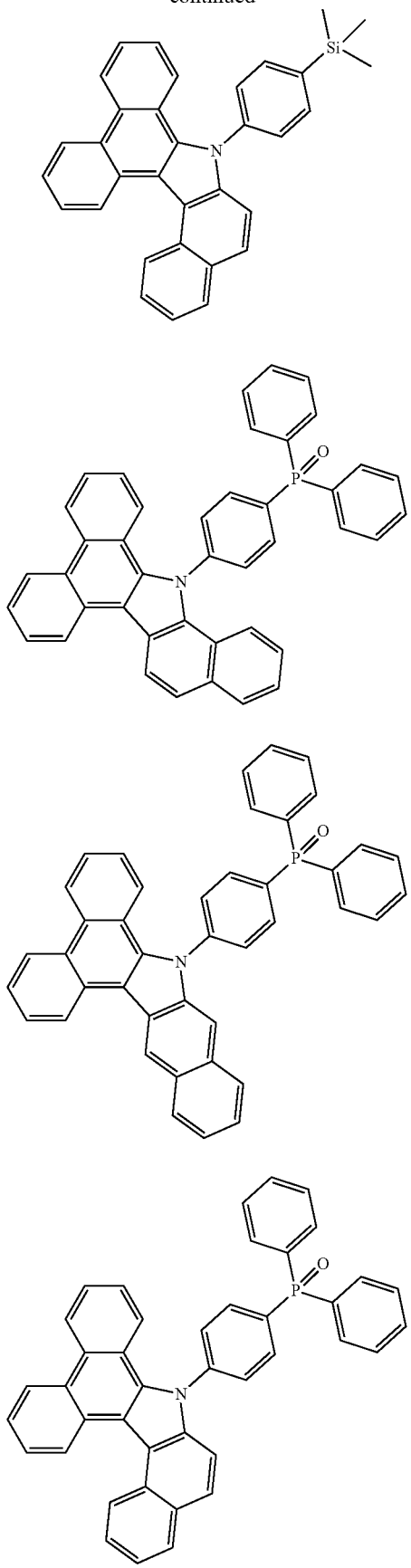

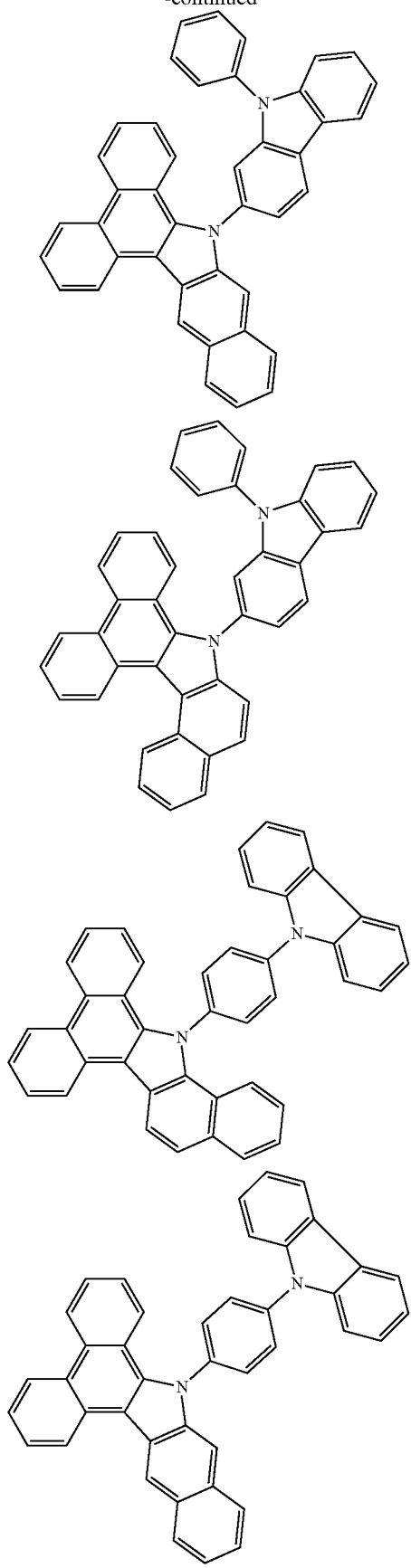
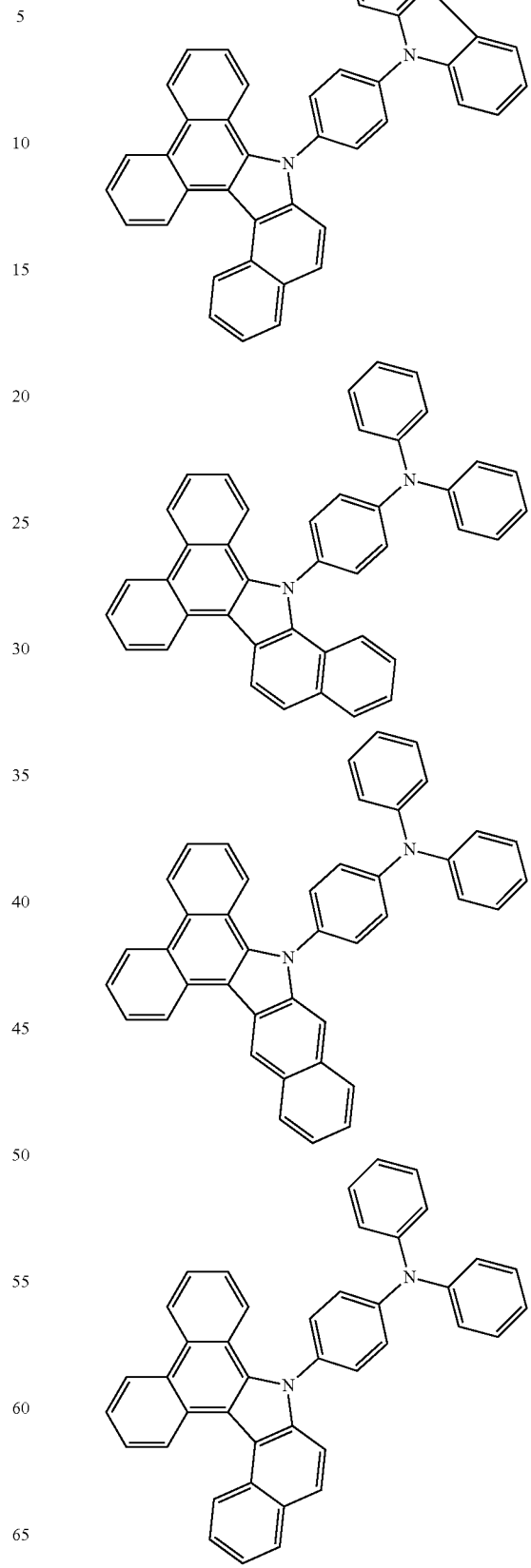

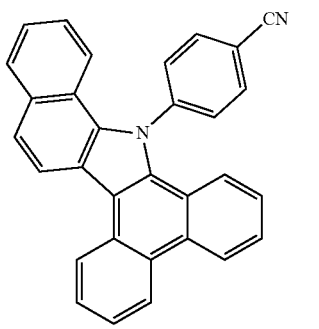
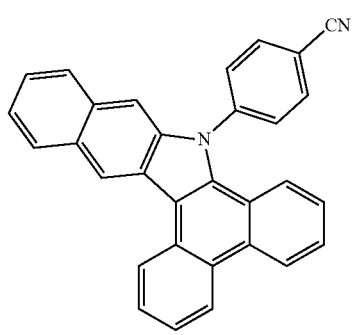
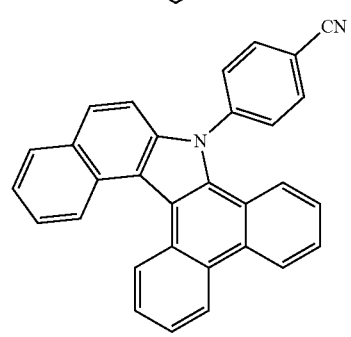
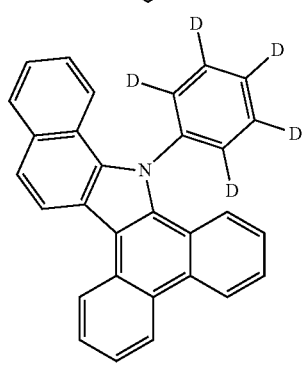
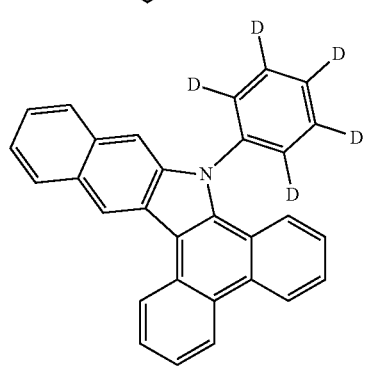
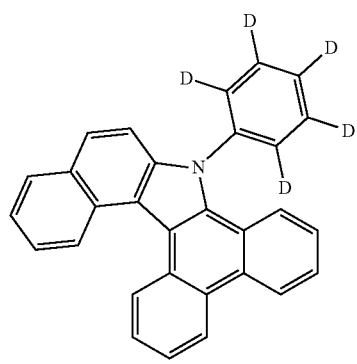
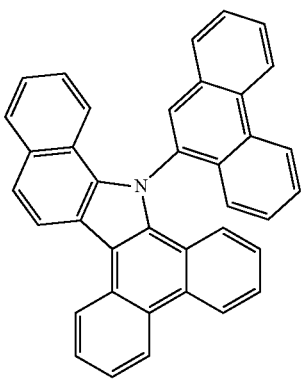
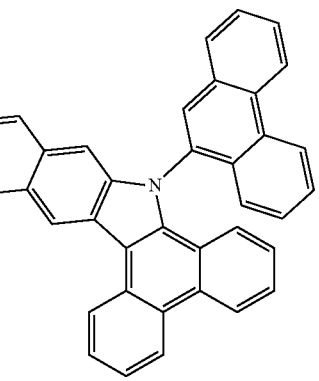
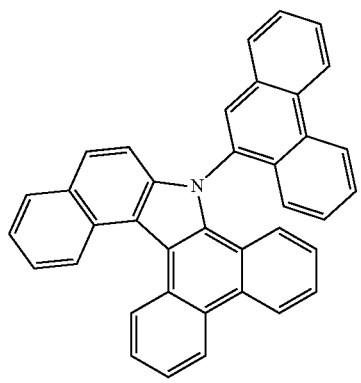

117
-continued
118
-continued
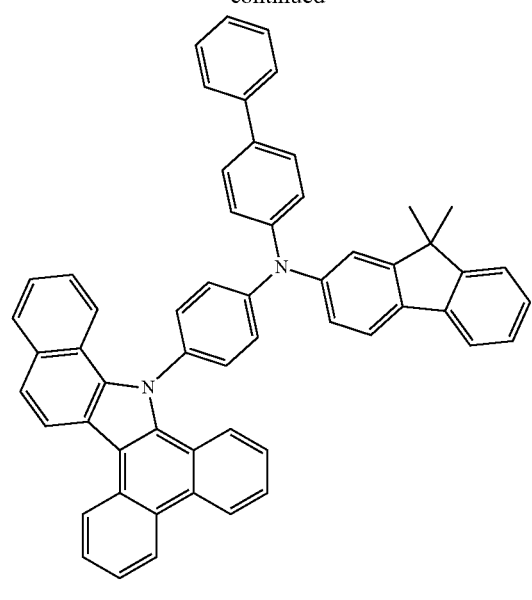
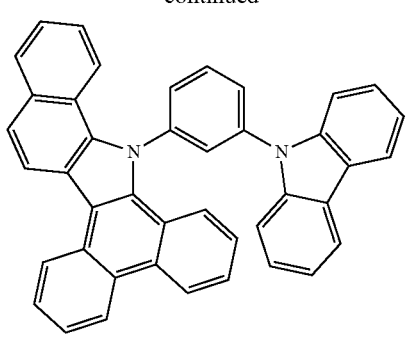
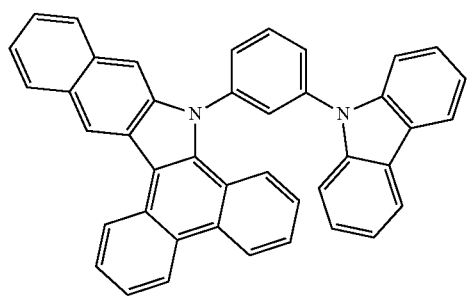
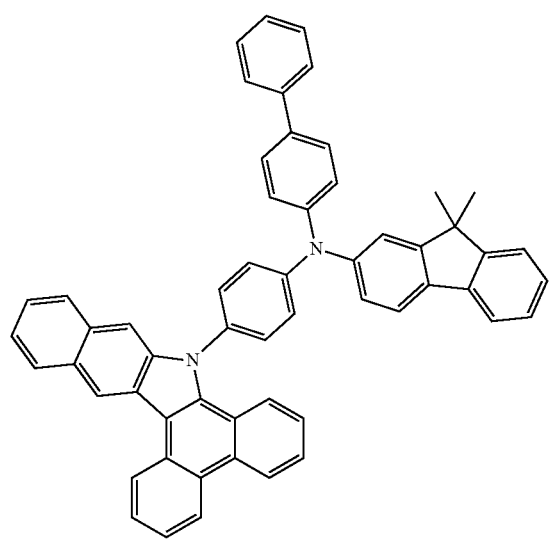
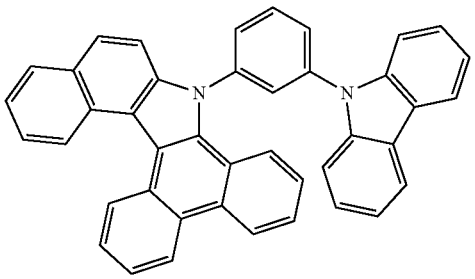
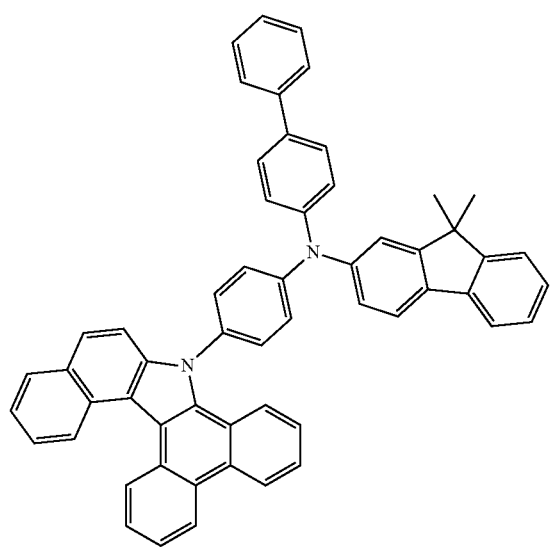
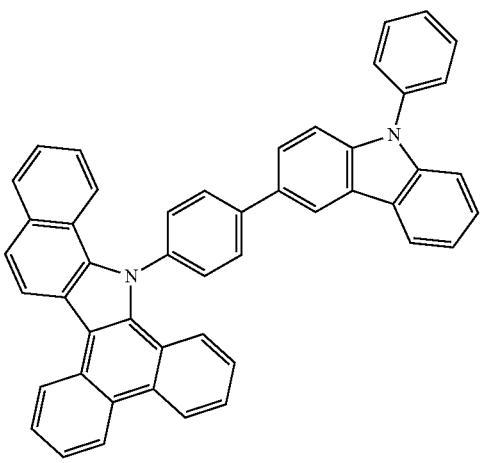

119
-continued
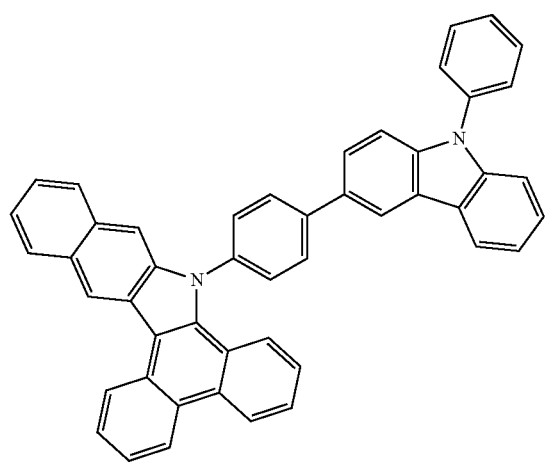
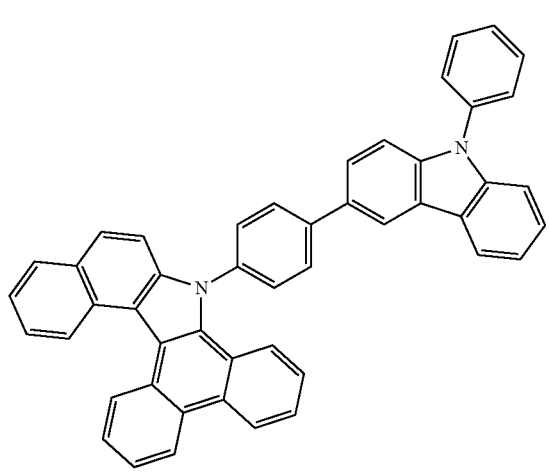
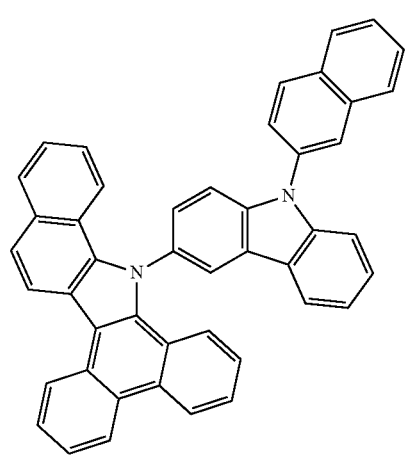
120
-continued
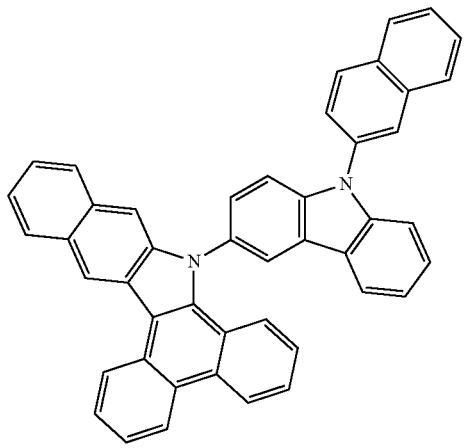
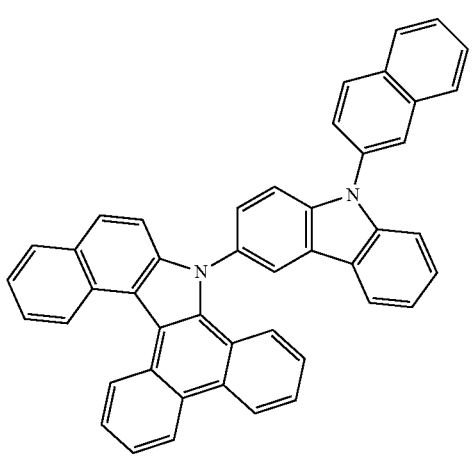
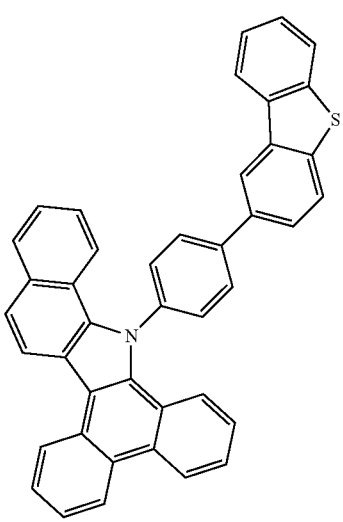

121
-continued
122
-continued
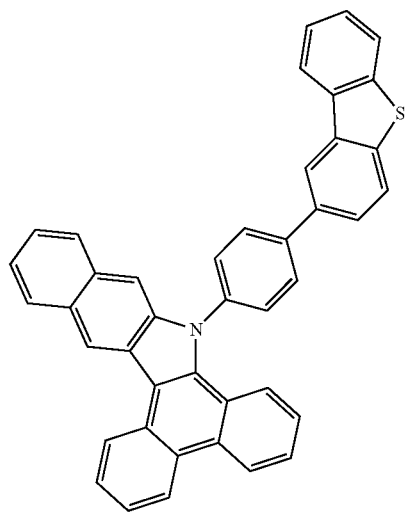
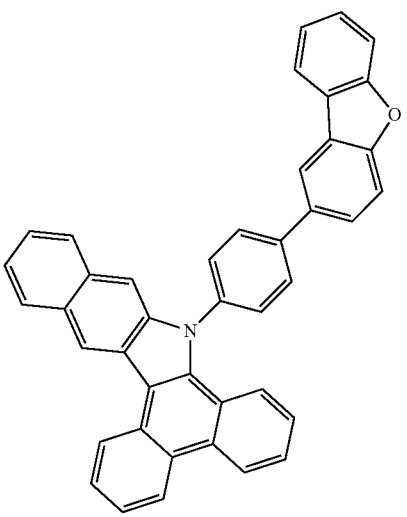
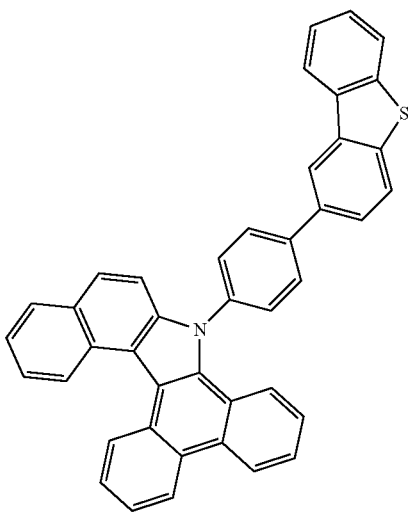
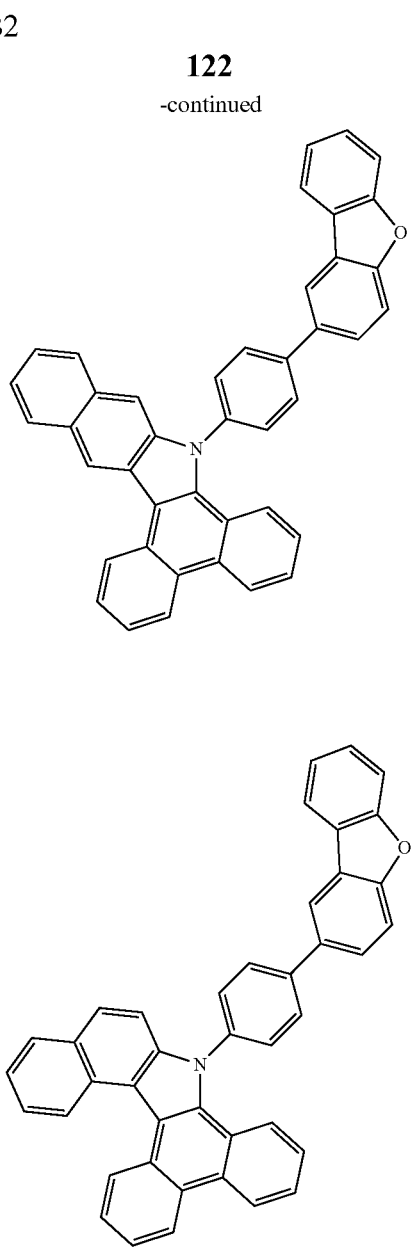
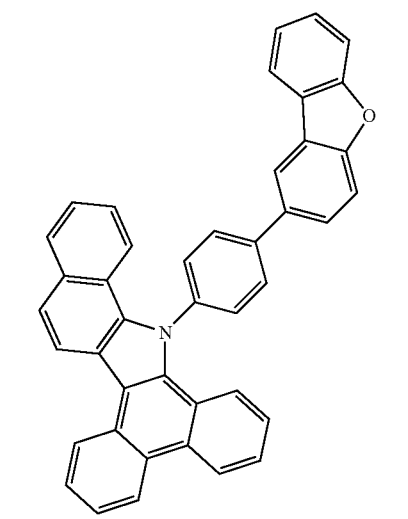
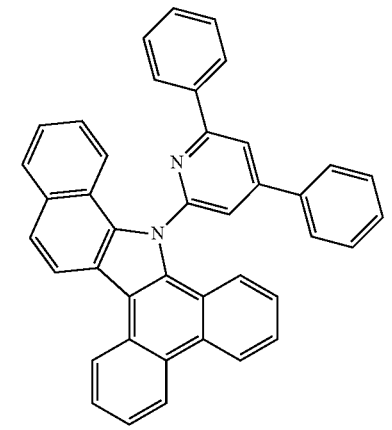

123
-continued
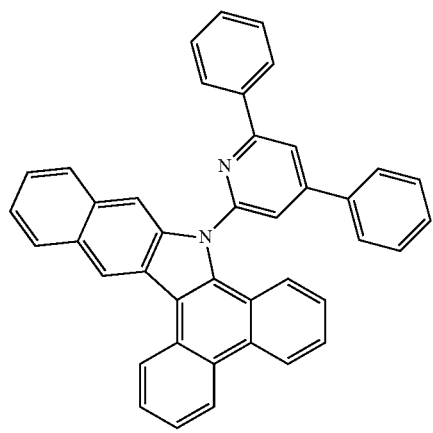
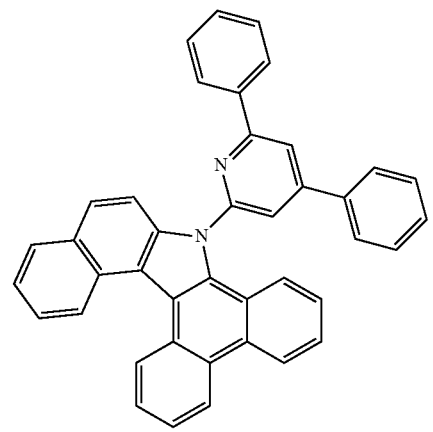
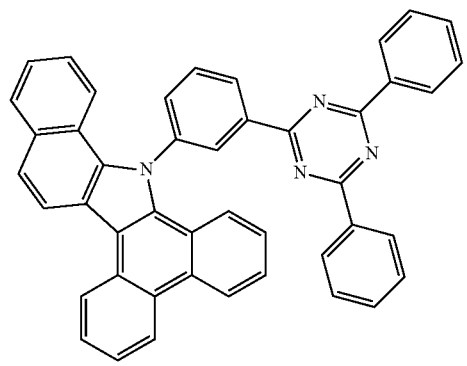
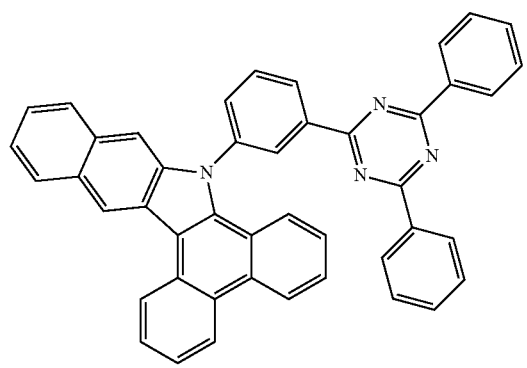
124
-continued
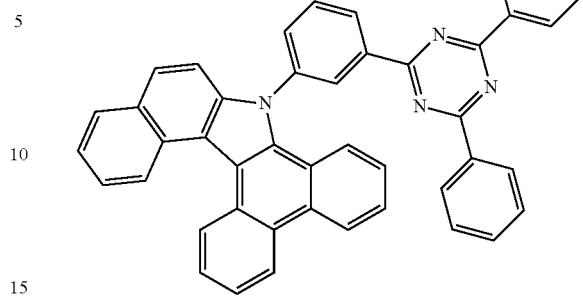
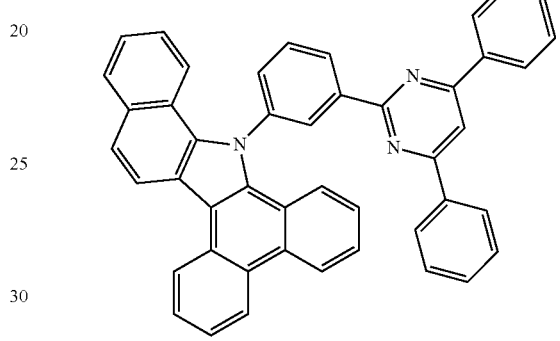
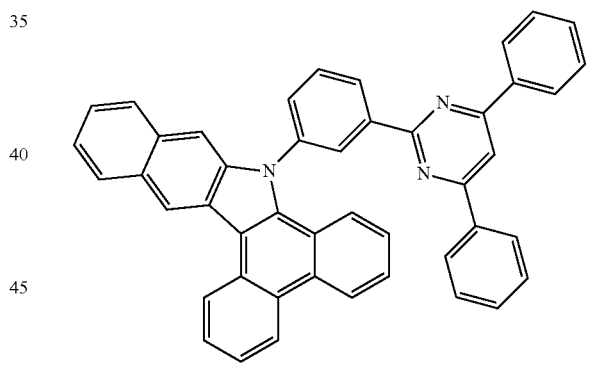
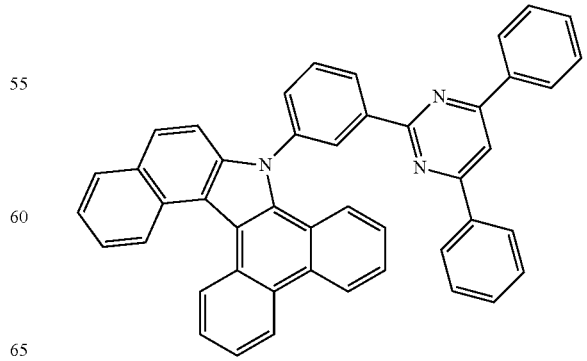

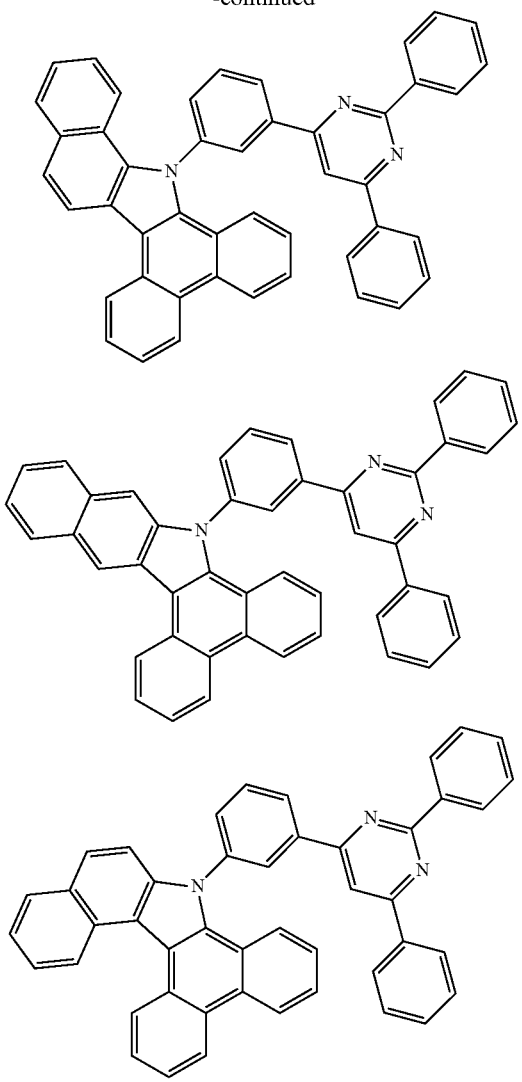
Chemical Formula 1 according to an exemplary embodiment of the present specification may be represented by Chemical Formula 1-1, and the core of the compound represented by Chemical Formula 1-1 may be prepared through the following Reaction Formula 1, but the preparation method is not limited thereto.
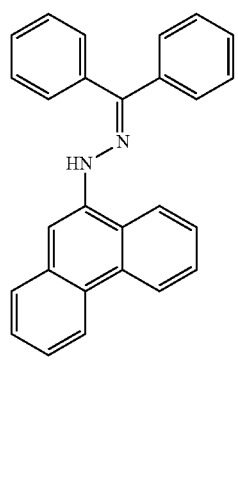
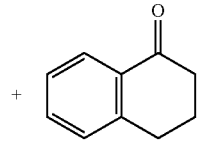
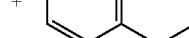
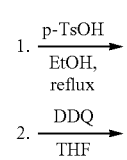
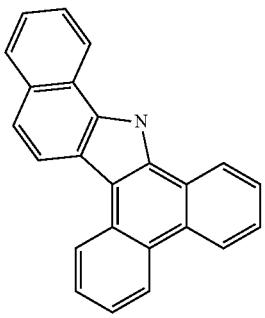
[Reaction Formula 1]
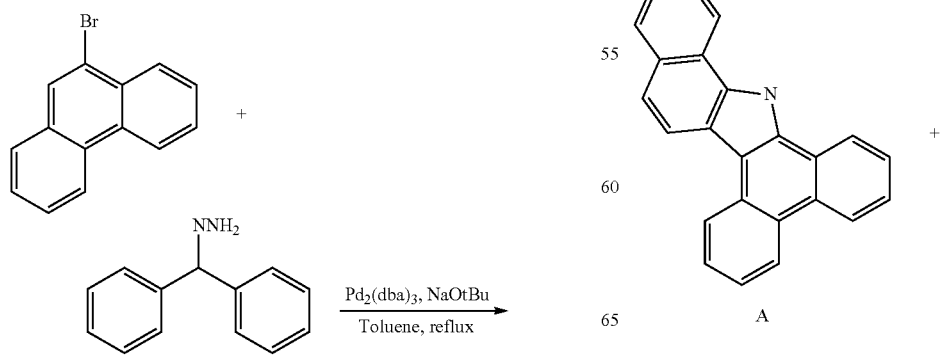

127

-continued

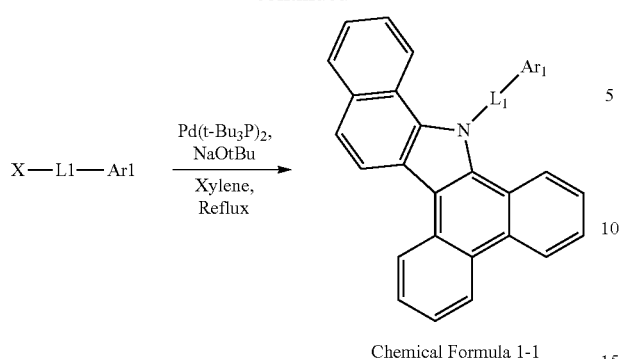

Chemical Formula 1-1

In Reaction Formula 1, X is a halogen group, and the definitions of L1 and Ar1 are the same as those in Chemical Formula 1.

Chemical Formula 1 according to an exemplary embodiment of the present specification may be represented by Chemical Formula 1-3, and the core of the compound represented by Chemical Formula 1-3 may be prepared through the following Reaction Formula 2, but the preparation method is not limited thereto.

[Reaction Formula 2]

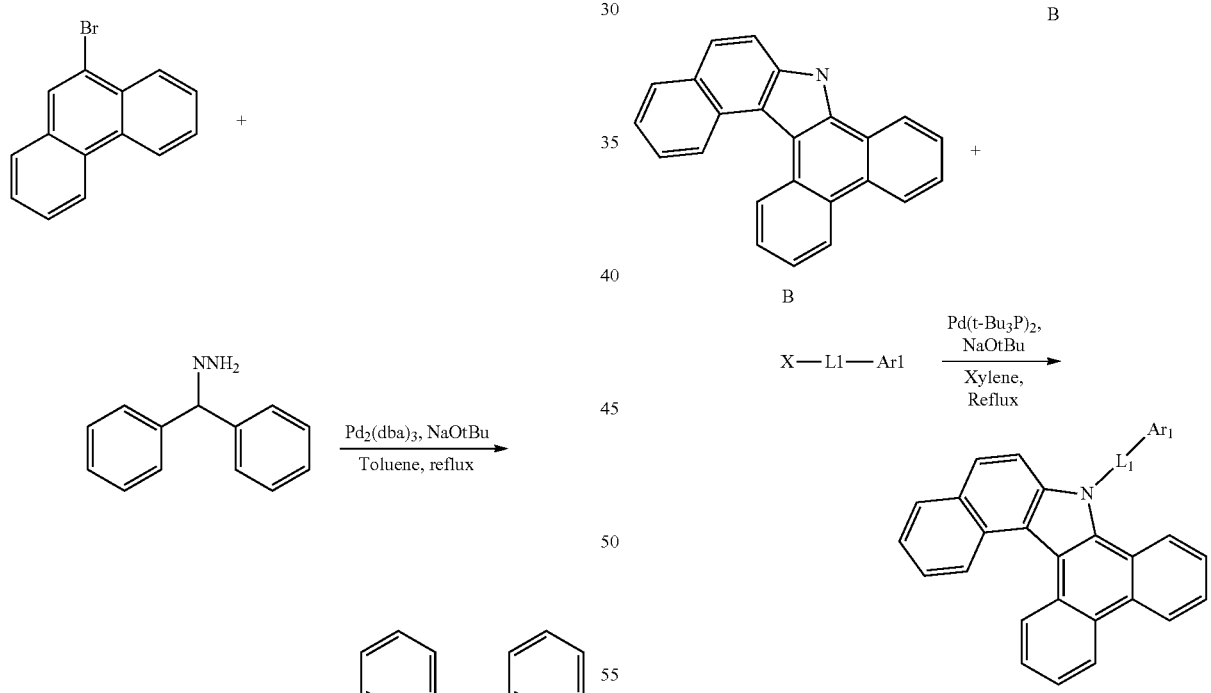

128

-continued

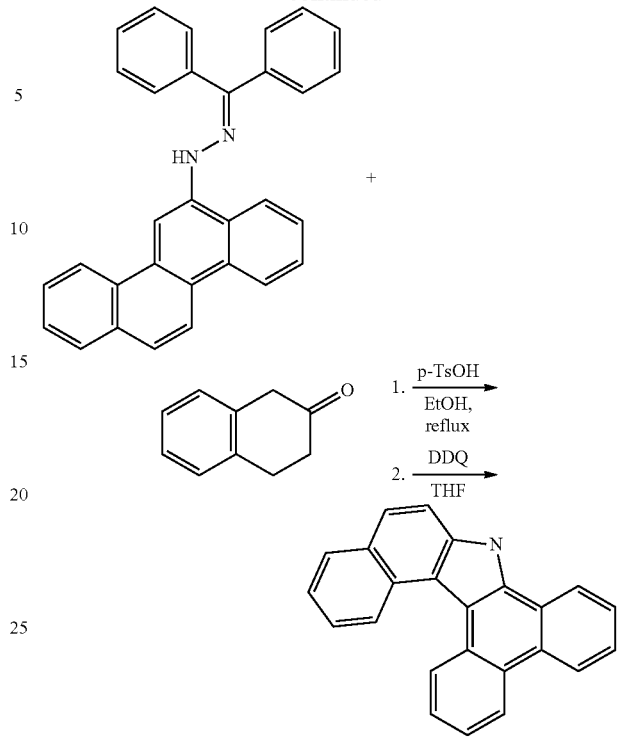

Chemical Formula 1-3

In Reaction Formula 2, X is a halogen group, and the definitions of L1 and Ar1 are the same as those in Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the hetero-cyclic compound represented by Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, an electron blocking layer, a light emitting layer, a hole blocking layer, an electron transport layer, an electron injection layer, and the like as organic material layers. However, the structure of the organic light emitting device is not limited thereto, and may include a fewer number of organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transport layer 70, a light emitting layer 40, an electron transport layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a hole injection layer or a hole transport layer, and the hole injection layer or the hole transport layer includes the hetero-cyclic compound represented by Chemical Formula 1.

According to an exemplary embodiment of the present specification, the organic material layer includes an electron blocking layer, and the electron blocking layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1 as a host of the light emitting layer.

According to an exemplary embodiment of the present specification, the organic material layer includes a light emitting layer, and the light emitting layer includes the hetero-cyclic compound represented by Chemical Formula 1 as a phosphorescent host or a fluorescent host of the light emitting layer.

According an exemplary embodiment of the present specification, the organic material layer includes the hetero-cyclic compound represented by Chemical Formula 1 as a host of the light emitting layer, and includes another organic compound, a metal or a metal compound as a dopant.

According to an exemplary embodiment of the present specification, the organic material layer includes a hole blocking layer, and the hole blocking layer includes the hetero-cyclic compound.

According to an exemplary embodiment of the present specification, the organic material layer includes an electron transport layer, an electron injection layer, or a layer which transports and injects electrons simultaneously, and the electron transport layer, the electron injection layer, or the layer which transports and injects electrons simultaneously includes the hetero-cyclic compound.

According to an exemplary embodiment of the present specification, the organic material layer further includes a hole injection layer or a hole transport layer, which includes a compound including an arylamino group, a carbazole group, or a benzocarbazole group, in addition to the organic material layer including the hetero-cyclic compound represented by Chemical Formula 1.

According to an exemplary embodiment of the present specification, the organic material layer includes a light emitting layer, and the light emitting layer includes a compound represented by the following Chemical Formula 1-A.

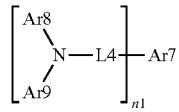

[Chemical Formula 1-A]

In Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Ar9 are a phenyl group which is unsubstituted or substituted with a trimethylgermanium group.

According to an exemplary embodiment of the present specification, Chemical Formula 1-A is represented by the following compound.

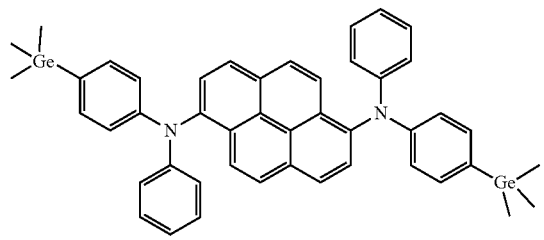

According to an exemplary embodiment of the present specification, the organic material layer includes a light emitting layer, and the light emitting layer includes a compound represented by the following Chemical Formula 2-A.

[Chemical Formula 2-A]

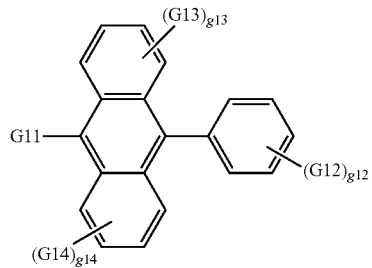

In Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

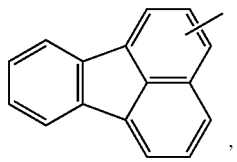

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

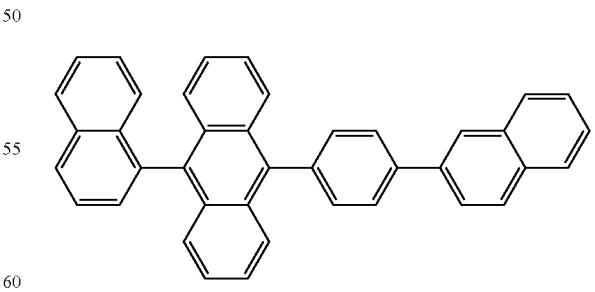

The organic light emitting device of the present specification may be manufactured by the materials and methods known in the art, except that one or more layers of the organic material layers include the hetero-cyclic compound of the present specification, that is, the hetero-cyclic compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which may be used as a second electrode, thereon, by using a physical vapor deposition (PVD) method such as sputtering or e-beam evaporation. In addition to the method as described above, an organic light emitting device may be made by sequentially depositing a negative electrode material, an organic material layer, and a first electrode material on a substrate. Further, the compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes into a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and the hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The electron blocking layer is a layer which may improve the lifetime and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

The light emitting material for the light emitting layer is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxyquinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material for the electron transport layer is suitably a material which may inject electrons well from a negative electrode and transfer the electrons to a light emitting layer, and has large mobility for the electrons. Specific examples thereof include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a positive electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

According to an exemplary embodiment of the present specification, the compound represented by Chemical Formula 1 may be included in an organic solar cell or an organic transistor in addition to the organic light emitting device.

Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

<Preparation Example 1> Preparation of Compound 1

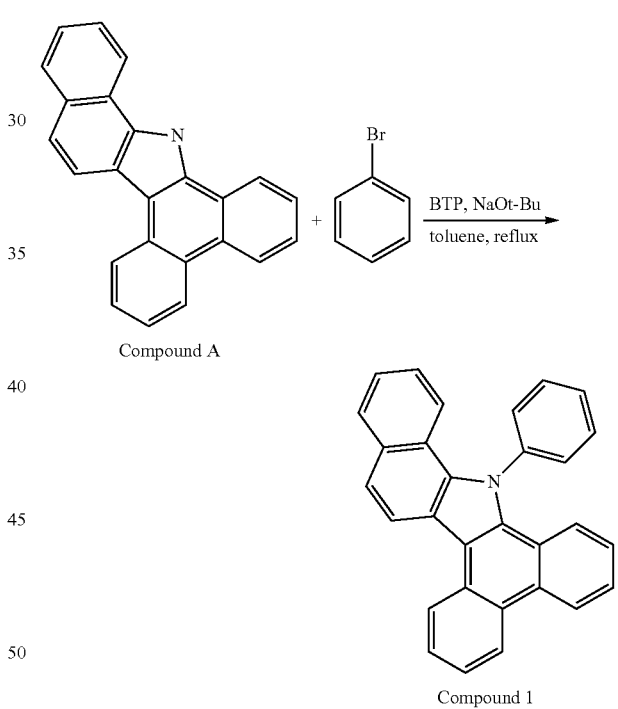

Compound A (10 g, 31.53 mmol), bromobenzene (3.41 g, 34.69 mmol), and NaOt-Bu (3.94 g, 40.99 mmol) were put into 250 ml of toluene, and then the temperature was increased while stirring the mixture. The mixture was warmed and then, when the reflux started, bis(tri-tert-butylphosphine)palladium (0.16 g, 0.32 mmol) was slowly added dropwise thereto. After 3 hours, the reaction was terminated, the temperature was lowered to normal temperature, and the resulting product was concentrated under reduced pressure, and then column-purified at a ratio of n-hexane:ethyl acetate=10:1 to prepare 10.84 g (87%) of Compound 1.

MS[M+H]$^+$=394

<Preparation Example 2> Preparation of Compound 2

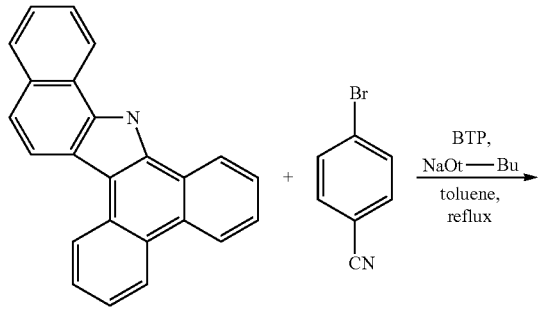

Compound A

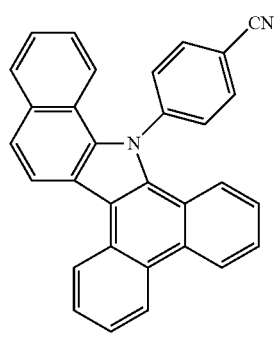

Compound 2

11.56 g of Compound 2 was prepared in the same manner as in Preparation Example 1, except that Compound A (10 g, 31.53 mmol) and para-bromobenzonitrile (4.24 g, 34.69 mmol) were used. (88%)

MS[M+H]$^+$=419

<Preparation Example 3> Preparation of Compound 3

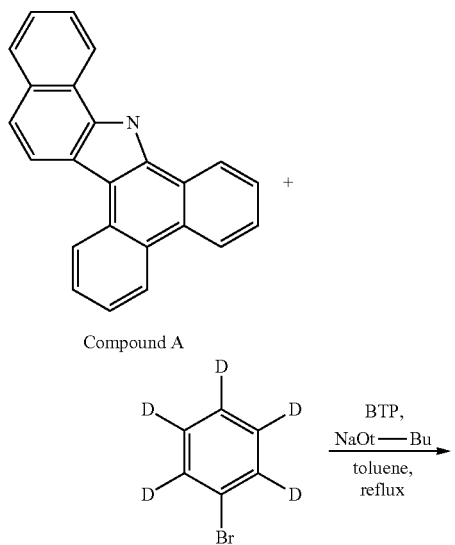

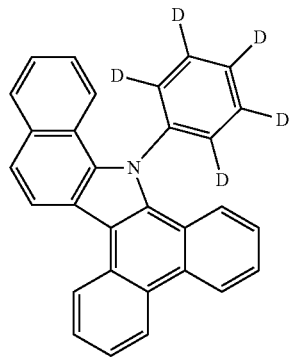

Compound 3

9.46 g of Compound 3 was prepared in the same manner as in Preparation Example 1, except that Compound A (10 g, 31.53 mmol) and para-bromobenzene-D5 (4.59 g, 34.69 mmol) were used. (75%)

MS[M+H]$^+$=399

<Preparation Example 4> Preparation of Compound 4

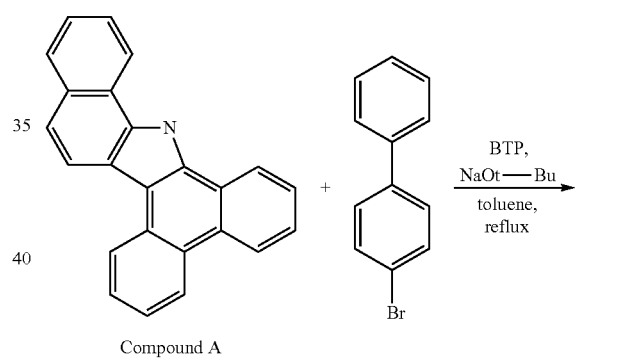

Compound A

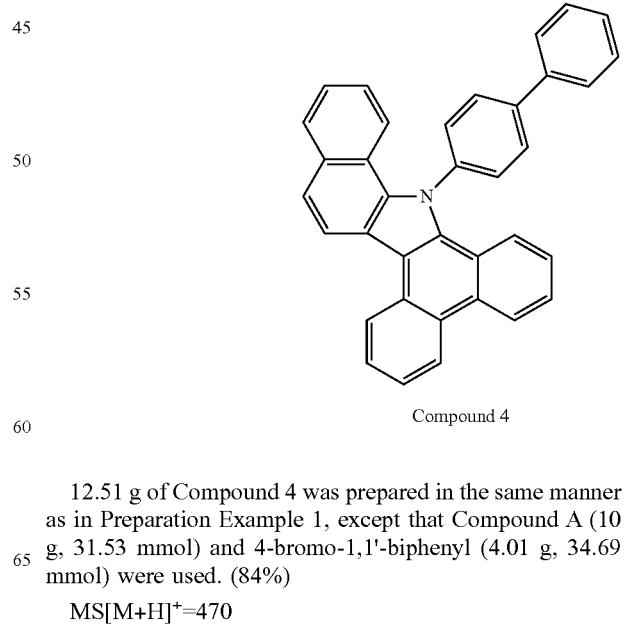

Compound 4

12.51 g of Compound 4 was prepared in the same manner as in Preparation Example 1, except that Compound A (10 g, 31.53 mmol) and 4-bromo-1,1'-biphenyl (4.01 g, 34.69 mmol) were used. (84%)

MS[M+H]$^+$=470

<Preparation Example 5> Preparation of Compound 5

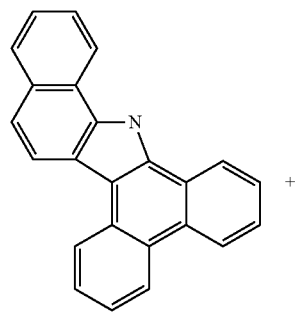

Compound A

+

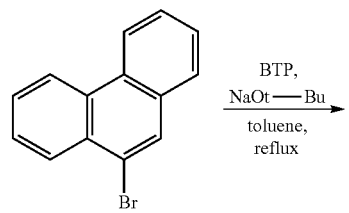

BTP,
NaOt—Bu
toluene,
reflux

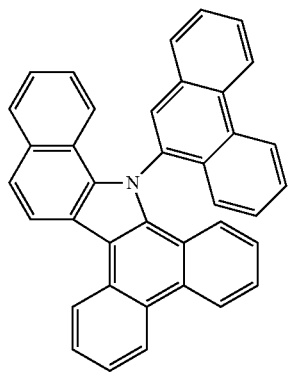

Compound 5

15.15 g of Compound 5 was prepared in the same manner as in Preparation Example 1, except that Compound A (10 g, 31.53 mmol) and 9-bromophenanthrene (5.88 g, 34.69 mmol) were used. (97%)
MS[M+H]$^+$=494

<Preparation Example 6> Preparation of Compound 6

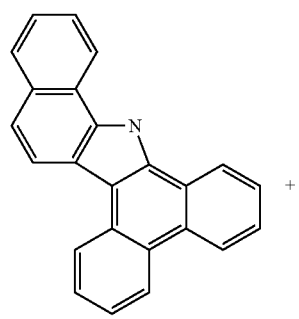

Compound A

+

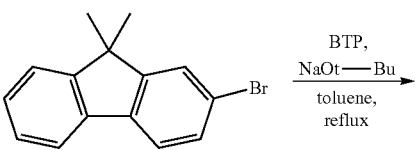

BTP,
NaOt—Bu
toluene,
reflux

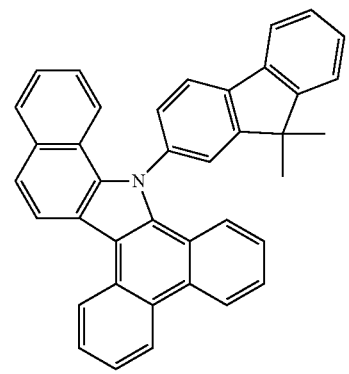

Compound 6

14.41 g of Compound 6 was prepared in the same manner as in Preparation Example 1, except that Compound A (10 g, 31.53 mmol) and 2-bromo-9,9-dimethyl-9H-fluorene (4.43 g, 34.69 mmol) were used. (90%)
MS[M+H]$^+$=510

<Preparation Example 7> Preparation of Compound 7

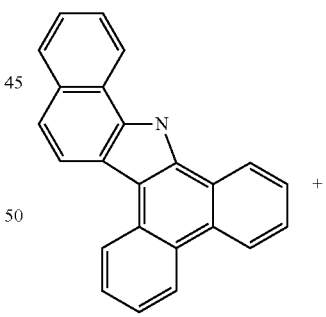

Compound A

+

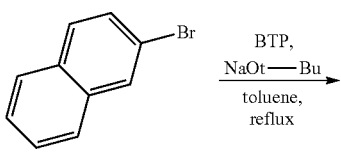

BTP,
NaOt—Bu
toluene,
reflux

-continued

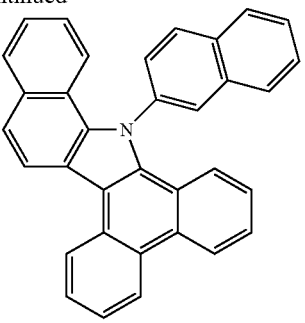

Compound 7

12.12 g of Compound 7 was prepared in the same manner as in Preparation Example 1, except that Compound A (10 g, 31.53 mmol) and 2-bromonaphthalene (4.15 g, 34.69 mmol) were used. (87%)
MS[M+H]⁺=444

<Preparation Example 8> Preparation of Compound 8

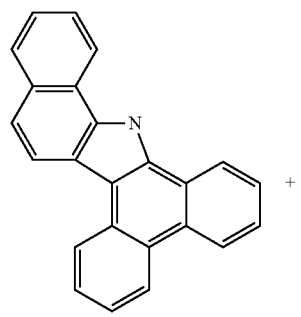

Compound A

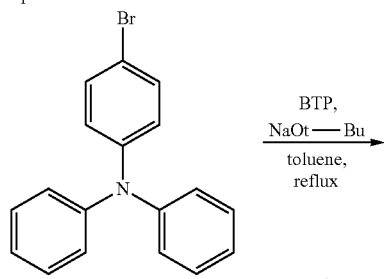

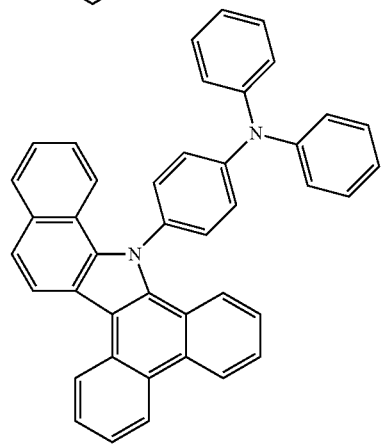

Compound 8

Compound A (10 g, 31.53 mmol), 4-bromo-N,N-diphenylaniline (10.21 g, 34.69 mmol), and sodium t-butoxide (3.94 g, 40.99 mmol) were put into 300 ml of toluene, and then the temperature was increased while stirring the mixture. The mixture was warmed and then, when the reflux started, bis(tri-tert-butylphosphine)palladium (0.16 g, 0.32 mmol) was slowly added dropwise thereto. After 5 hours, the reaction was terminated, the temperature was lowered to normal temperature, and the resulting product was concentrated under reduced pressure, and then column-purified at a ratio of n-hexane:ethyl acetate=15:1 to prepare 15.01 g of Compound 8. (85%)
MS[M+H]⁺=561

<Preparation Example 9> Preparation of Compound 9

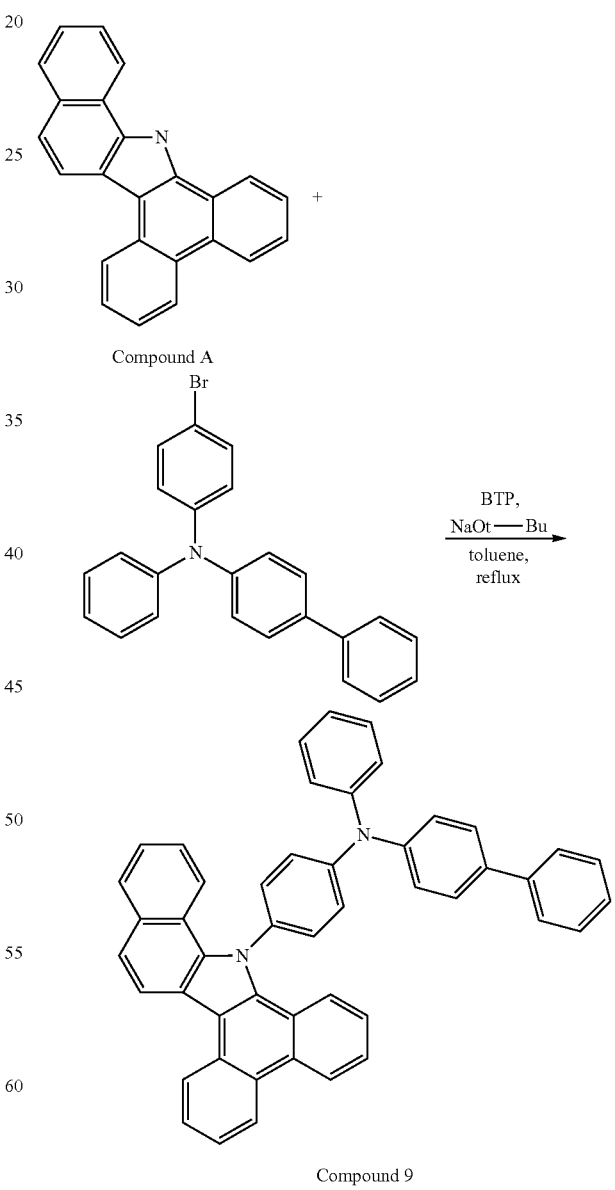

Compound 9

17.84 g of Compound 9 was prepared in the same manner as in Preparation Example 8, except that Compound A (10 g, 31.53 mmol) and N-(4-bromophenyl)-N-phenyl-[1,1'-biphenyl]-4-amine (10.88 g, 34.69 mmol) were used. (89%)

MS[M+H]⁺=637

<Preparation Example 10> Preparation of Compound 10

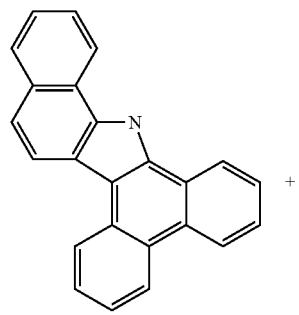

Compound A

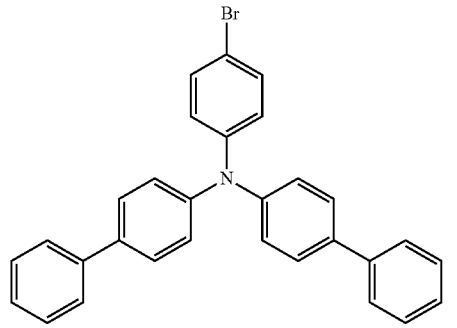

Compound 10

19.51 g of Compound 10 was prepared in the same manner as in Preparation Example 8, except that Compound A (10 g, 31.53 mmol) and N-([1,1'-biphenyl]-4-yl)-N-(4-bromophenyl)-[1,1'-biphenyl]-4-amine (11.48 g, 34.69 mmol) were used. (87%)

MS[M+H]⁺=713

<Preparation Example 11> Preparation of Compound 11

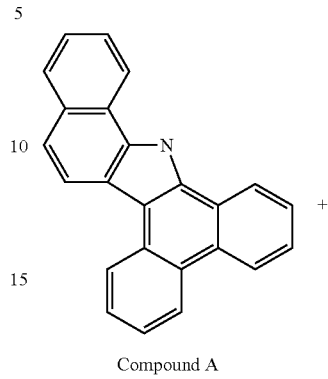

Compound A

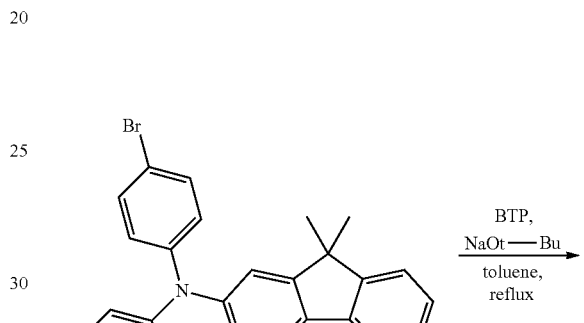

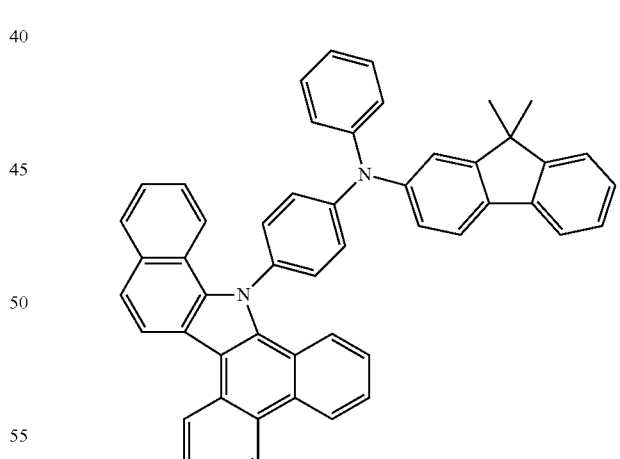

Compound 11

16.14 g of Compound 11 was prepared in the same manner as in Preparation Example 8, except that Compound A (10 g, 31.53 mmol) and N-(4-bromophenyl)-9,9-dimethyl-N-phenyl-9H-fluoren-2-amine (10.15 g, 34.69 mmol) were used. (81%)

MS[M+H]⁺=677

\<Preparation Example 12\> Preparation of Compound 12

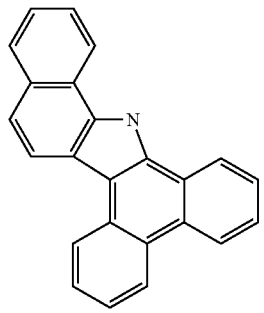

Compound A

+

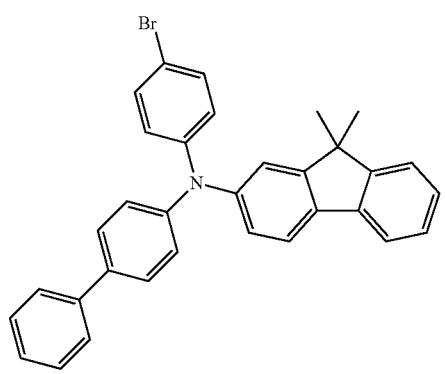

→ BTP, NaOt—Bu, toluene, reflux

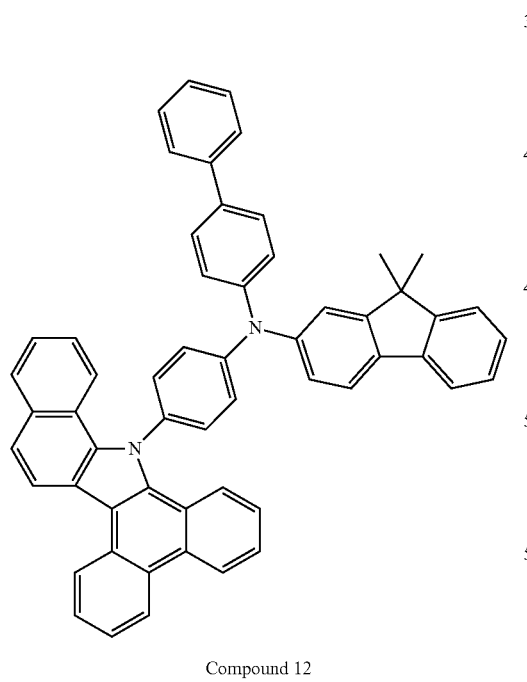

Compound 12

12.51 g of Compound 12 was prepared in the same manner as in Preparation Example 8, except that Compound A (10 g, 31.53 mmol) and N-([1,1'-biphenyl]-4-yl)-N-(4-bromophenyl)-9,9-dimethyl-9H-fluoren-2-amine (11.48 g, 34.69 mmol) were used. (58%)

MS[M+H]$^+$=753

\<Preparation Example 13\> Preparation of Compound 13

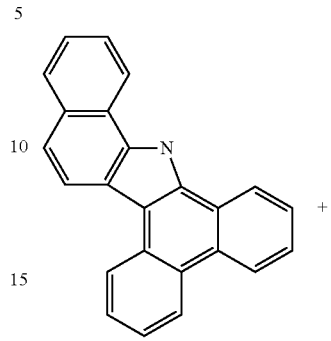

Compound A

+

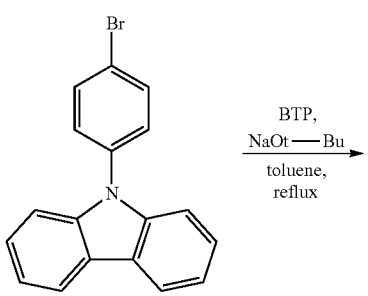

→ BTP, NaOt—Bu, toluene, reflux

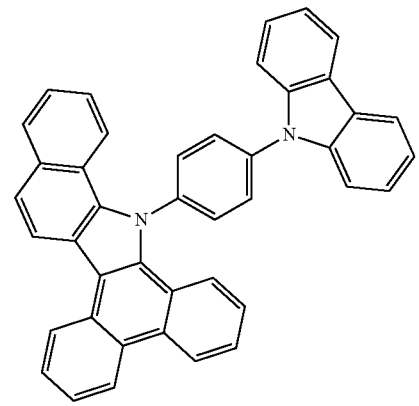

Compound 13

Compound A (10 g, 31.53 mmol), 9-(4-bromophenyl)-9H-carbazole (8.14 g, 34.69 mmol), and sodium t-butoxide (3.49 g, 40.99 mol) were put into 300 ml of toluene, and then the temperature was increased while stirring the mixture. The mixture was warmed and then, when the reflux started, bis(tri-tert-butylphosphine)palladium (0.16 g, 0.32 mmol) was slowly added dropwise thereto. After 8 hours, the reaction was terminated, the temperature was lowered to normal temperature, and the resulting product was concentrated under reduced pressure, and then column-purified to prepare 14.15 g of Compound 13 (80%).

MS[M+H]$^+$=559

<Preparation Example 14> Preparation of Compound 14

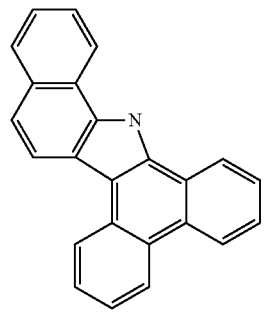

Compound A

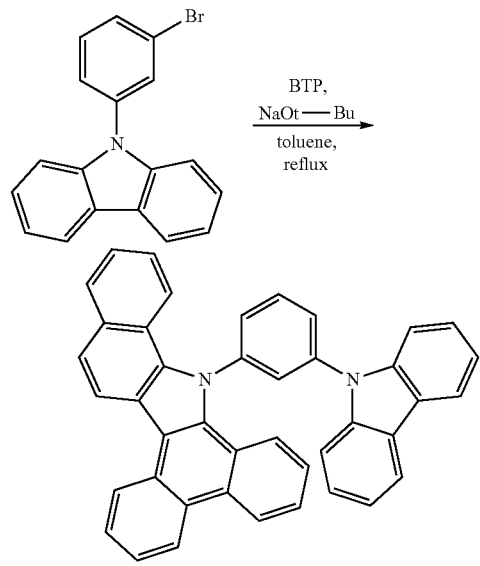

Compound 14

12.77 g of Compound 14 was prepared in the same manner as in Preparation Example 13, except that Compound A (10 g, 31.53 mmol) and 9-(3-bromophenyl)-9H-carbazole (8.14 g, 34.69 mmol) were used. (72%)

MS[M+H]$^+$=559

<Preparation Example 15> Preparation of Compound 15

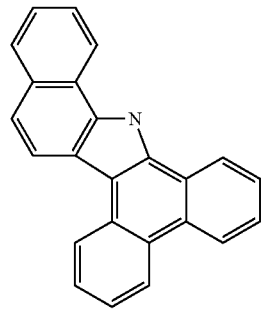

Compound A

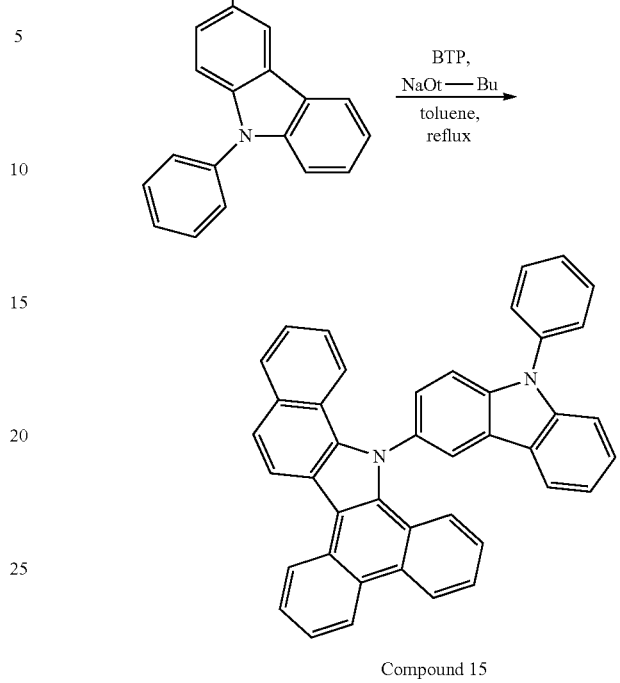

Compound 15

16.24 g of Compound 15 was prepared in the same manner as in Preparation Example 13, except that Compound A (10 g, 31.53 mmol) and 3-bromo-9-phenyl-9H-carbazole (8.14 g, 34.69 mmol) were used. (92%)

MS[M+H]$^+$=559

<Preparation Example 16> Preparation of Compound 16

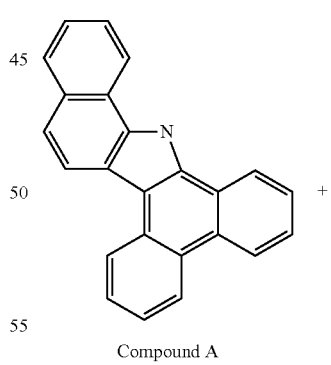

Compound A

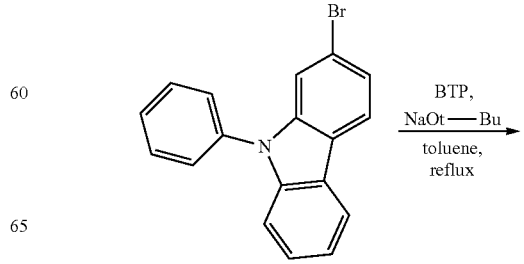

-continued

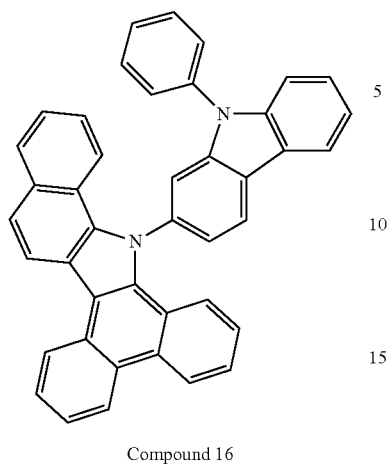

Compound 16

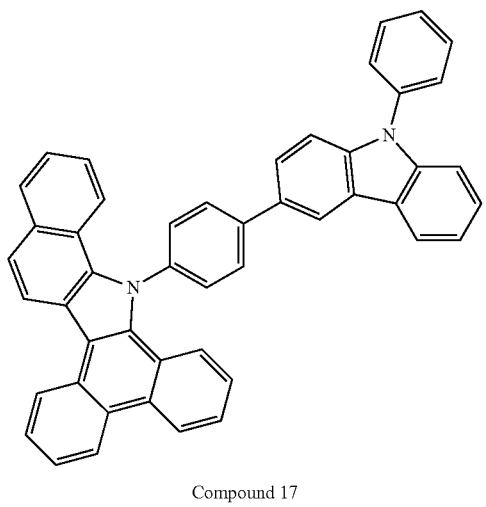

Compound 17

14.01 g of Compound 16 was prepared in the same manner as in Preparation Example 13, except that Compound A (10 g, 31.53 mmol) and 2-bromo-9-phenyl-9H-carbazole (8.14 g, 34.69 mmol) were used. (79%)

MS[M+H]$^+$=559

<Preparation Example 17> Preparation of Compound 17

7.2 g of Compound 17 was prepared in the same manner as in Preparation Example 13, except that Compound A (10 g, 31.53 mmol) and 3-(4-bromophenyl)-9-phenyl-9H-carbazole (8.97 g, 34.69 mmol) were used. (92%)

MS[M+H]$^+$=725

<Preparation Example 18> Preparation of Compound 18

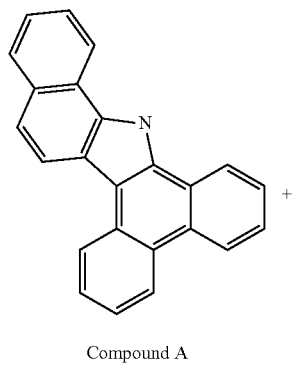

Compound A

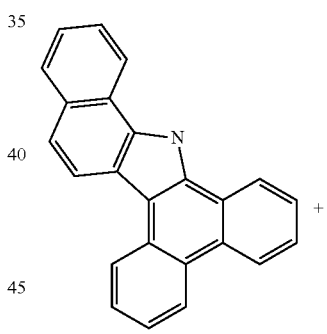

Compound A

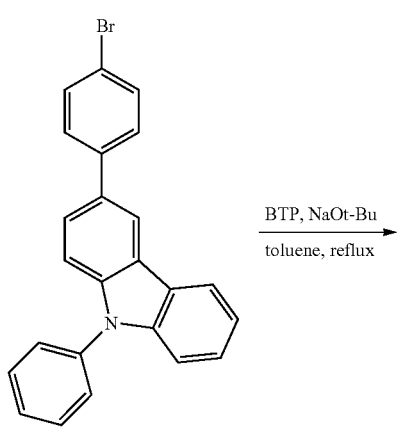

BTP, NaOt-Bu
toluene, reflux
→

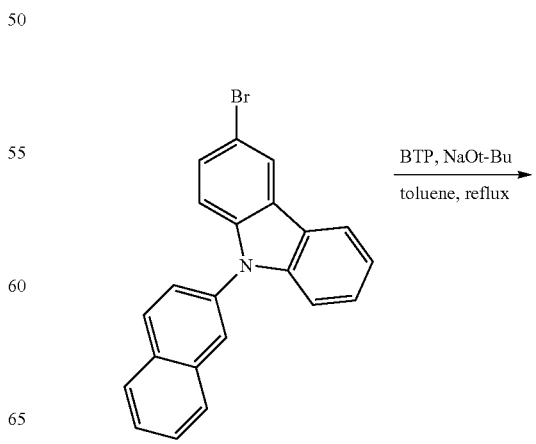

BTP, NaOt-Bu
toluene, reflux
→

-continued

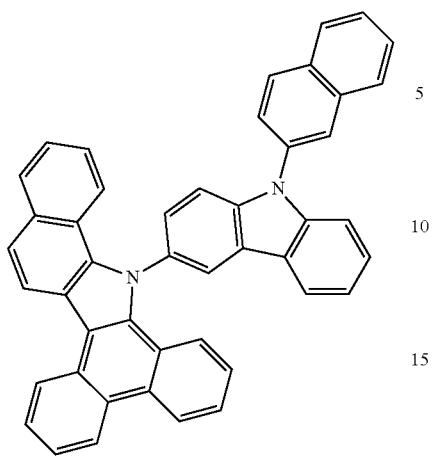

Compound 18

7.2 g of Compound 18 was prepared in the same manner as in Preparation Example 13, except that Compound A (10 g, 31.53 mmol) and 3-bromo-9-(naphthalen2-yl)-9H-carbazole (8.67 g, 34.69 mmol) were used. (92%)

MS[M+H]$^+$=609

<Preparation Example 19> Preparation of Compound 19

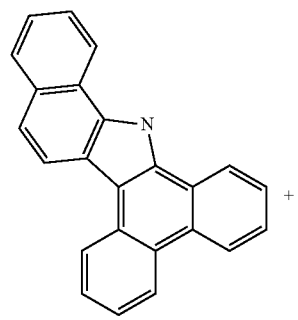

Compound A

-continued

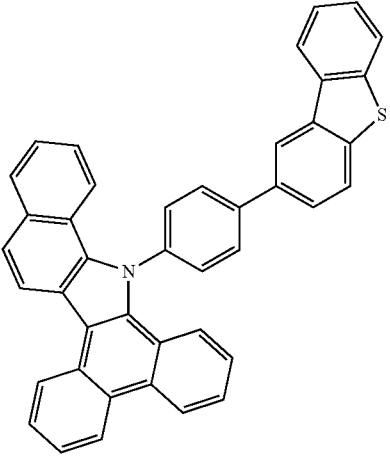

Compound 19

Compound A (10 g, 31.53 mmol), 2-(4-bromophenyl)dibenzo[b,d]thiophene (7.13 g, 12.8 mmol), and sodium t-butoxide (3.94 g, 40.99 mmol) were put into 250 ml of toluene, and then the temperature was increased while stirring the mixture. The mixture was warmed and then, when the reflux started, bis(tri-tert-butylphosphine)palladium (0.16 g, 0.32 mmol) was slowly added dropwise thereto. After 3 hours, the reaction was terminated, the temperature was lowered to normal temperature, and the resulting product was concentrated under reduced pressure, and then column-purified at a ratio of n-hexane:ethyl acetate=10:1 to prepare 6.5 g of Compound 19.

MS[M+H]$^+$=576

<Preparation Example 20> Preparation of Compound 20

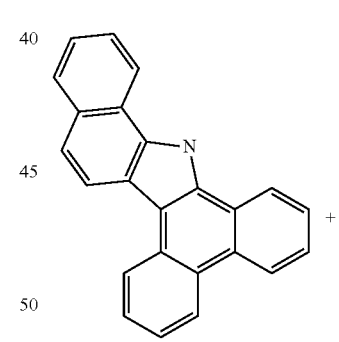

Compound A

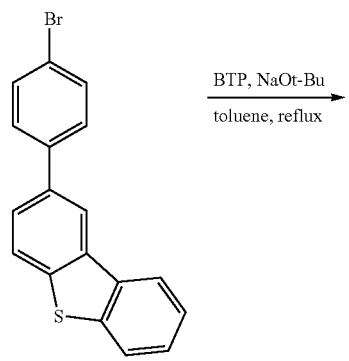

-continued

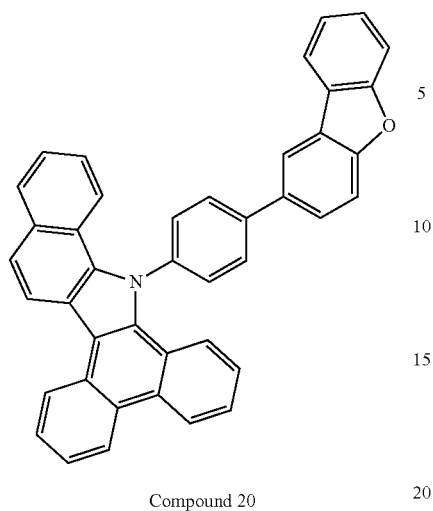

Compound 20

Compound A (10 g, 31.53 mmol), 2-(4-bromophenyl)dibenzo[b,d]furan (7.98 g, 12.8 mmol), and sodium t-butoxide (3.94 g, 40.99 mmol) were put into 250 ml of toluene, and then the temperature was increased while stirring the mixture. The mixture was warmed and then, when the reflux started, bis(tri-tert-butylphosphine)palladium (0.16 g, 0.32 mmol) was slowly added dropwise thereto. After 3 hours, the reaction was terminated, the temperature was lowered to normal temperature, and the resulting product was concentrated under reduced pressure, and then column-purified at a ratio of n-hexane:ethyl acetate=10:1 to prepare 6.1 g of Compound 20.

MS[M+H]$^+$=560

<Preparation Example 21> Preparation of Compound 21

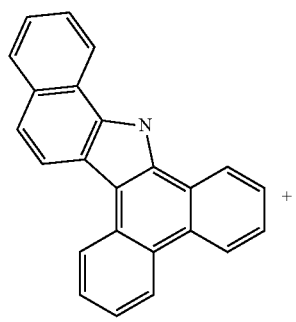

Compound A

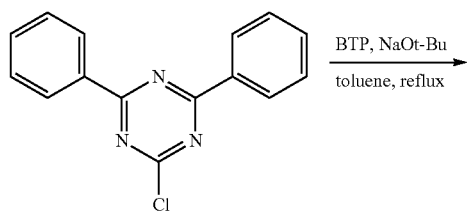

-continued

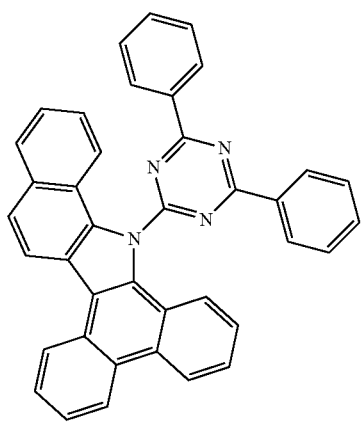

Compound 21

Compound A (10 g, 31.53 mmol), 2-chloro-4,6-diphenyl-1,3,5-triazine (7.53 g, 34.69 mmol), and K$_3$PO$_4$ (4.88 g, 23 mmol) were put into 21 ml of xylene and 7 ml of N,N-dimethylacetamide, and then the temperature was increased while stirring the mixture. The mixture was warmed and then, 7 hours after the mixture started to be refluxed, the reaction was terminated, the temperature was lowered to normal temperature, and the resulting product was concentrated under reduced pressure, and then column-purified to prepare 6.7 g of Compound 21.

MS[M+H]$^+$=549

<Preparation Example 22> Preparation of Compound 22

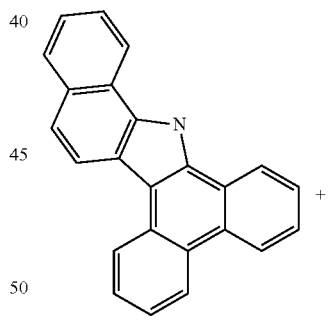

Compound A

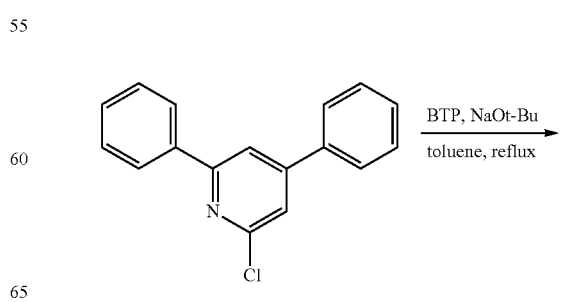

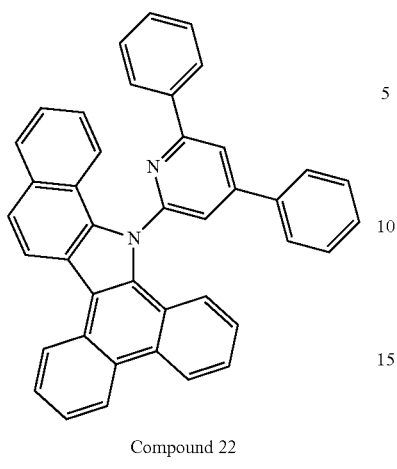

Compound 22

Compound A (10 g, 31.53 mmol), 2-chloro-4,6-diphenylpyridine (7.37 g, 12.7 mmol), and K$_3$PO$_4$ (4.88 g, 23 mmol) were put into 21 ml of xylene and 7 ml of N,N-dimethylacetamide, and then the temperature was increased while stirring the mixture. The mixture was warmed and then, 9 hours after the mixture started to be refluxed, the reaction was terminated, the temperature was lowered to normal temperature, and the resulting product was concentrated under reduced pressure, and then column-purified to prepare 6.4 g of Compound 22.

MS[M+H]$^+$=547

<Preparation Example 23> Preparation of Compound 23

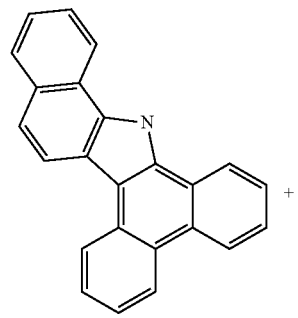

Compound A

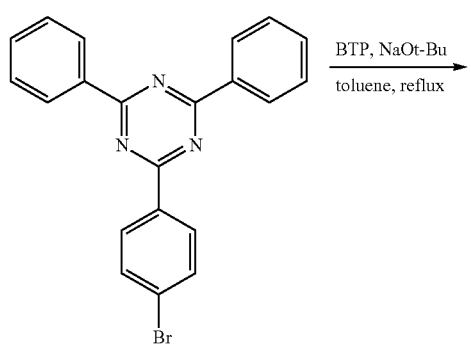

$\xrightarrow{\text{BTP, NaOt-Bu}}_{\text{toluene, reflux}}$

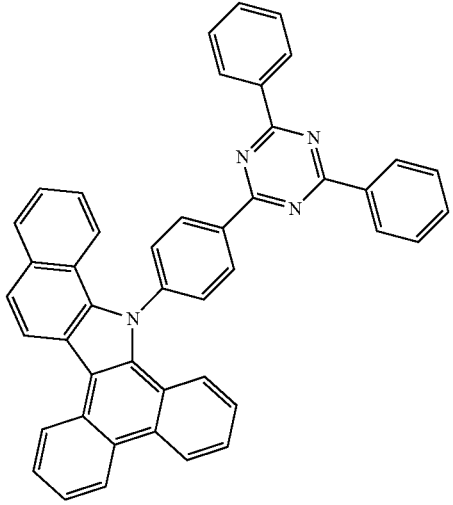

Compound 23

Compound A (10 g, 31.53 mmol), 2-(4-bromophenyl)4,6-diphenyl-1,3,5-triazine (9.15 g, 12.7 mmol), and sodium t-butoxide (1.3 g, 13.8 mmol) were put into 40 ml of toluene, and then the temperature was increased while stirring the mixture. The mixture was warmed and then, when the reflux started, bis(tri-tert-butylphosphine)palladium (0.11 g, 0.23 mmol) was slowly added dropwise thereto. After 6 hours, the reaction was terminated, the temperature was lowered to normal temperature, and the resulting product was concentrated under reduced pressure, and then column-purified to prepare 7.3 g of Compound 23.

MS[M+H]$^+$=625

<Preparation Example 24> Preparation of Compound 24

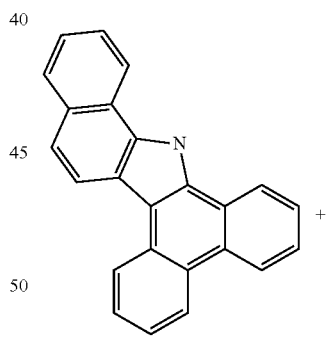

Compound A

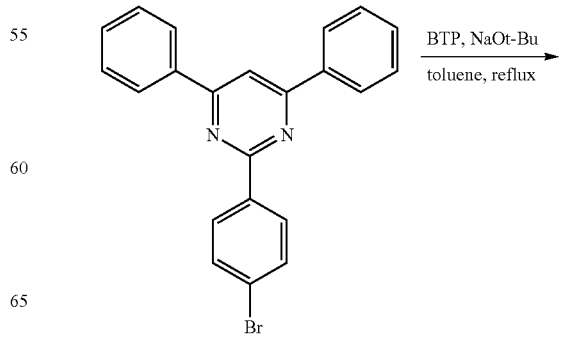

$\xrightarrow{\text{BTP, NaOt-Bu}}_{\text{toluene, reflux}}$

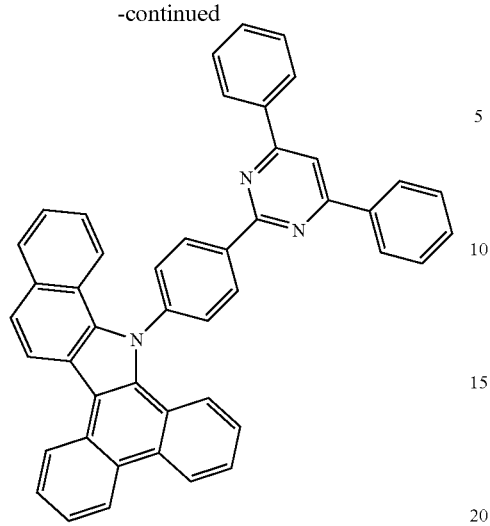

Compound 24

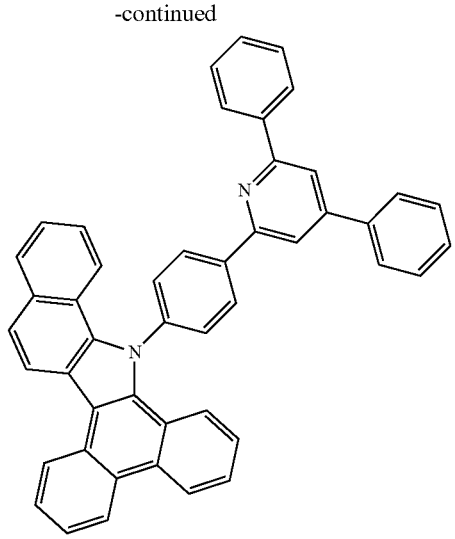

Compound 25

Compound A (10 g, 31.53 mmol), 2-(4-bromophenyl)4,6-diphenylpyrimidine (9.15 g, 34.69 mmol), and sodium t-butoxide (1.3 g, 13.8 mmol) were put into 40 ml of toluene, and then the temperature was increased while stirring the mixture. The mixture was warmed and then, when the reflux started, bis(tri-tert-butylphosphine)palladium (0.11 g, 0.23 mmol) was slowly added dropwise thereto. After 8 hours, the reaction was terminated, the temperature was lowered to normal temperature, and the resulting product was concentrated under reduced pressure, and then column-purified to prepare 7.0 g of Compound 24.

MS[M+H]$^+$=624

<Preparation Example 25> Preparation of Compound 25

6.8 g of Compound 25 was prepared in the same manner as in the preparation of Compound 23, except that Compound A (10 g, 31.53 mmol) and 2-(4-bromophenyl)4,6-diphenylpyridine (9.15 g, 34.69 mmol) were used.

MS[M+H]$^+$=713

<Preparation Example 26> Preparation of Compound 26

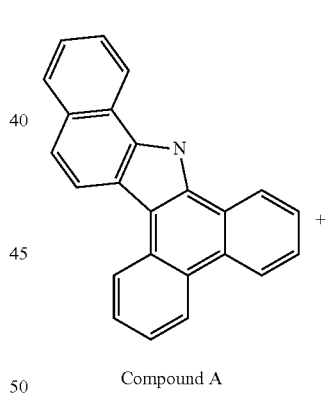

Compound A

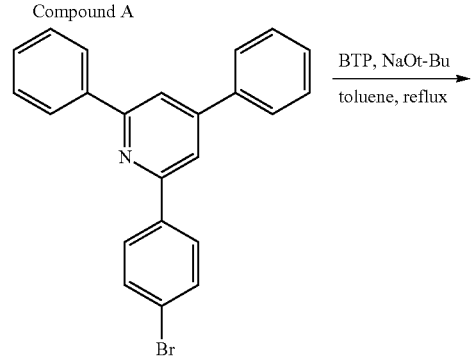

Compound A

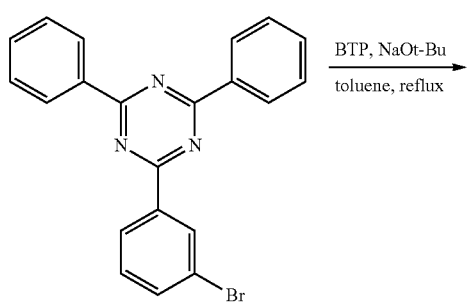

-continued

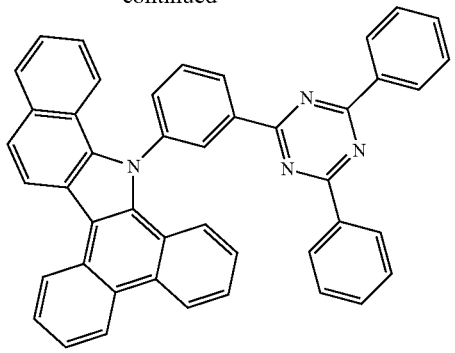

Compound 26

7.2 g of Compound 26 was prepared in the same manner as in the preparation of Compound 23, except that Compound A (10 g, 31.53 mmol) and 2-(3-bromophenyl)4,6-diphenyl-1,3,5-triazine (9.14 g, 34.69 mmol) were used.
MS[M+H]⁺=625

<Preparation Example 27> Preparation of Compound 27

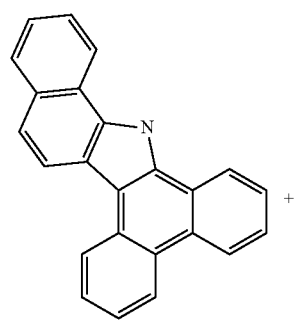

Compound A

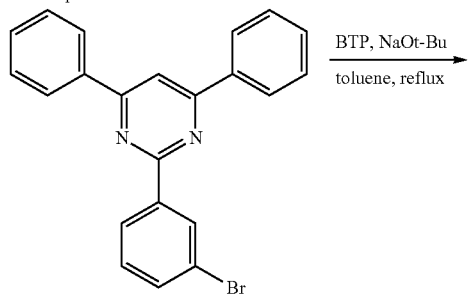

Compound 27

7.0 g of Compound 27 was prepared in the same manner as in the preparation of Compound 23, except that Compound A (10 g, 31.53 mmol) and 2-(3-bromophenyl)4,6-diphenylpyrimidine (9.64 g, 34.69 mmol) were used.
MS[M+H]⁺=624

<Preparation Example 28> Preparation of Compound 28

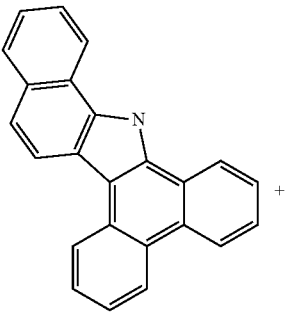

Compound A

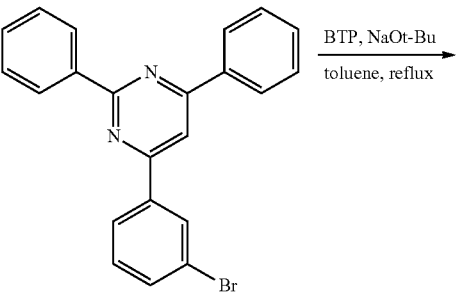

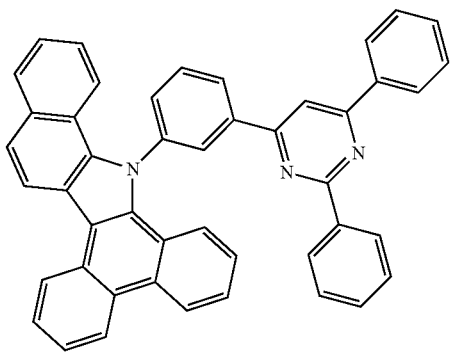

Compound 28

6.8 g of Compound 28 was prepared in the same manner as in the preparation of Compound 23, except that Compound A (10 g, 31.53 mmol) and 4-(3-bromophenyl)-2,6-diphenylpyrimidine (9.63 g, 34.69 mmol) were used.
MS[M+H]⁺=623

<Preparation Example 29> Preparation of Compound 29

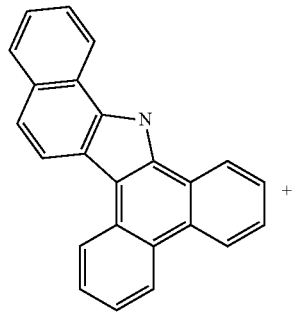

Compound A

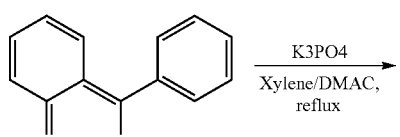

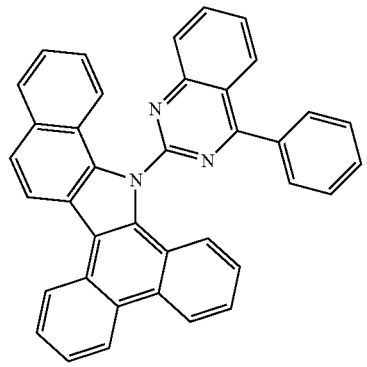

Compound 29

Compound A (10 g, 31.53 mmol), 2-chloro-4-phenylquinazoline (9.05 g, 34.69 mmol), and K₃PO₄ (4.88 g, 23 mmol) were put into 21 ml of xylene and 7 ml of N,N-dimethylacetamide, and then the temperature was increased while stirring the mixture. The mixture was warmed and then, 5 hours after the mixture started to be refluxed, the reaction was terminated, the temperature was lowered to normal temperature, and the resulting product was concentrated under reduced pressure, and then column-purified to prepare 6.0 g of Compound 29.
MS[M+H]⁺=522

<Preparation Example 30> Preparation of Compound 30

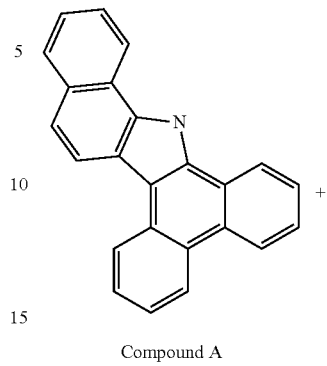

Compound A

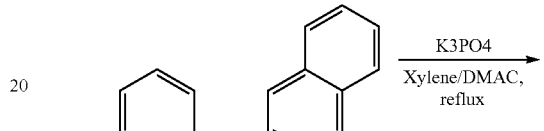

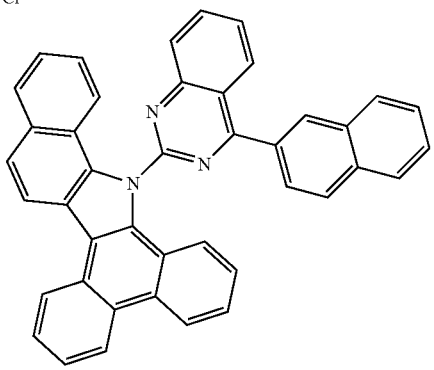

Compound 30

6.7 g of Compound 30 was prepared in the same manner as in Compound 29, except that Compound A (10 g, 31.53 mmol) and 2-chloro-4-(naphthalene-2-yl)quinazoline (10.68 g, 34.69 mmol) were used.
MS[M+H]⁺=572

<Preparation Example 31> Preparation of Compound 31

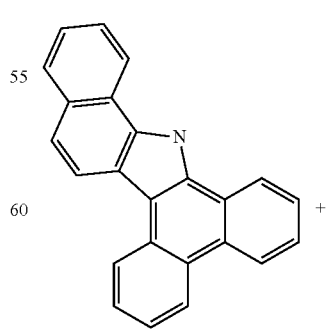

Compound A

-continued

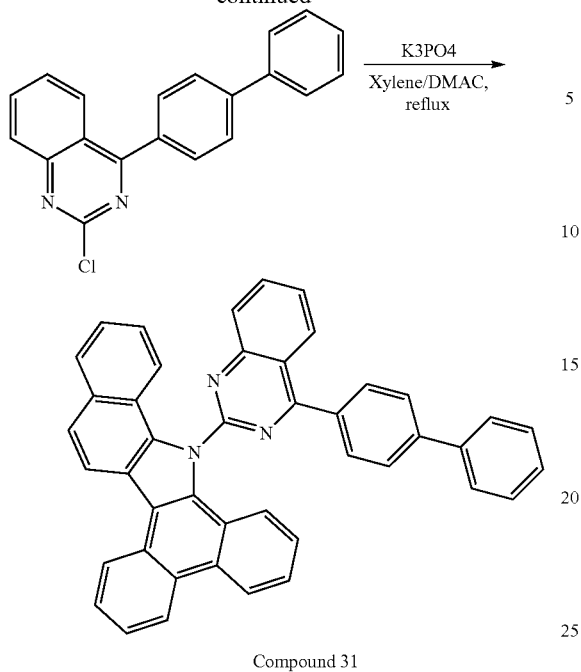

Compound 31

6.8 g of Compound 31 was prepared in the same manner as in Compound 29, except that Compound A (10 g, 31.53 mmol) and 4-([1,1'-biphenyl]-4-yl)2-chloroquinazoline (10.01 g, 34.69 mmol) were used.
MS[M+H]$^+$=598

<Preparation Examples 32 to 62> Preparation of Compounds 32 to 62

The following Compounds 32 to 62 were prepared in the same manner as in Preparation Examples 1 to 31, except that Compound B was used instead of Compound A as a starting material in Preparation Examples 1 to 31.

32

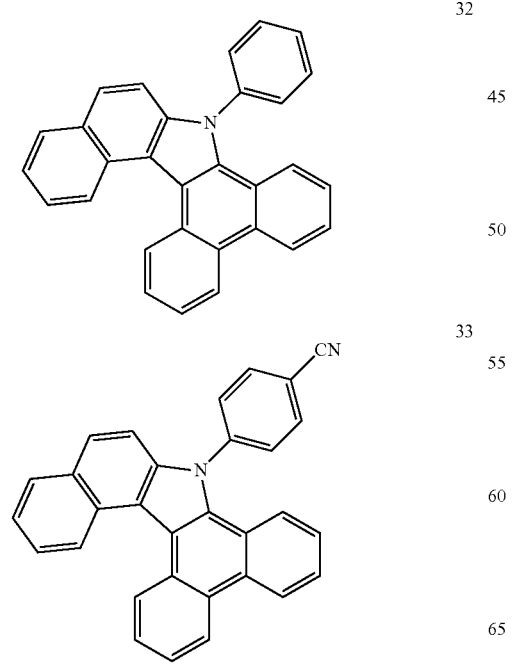

33

-continued

34

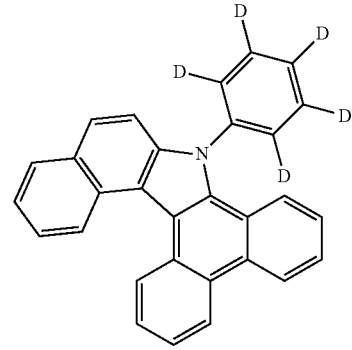

35

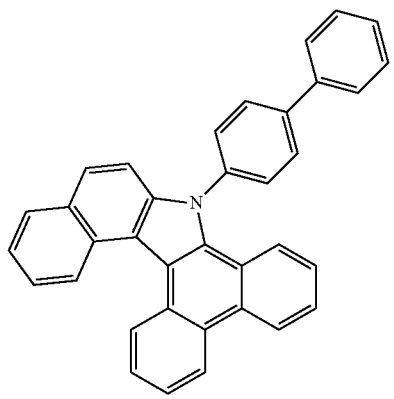

36

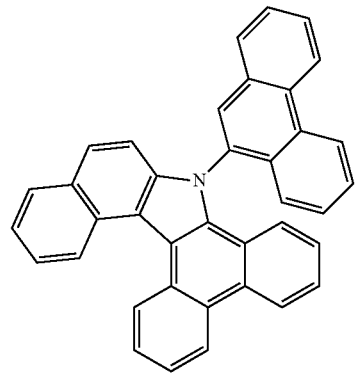

37

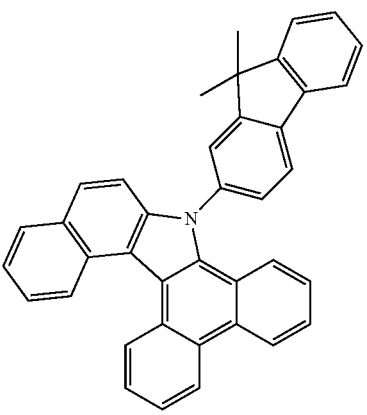

38
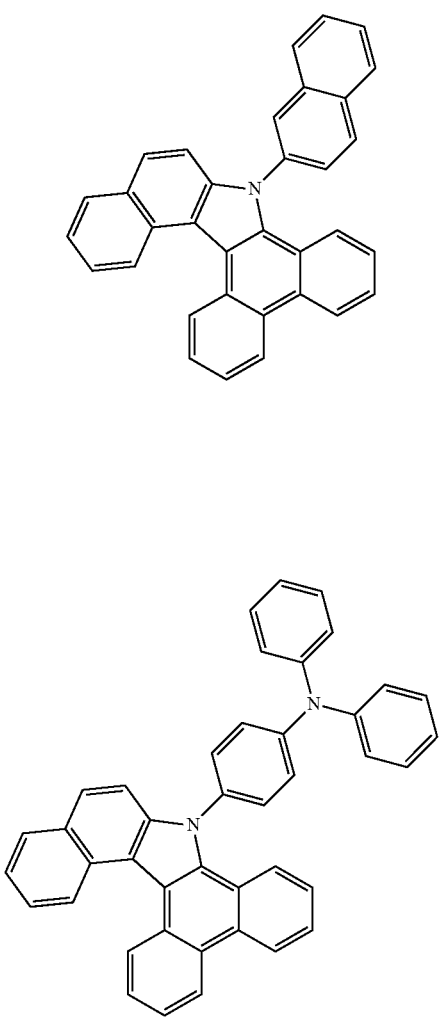
39
42
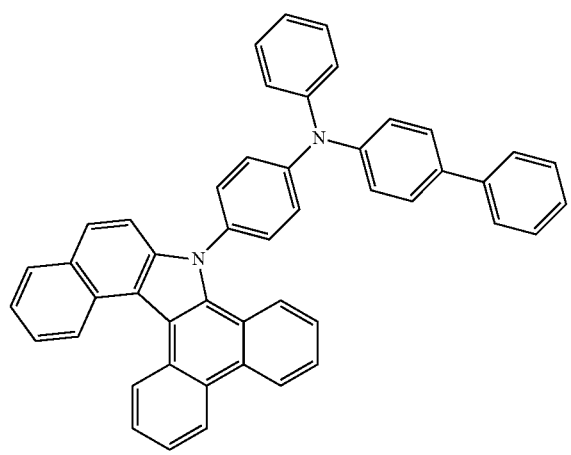
41
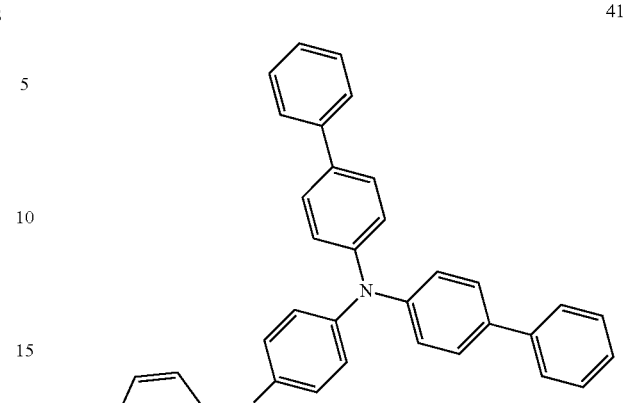
42
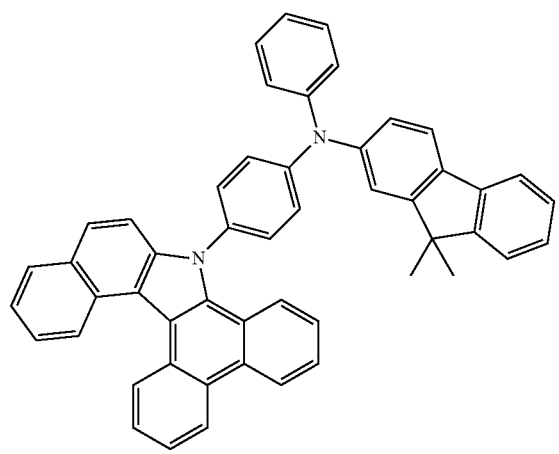
43
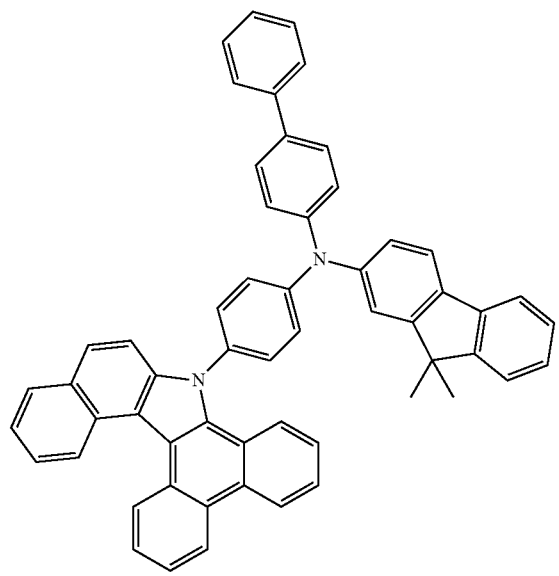

-continued
44
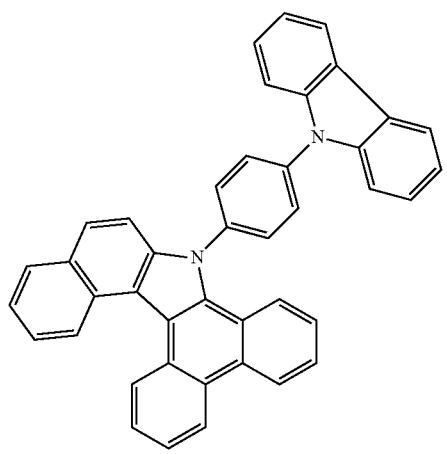
45
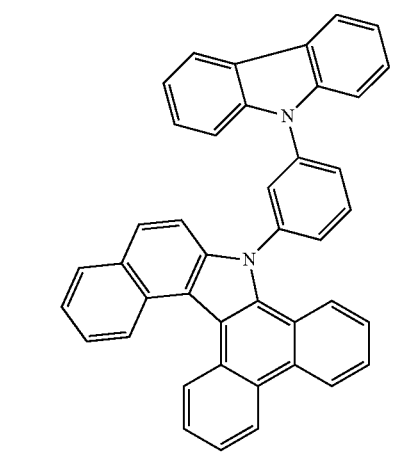
46
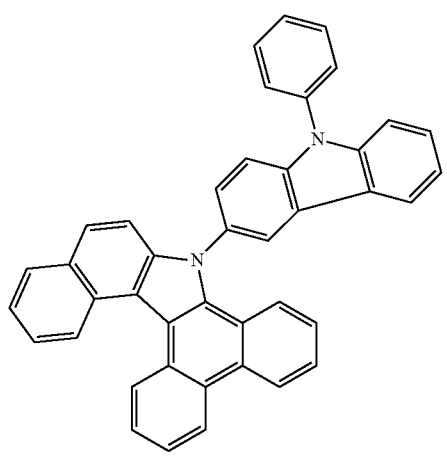
-continued
47
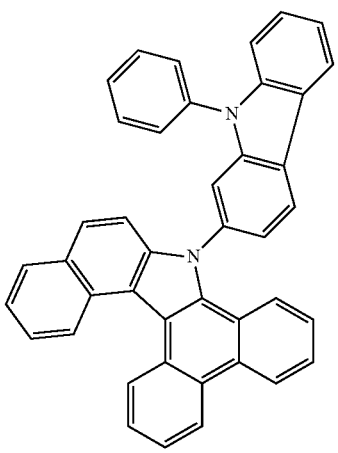
48
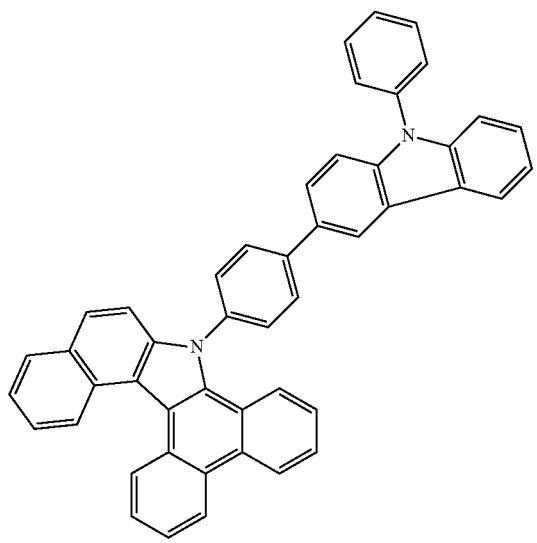
49
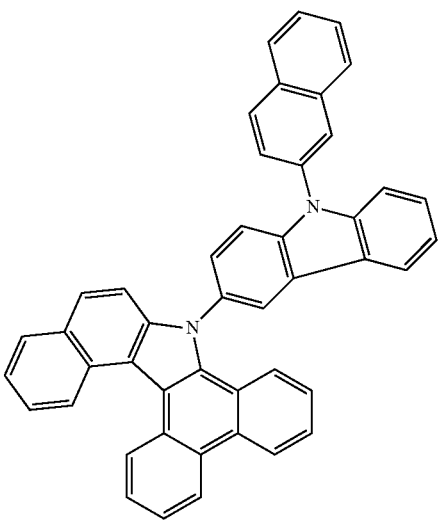

169
-continued
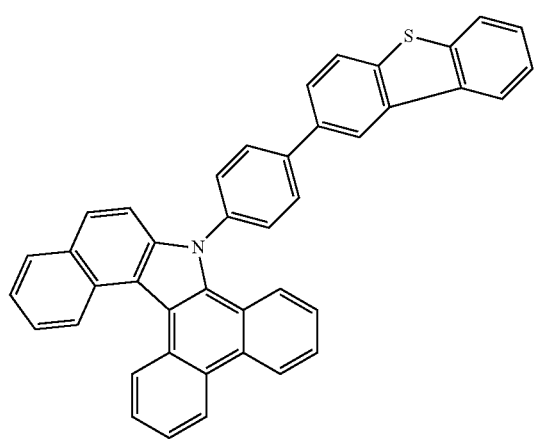
50
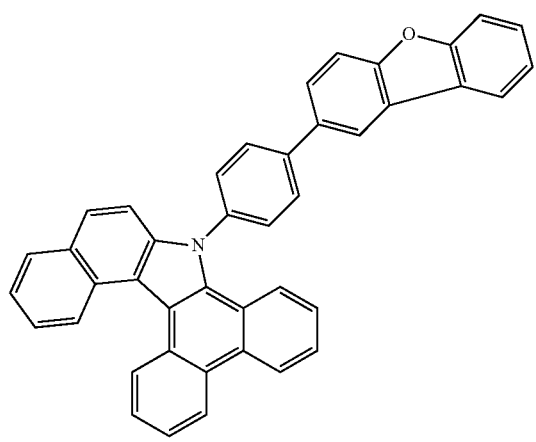
51
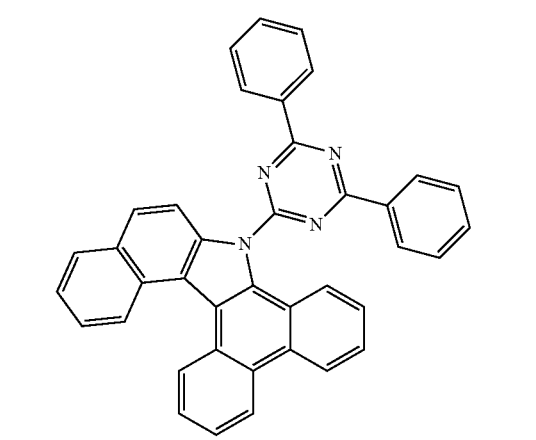
52
170
-continued
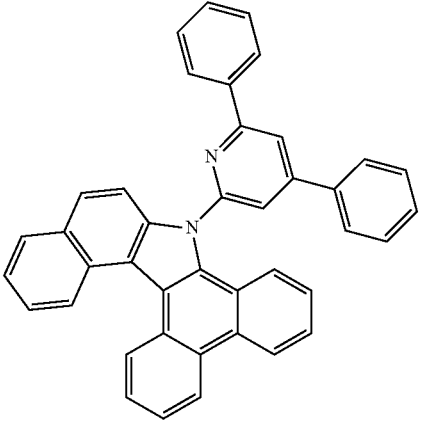
53
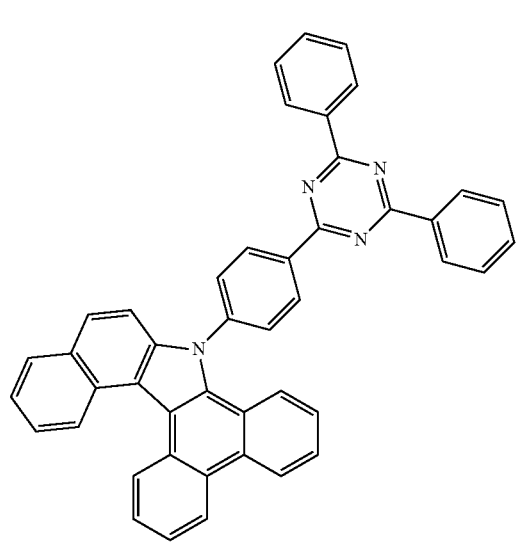
54
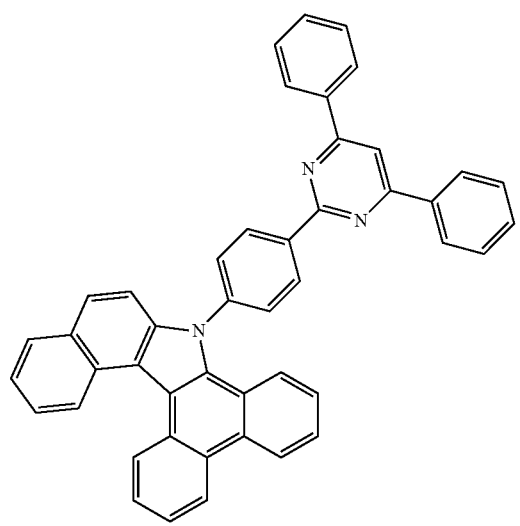
55

-continued
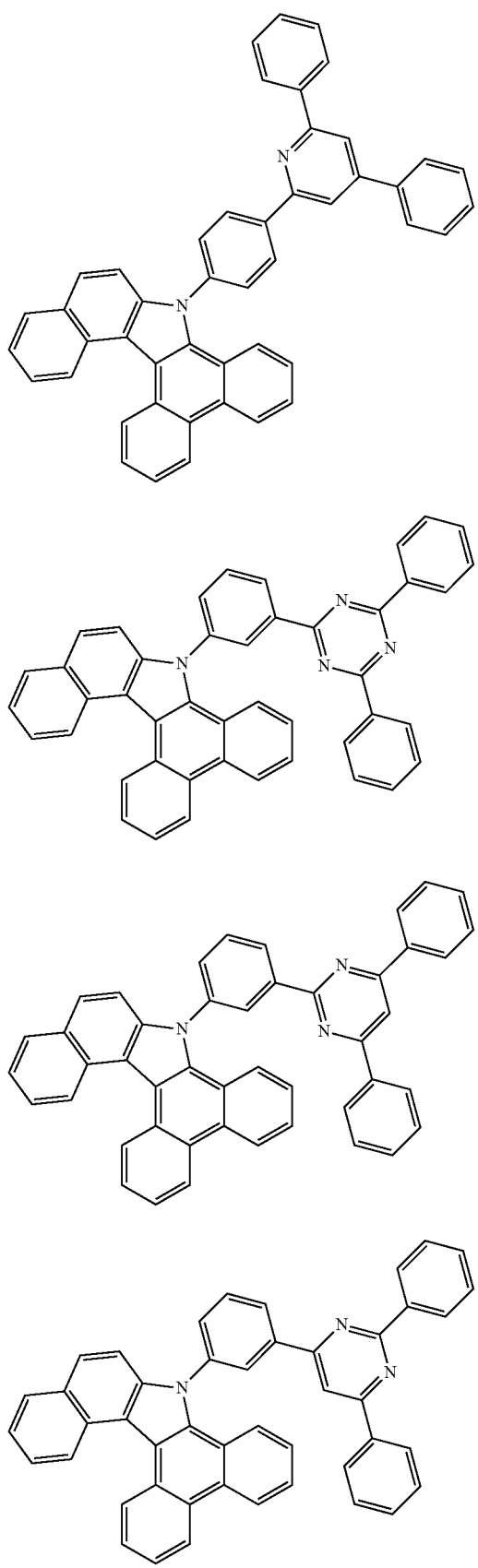
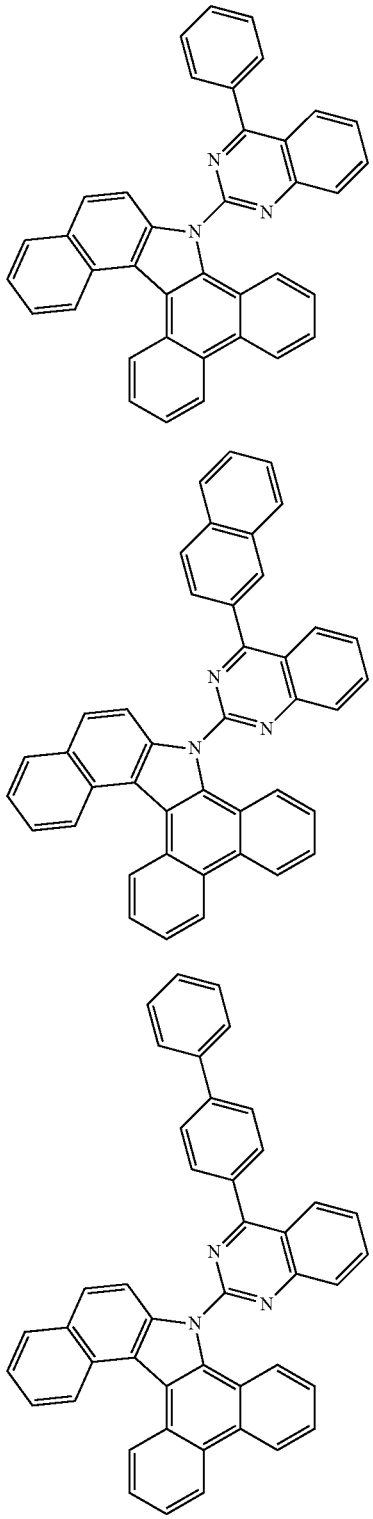
Experimental Example 1-1
A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

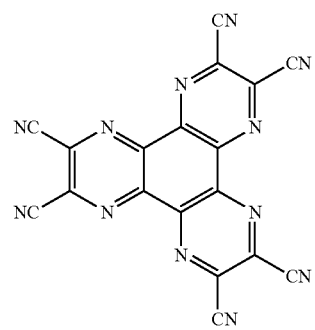

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

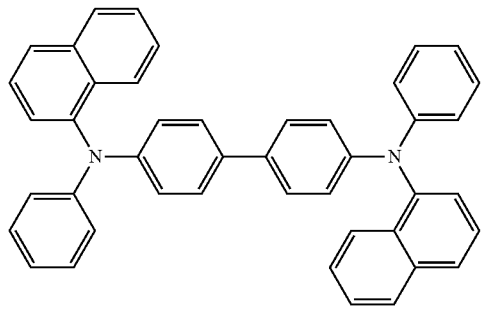

[NPB]

Subsequently, the following Compound 1 was vacuum deposited to have a film thickness of 100 Å on the hole transport layer, thereby forming an electron blocking layer.

Subsequently, the following BH and BD were vacuum deposited at a weight ratio of 25:1 to have a film thickness of 300 Å on the electron blocking layer, thereby forming a light emitting layer.

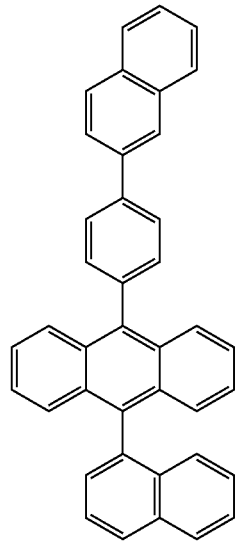

[BH]

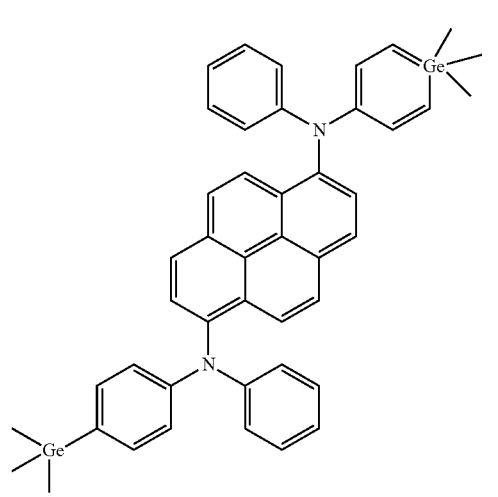

[BD]

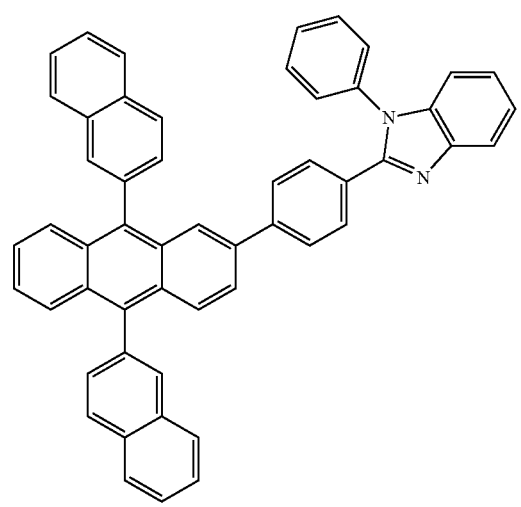

[ET1]

-continued

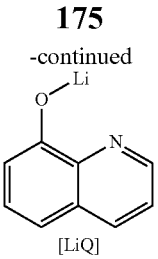

[LiQ]

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 1-2

An organic light emitting device was manufactured in the same manner as in Experimental Example 1-1, except that Compound 4 was used instead of Compound 1 in Experimental Example 1-1.

Experimental Example 1-3

An organic light emitting device was manufactured in the same manner as in Experimental Example 1-1, except that Compound 6 was used instead of Compound 1 in Experimental Example 1-1.

Experimental Example 1-4

An organic light emitting device was manufactured in the same manner as in Experimental Example 1-1, except that Compound 8 was used instead of Compound 1 in Experimental Example 1-1.

Experimental Example 1-5

An organic light emitting device was manufactured in the same manner as in Experimental Example 1-1, except that Compound 9 was used instead of Compound 1 in Experimental Example 1-1.

Experimental Example 1-6

An organic light emitting device was manufactured in the same manner as in Experimental Example 1-1, except that Compound 10 was used instead of Compound 1 in Experimental Example 1-1.

Experimental Example 1-7

An organic light emitting device was manufactured in the same manner as in Experimental Example 1-1, except that Compound 11 was used instead of Compound 1 in Experimental Example 1-1.

Experimental Example 1-8

An organic light emitting device was manufactured in the same manner as in Experimental Example 1-1, except that Compound 12 was used instead of Compound 1 in Experimental Example 1-1.

Experimental Example 1-9

An organic light emitting device was manufactured in the same manner as in Experimental Example 1-1, except that Compound 32 was used instead of Compound 1 in Experimental Example 1-1.

Experimental Example 1-10

An organic light emitting device was manufactured in the same manner as in Experimental Example 1-1, except that Compound 35 was used instead of Compound 1 in Experimental Example 1-1.

Experimental Example 1-11

An organic light emitting device was manufactured in the same manner as in Experimental Example 1-1, except that Compound 37 was used instead of Compound 1 in Experimental Example 1-1.

Experimental Example 1-12

An organic light emitting device was manufactured in the same manner as in Experimental Example 1-1, except that Compound 39 was used instead of Compound 1 in Experimental Example 1-1.

Experimental Example 1-13

An organic light emitting device was manufactured in the same manner as in Experimental Example 1-1, except that Compound 40 was used instead of Compound 1 in Experimental Example 1-1.

Experimental Example 1-14

An organic light emitting device was manufactured in the same manner as in Experimental Example 1-1, except that Compound 41 was used instead of Compound 1 in Experimental Example 1-1.

Experimental Example 1-15

An organic light emitting device was manufactured in the same manner as in Experimental Example 1-1, except that Compound 42 was used instead of Compound 1 in Experimental Example 1-1.

Experimental Example 1-16

An organic light emitting device was manufactured in the same manner as in Experimental Example 1-1, except that Compound 43 was used instead of Compound 1 in Experimental Example 1-1.

Comparative Example 1-1

An organic light emitting device was manufactured in the same manner as in Experimental Example 1-1, except that EB 1 (TCTA) was used instead of Compound 1 in Experimental Example 1-1.

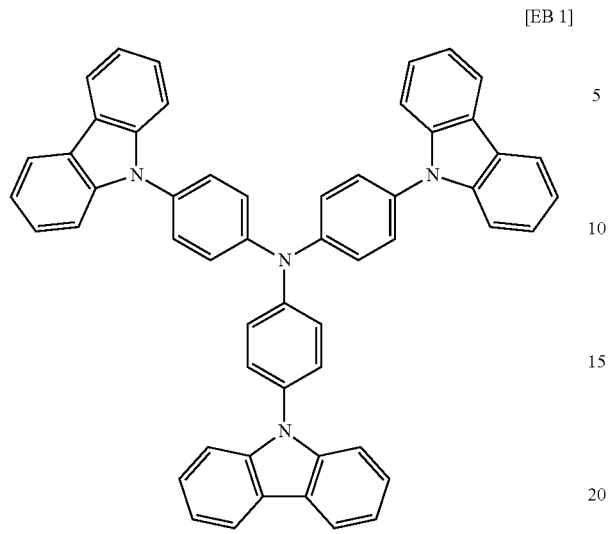
[EB 1]

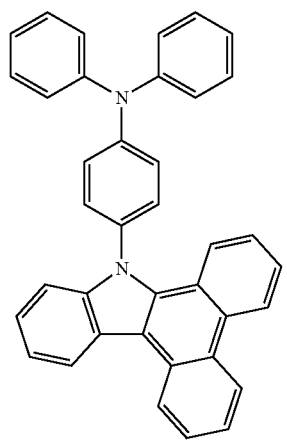
[EB 2]

Comparative Example 1-2

An organic light emitting device was manufactured in the same manner as in Experimental Example 1-1, except that EB 2 was used instead of Compound 1 in Experimental Example When current was applied to the organic light emitting devices manufactured in Experimental Examples 1-1 to 1-16 and Comparative Examples 1-1 and 1-2, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.61 | 5.65 | (0.139, 0.122) |
| Experimental Example 1-2 | Compound 4 | 3.63 | 5.68 | (0.138, 0.126) |
| Experimental Example 1-3 | Compound 6 | 3.62 | 5.61 | (0.138, 0.127) |
| Experimental Example 1-4 | Compound 8 | 3.64 | 5.62 | (0.137, 0.125) |
| Experimental Example 1-5 | Compound 9 | 3.60 | 5.63 | (0.136, 0.125) |
| Experimental Example 1-6 | Compound 10 | 3.65 | 5.67 | (0.136, 0.127) |
| Experimental Example 1-7 | Compound 11 | 3.60 | 5.68 | (0.136, 0.125) |
| Experimental Example 1-8 | Compound 12 | 3.68 | 5.68 | (0.137, 0.125) |
| Experimental Example 1-9 | Compound 32 | 3.87 | 5.41 | (0.138, 0.125) |
| Experimental Example 1-10 | Compound 35 | 3.81 | 5.35 | (0.136, 0.125) |
| Experimental Example 1-11 | Compound 37 | 3.83 | 5.48 | (0.137, 0.125) |
| Experimental Example 1-12 | Compound 39 | 3.82 | 5.41 | (0.136, 0.125) |
| Experimental Example 1-13 | Compound 40 | 3.94 | 5.32 | (0.138, 0.126) |
| Experimental Example 1-14 | Compound 41 | 3.90 | 5.33 | (0.137, 0.125) |
| Experimental Example 1-15 | Compound 42 | 3.85 | 5.47 | (0.136, 0.127) |

TABLE 1-continued

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-16 | Compound 43 | 3.80 | 5.48 | (0.135, 0.127) |
| Comparative Example 1-1 | EB 1 | 4.86 | 3.83 | (0.138, 0.127) |
| Comparative Example 1-2 | EB 2 | 4.31 | 4.48 | (0.139, 0.122) |

As observed in Table 1, it can be seen that Experimental Examples 1-1 to 1-8 where a compound in which Compound A being a core compound of Chemical Formula 1-1 of the present invention is a center is used and Experimental Examples 1-9 to 1-16 where a compound in which Compound B being a core compound of Chemical Formula 1-3 of the present invention is a center is used exhibit lower voltage and higher efficiency characteristics than EB 1 (TCTA) of Comparative Example 1-1, which is frequently used as an electron blocking layer in the case of an organic light emitting device, and Comparative Example 1-2 being a compound in which a core is similar to that of Chemical Formula 1 of the present invention, but the core does not form a fused ring.

In particular, it can be seen that the organic light emitting devices in Experimental Examples 1-1 to 1-8 where Compound A being a core compound of Chemical Formula 1-1 of the present invention is a center have excellent characteristics.

It could be confirmed that the compound derivatives of the Formulae according to the present invention have excellent electron blocking capability to exhibit low voltage and high efficiency characteristics, and may be applied to an organic light emitting device.

Experimental Examples 2-1 to 2-16

An experiment was performed in the same manner as in Experimental Example 1-1, except that EB 1 was used as the electron blocking layer, and the compounds in Experimental Examples 1-1 to 1-16 were used instead of NPB as the hole transport layer.

Comparative Example 2-1

An experiment was performed in the same manner as in Experimental Example 1-1, except that EB 1 was used as the electron blocking layer, and HT 1 was used as the hole transport layer.

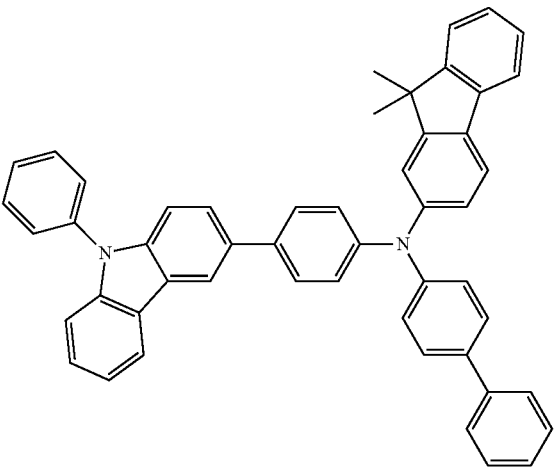

[HT 1]

Comparative Example 2-2

An experiment was performed in the same manner as in Experimental Example 1-1, except that EB 1 was used as the electron blocking layer, and HT 2 was used as the hole transport layer.

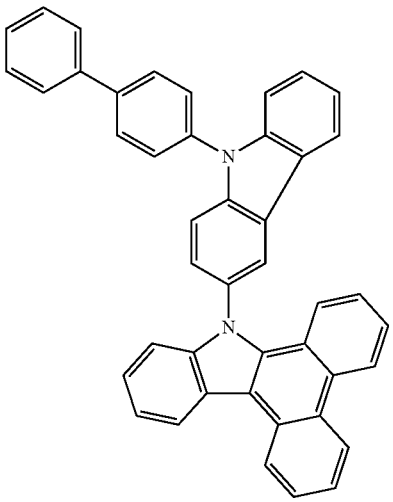

[HT 2]

When current was applied to the organic light emitting devices manufactured in Experimental Examples 2-1 to 2-16 and Comparative Examples 2-1 and 2-2, the results of Table 2 were obtained.

TABLE 2

| | Compound (Hole transport layer) | Voltage (V@10 mA/cm$^2$) | Efficiency (cd/A@10 mA/cm$^2$) | Color coordinate (x, y) |
|---|---|---|---|---|
| Experimental Example 2-1 | Compound 1 | 4.21 | 5.35 | (0.139, 0.122) |
| Experimental Example 2-2 | Compound 4 | 4.23 | 5.38 | (0.138, 0.126) |
| Experimental Example 2-3 | Compound 6 | 4.22 | 5.31 | (0.138, 0.127) |
| Experimental Example 2-4 | Compound 8 | 4.14 | 5.22 | (0.137, 0.125) |
| Experimental Example 2-5 | Compound 9 | 4.10 | 5.23 | (0.136, 0.125) |
| Experimental Example 2-6 | Compound 10 | 4.15 | 5.27 | (0.136, 0.127) |
| Experimental Example 2-7 | Compound 11 | 4.10 | 5.28 | (0.136, 0.125) |
| Experimental Example 2-8 | Compound 12 | 4.18 | 5.28 | (0.137, 0.125) |
| Experimental Example 2-9 | Compound 32 | 4.37 | 5.01 | (0.138, 0.125) |
| Experimental Example 2-10 | Compound 35 | 4.31 | 5.05 | (0.136, 0.125) |
| Experimental Example 2-11 | Compound 37 | 4.32 | 5.08 | (0.137, 0.125) |
| Experimental Example 2-12 | Compound 39 | 4.32 | 5.11 | (0.136, 0.125) |
| Experimental Example 2-13 | Compound 40 | 4.34 | 5.12 | (0.138, 0.126) |
| Experimental Example 2-14 | Compound 41 | 4.30 | 5.13 | (0.137, 0.125) |
| Experimental Example 2-15 | Compound 42 | 4.35 | 5.17 | (0.136, 0.127) |
| Experimental Example 2-16 | Compound 43 | 4.30 | 5.18 | (0.135, 0.127) |
| Comparative Example 2-1 | HT 1 | 5.16 | 4.53 | (0.138, 0.127) |
| Comparative Example 2-2 | HT 2 | 5.21 | 4.38 | (0.137, 0.125) |

As observed in Table 2, it can be seen that Experimental Examples 2-1 to 2-8 where a compound in which Compound A being a core compound of Chemical Formula 1-1 of the present invention is a center is used and Experimental Examples 2-9 to 2-16 where a compound in which Compound B being a core compound of Chemical Formula 1-3 of the present invention is a center is used exhibit lower voltage and higher efficiency characteristics than Compound HT-1 of Comparative Example 2-1, which is frequently used as a hole transport layer in the case of an organic light emitting device, and, but Comparative Example 2-2 being a compound in which a core is similar to that of Chemical Formula 1 of the present invention, but the core does not form a fused ring.

In particular, it can be seen that the organic light emitting devices in Experimental Examples 2-1 to 2-8 where Compound A being a core compound of Chemical Formula 1-1 of the present invention is a center have excellent characteristics.

It could be confirmed that the organic light emitting device manufactured by using the compound represented by Chemical Formula 1 according to the present invention also has excellent hole transport capability to exhibit low voltage and high efficiency characteristics, and may be applied to an organic light emitting device.

Experimental Example 3-1

The compounds prepared in the Preparation Examples were subjected to high-purity sublimation purification by a typically known method, and then green organic light emitting devices were manufactured by the following method.

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

An organic EL device was manufactured by configuring the light emitting device in the order of m-MTDATA (60 nm)/TCTA (80 nm)/Compound 21+10% Ir(ppy)$_3$ (300 nm)/BCP (10 nm)/Alq$_3$ (30 nm)/LiF (1 nm)/Al (200 nm) on the thus prepared ITO transparent electrode by using Compound 21 as a host.

The structures of m-MTDATA, TCTA, Ir(ppy)$_3$, and BCP are as follows.

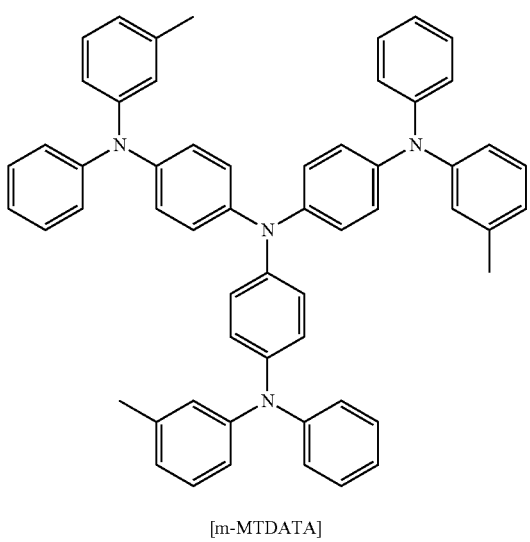

[m-MTDATA]

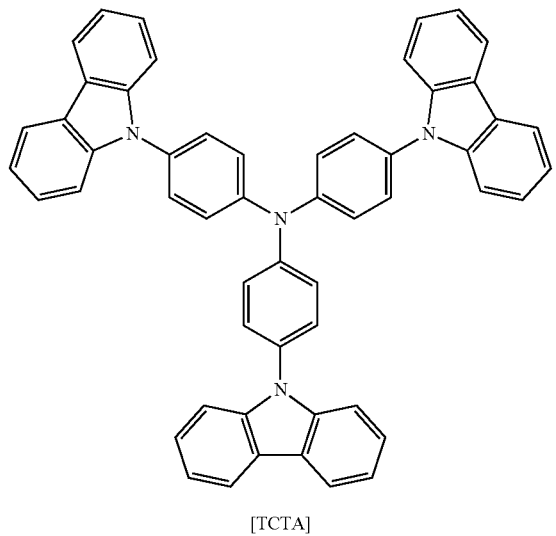

[TCTA]

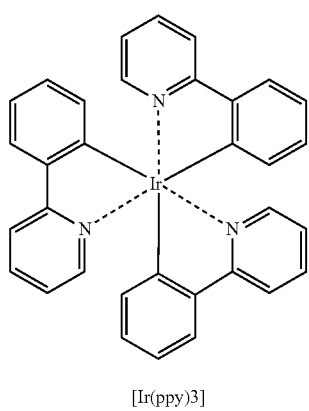

[Ir(ppy)3]

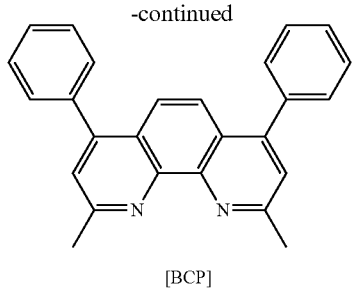

[BCP]

Experimental Example 3-2

An organic light emitting device was manufactured in the same manner as in Experimental Example 3-1, except that Compound 22 was used instead of Compound 21 in Experimental Example 3-1.

Experimental Example 3-3

An organic light emitting device was manufactured in the same manner as in Experimental Example 3-1, except that Compound 23 was used instead of Compound 21 in Experimental Example 3-1.

Experimental Example 3-4

An organic light emitting device was manufactured in the same manner as in Experimental Example 3-1, except that Compound 24 was used instead of Compound 21 in Experimental Example 3-1.

Experimental Example 3-5

An organic light emitting device was manufactured in the same manner as in Experimental Example 3-1, except that Compound 25 was used instead of Compound 21 in Experimental Example 3-1.

Experimental Example 3-6

An organic light emitting device was manufactured in the same manner as in Experimental Example 3-1, except that Compound 26 was used instead of Compound 21 in Experimental Example 3-1.

Experimental Example 3-7

An organic light emitting device was manufactured in the same manner as in Experimental Example 3-1, except that Compound 27 was used instead of Compound 21 in Experimental Example 3-1.

Experimental Example 3-8

An organic light emitting device was manufactured in the same manner as in Experimental Example 3-1, except that Compound 28 was used instead of Compound 21 in Experimental Example 3-1.

Experimental Example 3-9

An organic light emitting device was manufactured in the same manner as in Experimental Example 3-1, except that Compound 51 was used instead of Compound 21 in Experimental Example 3-1.

Experimental Example 3-10

An organic light emitting device was manufactured in the same manner as in Experimental Example 3-1, except that Compound 52 was used instead of Compound 21 in Experimental Example 3-1.

Experimental Example 3-11

An organic light emitting device was manufactured in the same manner as in Experimental Example 3-1, except that Compound 53 was used instead of Compound 21 in Experimental Example 3-1.

Experimental Example 3-12

An organic light emitting device was manufactured in the same manner as in Experimental Example 3-1, except that Compound 54 was used instead of Compound 21 in Experimental Example 3-1.

Comparative Example 3-1

An organic light emitting device was manufactured in the same manner as in Experimental Example 3-1, except that GH 1 (CBP) was used instead of Compound 21 in Experimental Example 3-1.

[GH 1]

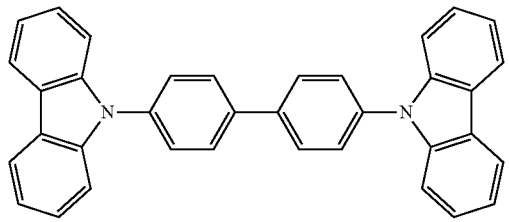

Comparative Example 3-2

An organic light emitting device was manufactured in the same manner as in Experimental Example 3-1, except that GH 2 was used instead of Compound 21 in Experimental Example 3-1.

[GH 2]

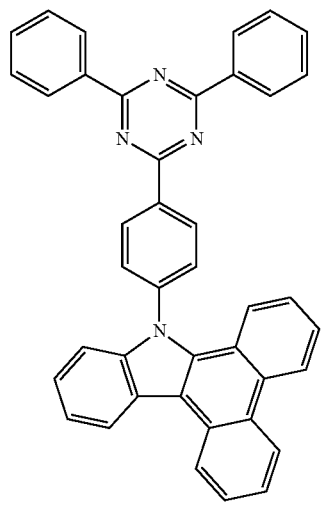

Comparative Example 3-3

An organic light emitting device was manufactured in the same manner as in Experimental Example 3-1, except that GH 3 was used instead of Compound 21 in Experimental Example 3-1.

[GH 3]

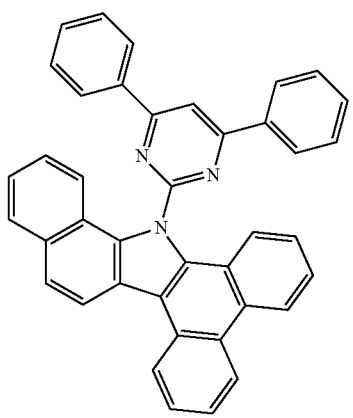

When current was applied to the organic light emitting devices manufactured in Experimental Examples 3-1 to 3-12 and Comparative Examples 3-1 to 3-3, the results of Table 3 were obtained.

TABLE 3

| | Compound (Host) | Voltage (V@10 mA/ cm$^2$) | Efficiency (cd/A@10 mA/ cm$^2$) | Light emitting peak (nm) |
|---|---|---|---|---|
| Experimental Example 3-1 | Compound 21 | 6.11 | 46.93 | 517 |
| Experimental Example 3-2 | Compound 22 | 6.16 | 45.79 | 518 |
| Experimental Example 3-3 | Compound 23 | 6.24 | 46.15 | 517 |
| Experimental Example 3-4 | Compound 24 | 6.28 | 47.31 | 515 |

TABLE 3-continued

| | Compound (Host) | Voltage (V@10 mA/cm$^2$) | Efficiency (cd/A@10 mA/cm$^2$) | Light emitting peak (nm) |
|---|---|---|---|---|
| Experimental Example 3-5 | Compound 25 | 6.21 | 45.63 | 516 |
| Experimental Example 3-6 | Compound 26 | 6.25 | 45.62 | 516 |
| Experimental Example 3-7 | Compound 27 | 6.26 | 46.64 | 517 |
| Experimental Example 3-8 | Compound 28 | 6.24 | 46.68 | 518 |
| Experimental Example 3-9 | Compound 51 | 6.18 | 46.83 | 517 |
| Experimental Example 3-10 | Compound 52 | 6.25 | 45.24 | 516 |
| Experimental Example 3-11 | Compound 53 | 6.20 | 46.95 | 517 |
| Experimental Example 3-12 | Compound 54 | 6.23 | 45.31 | 515 |
| Comparative Example 3-1 | GH 1 (CBP) | 7.41 | 32.72 | 517 |
| Comparative Example 3-2 | GH 2 | 7.05 | 34.56 | 517 |
| Comparative Example 3-3 | GH 3 | 7.25 | 33.41 | 517 |

As observed in Table 3, it could be confirmed that the green organic light emitting devices in Experimental Examples 3-1 to 3-12 where the hetero-cyclic compound according to an exemplary embodiment of the present specification was used as a host material of the light emitting layer exhibited a better performance in terms of current efficiency and driving voltage than the green organic light emitting devices in Comparative Example 3-1 where CBP in the related art was used, Comparative Example 3-2 being a compound in which a core is similar to that of Chemical Formula 1 of the present invention, but the core did not form a fused ring, and Comparative Example 3-3 being a compound in which L1 of Chemical Formula 1 of the present invention is a direct bond and Ar1 is a pyrimidyl group substituted with a phenyl group.

Experimental Example 4-1

The compounds prepared in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted on a vacuum chamber, and then the base pressure was allowed to be 1×10$^{-6}$ torr, and then for the organic material, DNTPD (700 Å), a-NPB (300 Å), and Compound 29 were used as hosts (90 wt %) on the ITO, the following (piq)$_2$Ir(acac) (10 wt %) was co-deposited as a dopant, films were formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

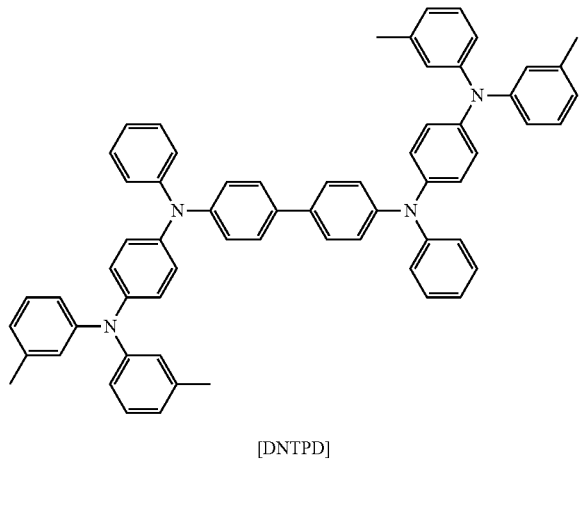

[DNTPD]

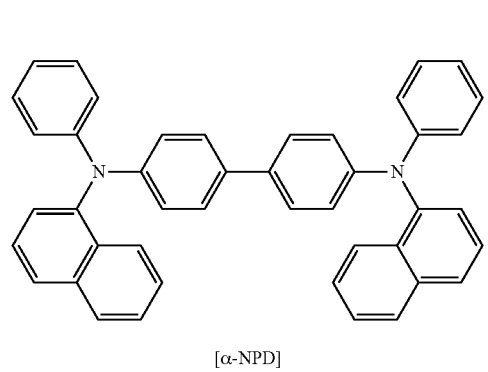

[α-NPD]

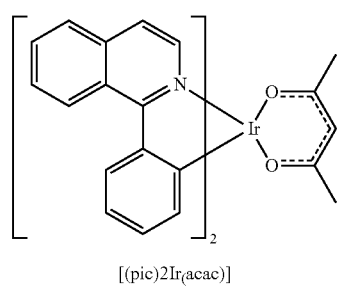

[(pic)2Ir(acac)]

-continued

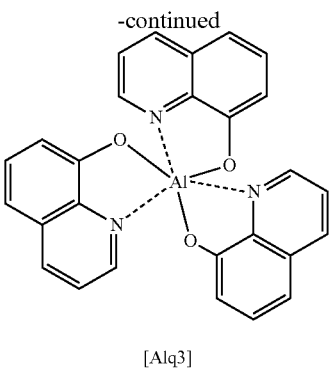

[Alq3]

Experimental Example 4-2

An organic light emitting device was manufactured in the same manner as in Experimental Example 4-1, except that Compound 30 was used instead of Compound 29 in Experimental Example 4-1.

Experimental Example 4-3

An organic light emitting device was manufactured in the same manner as in Experimental Example 4-1, except that Compound 31 was used instead of Compound 29 in Experimental Example 4-1.

Experimental Example 4-4

An organic light emitting device was manufactured in the same manner as in Experimental Example 4-1, except that Compound 59 was used instead of Compound 29 in Experimental Example 4-1.

Experimental Example 4-5

An organic light emitting device was manufactured in the same manner as in Experimental Example 4-1, except that Compound 60 was used instead of Compound 29 in Experimental Example 4-1.

Experimental Example 4-6

An organic light emitting device was manufactured in the same manner as in Experimental Example 4-1, except that Compound 61 was used instead of Compound 29 in Experimental Example 4-1.

Comparative Example 4-1

An organic light emitting device was manufactured in the same manner as in Experimental Example 4-1, except that RH 1 (CBP) was used instead of Compound 26 in Experimental Example 4-1.

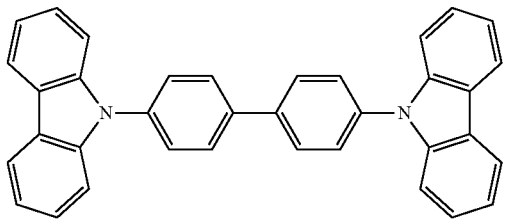

[RH 1]

For the organic light emitting devices manufactured according to Experimental Examples 4-1 to 4-6 and Comparative Example 4-1, the voltages, current densities, luminances, color coordinates, and lifetimes were measured, and the results are shown in the following Table 4. T95 means the time taken for the luminance to be reduced to 95% of the initial luminance (5,000 nit).

TABLE 4

| Classification | Compound (Host) | Dopant | Voltage (V) | Luminance (cd/m$^2$) | Color coordinate (x, y) | T95 (hr) |
| --- | --- | --- | --- | --- | --- | --- |
| Experimental Example 4-1 | Compound 29 | (piq)$_2$Ir(acac) | 4.4 | 1660 | (0.670, 0.329) | 465 |
| Experimental Example 4-2 | Compound 30 | (piq)$_2$Ir(acac) | 4.3 | 1750 | (0.674, 0.325) | 415 |
| Experimental Example 4-3 | Compound 31 | (piq)$_2$Ir(acac) | 4.2 | 1800 | (0.672, 0.327) | 440 |
| Experimental Example 4-4 | Compound 59 | (piq)$_2$Ir(acac) | 4.4 | 1640 | (0.673, 0.335) | 435 |
| Experimental Example 4-5 | Compound 60 | (piq)$_2$Ir(acac) | 4.1 | 1990 | (0.675, 0.333) | 405 |
| Experimental Example 4-6 | Compound 61 | (piq)$_2$Ir(acac) | 4.3 | 1810 | (0.670, 0.339) | 420 |
| Comparative Example 4-1 | RH 1 | (piq)$_2$Ir(acac) | 6.21 | 1200 | (0.670, 0.327) | 215 |

As observed in Table 4, it could be confirmed that the red organic light emitting devices of Experimental Examples 4-1 to 4-6 in which the hetero-cyclic compound according to an exemplary embodiment of the present specification was used as a host material of the light emitting layer exhibited better performances in terms of current efficiency and driving voltage than the red organic light emitting device of Comparative Example 4-1 in which RH1 (CBP) in the related art was used.

Although the preferred exemplary embodiments (an electron blocking layer, a hole transport layer, a green light emitting layer, and a red light emitting layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transport layer
80: Electron transport layer
90: Electron injection layer

The invention claimed is:
1. A hetero-cyclic compound represented by the following Chemical Formula 1:

[Chemical Formula 1]

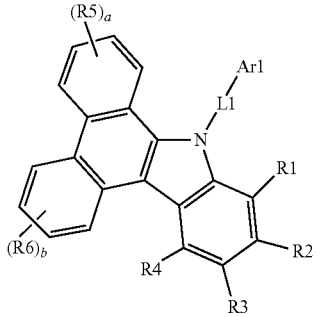

in Chemical Formula 1,
L1 is a direct bond; a substituted or unsubstituted arylene group; or a substituted or unsubstituted heteroarylene group,
Ar1 is deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted silyl group; a substituted or unsubstituted boron group; an amine group unsubstituted or substituted with one or more substituents selected from the group consisting deuterium, a halogen group, a nitrile group, a nitro group, an imide group, an amide group, a carbonyl group, an ester group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, and a substituted or unsubstituted aryl group, and substituted or unsubstituted heteroaryl group containing N; a substituted or unsubstituted arylphosphine group; a phenyl group unsubstituted or substituted with one or more substituents selected from the group consisting of deuterium, a halogen group, a nitrile group, a nitro group; an imide group, an amide group, a carbonyl group, an ester group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group; a substituted or unsubstituted phosphine oxide group, and a substituted or unsubstituted aryl group; a substituted or unsubstituted phosphine oxide group; a substituted or unsubstituted polycyclic aryl group; a pyridyl group unsubstituted or substituted with one or more substituents selected from the group consisting deuterium, a halogen group, a nitrile group, a nitro group, an imide group, an amide group, a carbonyl group, an ester group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, and substituted or unsubstituted heteroaryl group; a substituted or unsubstituted pyrimidyl group; a substituted or unsubstituted triazinyl group; a substituted or unsubstituted pyridazinyl group; a substituted or unsubstituted pyrazinyl group; or a substituted or unsubstituted polycyclic heteroaryl group, R1 and R2, R2 and R3, or R3 and R4 in R1 to R6 combine with each other to form a ring substituted with (R7)c, and the others and R7 are hydrogen, a to c are each an integer of 1 to 4, and provided that when Ar1 is a substituted or unsubstituted pyrimidyl group, L1 is a substituted or unsubstituted arylene group; or a substituted or unsubstituted heteroarylene group.

2. The hetero-cyclic compound of claim 1, wherein Chemical Formula 1 is represented by any one of the following Chemical Formulae 1-1 to 1-3:

[Chemical Formula 1-1]

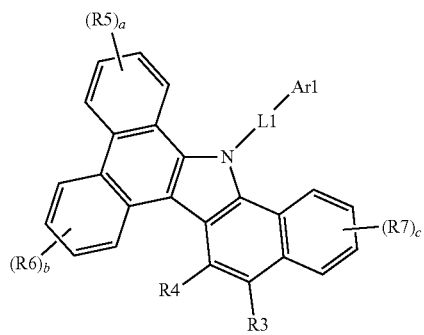

[Chemical Formula 1-2]

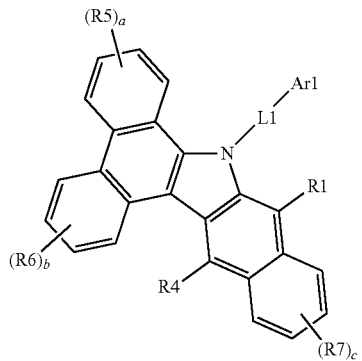

[Chemical Formula 1-3]

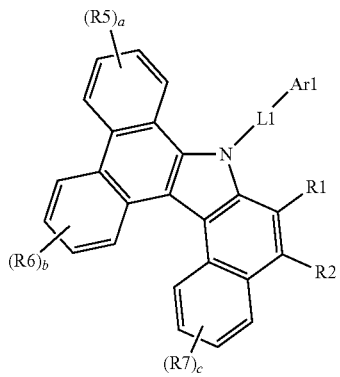

in Chemical Formulae 1-1 to 1-3, the definitions of L1, Ar1, and R1 to R7 are the same as those in Chemical Formula 1.

3. The hetero-cyclic compound of claim 1, wherein Ar1 is selected from the group consisting of the phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; the pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quarterphenylfluorenylamine group; a substituted or unsubstituted N-terphenylfluorenylamine group; a substituted or unsubstituted N-biphenyl terphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenyl terphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; substituted or unsubstituted

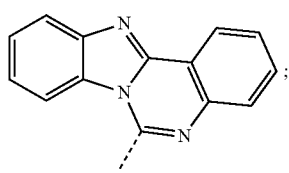

substituted or unsubstituted

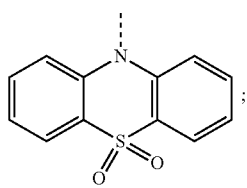

and a structure represented by the following Chemical Formula a,
--- is a moiety bonded to Chemical Formula 1 via L1,

[Chemical Formula a]

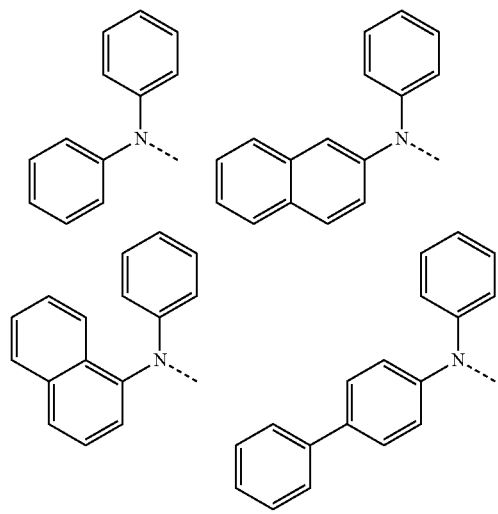

in Chemical Formula a,
one of X1 to X12 is a moiety bonded to Chemical Formula 1 via L1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

4. The hetero-cyclic compound of claim 1, wherein Ar1 is represented by any one of the following structural formulae [A-1] to [A-5]:

[A-1]

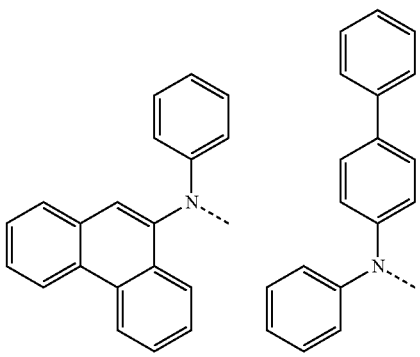

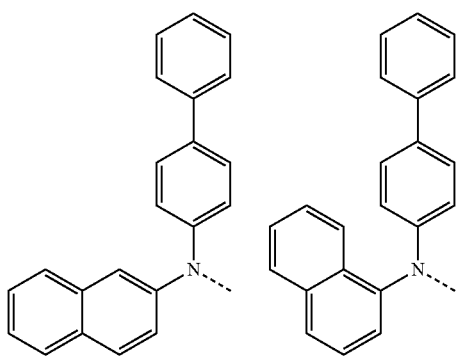

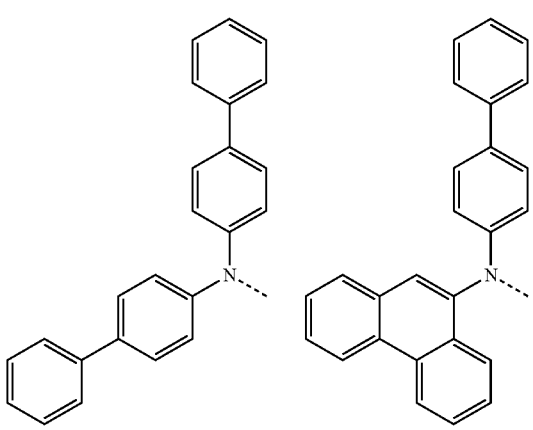

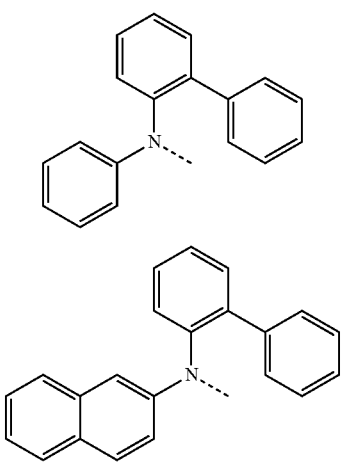

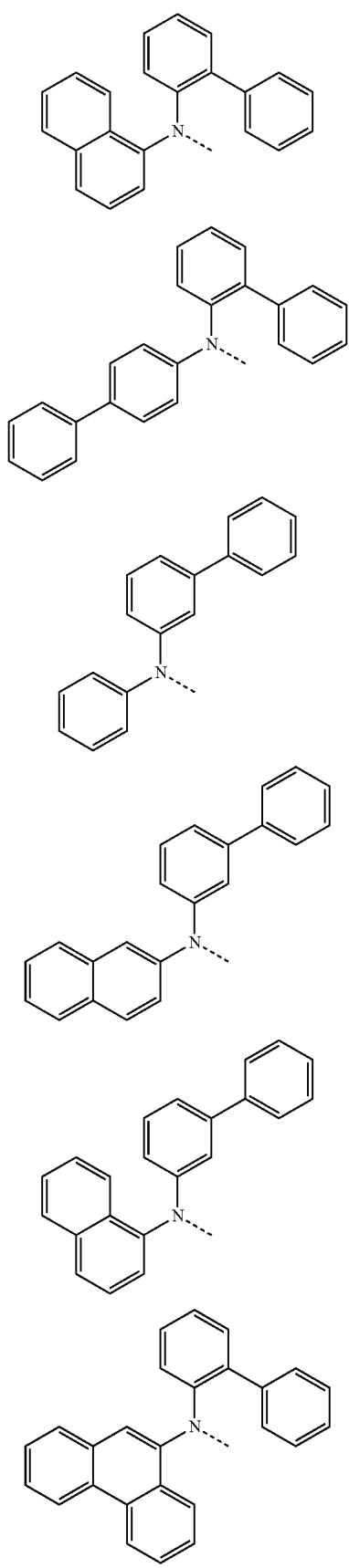
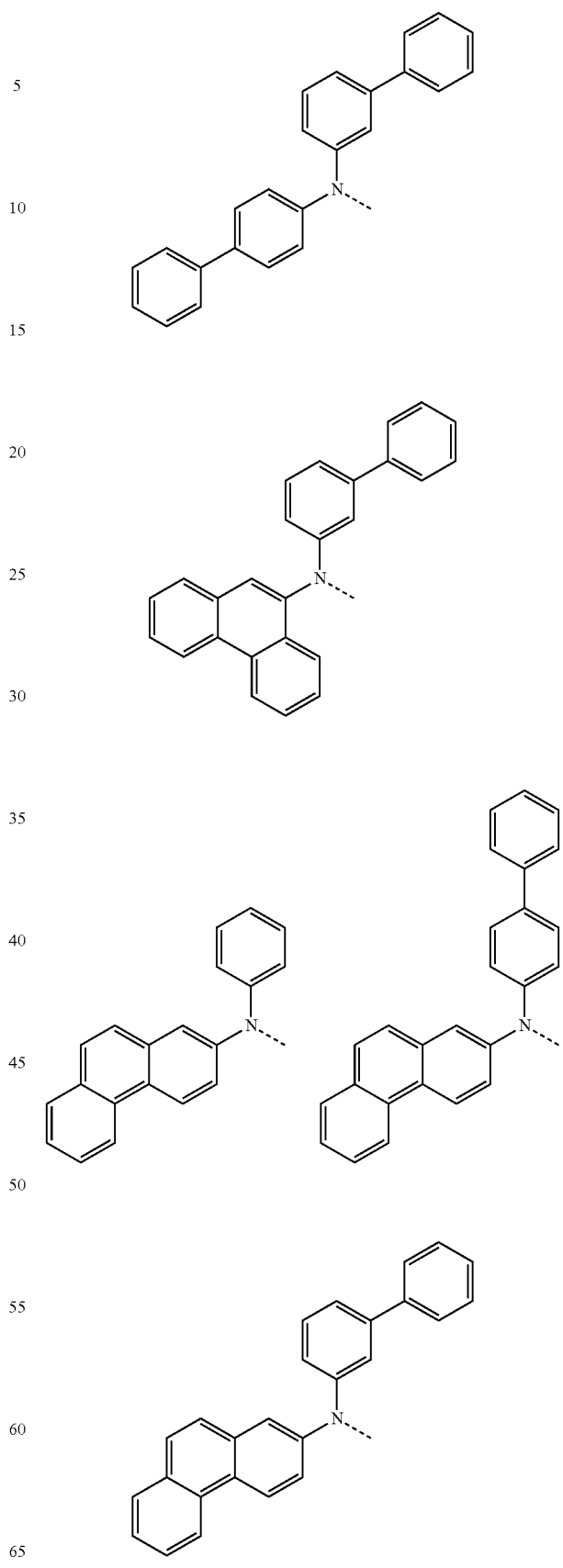

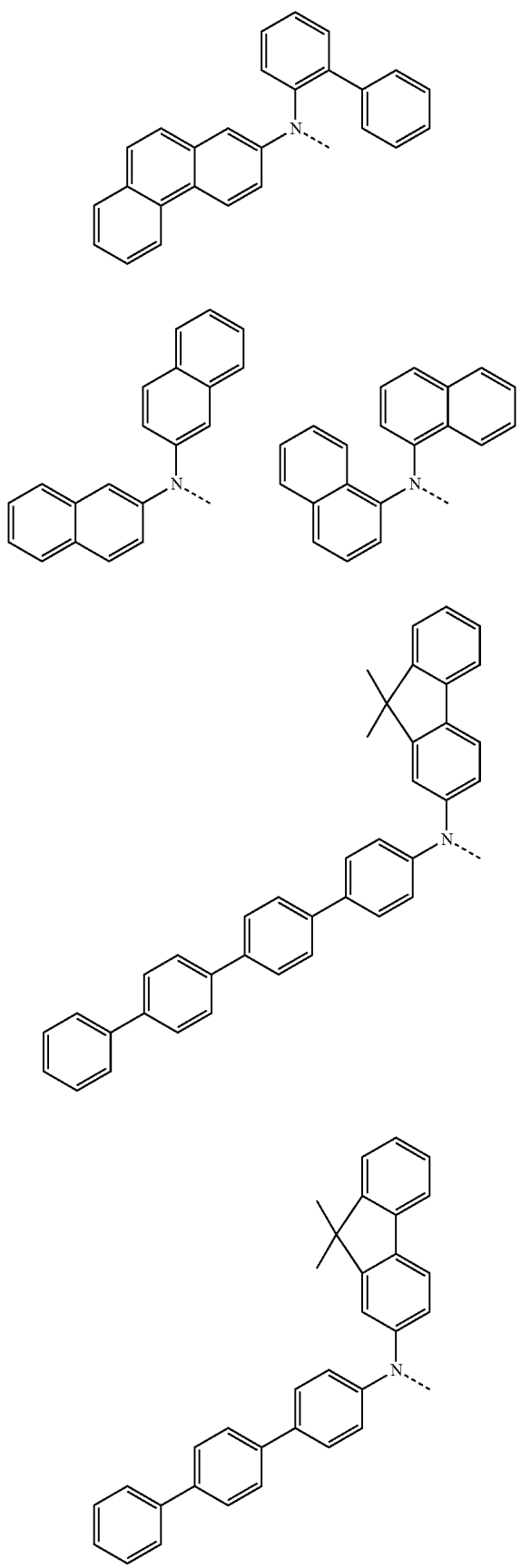
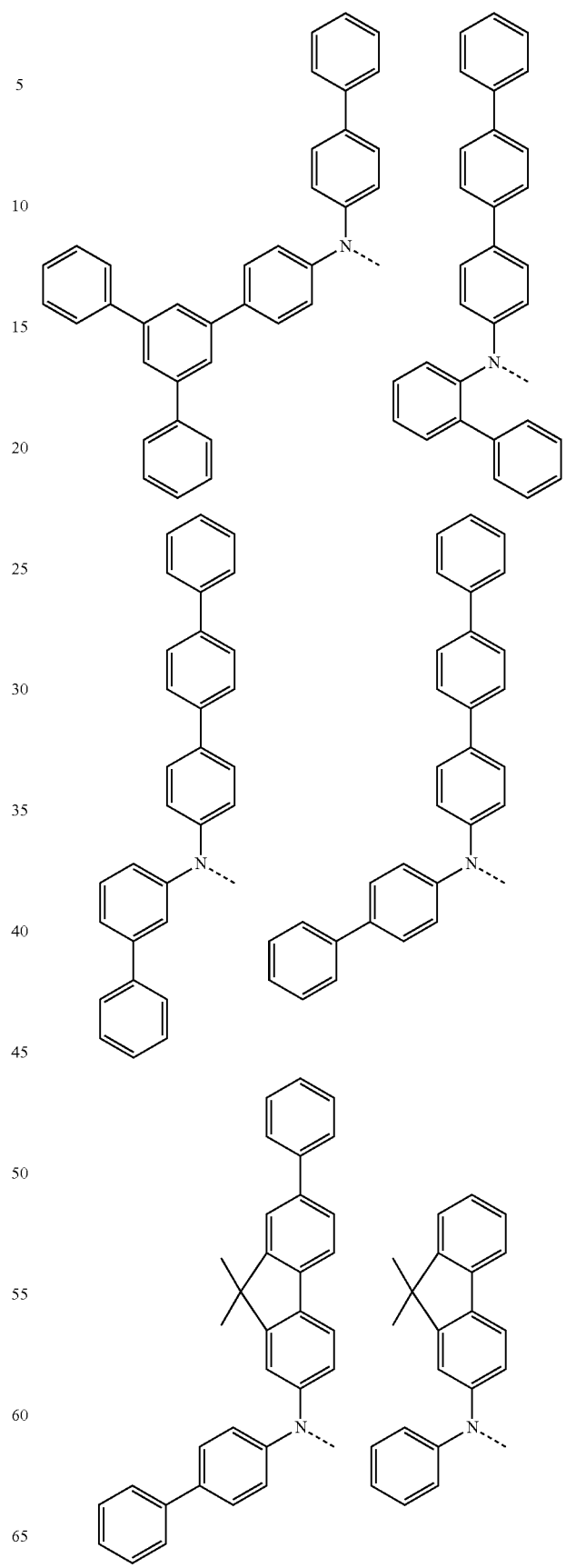

201
-continued
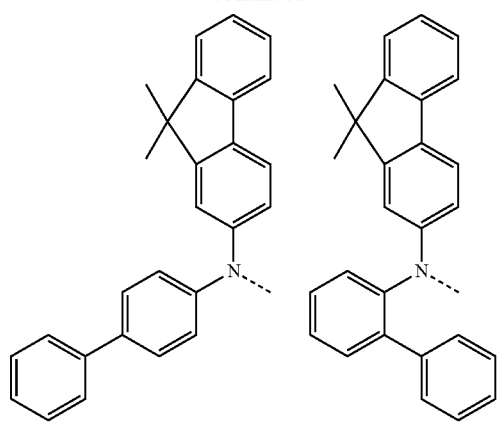
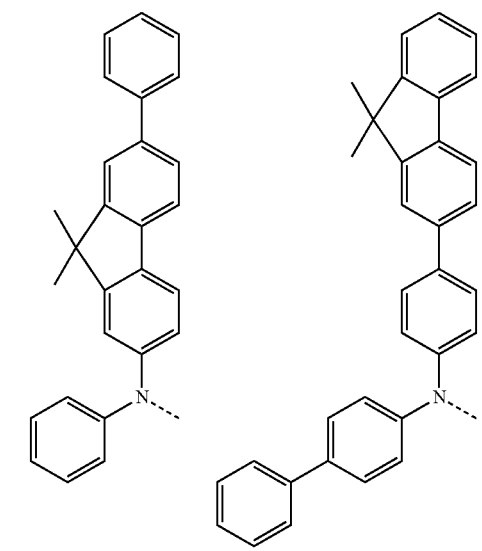
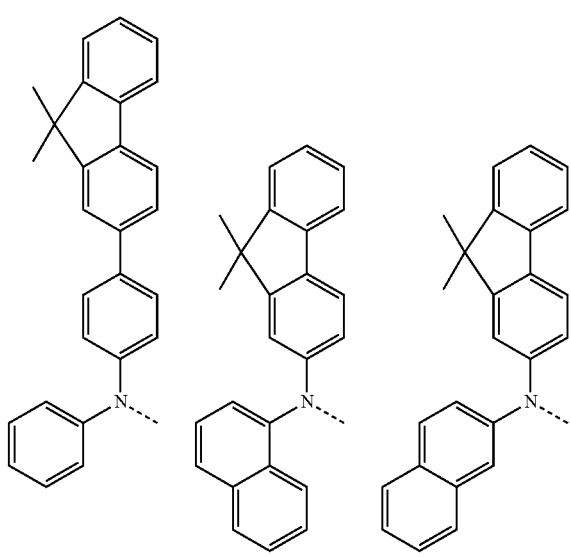
202
-continued
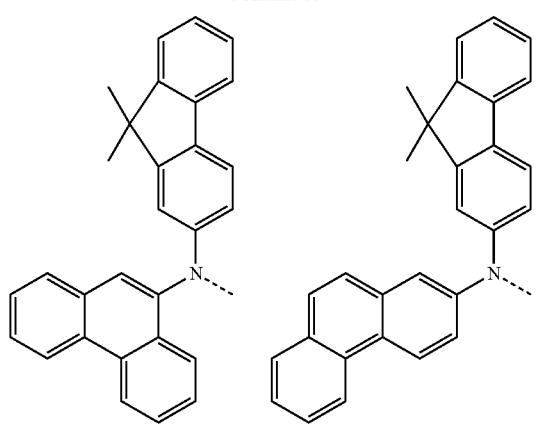
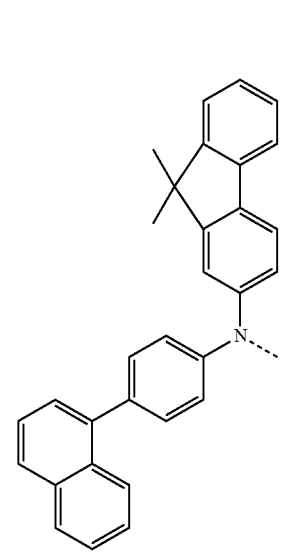
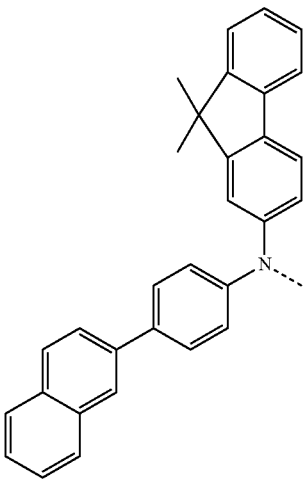

203
-continued
204
-continued
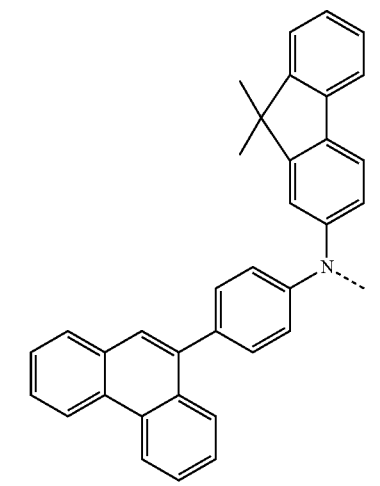
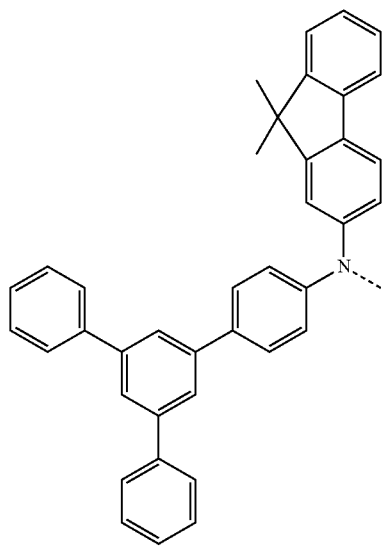

205
-continued
206
-continued
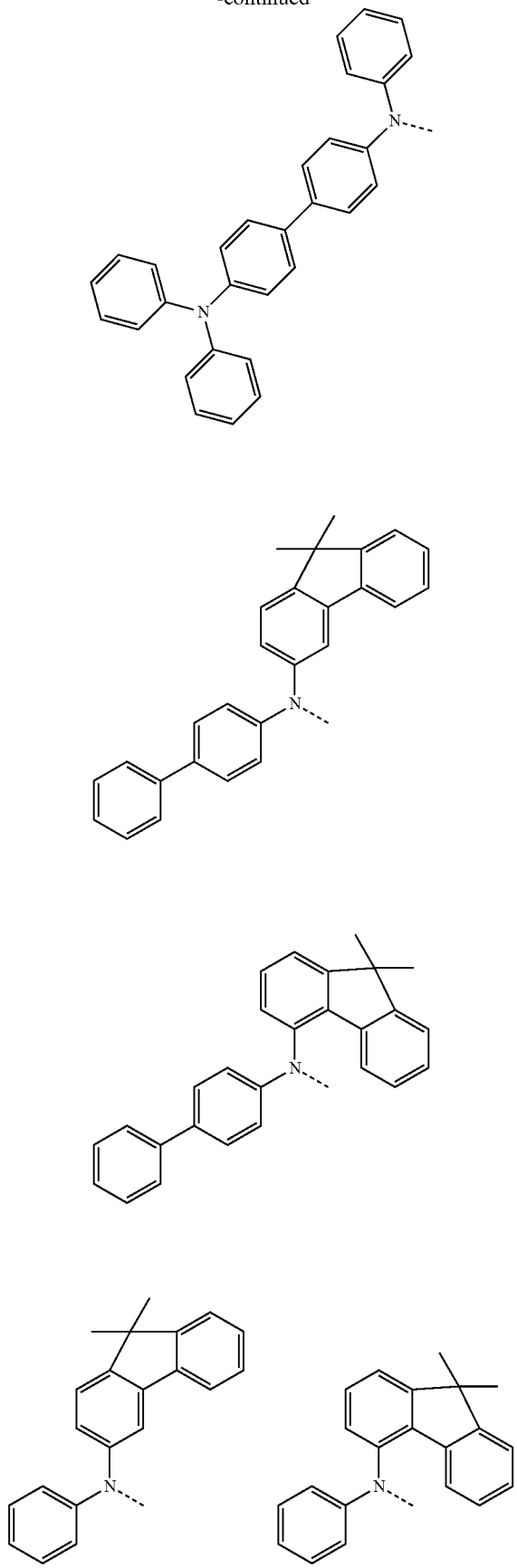
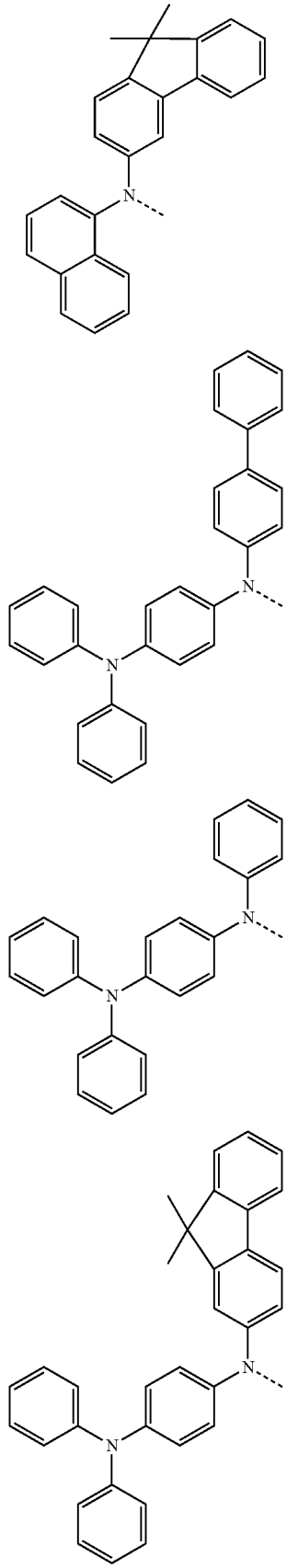

207
-continued
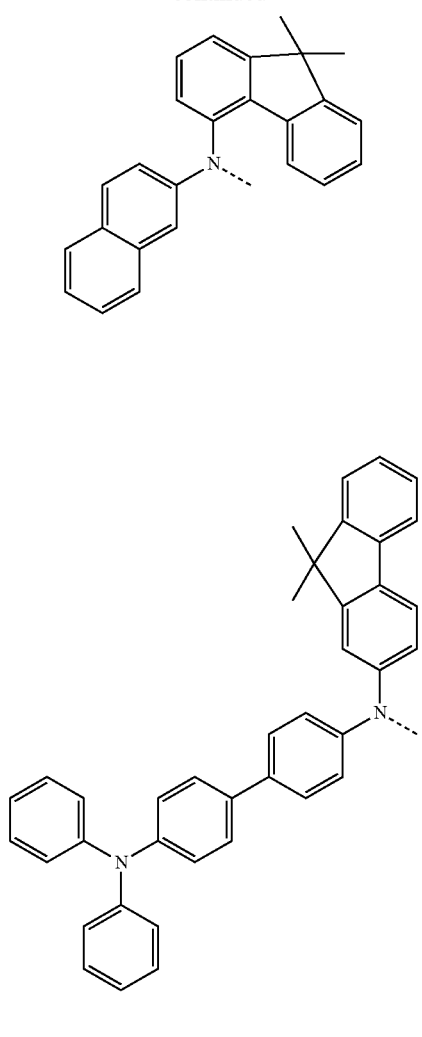
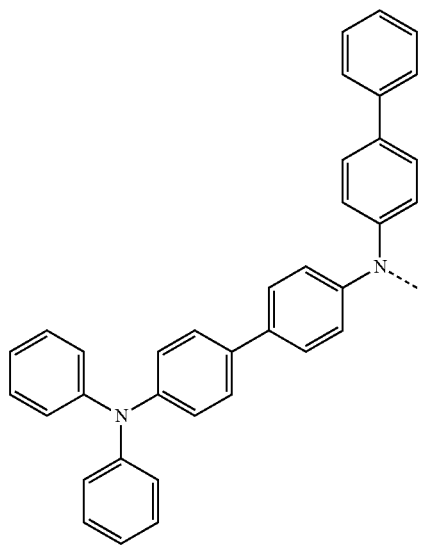
208
-continued
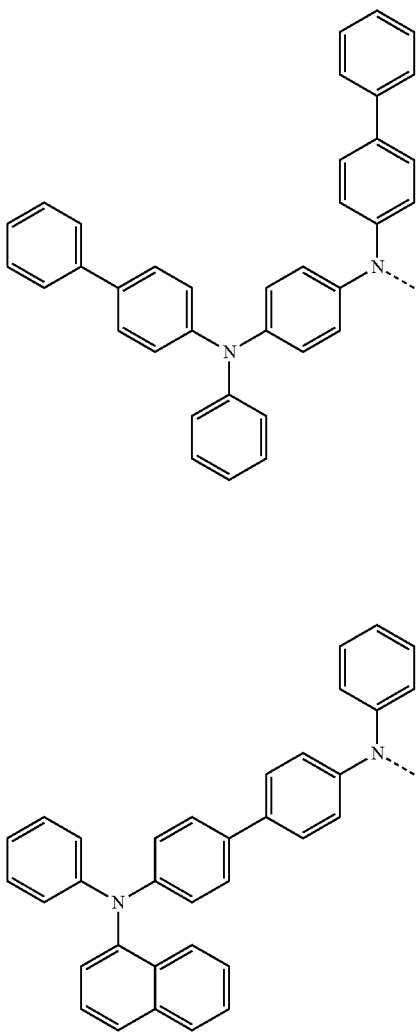
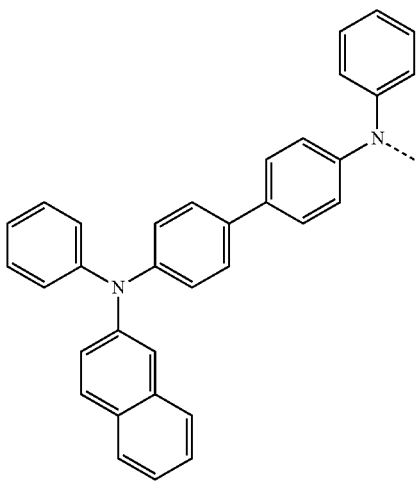

209
-continued
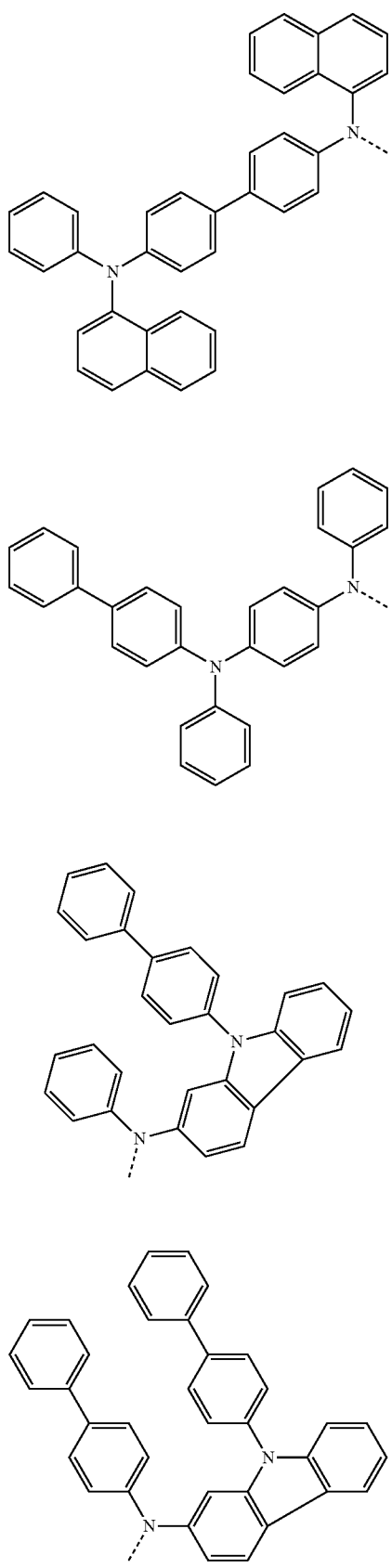
210
-continued
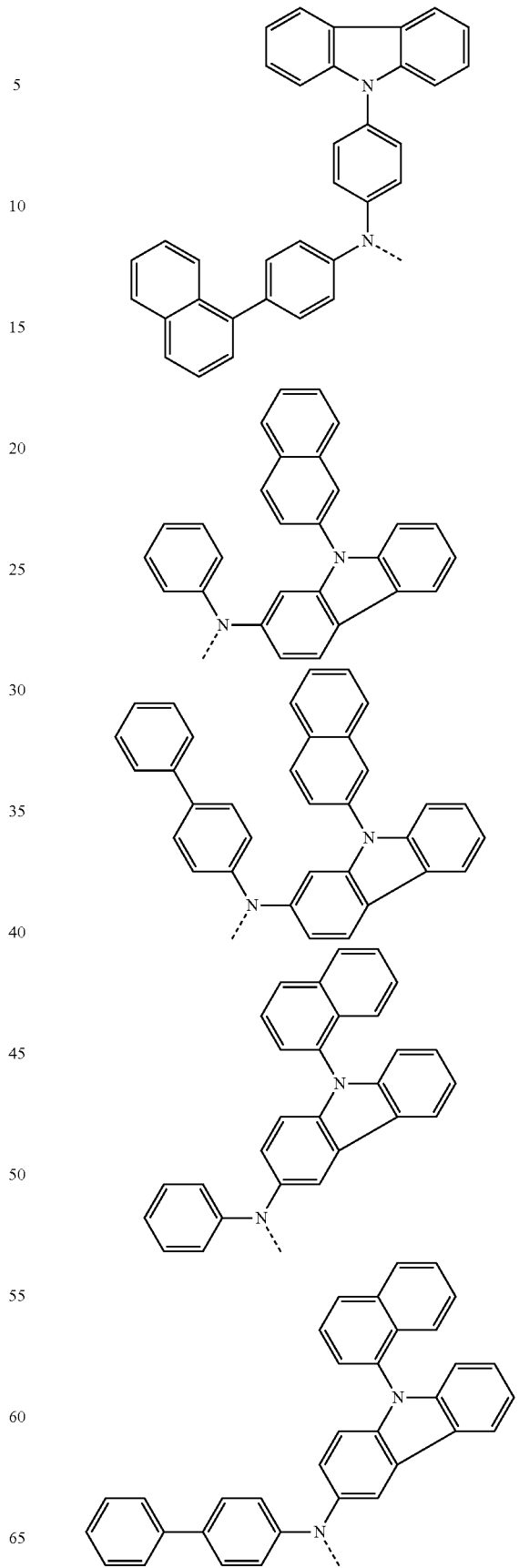

211
-continued
212
-continued
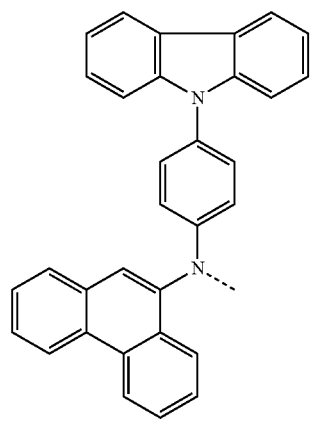
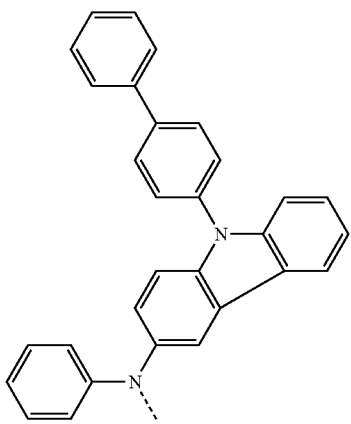

213
-continued
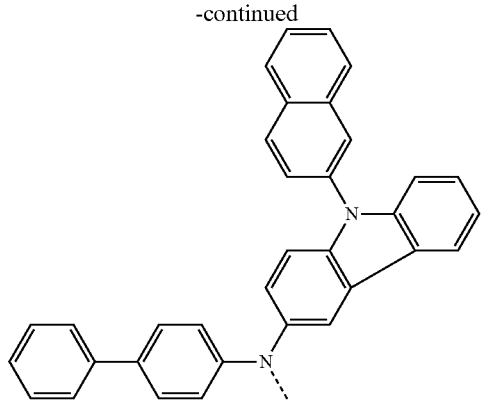
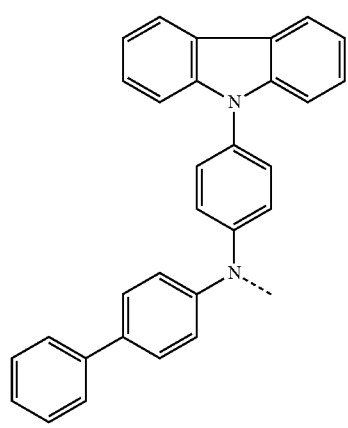
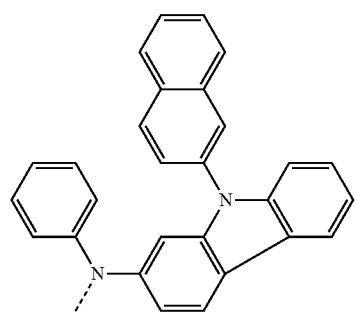
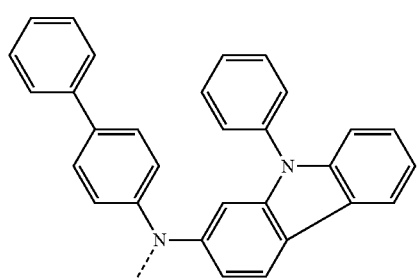
214
-continued
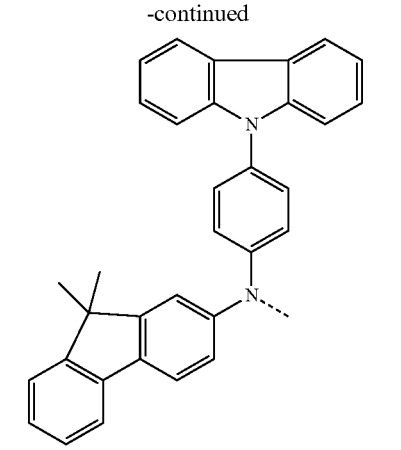
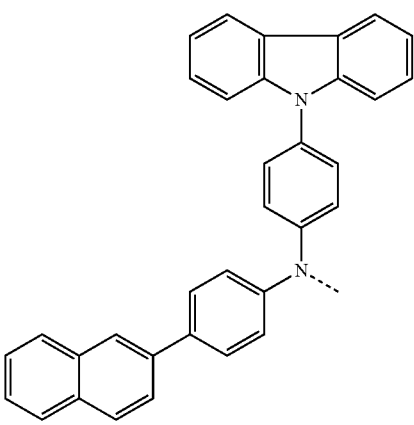
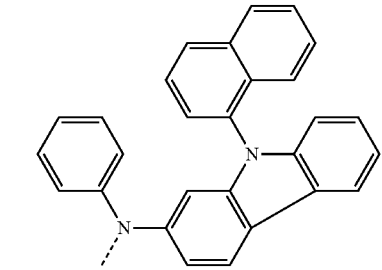
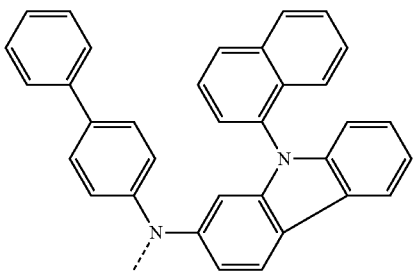
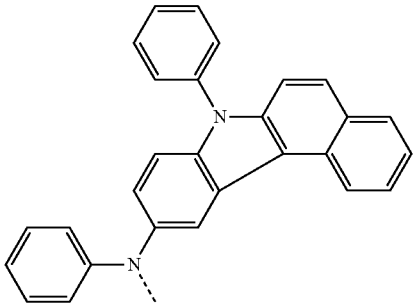

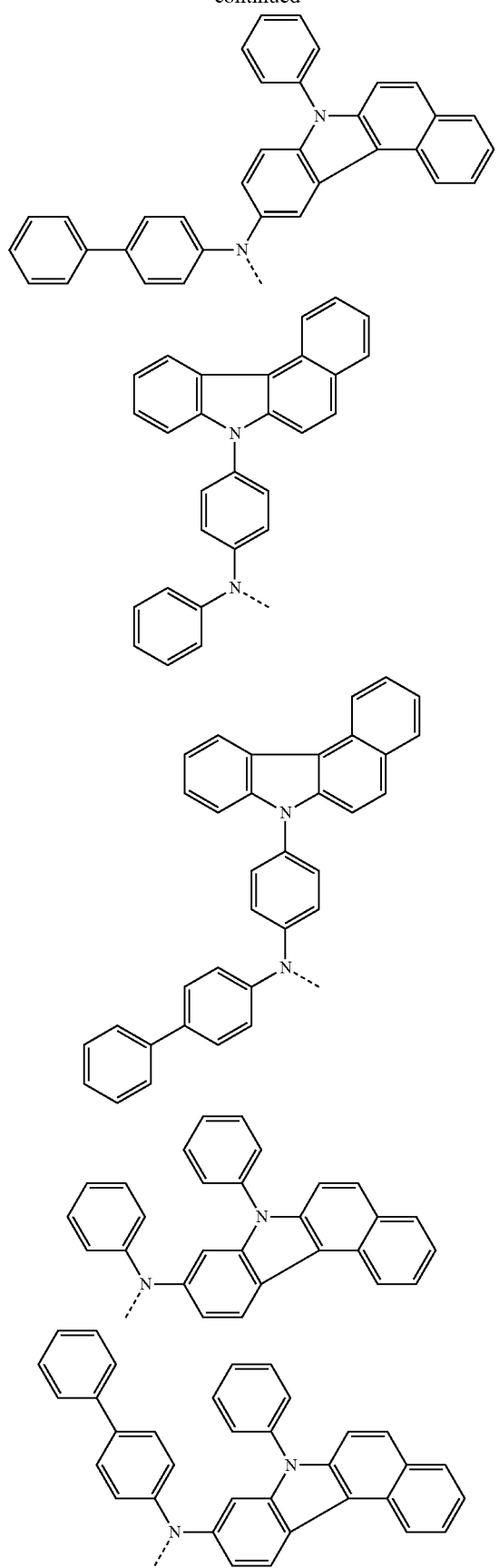
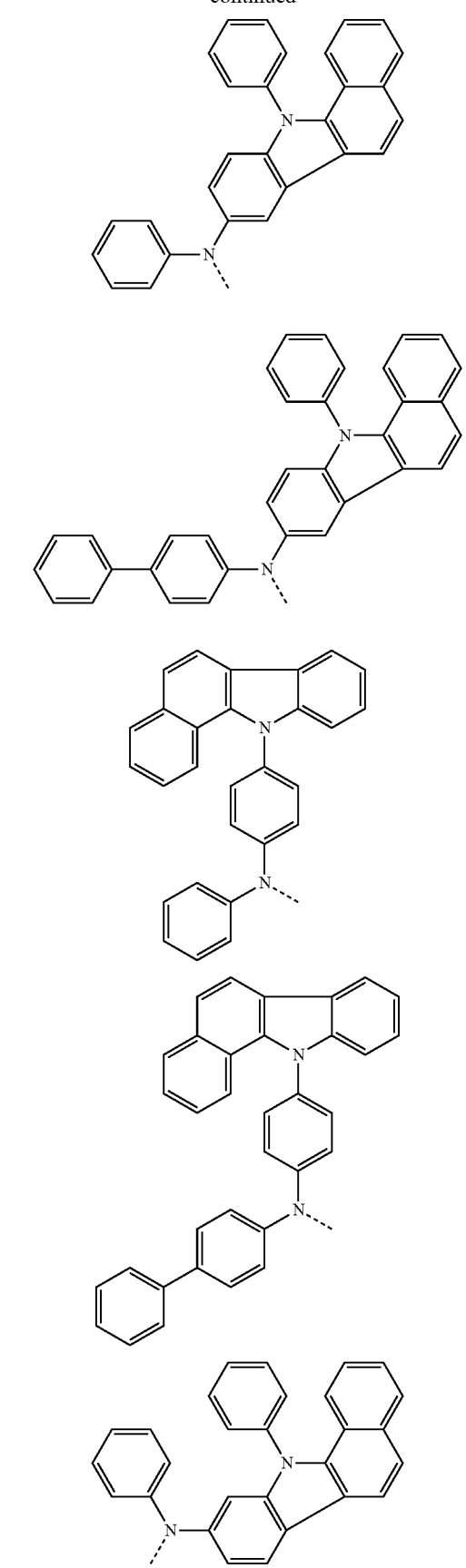

217
-continued
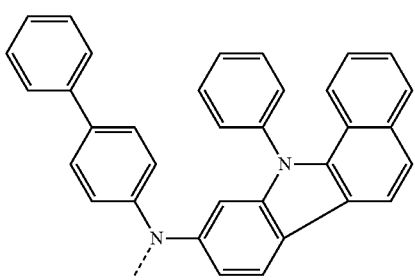
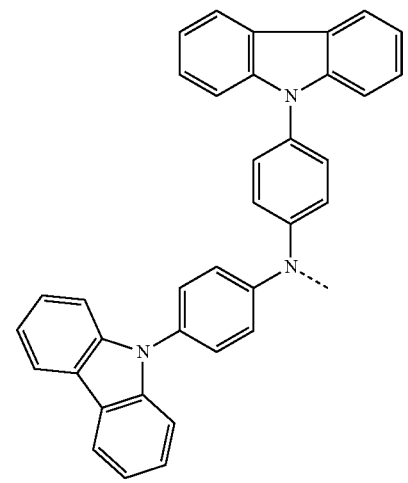
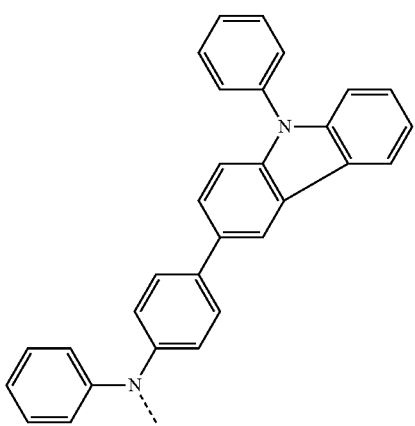
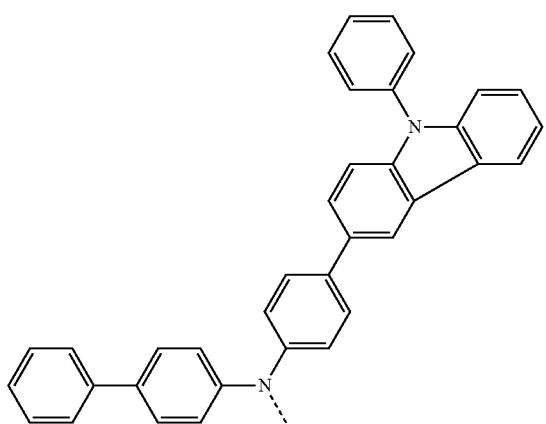
218
-continued
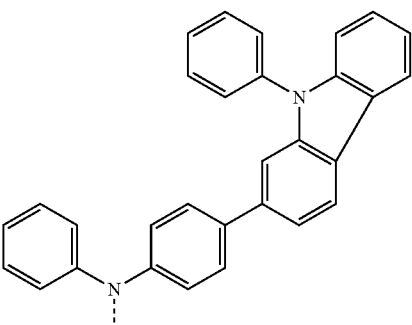
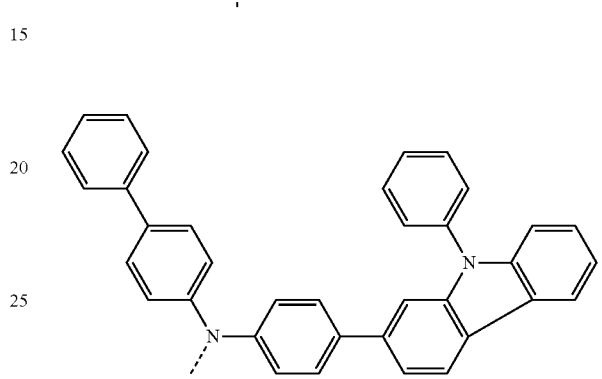
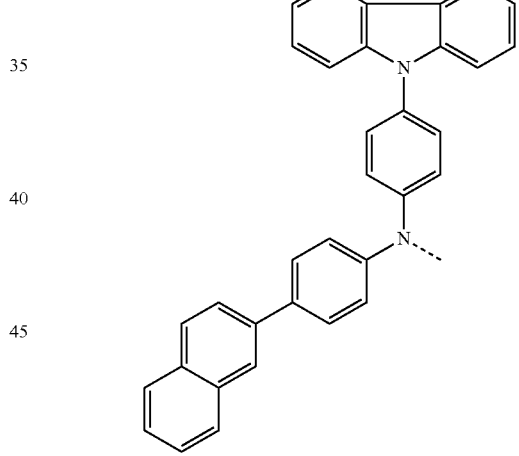
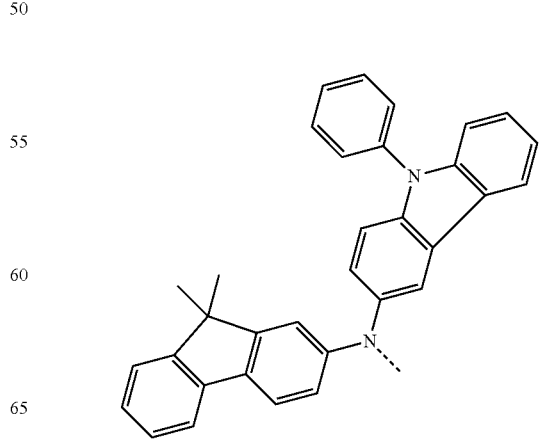

219
-continued
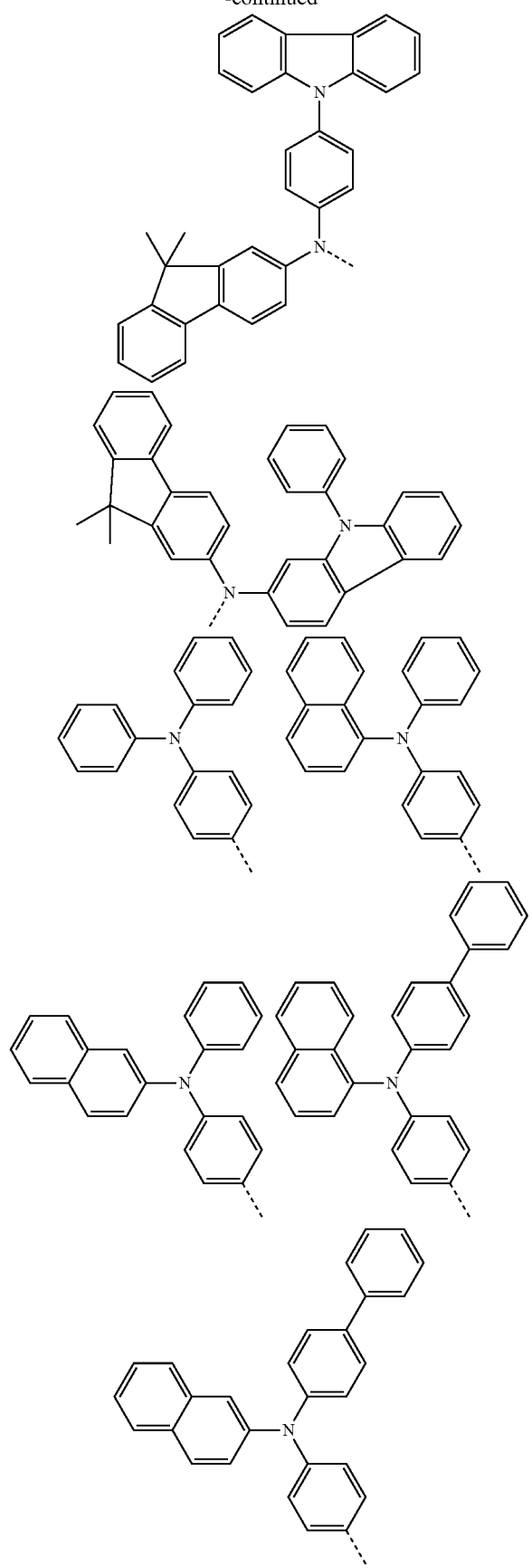
220
-continued
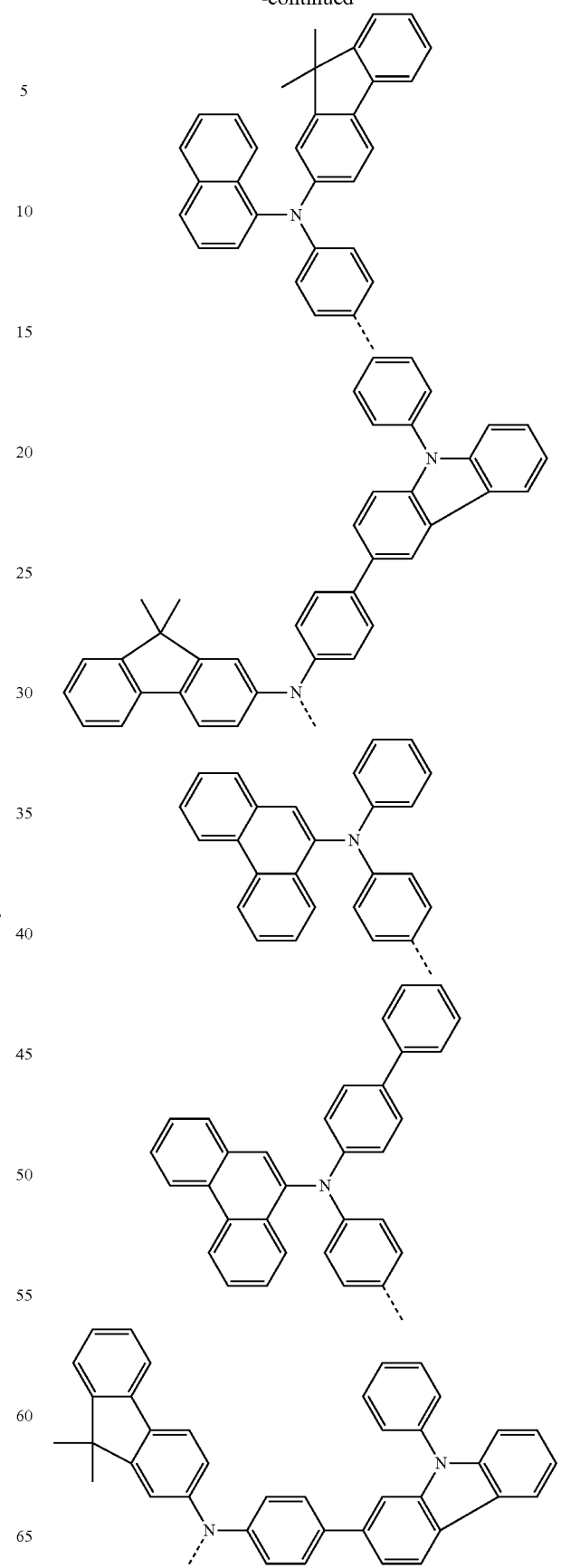

221
-continued
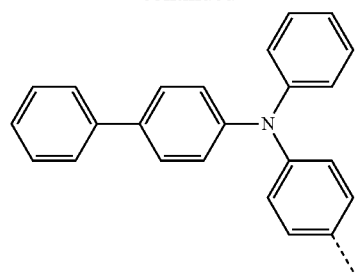
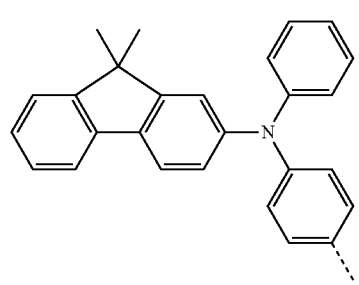
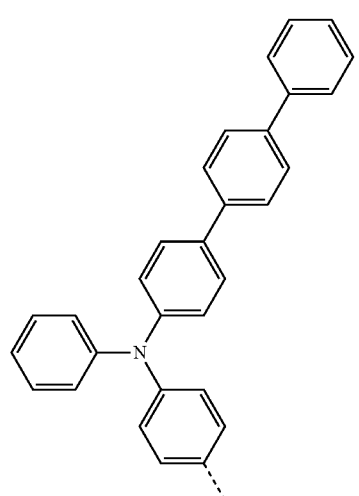
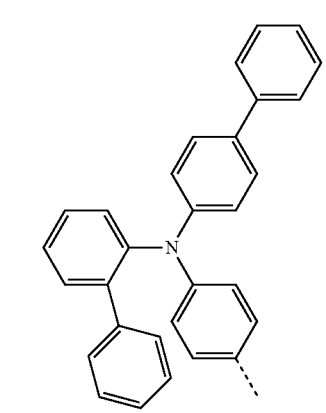
222
-continued
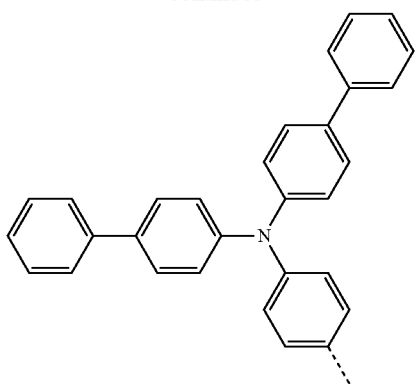
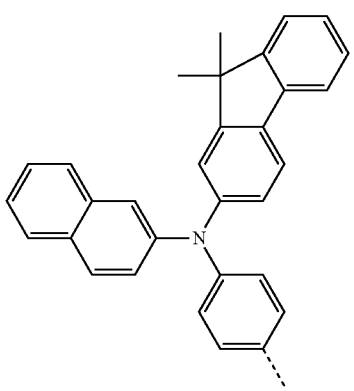
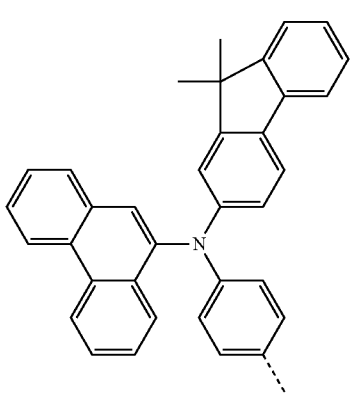
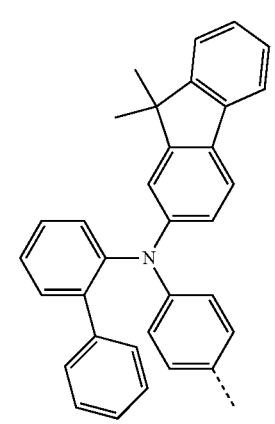

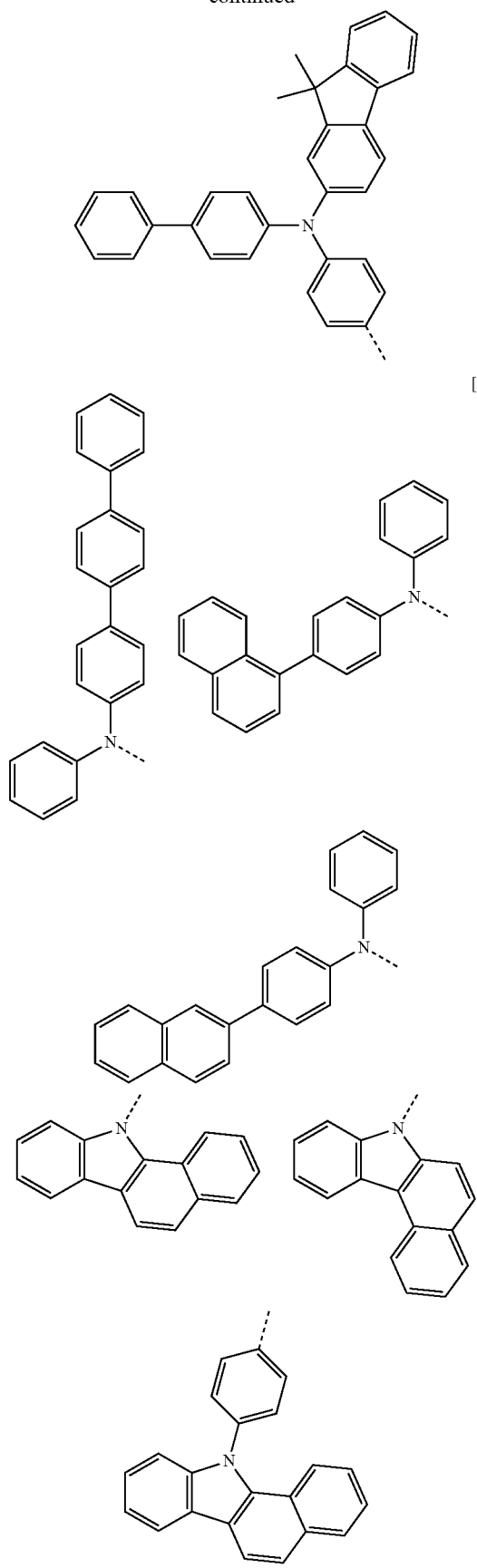
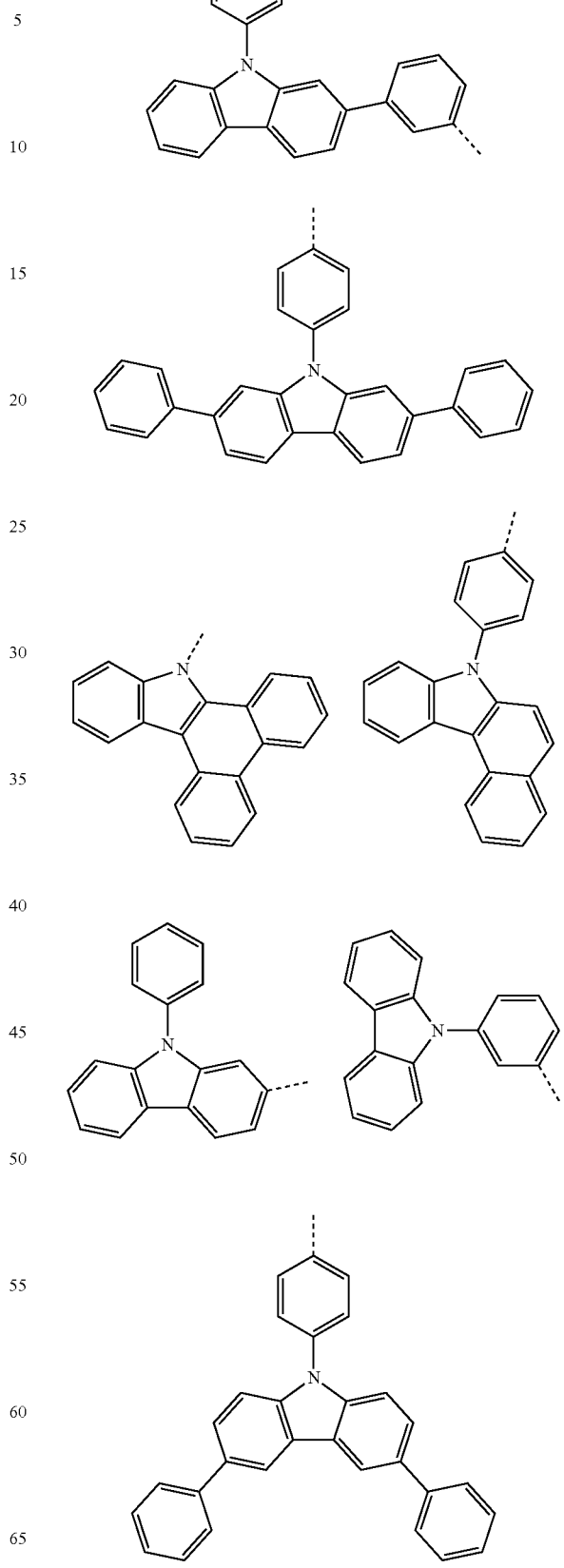

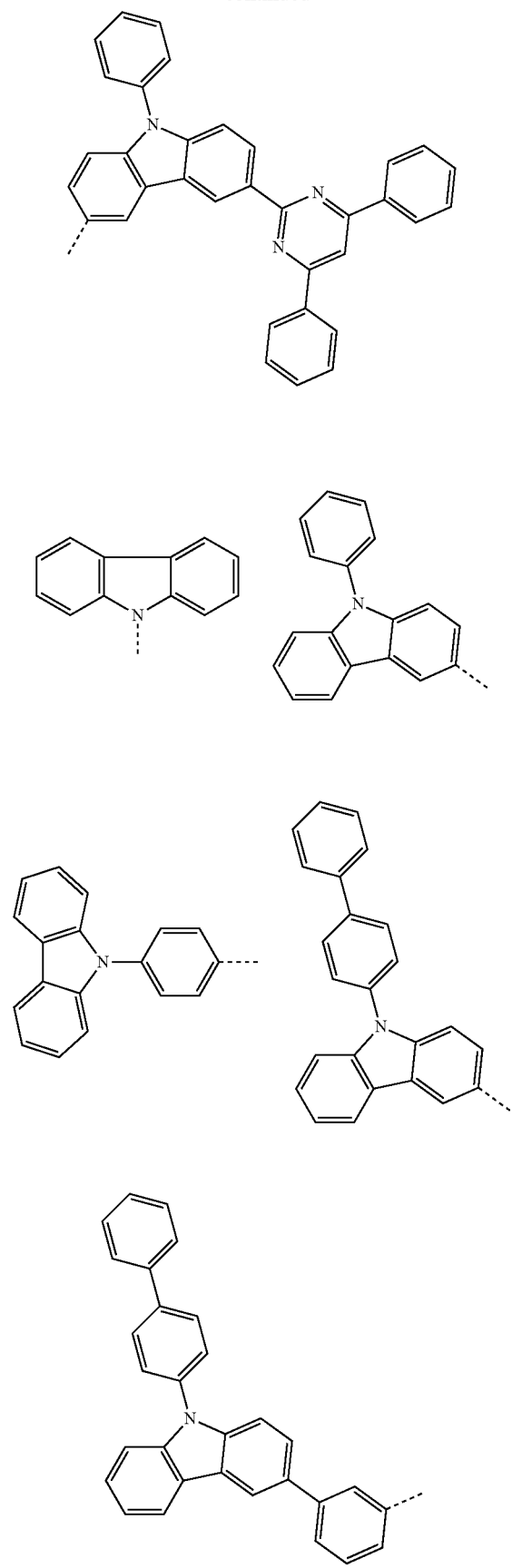
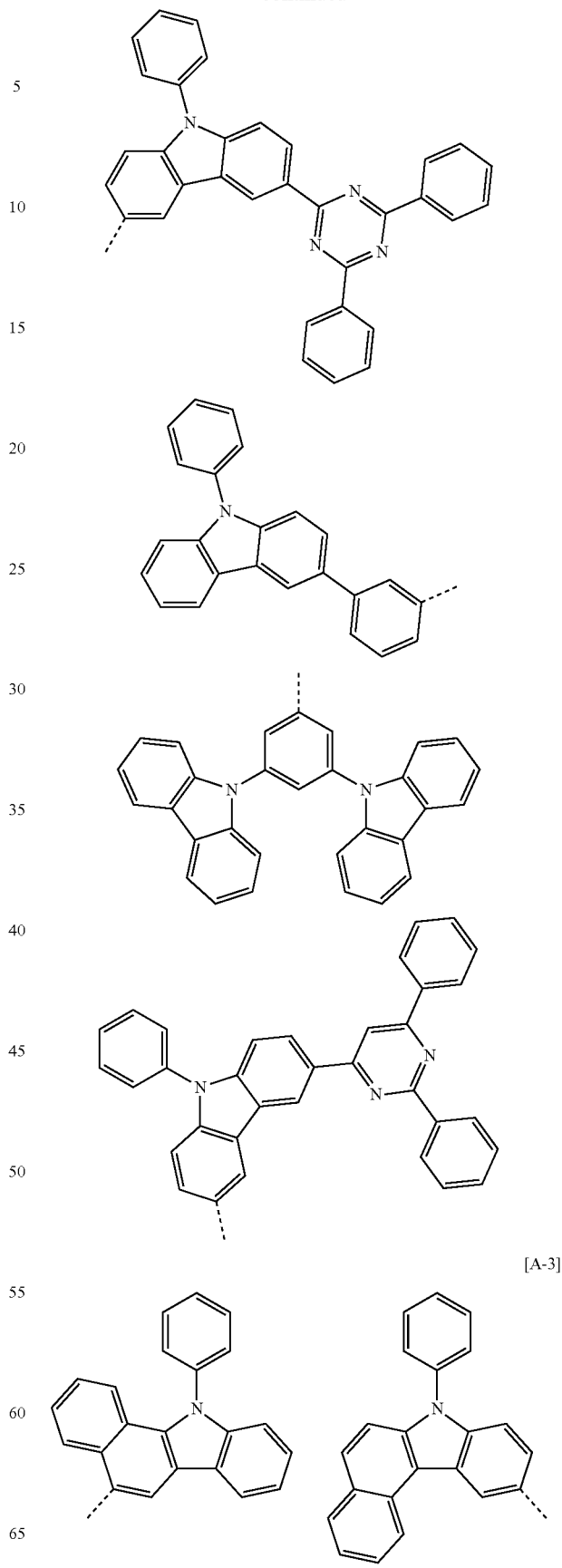
[A-3]

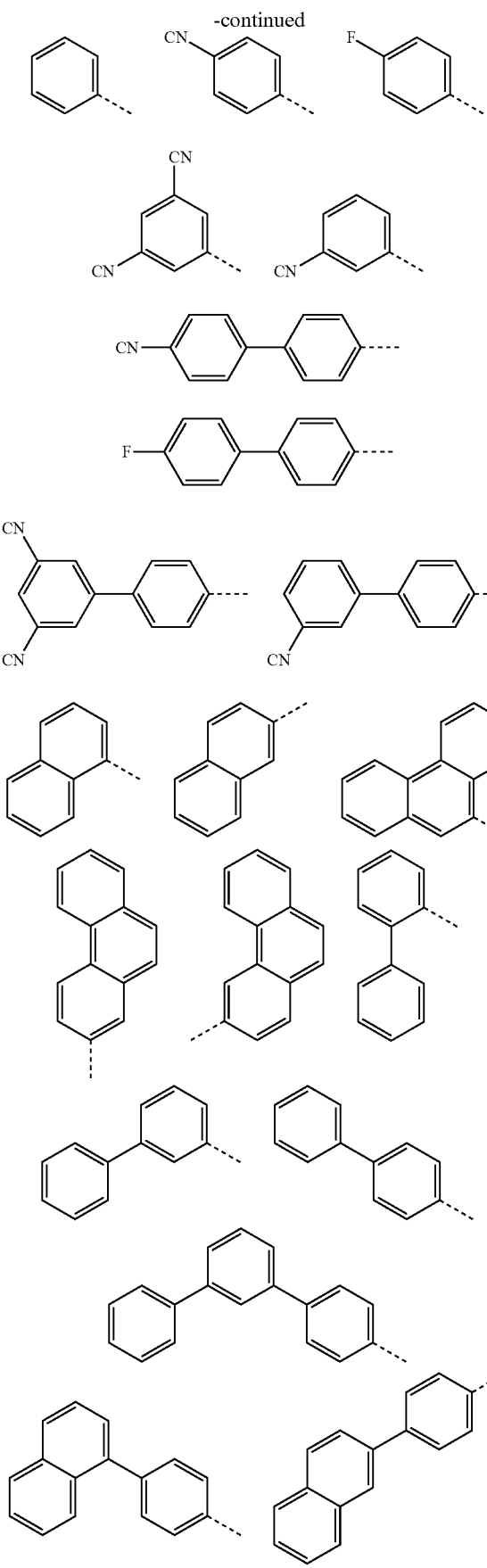
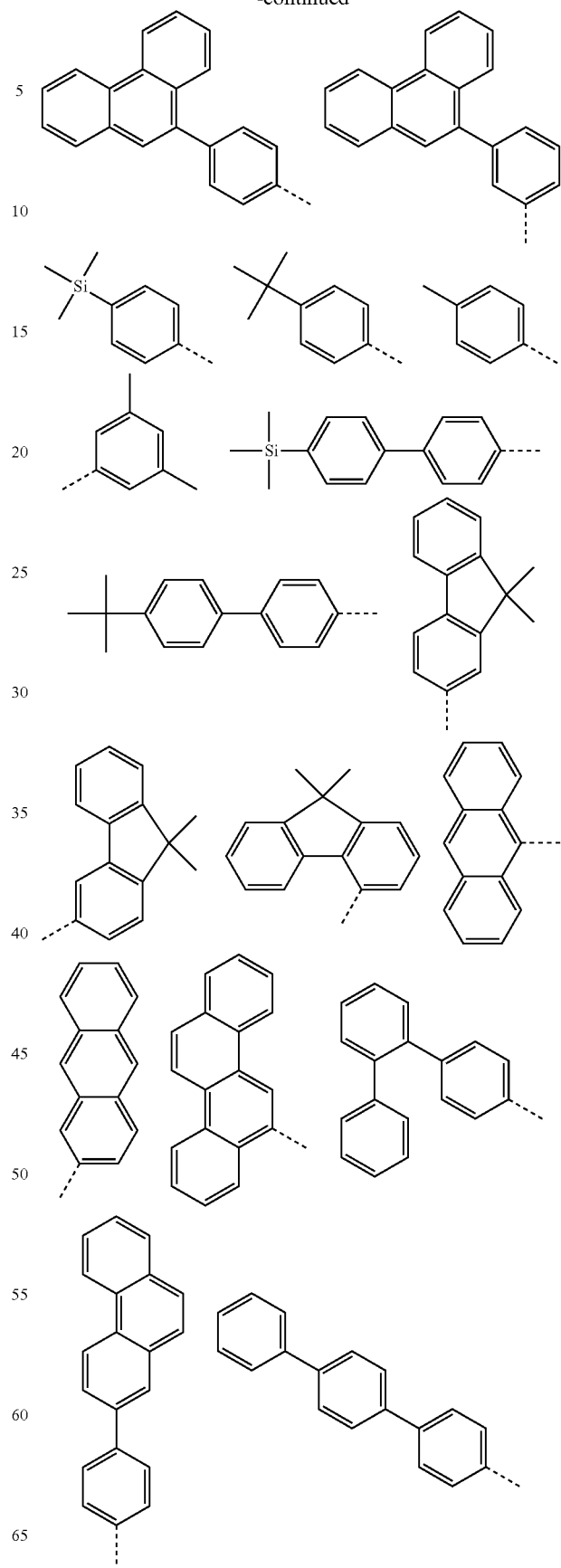

229
-continued
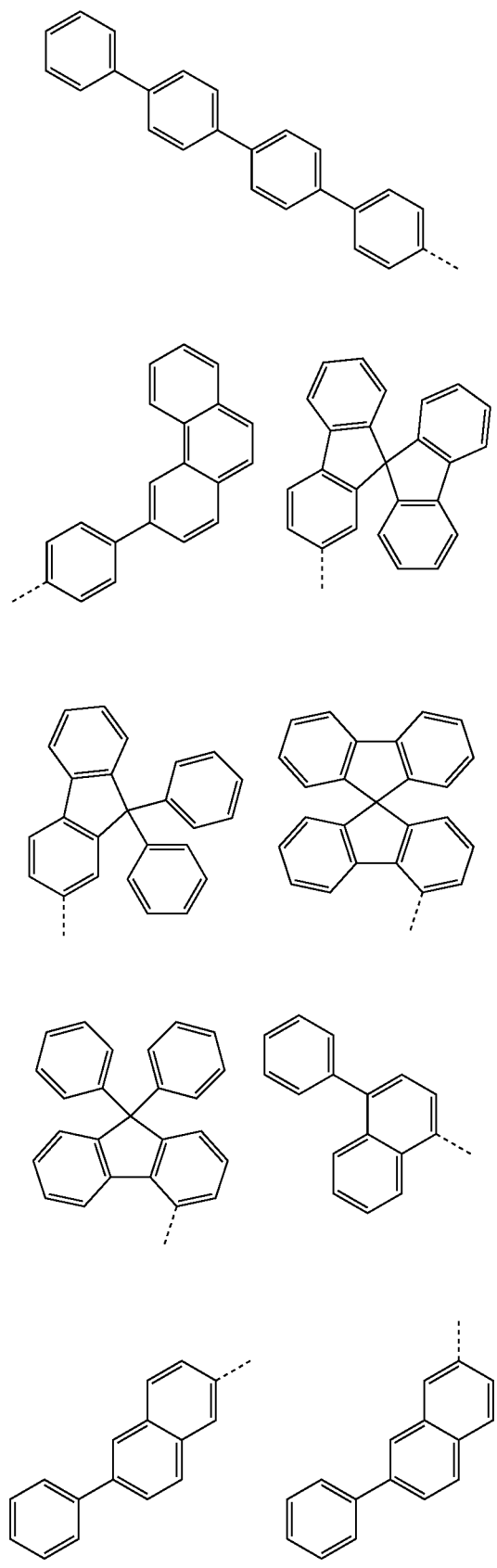
230
-continued
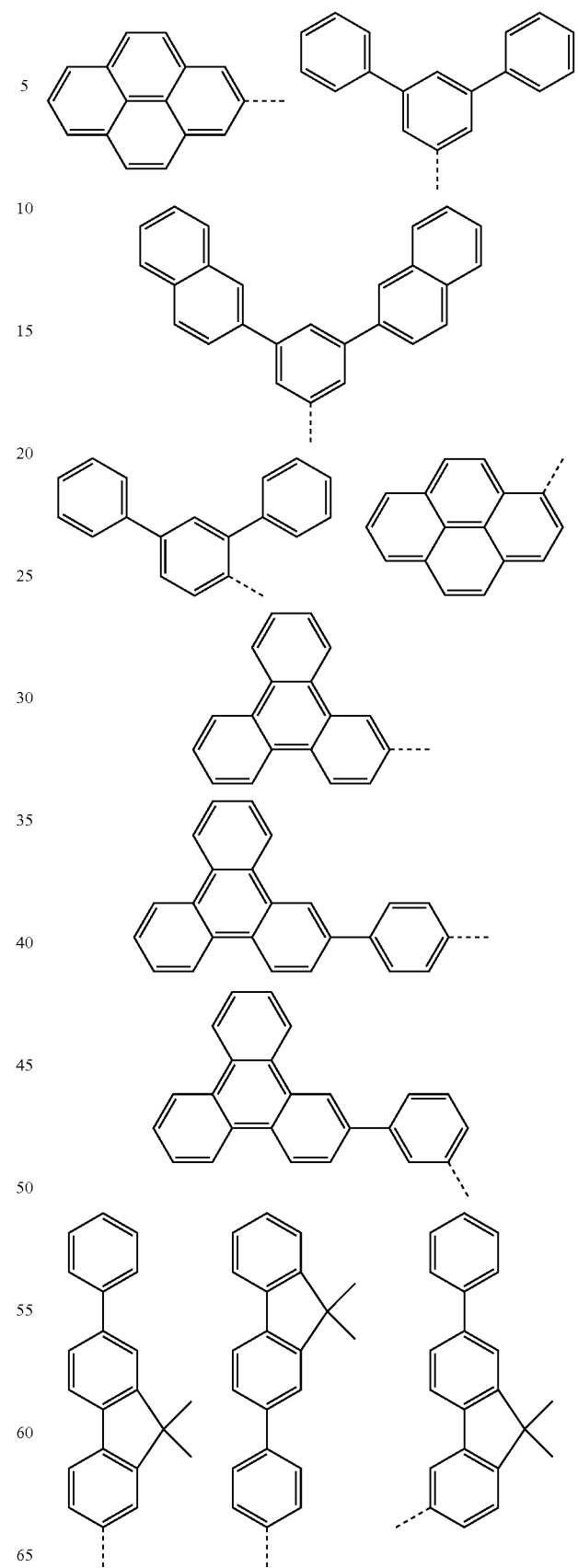

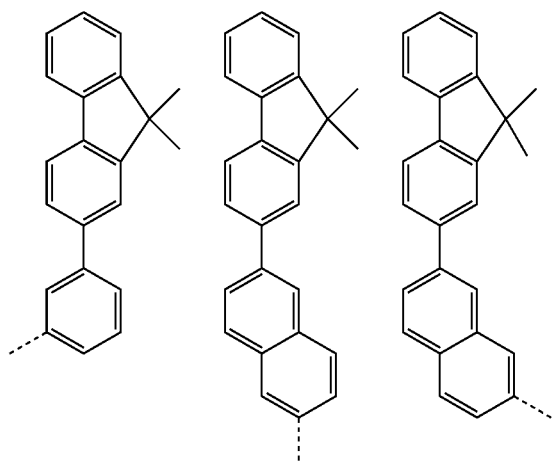
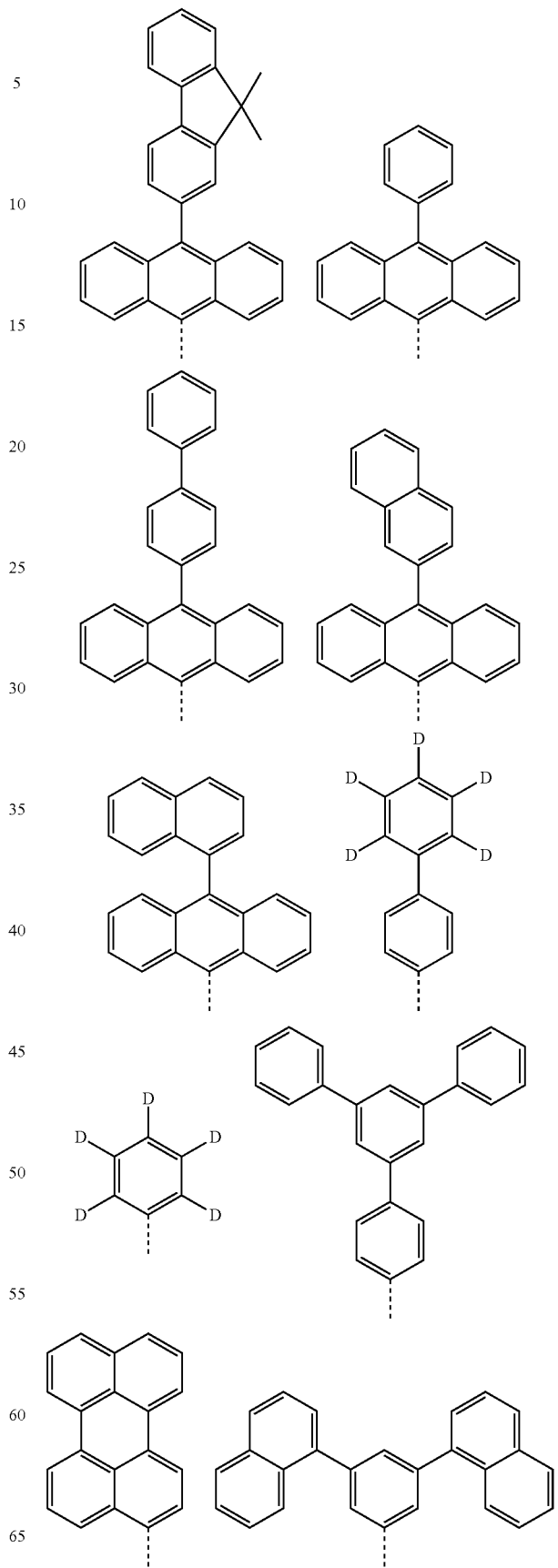

233
-continued
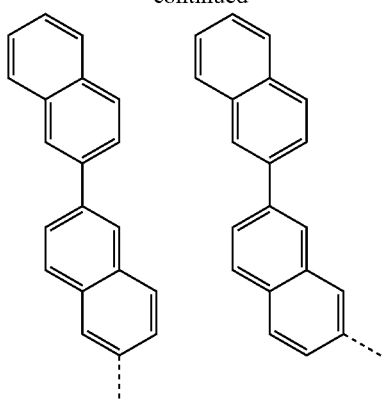
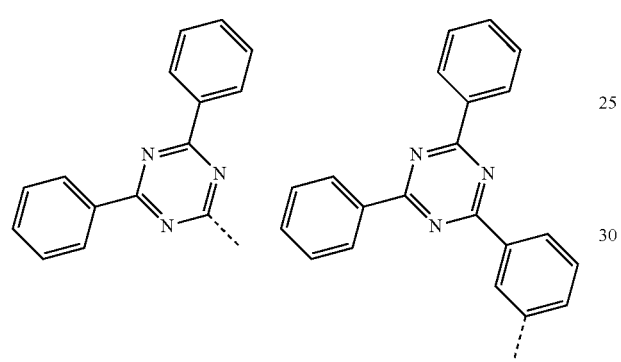
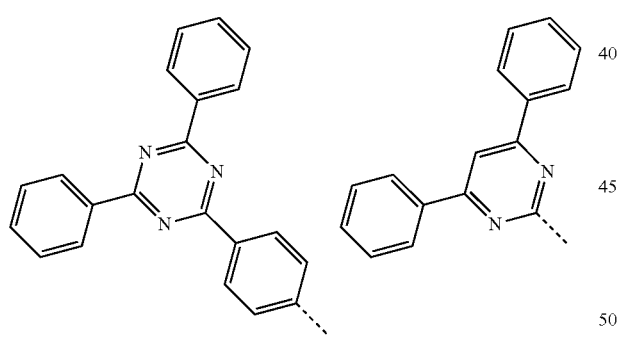
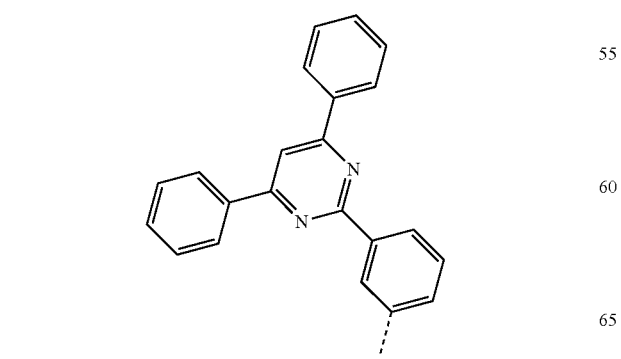
234
-continued
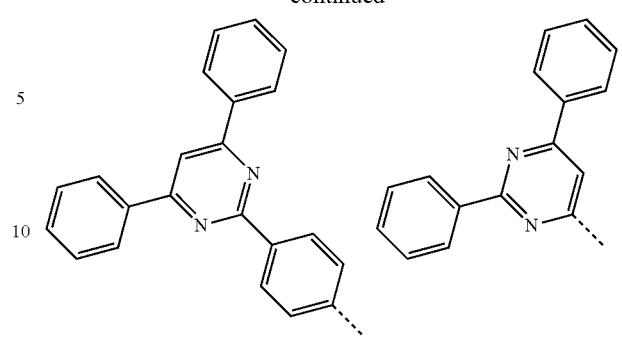
[A-4]
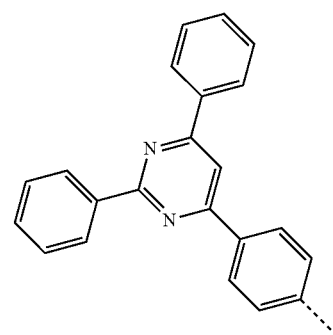
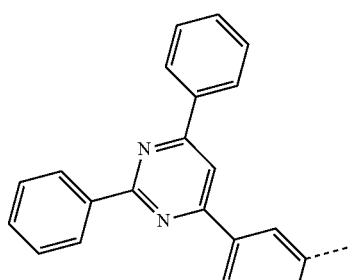
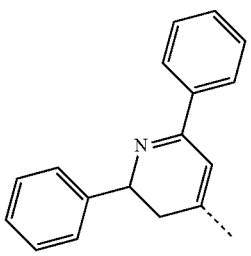
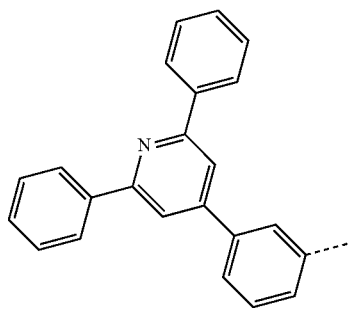

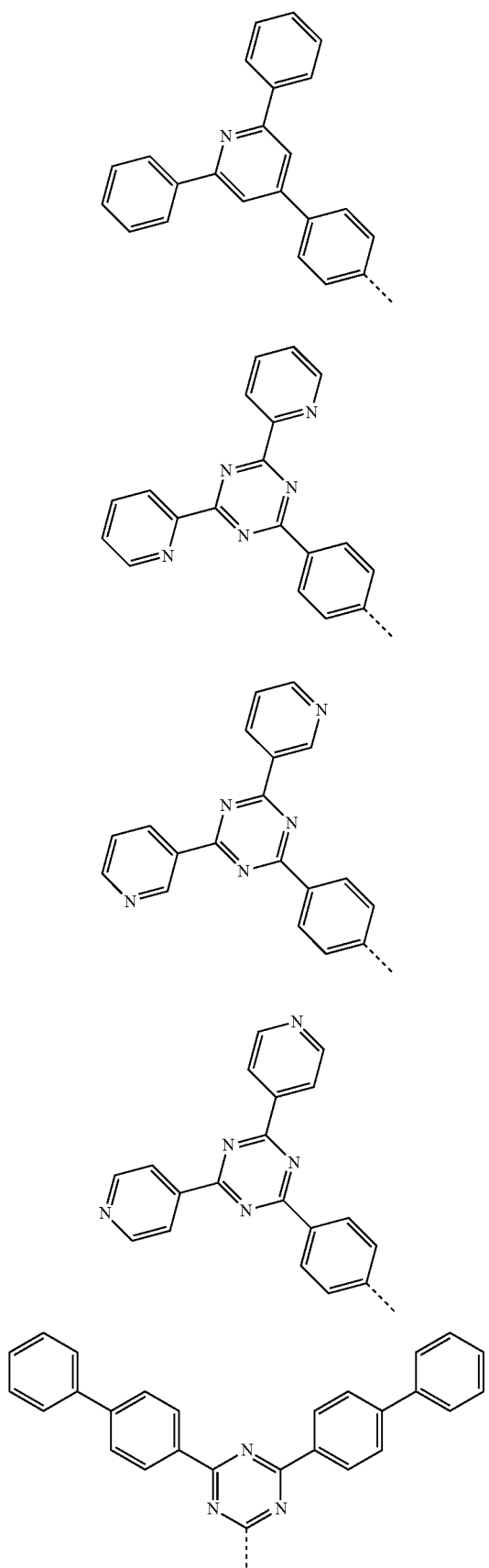
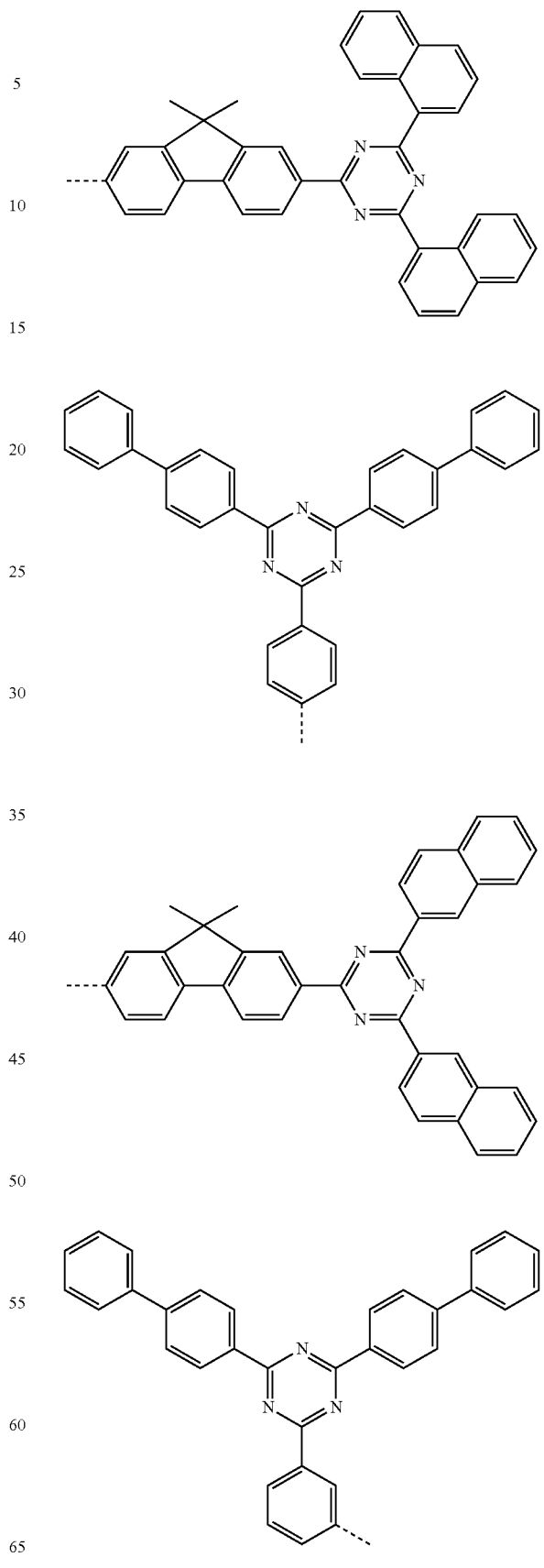

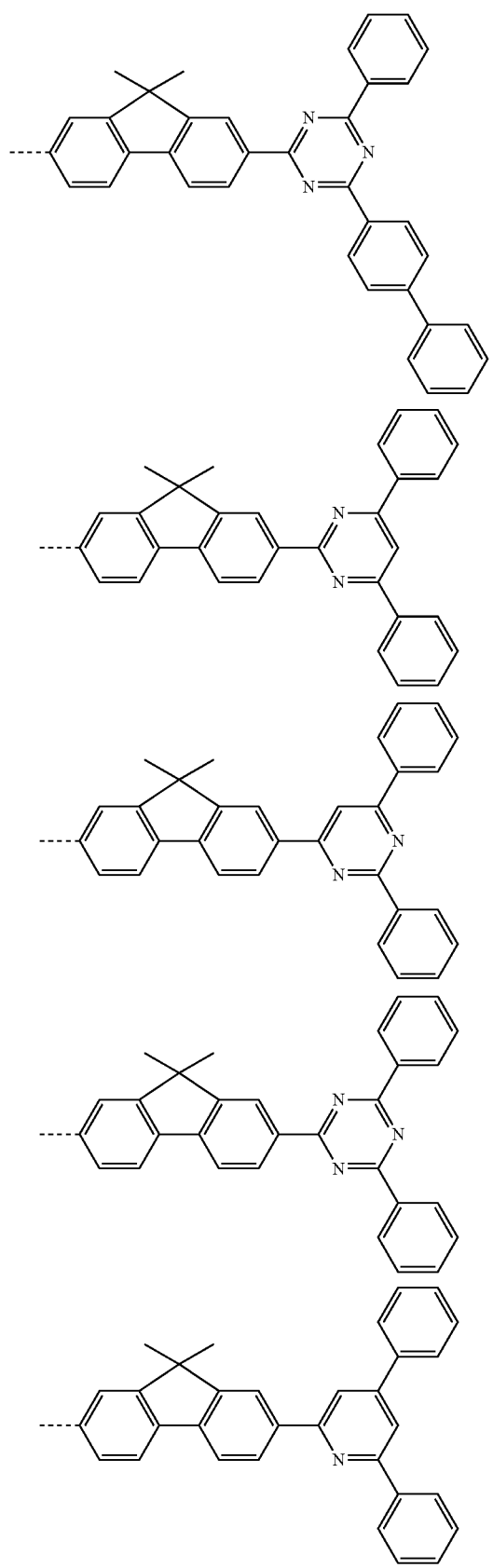
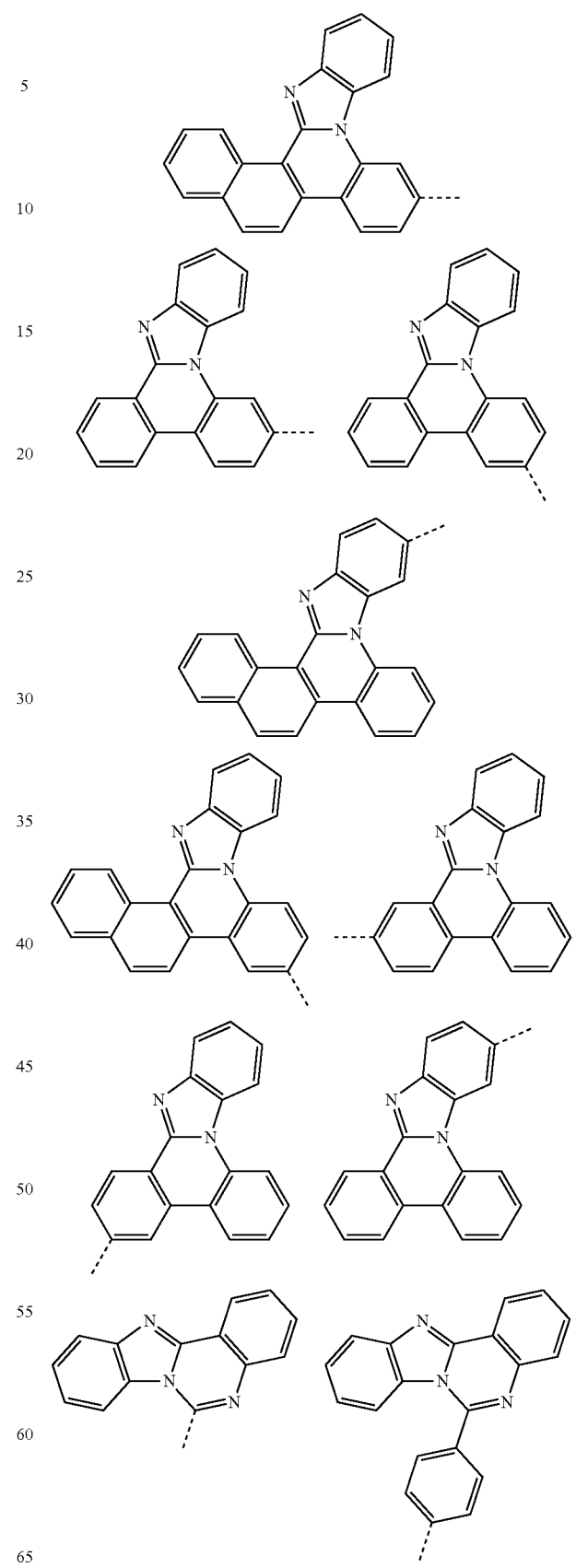

239
-continued
240
-continued
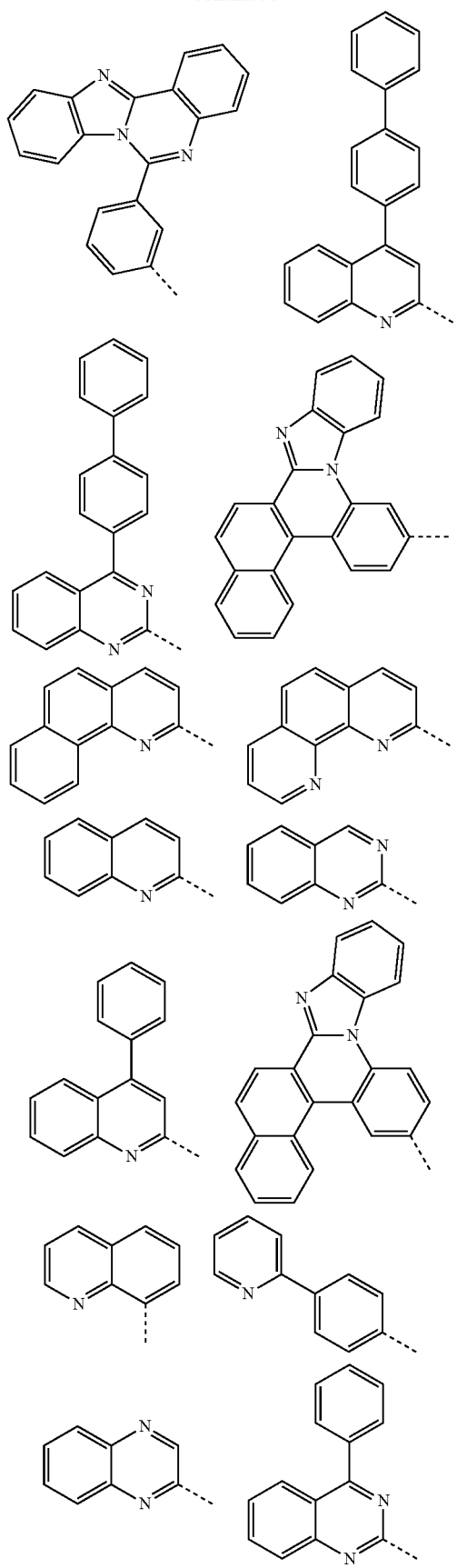
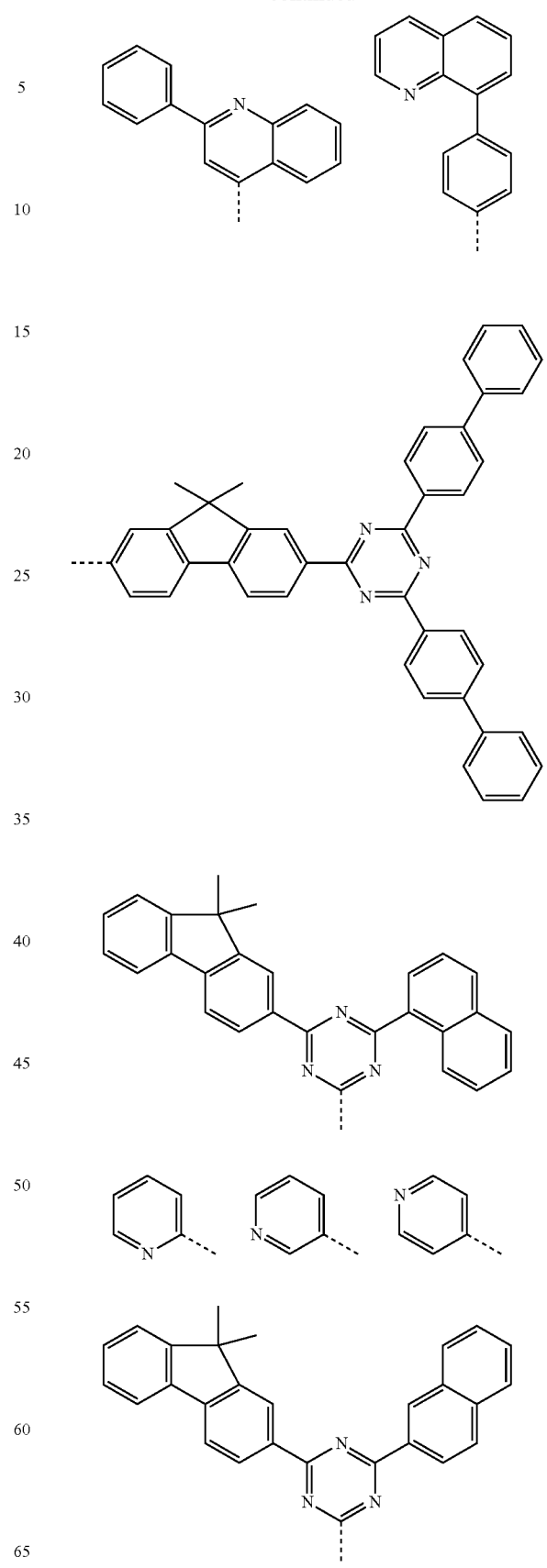

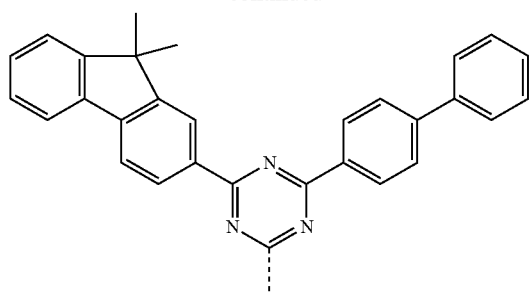
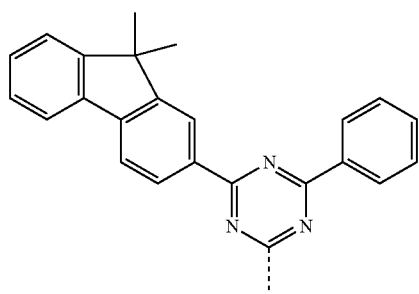
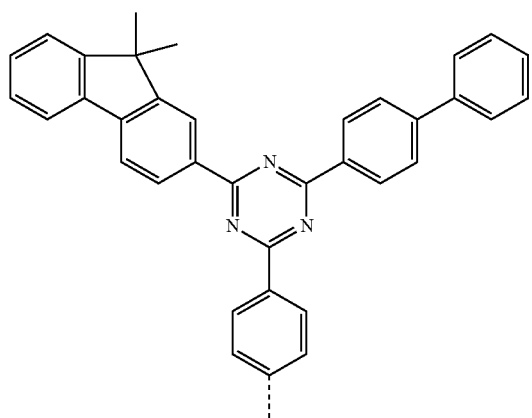
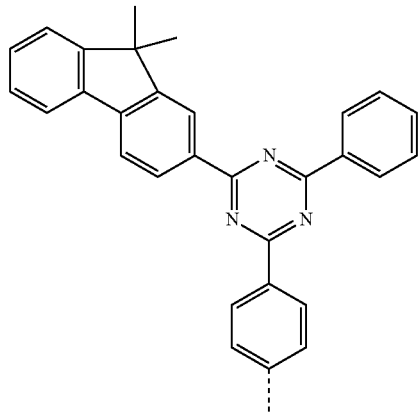
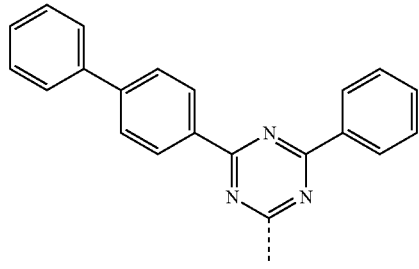
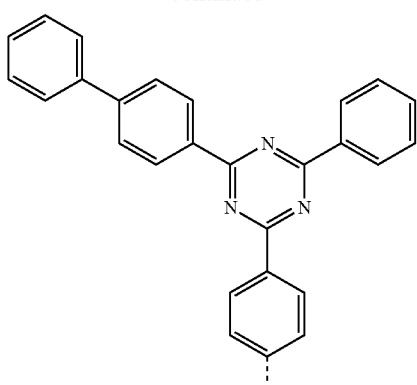
[A-5]
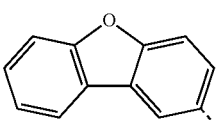 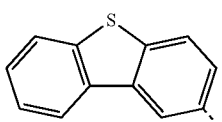
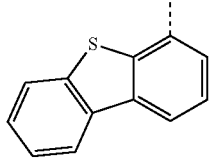 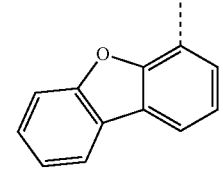
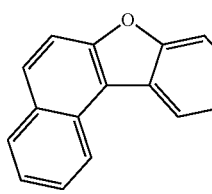 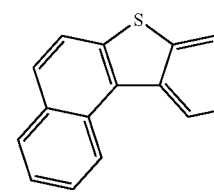
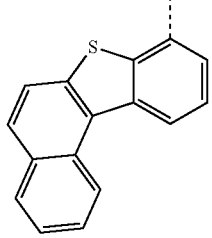 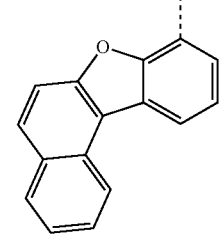
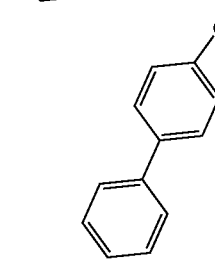 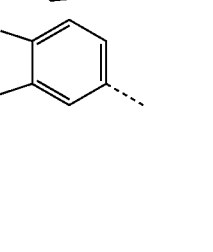
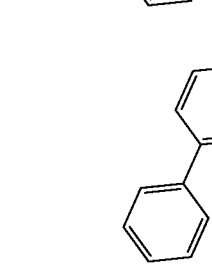
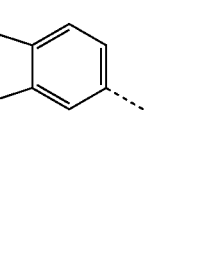

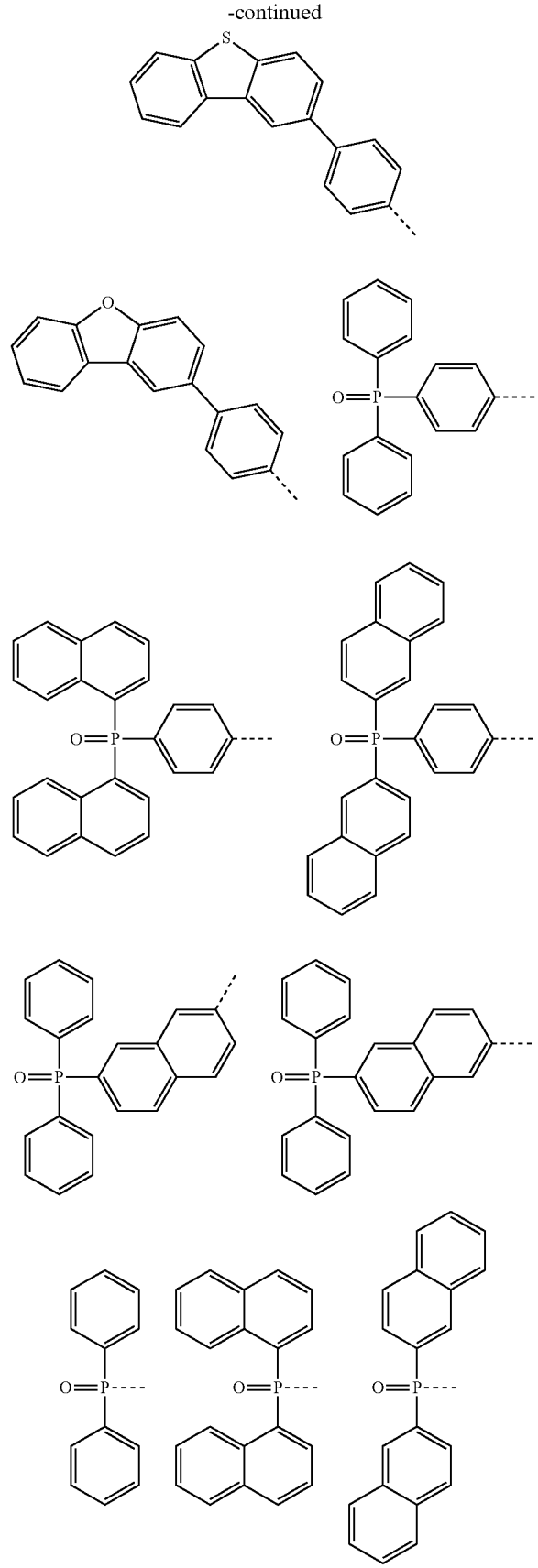
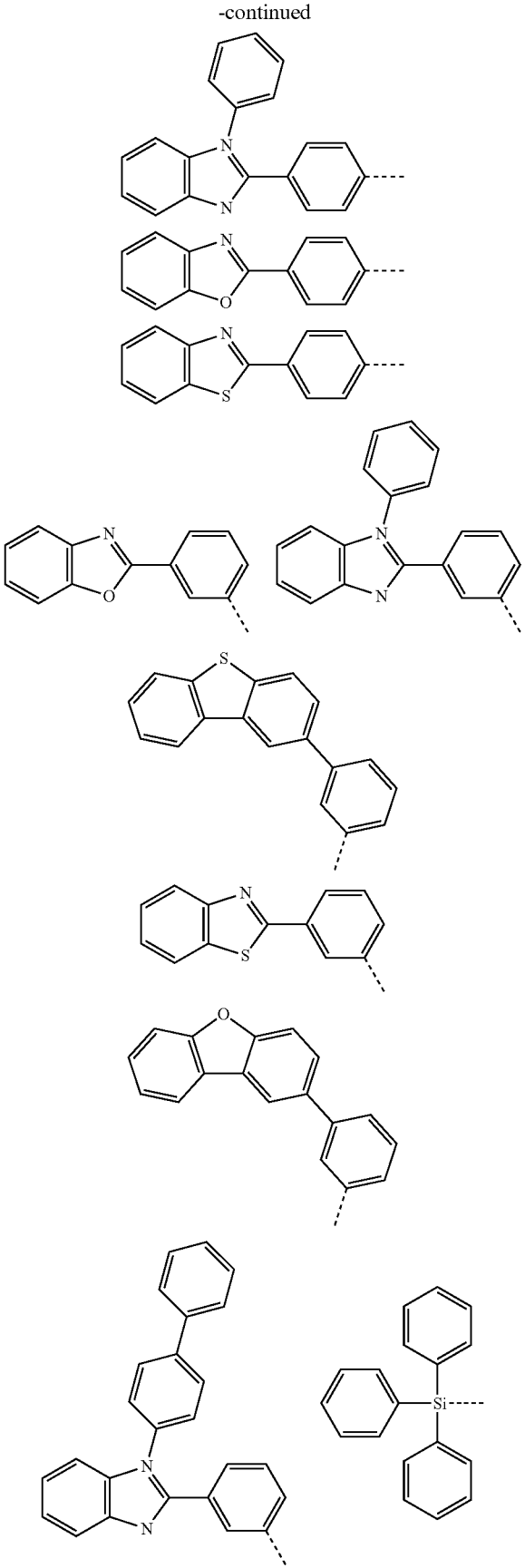

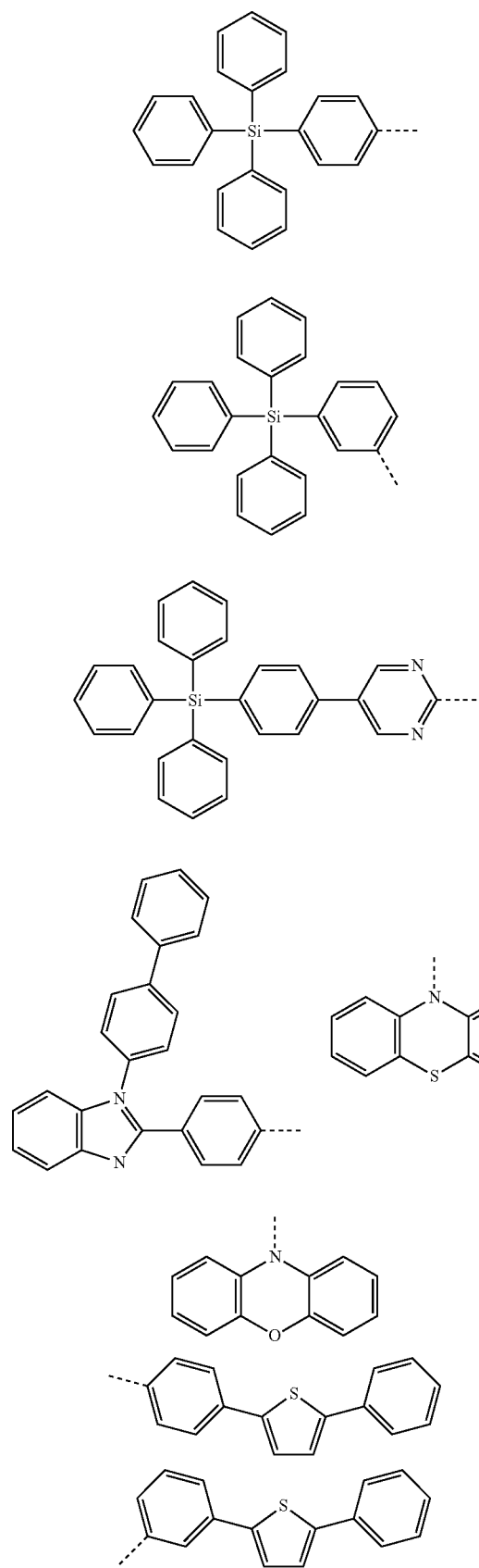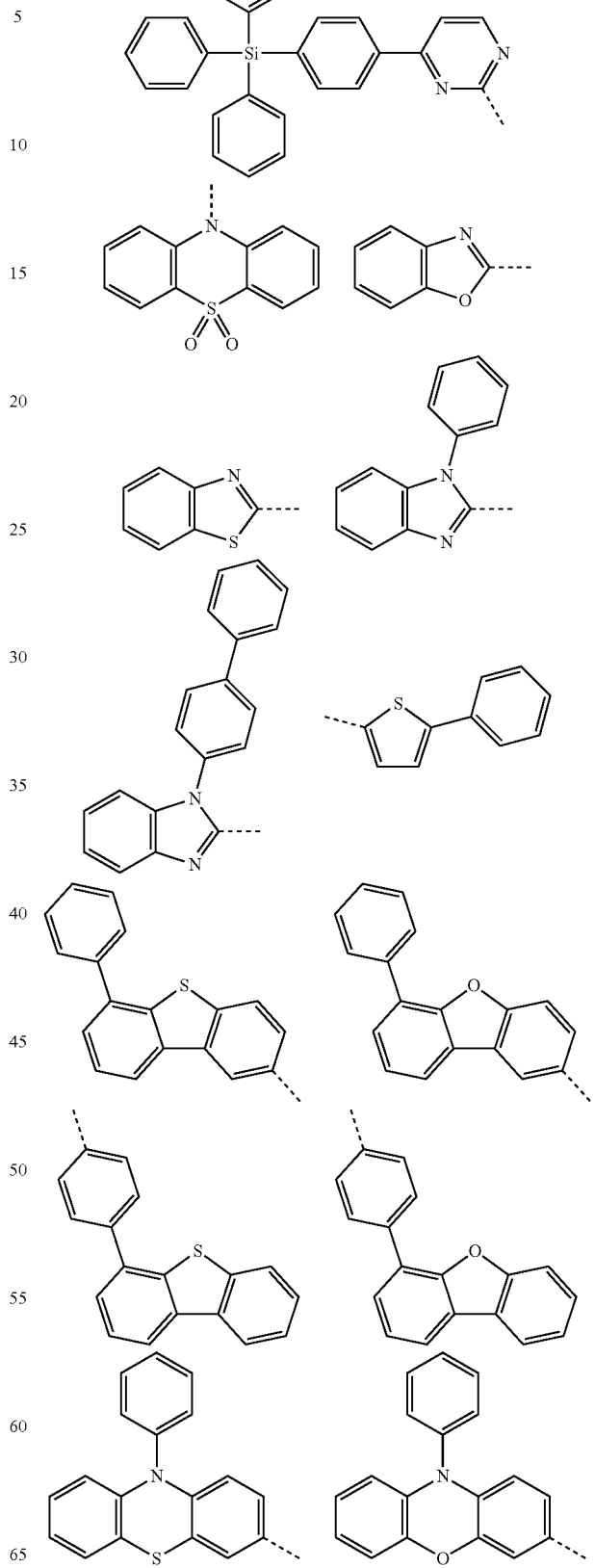

in the structural formulae, ---- means a moiety bonded to Chemical Formula 1 via L1.
5. The hetero-cyclic compound of claim 1, wherein Chemical Formula 1 is represented by any one of the following compounds:
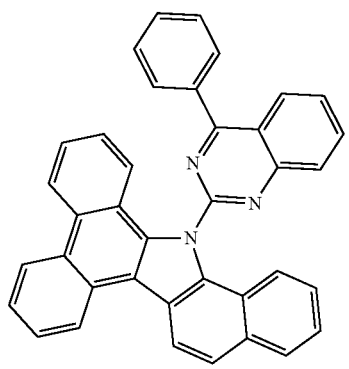
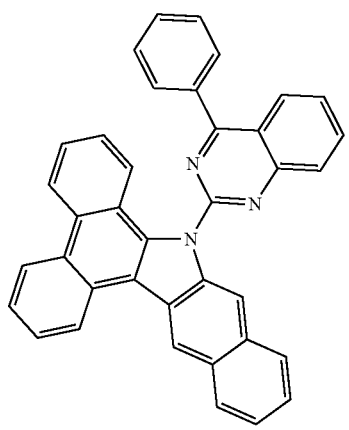
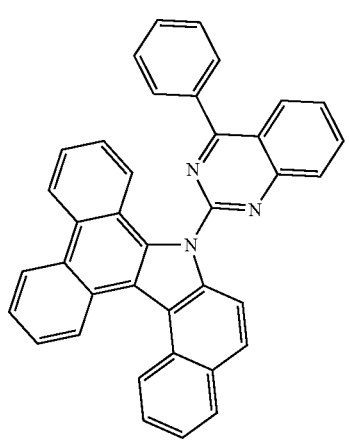
-continued
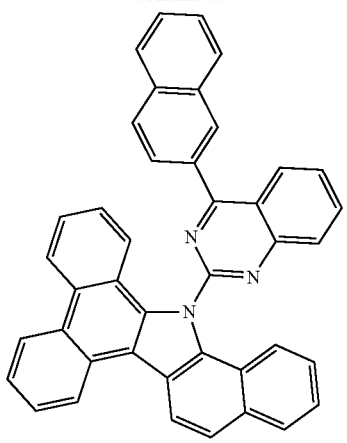
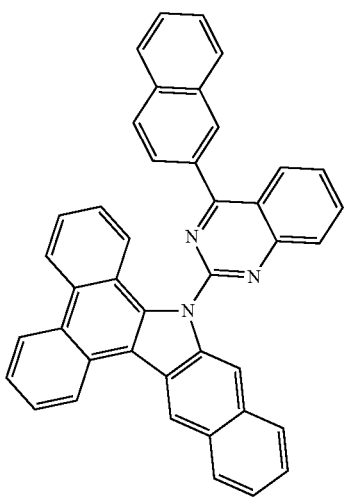
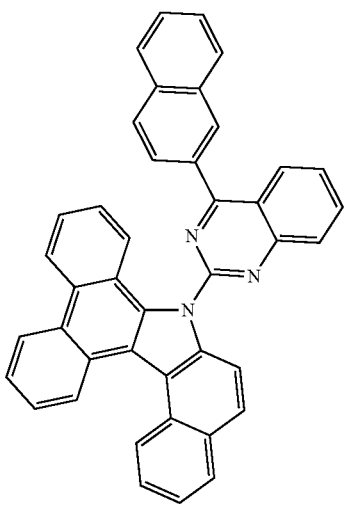

249
-continued
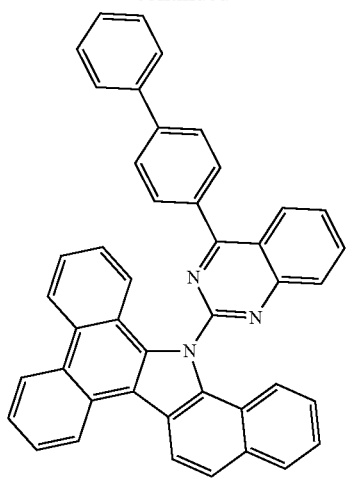
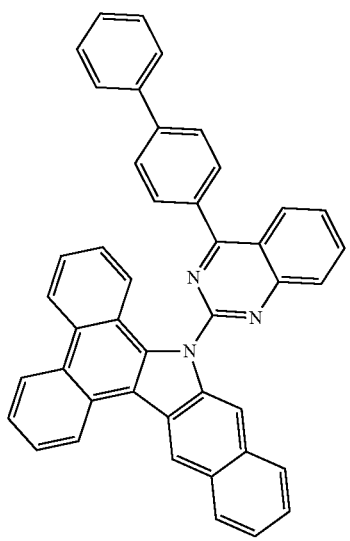
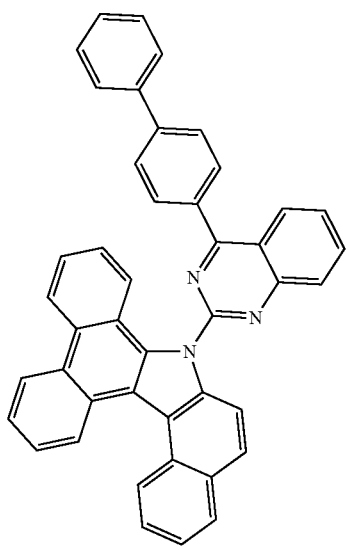
250
-continued
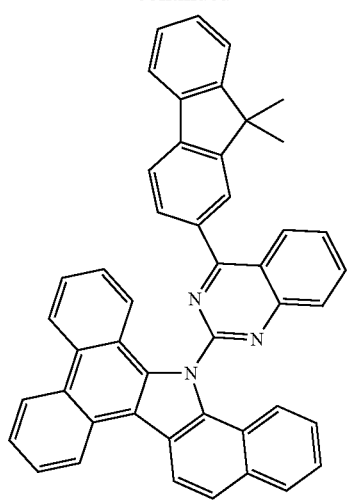
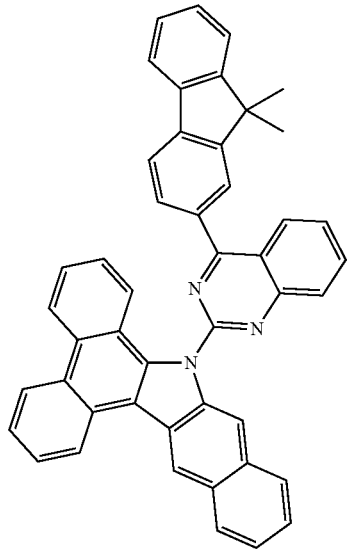
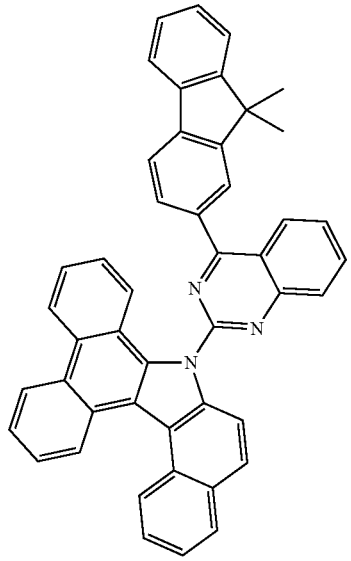

251
-continued
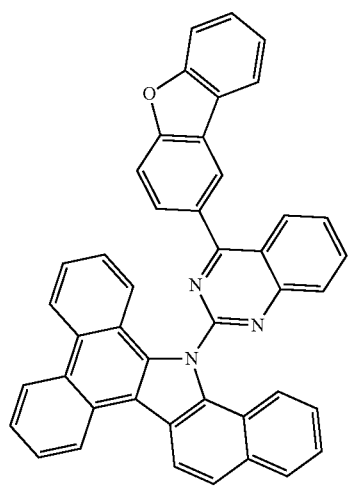
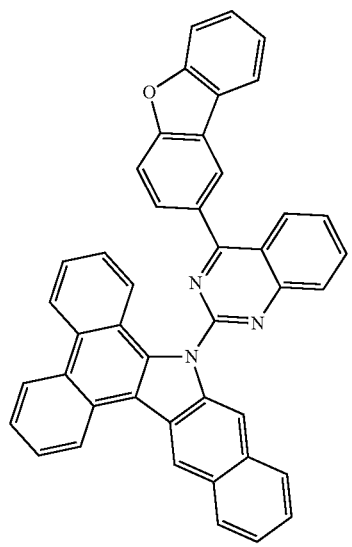
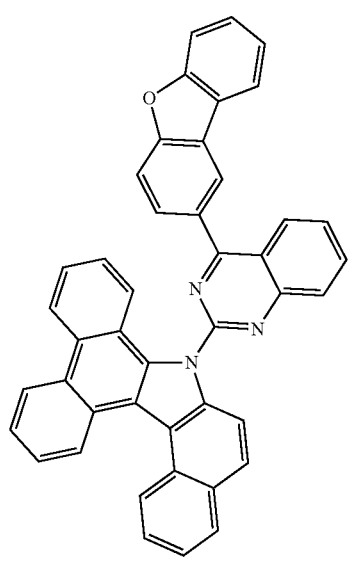
252
-continued
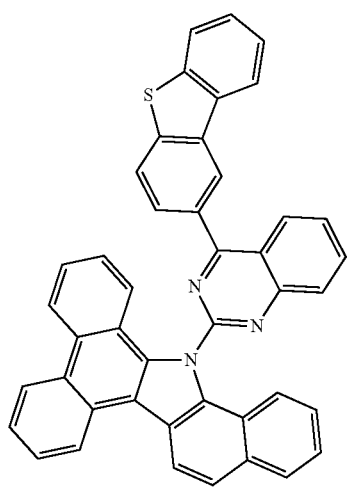
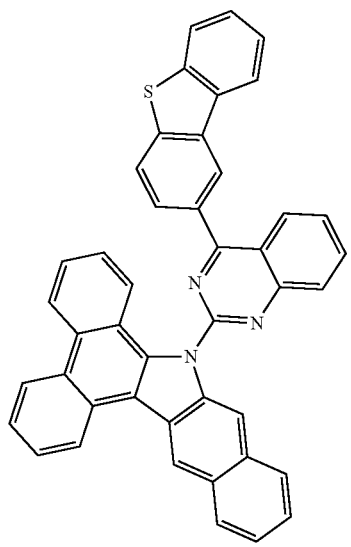
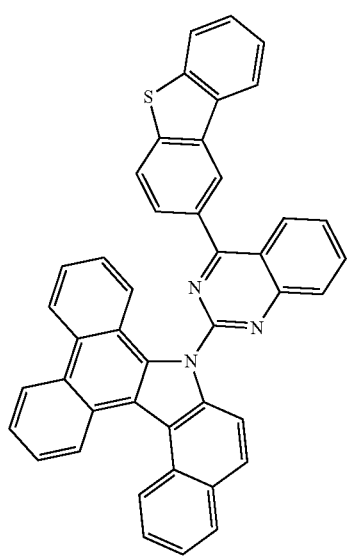

253
-continued
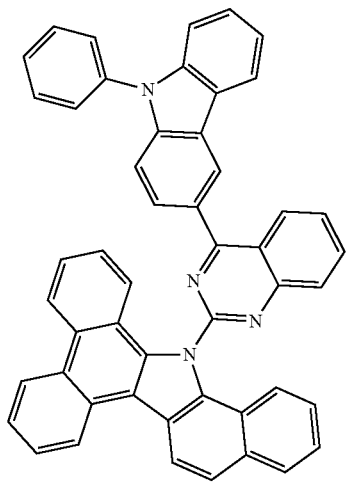
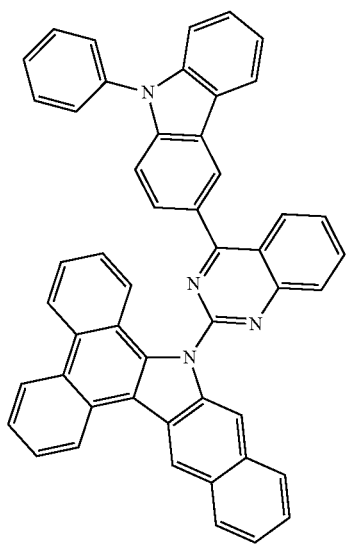
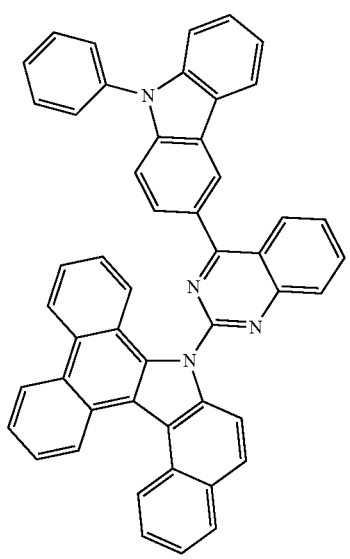
254
-continued
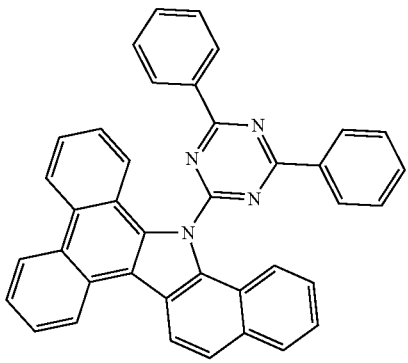
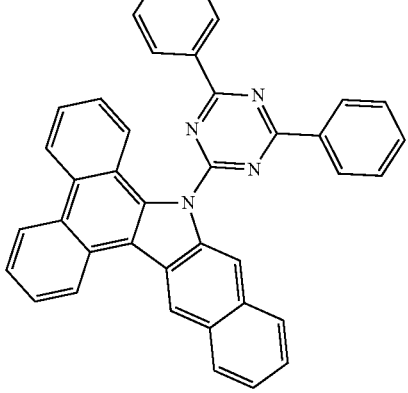
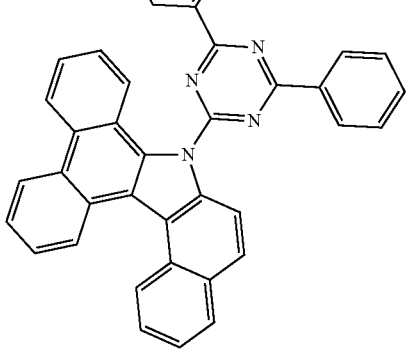
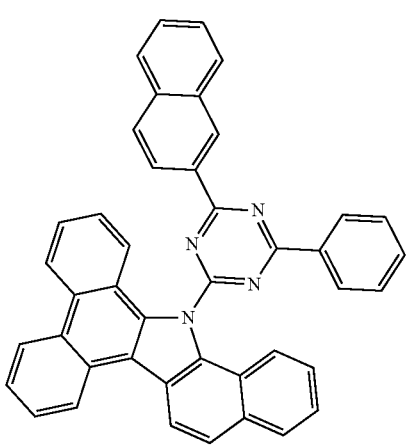

255
-continued
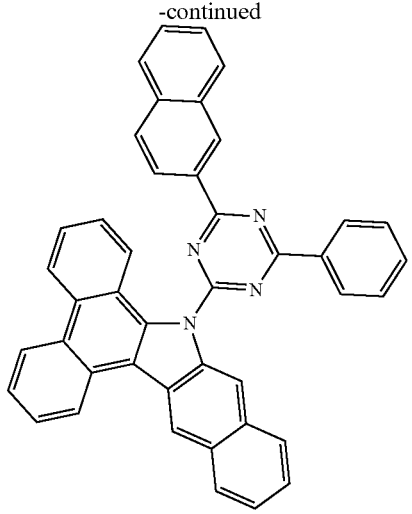
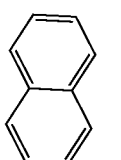
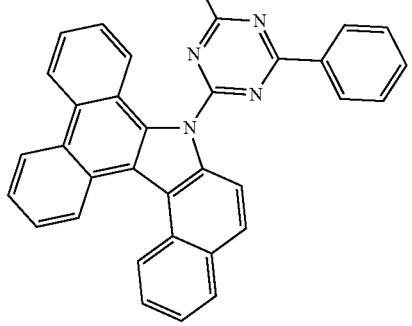
256
-continued
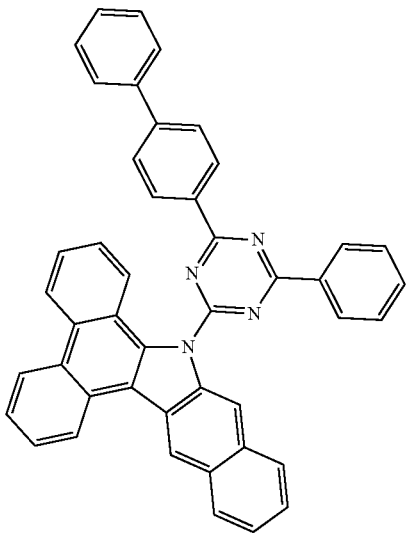
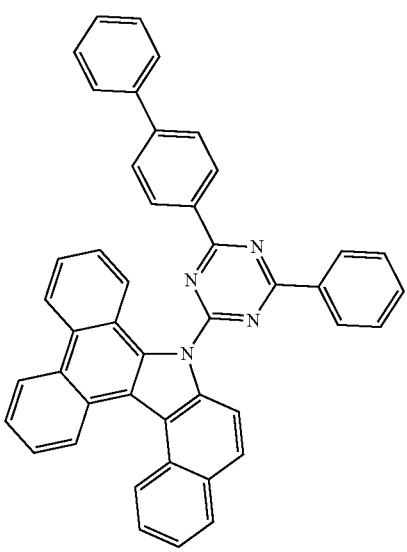
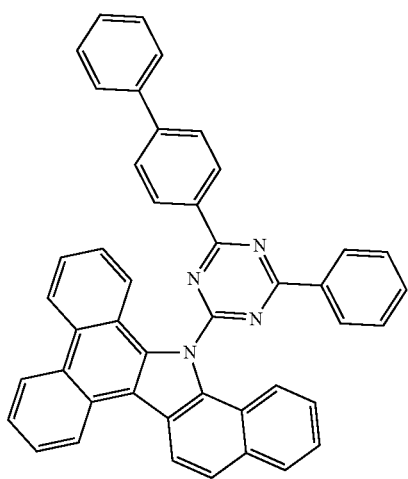
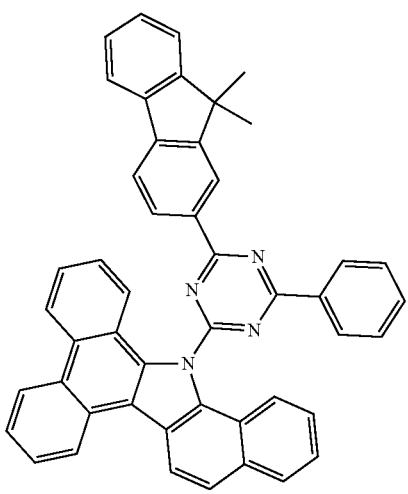

257
-continued
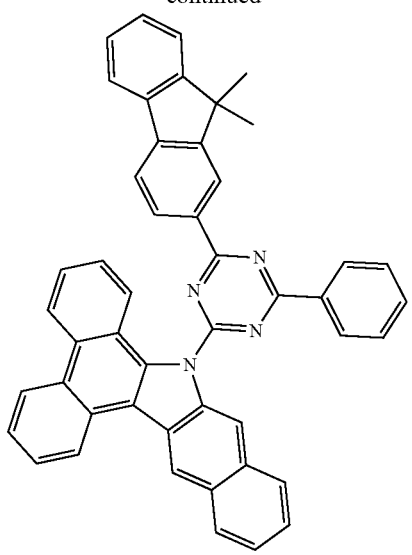
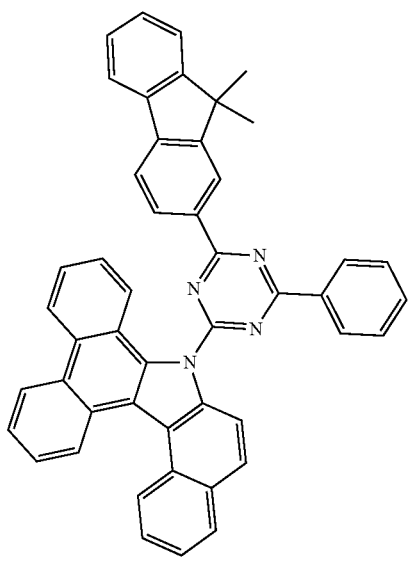
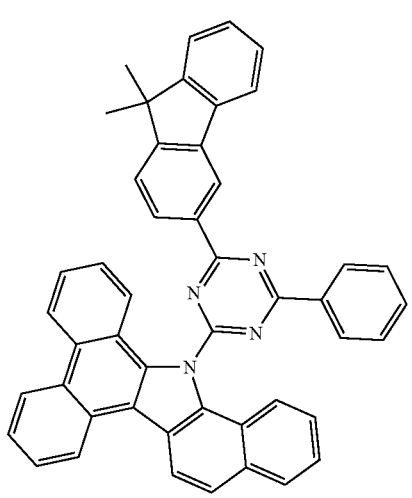
258
-continued
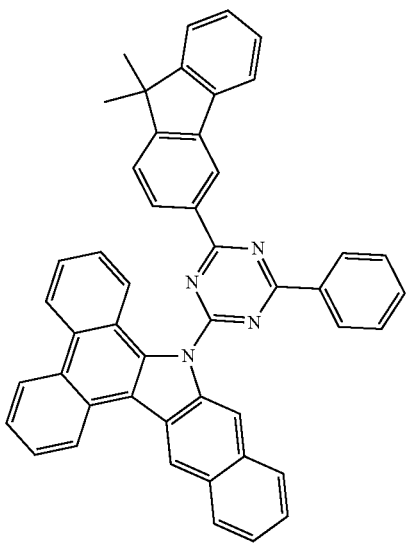
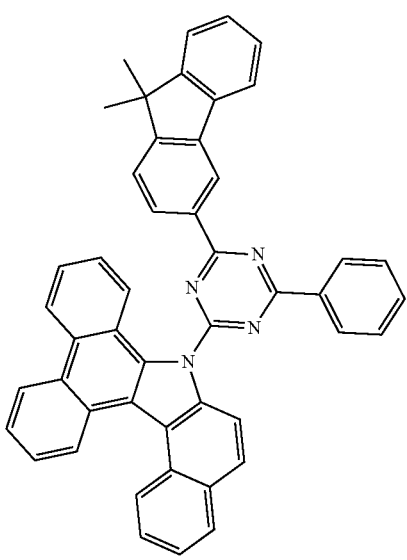
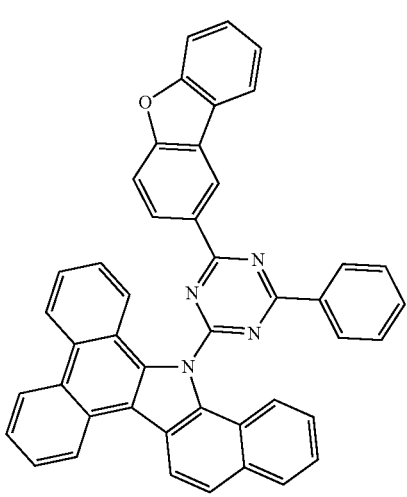

259
-continued
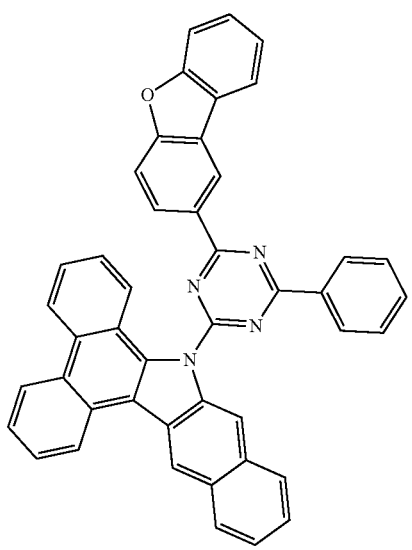
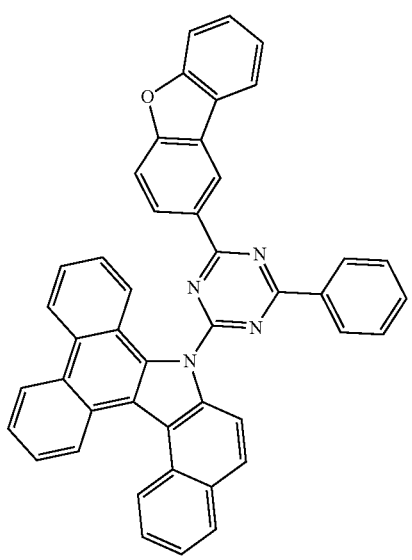
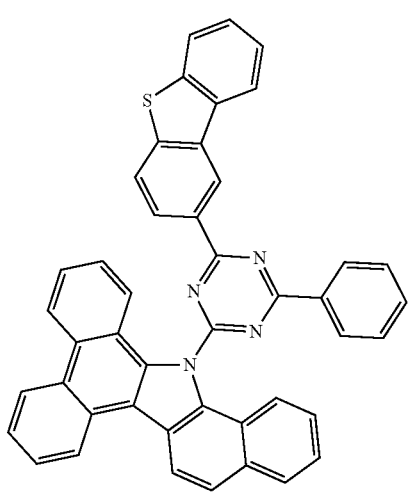
260
-continued
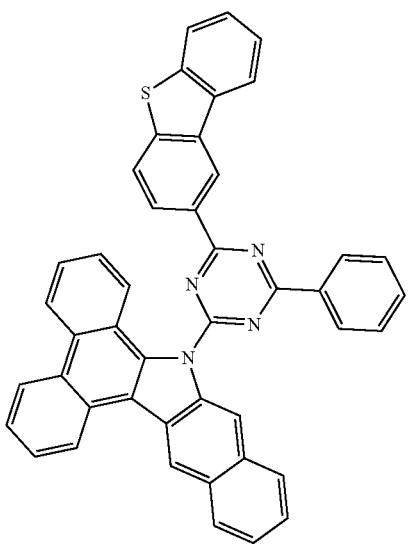
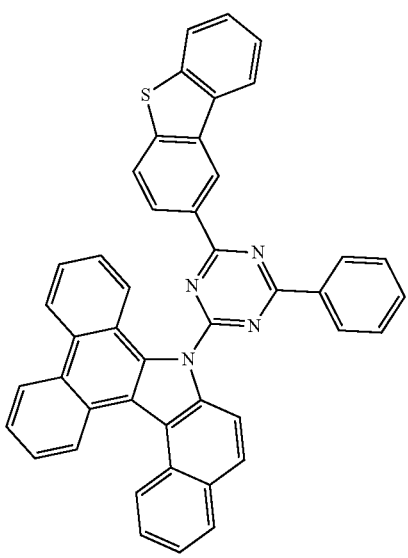
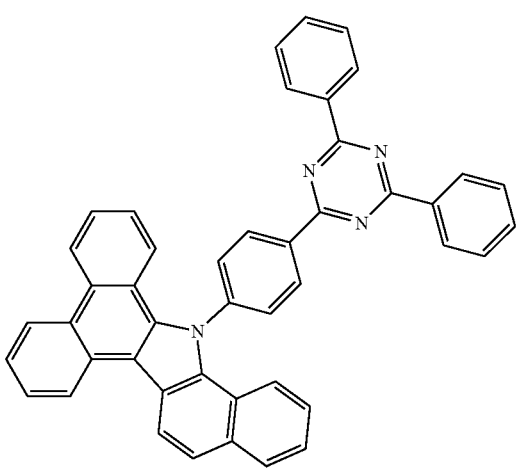

261
-continued
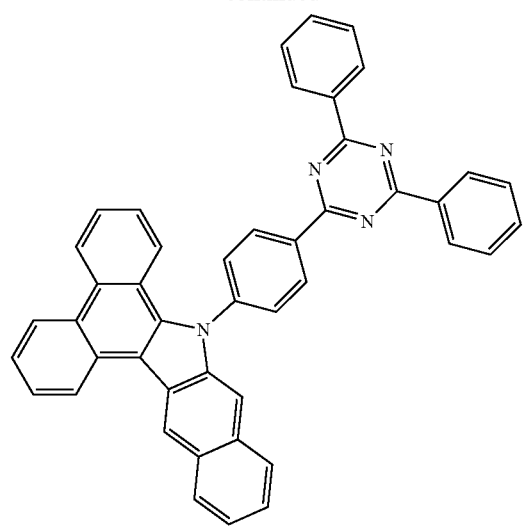
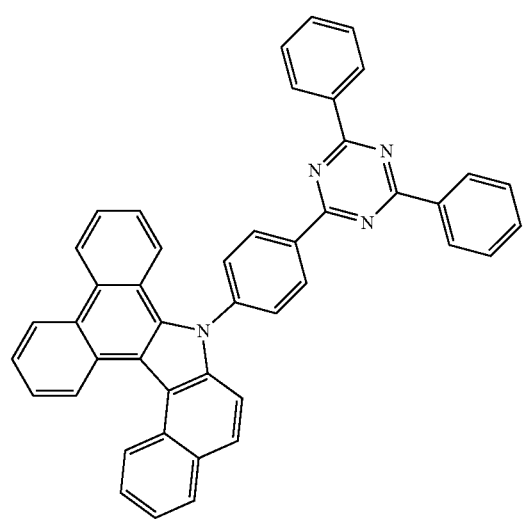
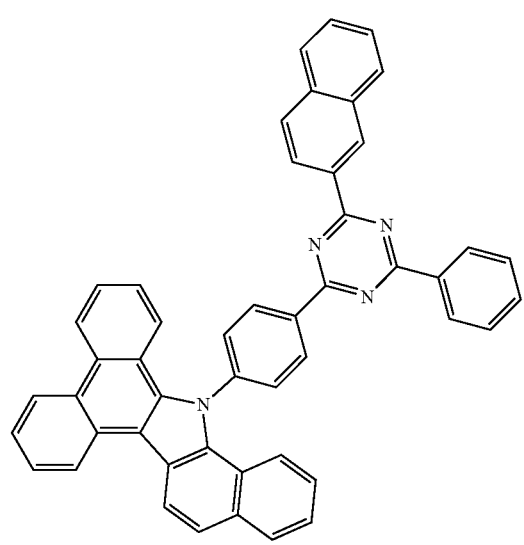
262
-continued
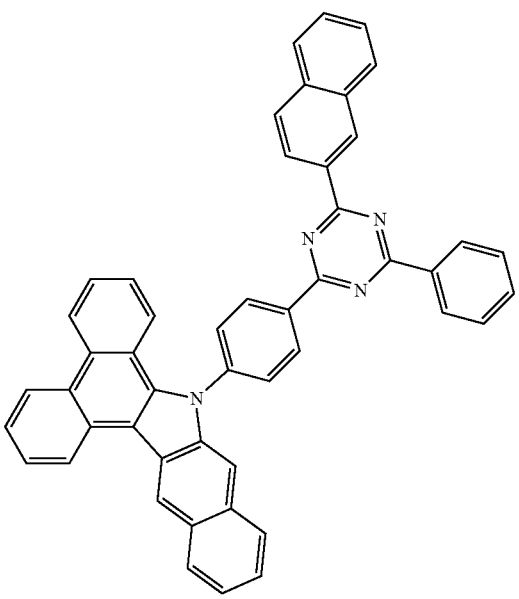
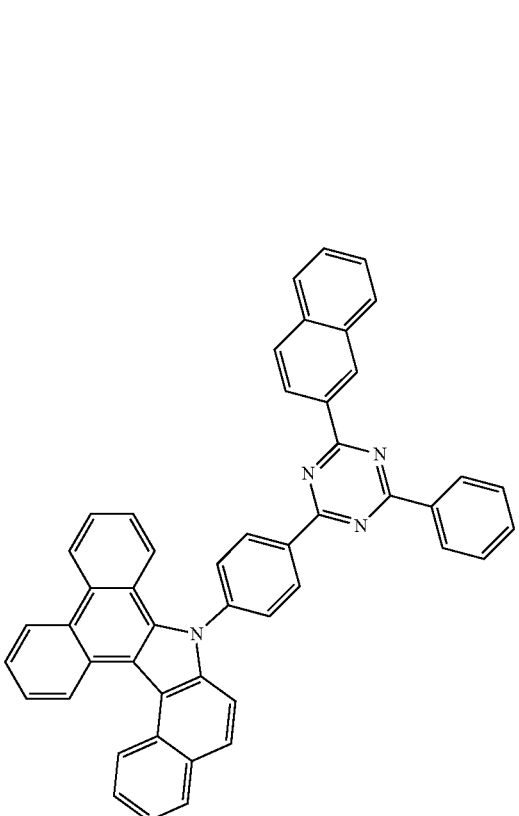

263
-continued
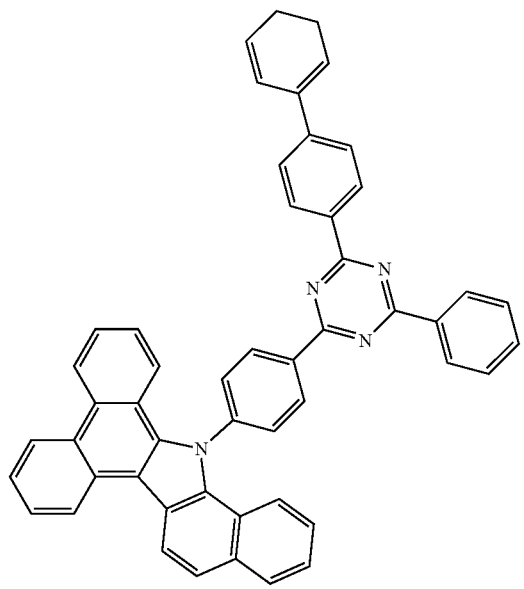
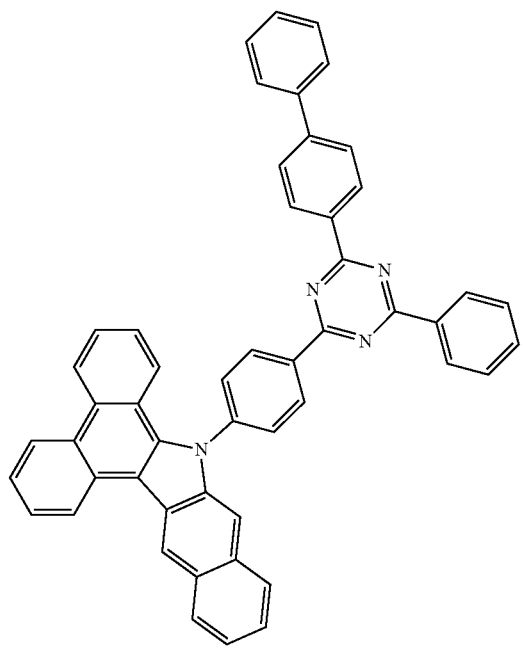
264
-continued
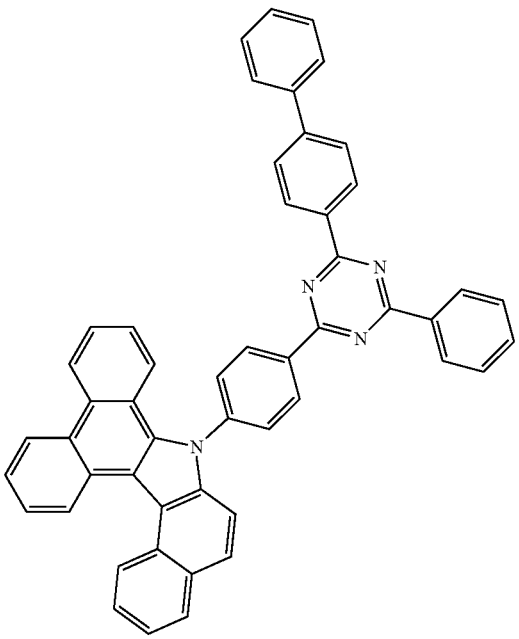
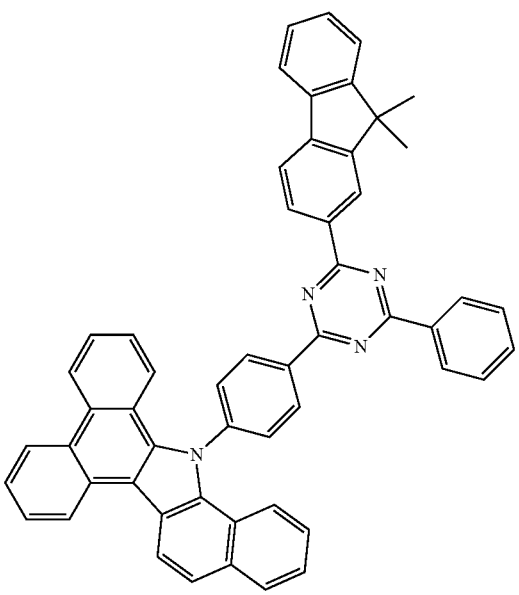

-continued
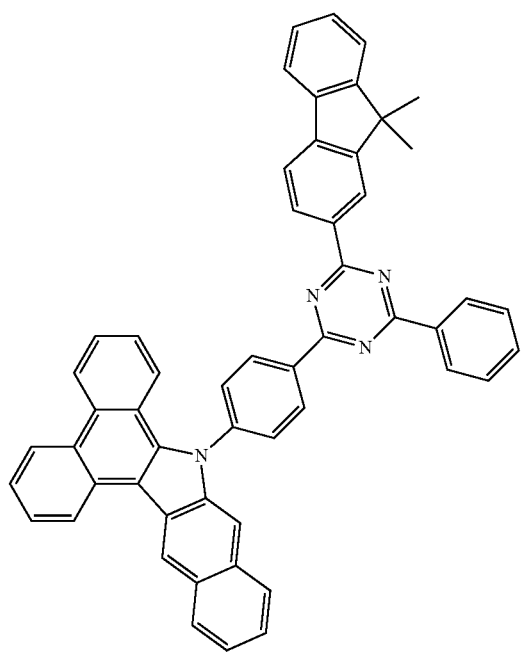
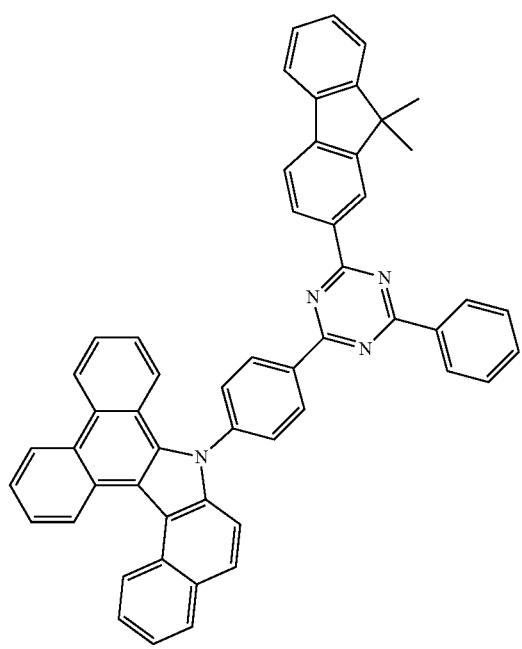
-continued
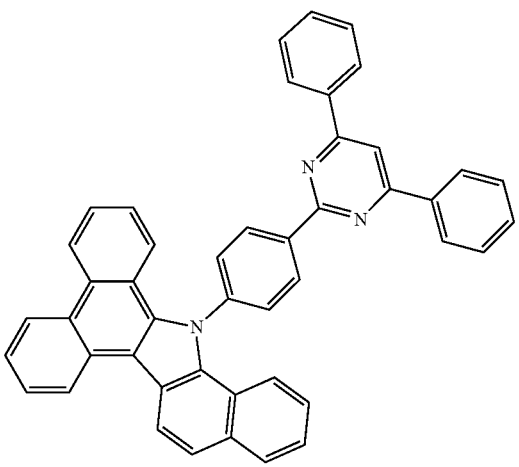
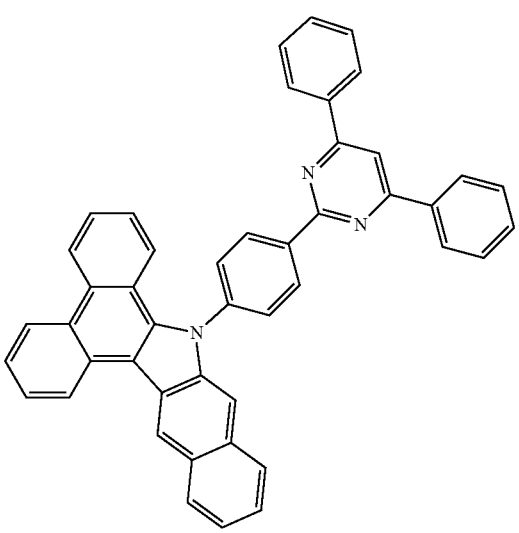
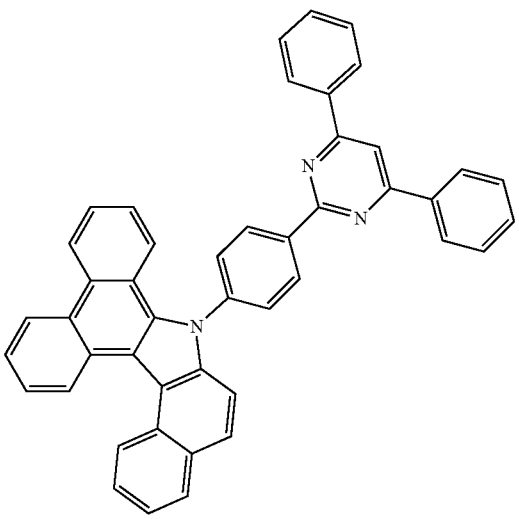

267
-continued
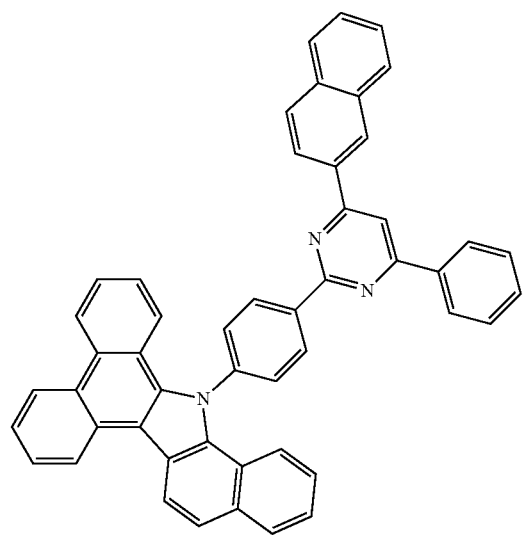
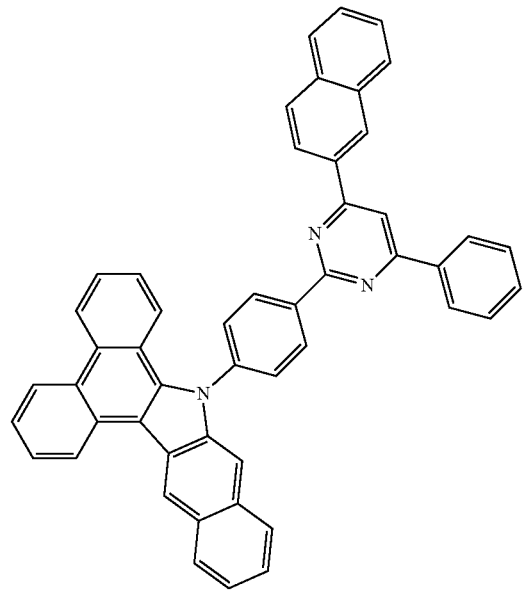
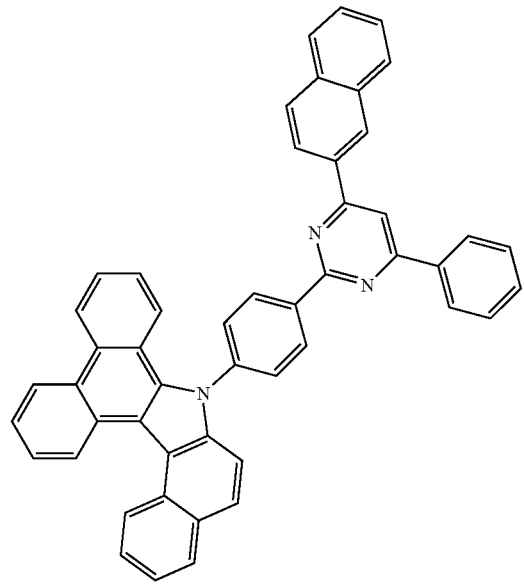
268
-continued
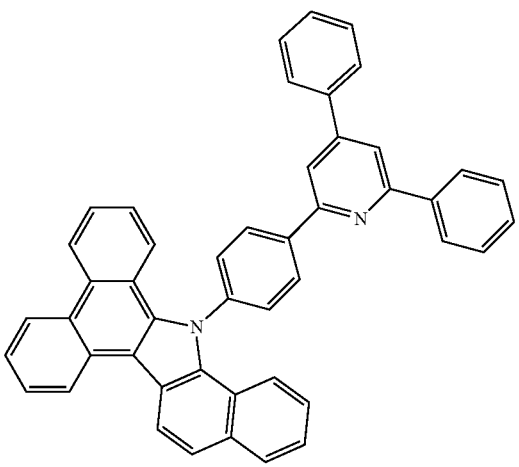
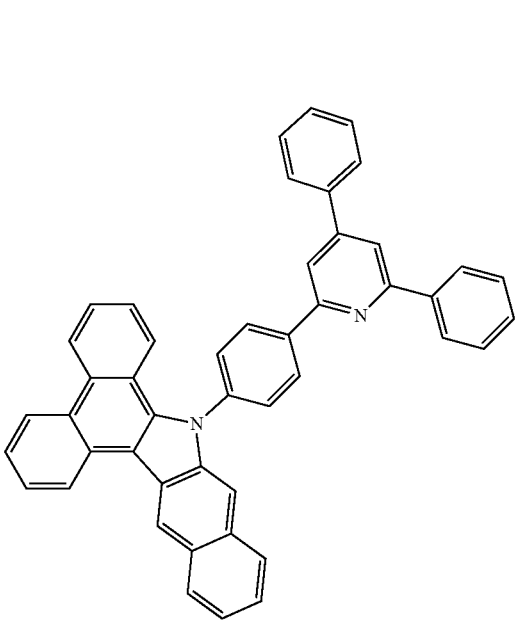
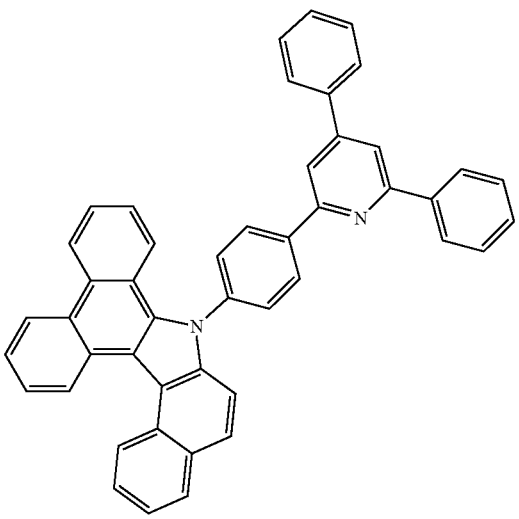

269
-continued
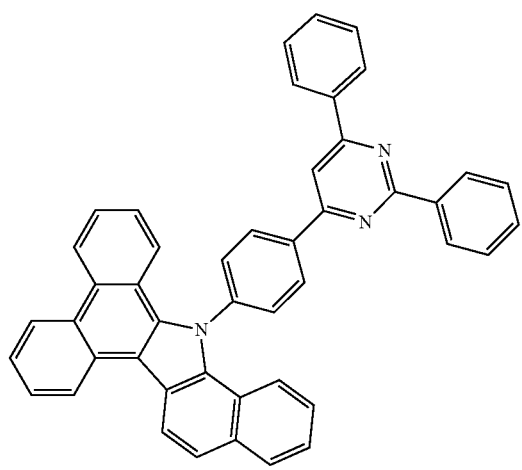
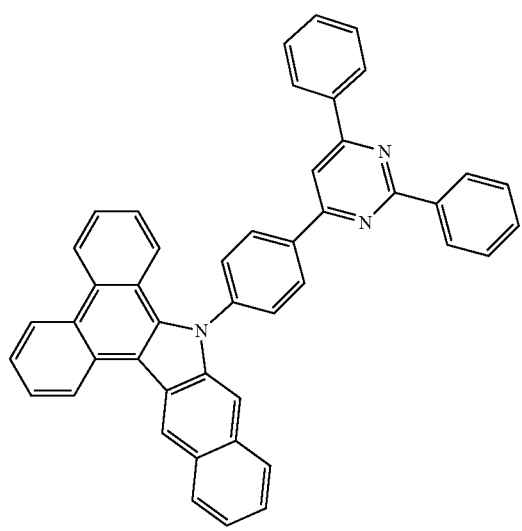
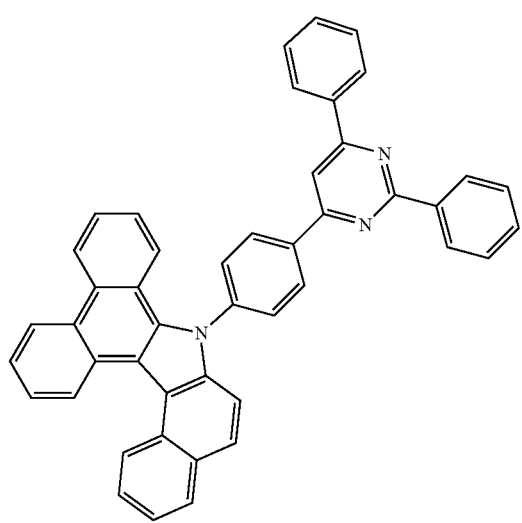
270
-continued
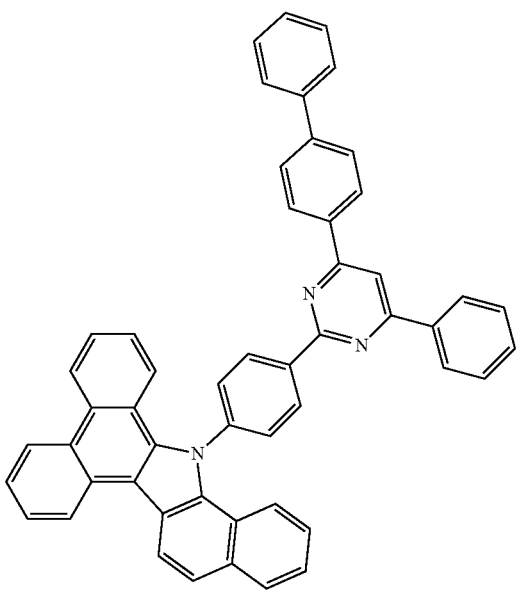
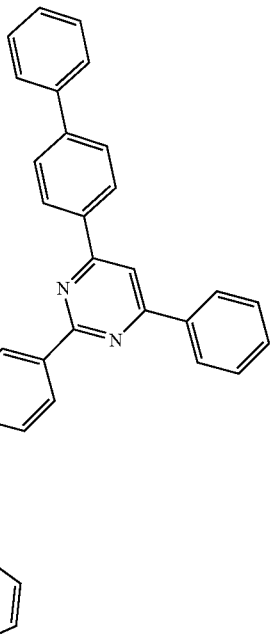

271
-continued
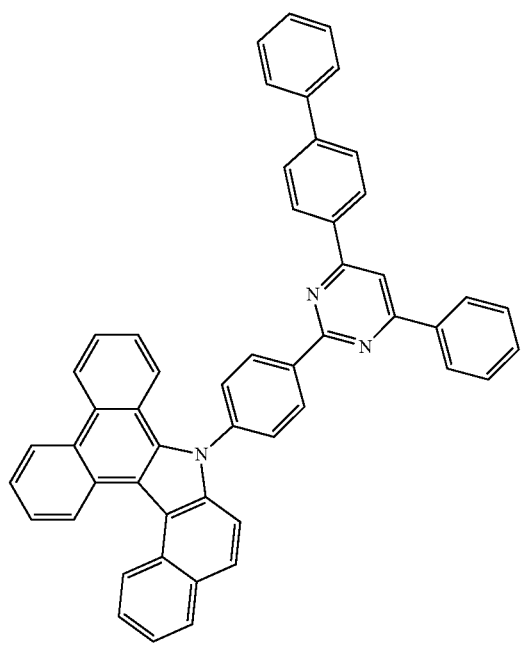
272
-continued
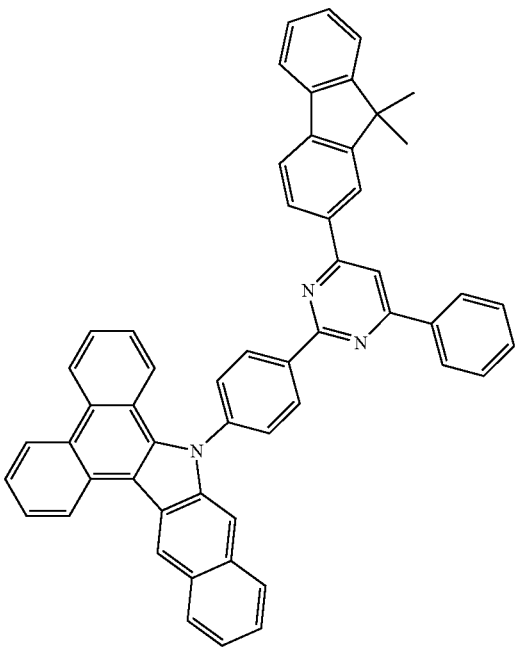
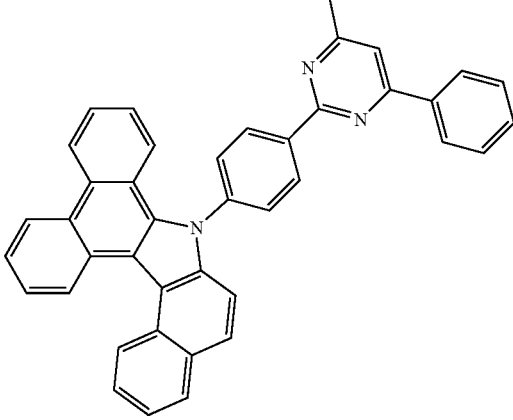
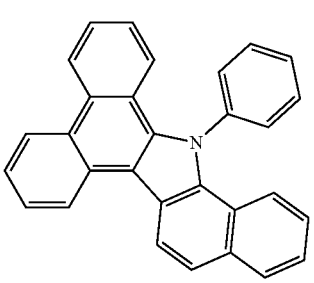

273
-continued
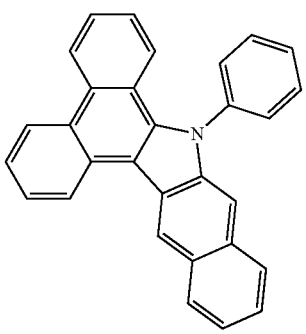
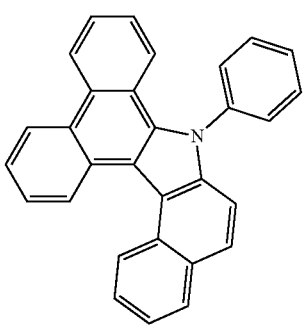
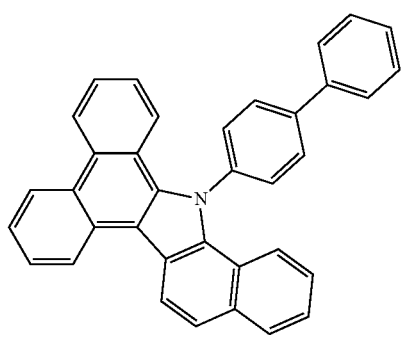
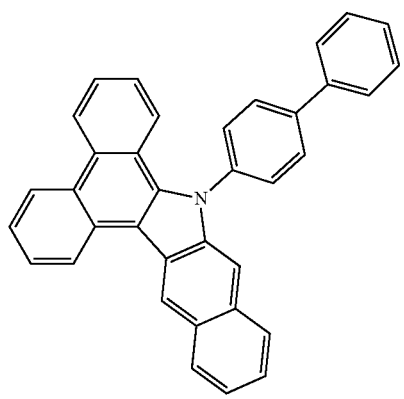
274
-continued
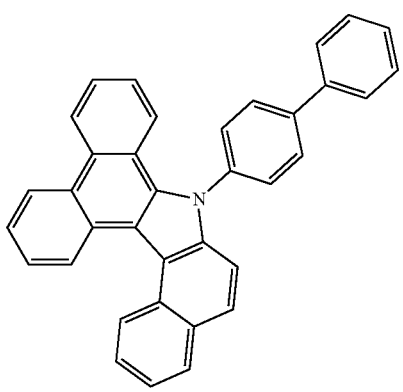
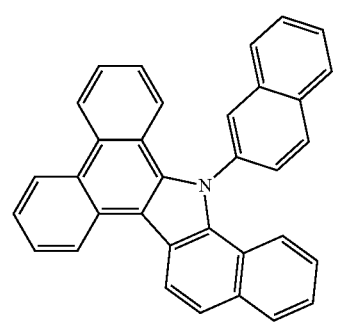
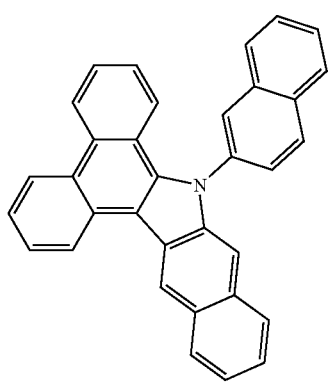
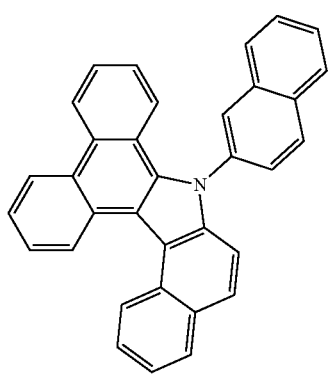

275
-continued
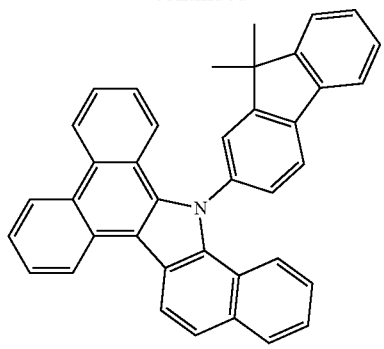
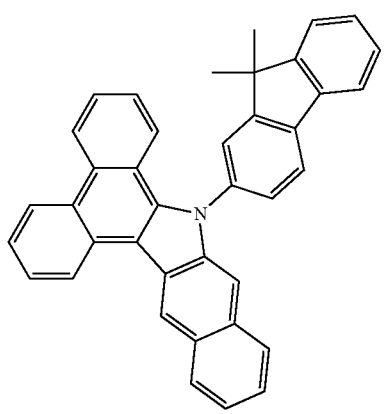
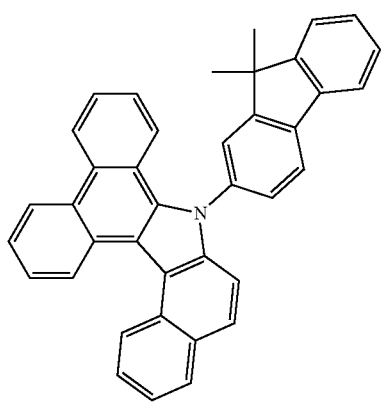
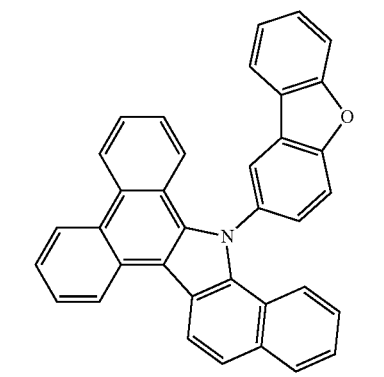
276
-continued
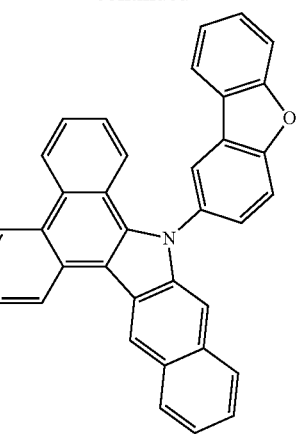
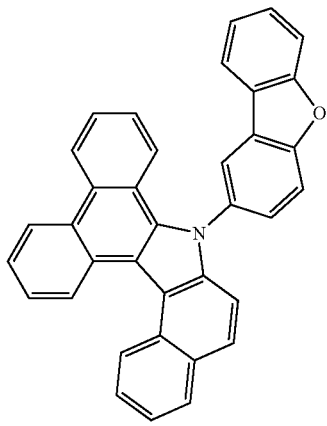
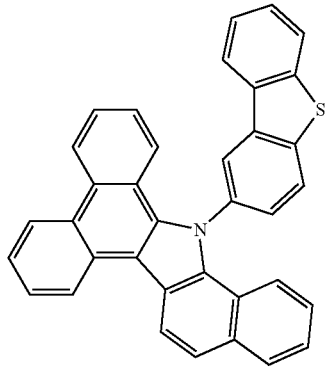
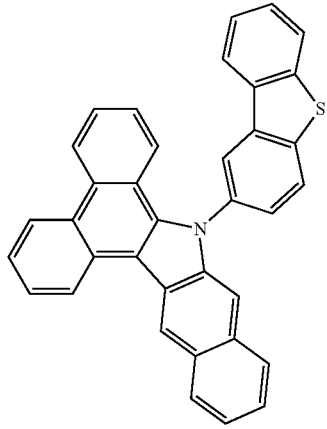

277
-continued
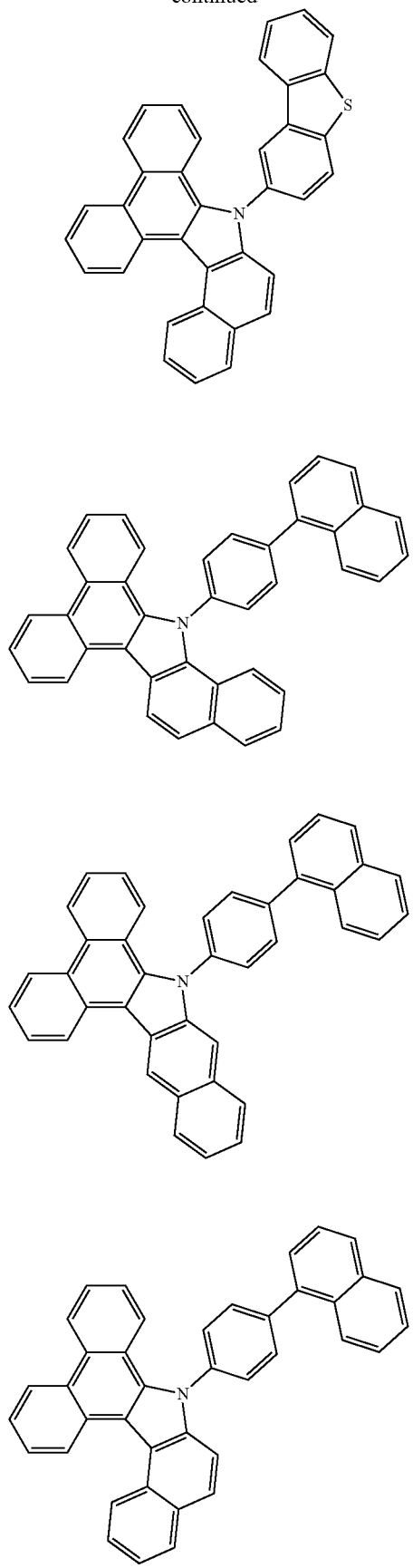
278
-continued
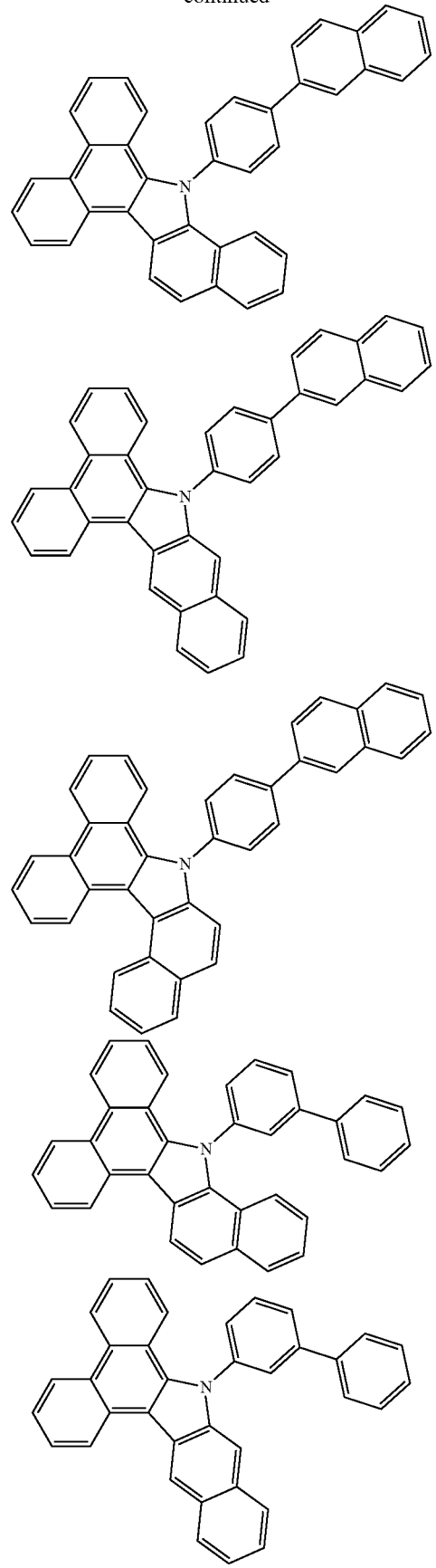

279
-continued
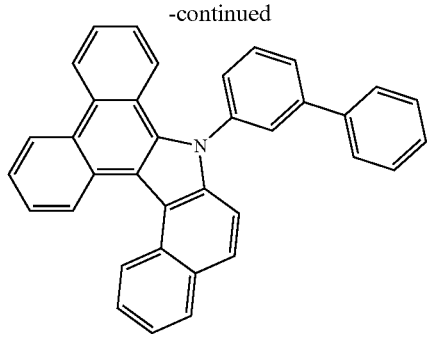
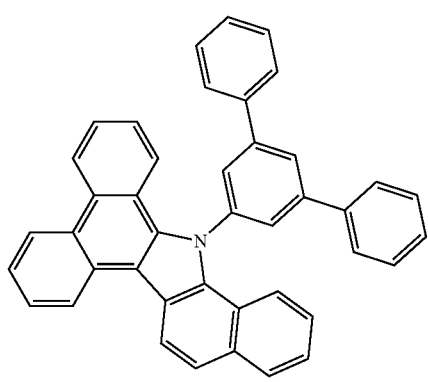
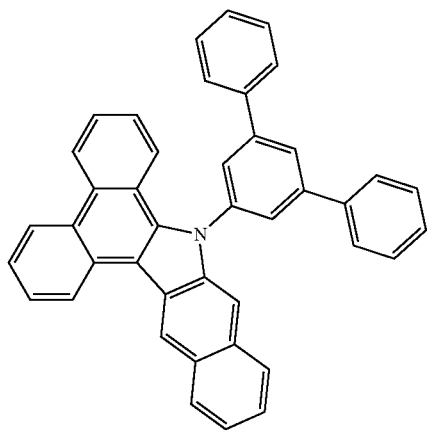
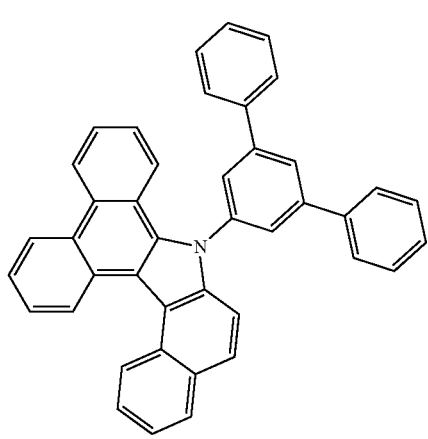
280
-continued
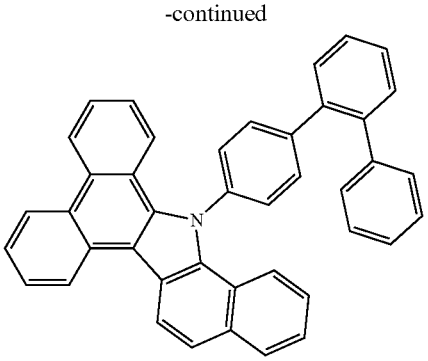
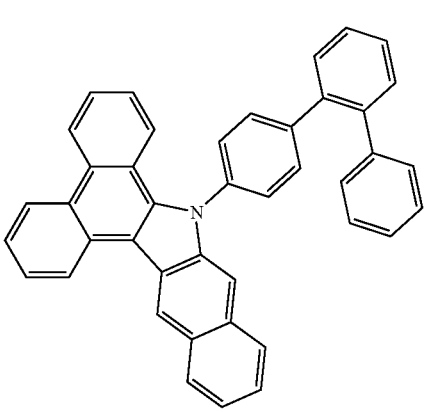
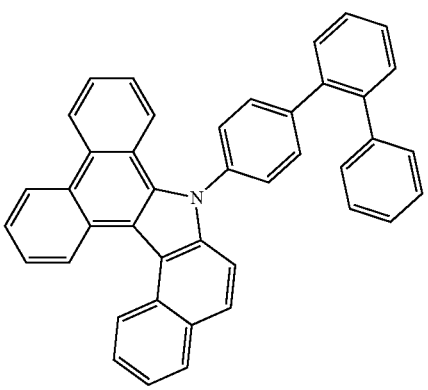
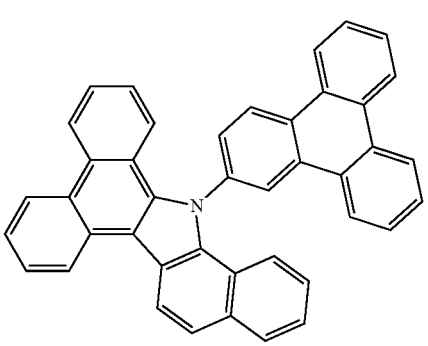

281
-continued
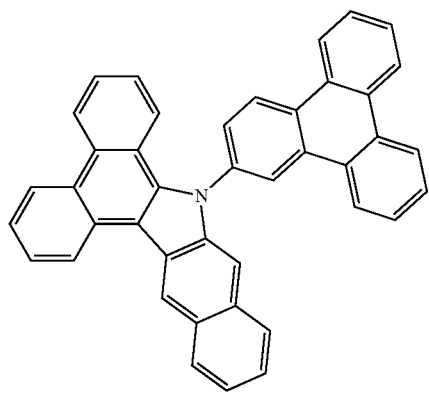
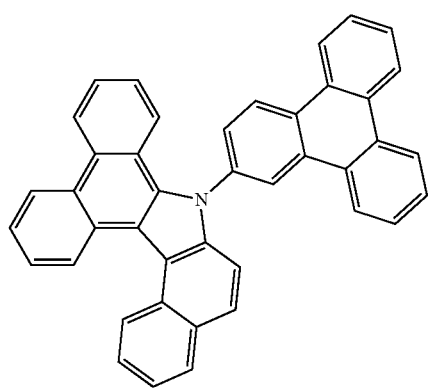
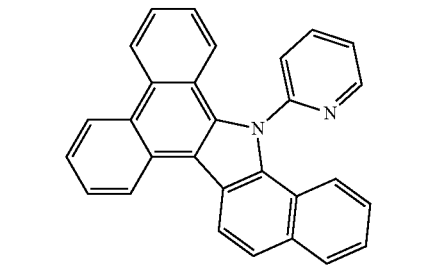
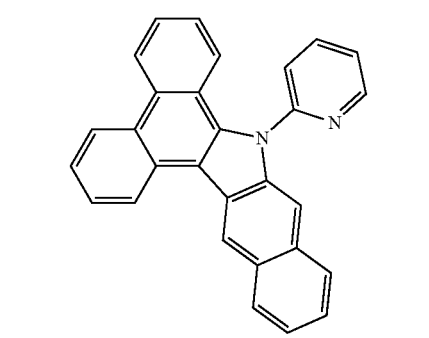
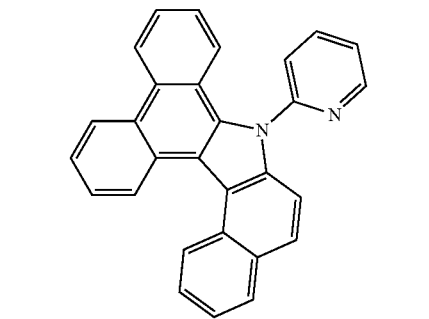
282
-continued
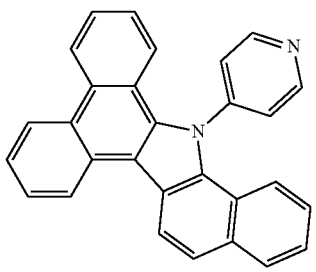
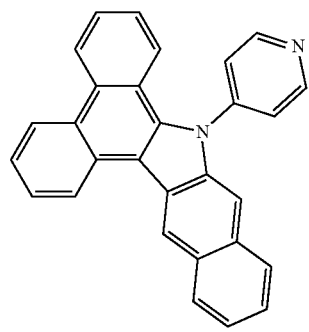
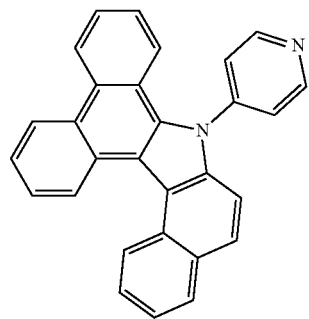
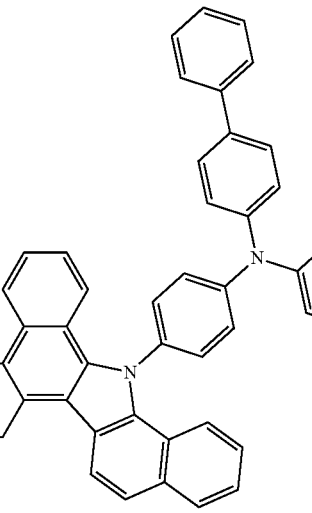

283
-continued
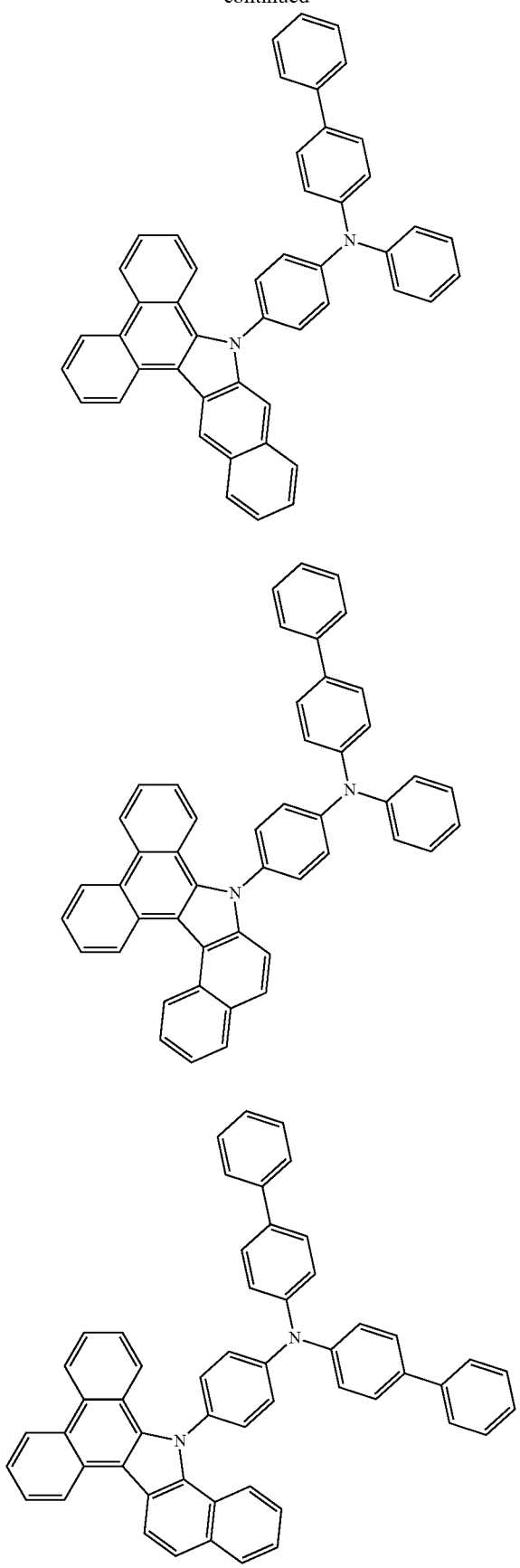
284
-continued
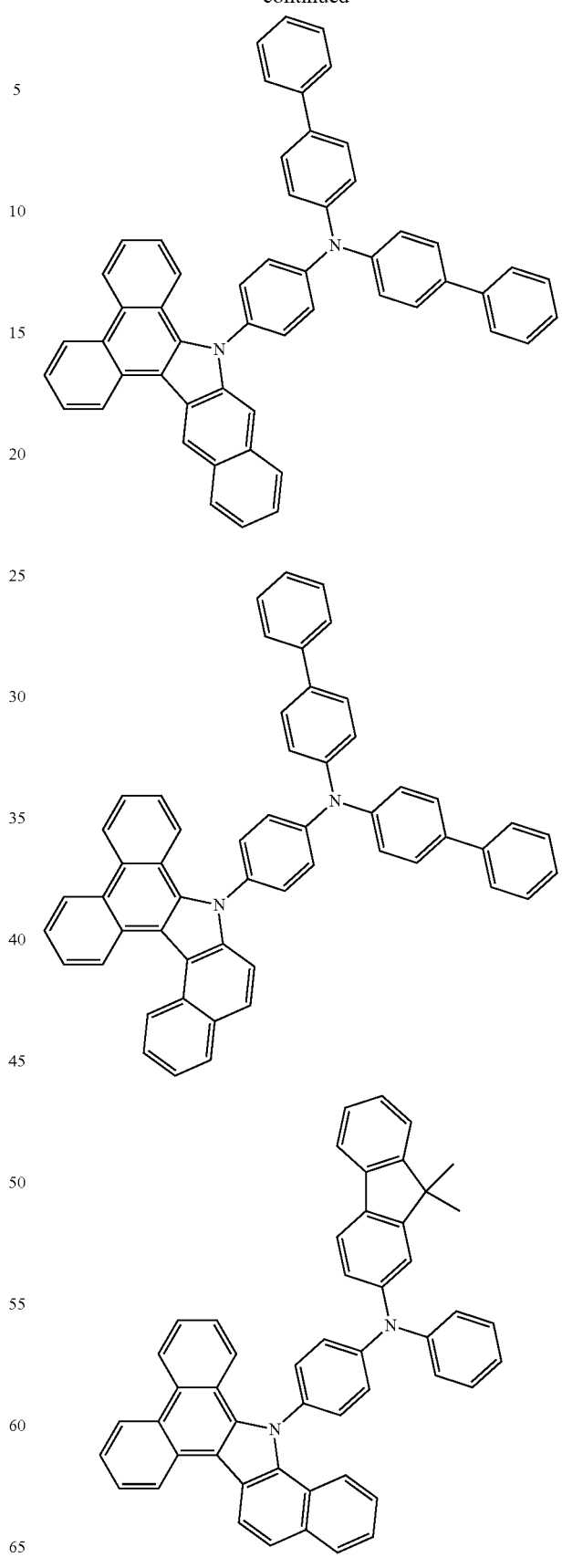

285
-continued
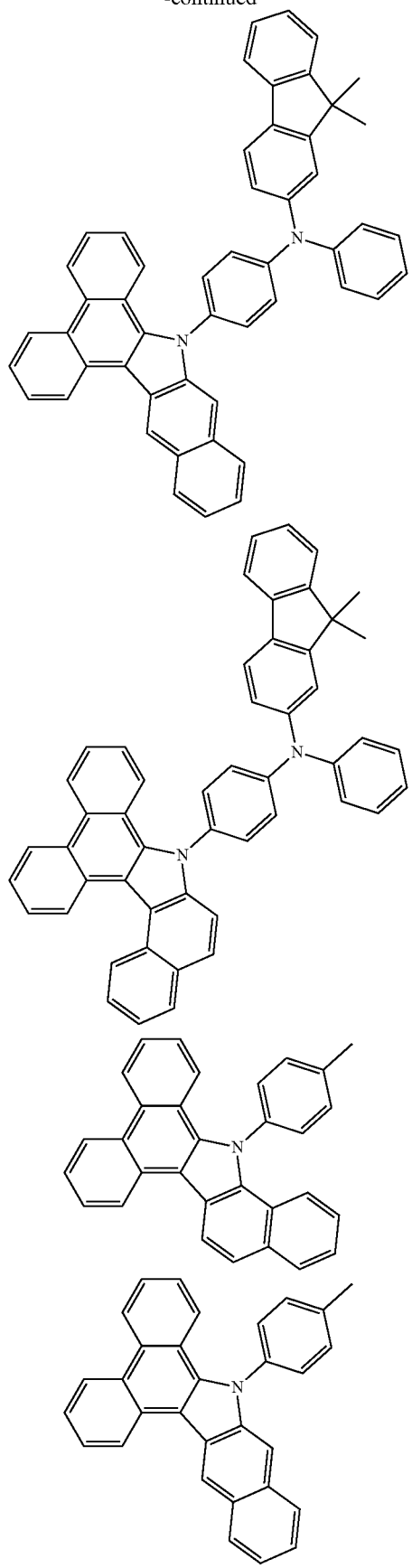
286
-continued
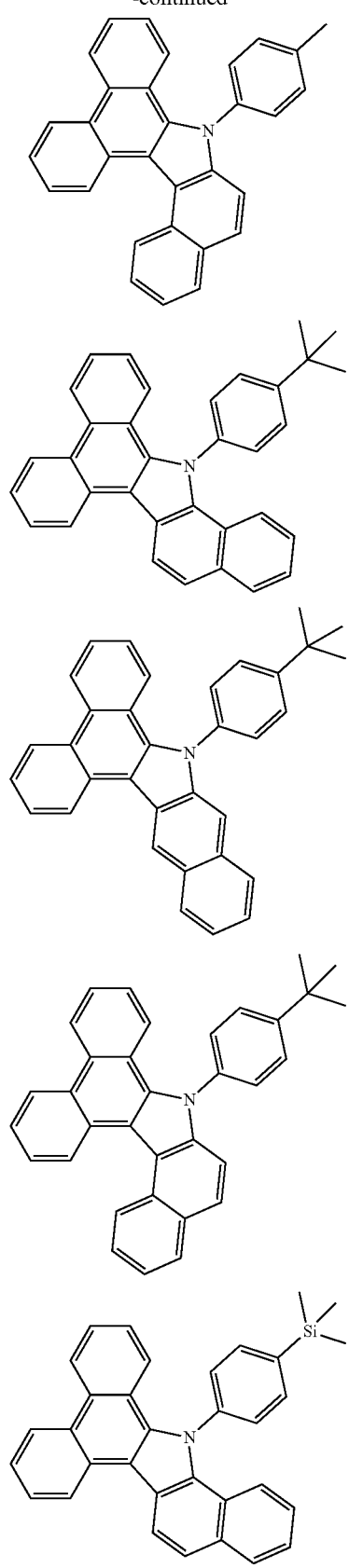

287
-continued
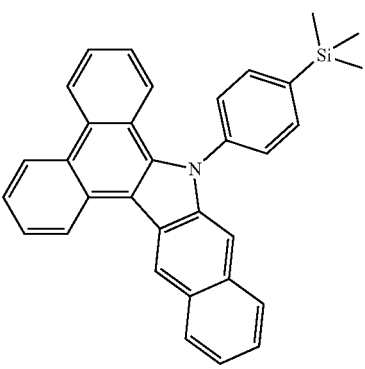
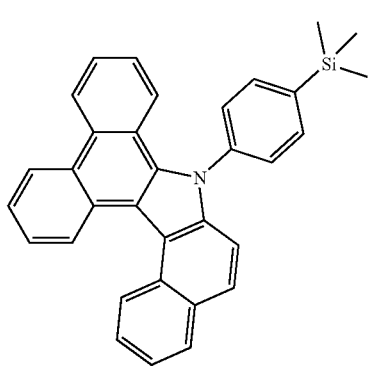
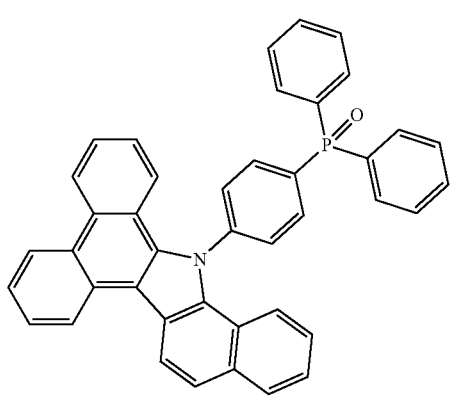
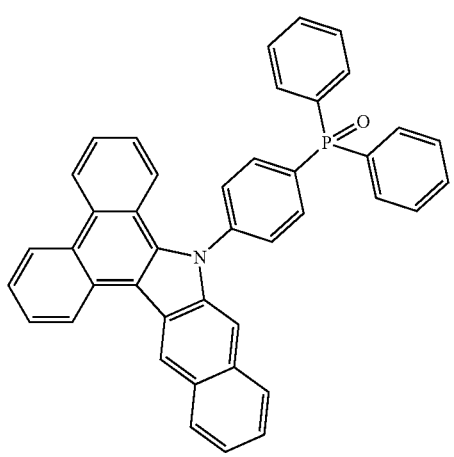
288
-continued
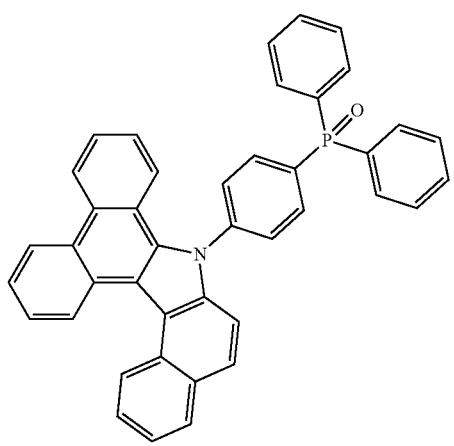
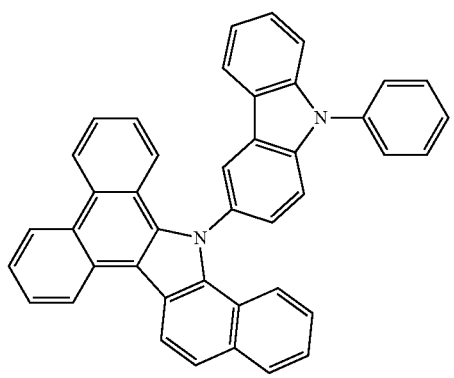
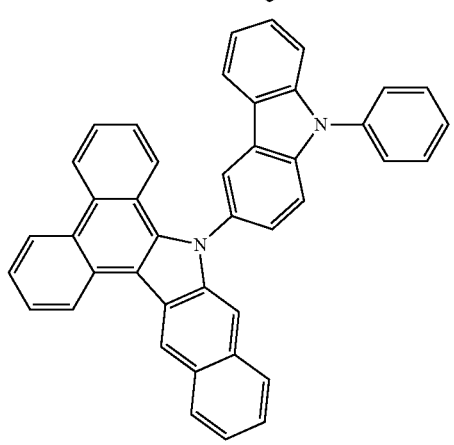
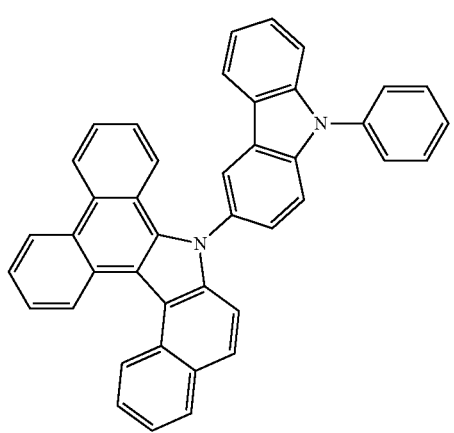

289
-continued
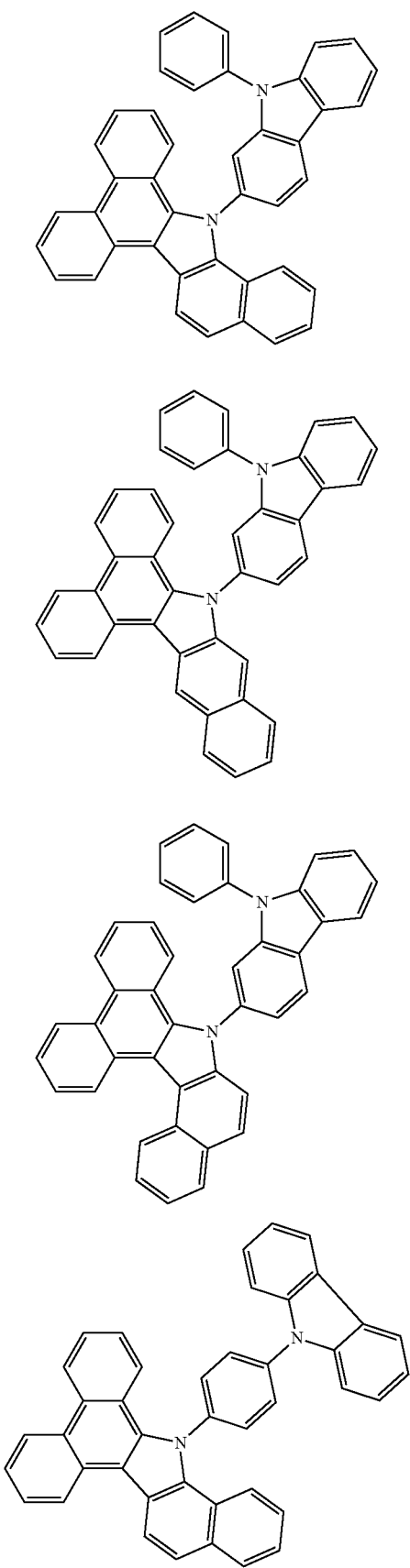
290
-continued
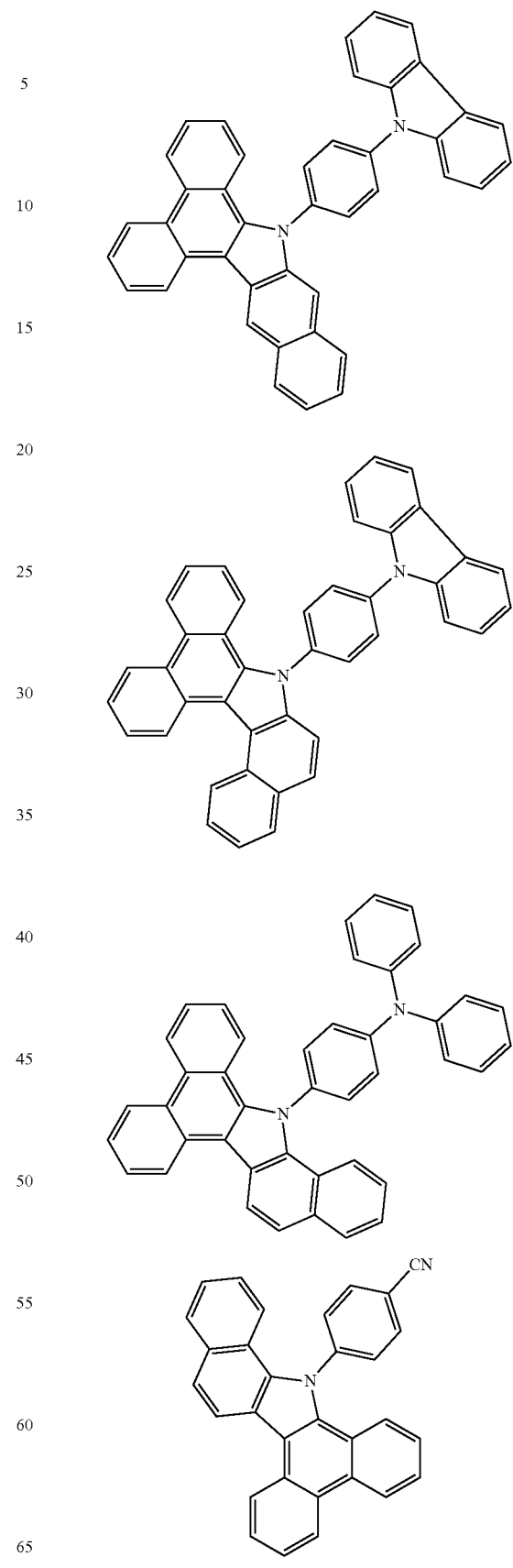

291
-continued
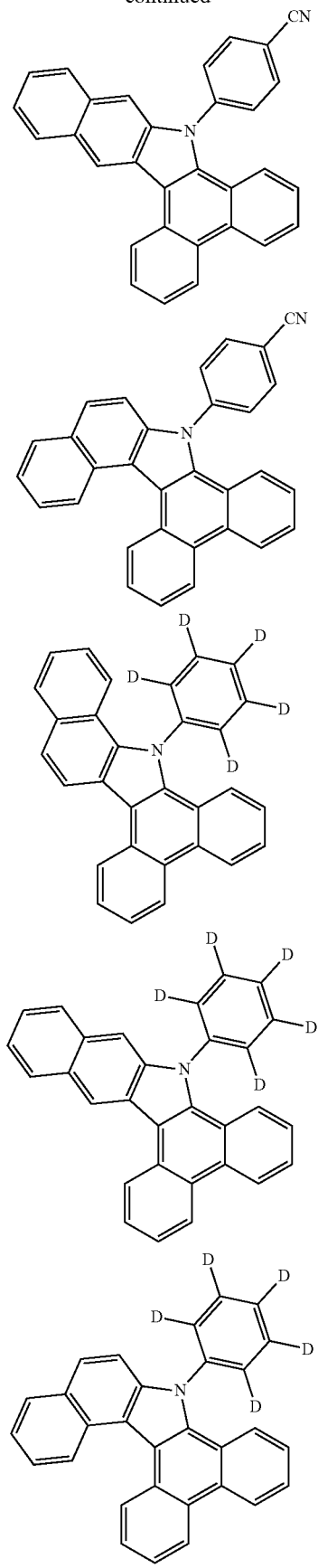
292
-continued
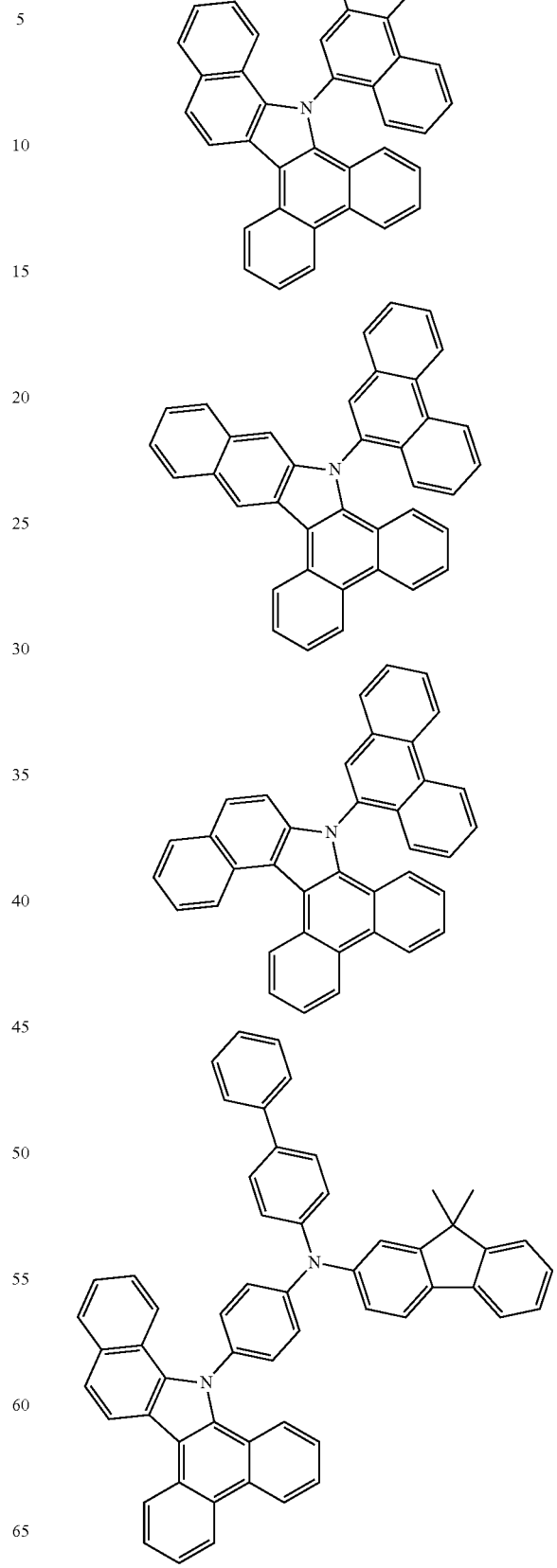

293
-continued
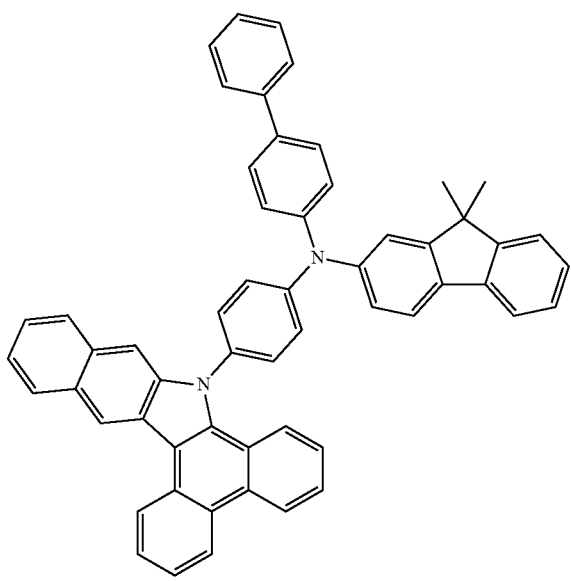
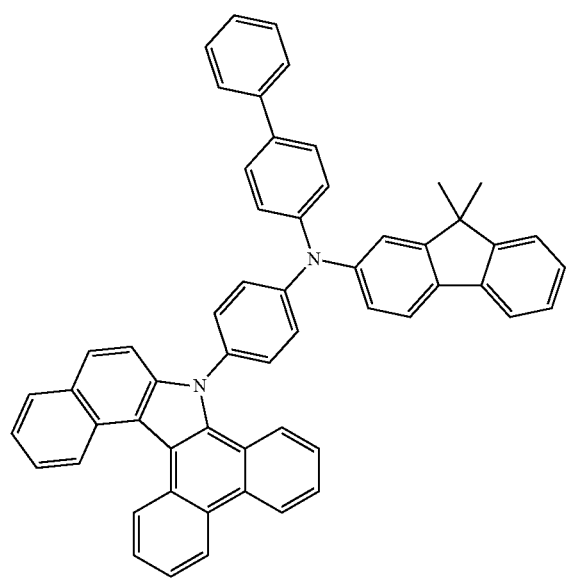
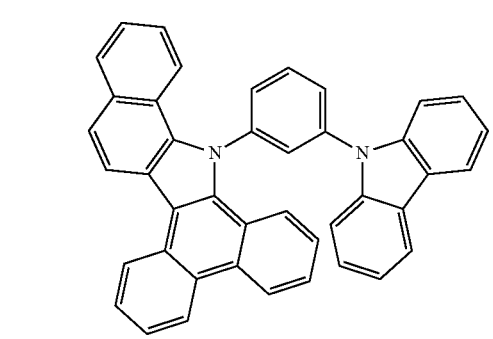
294
-continued
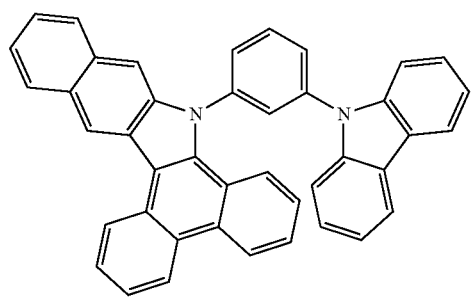
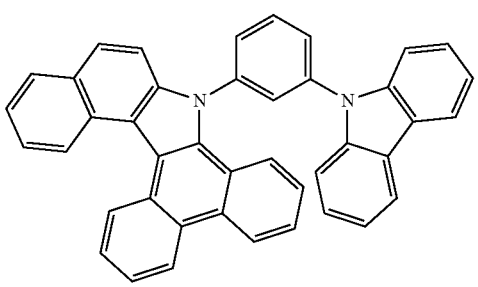
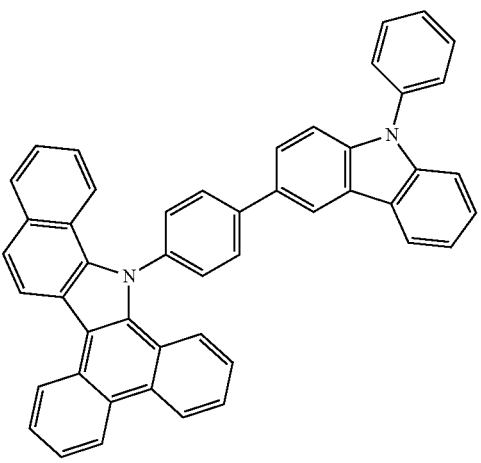
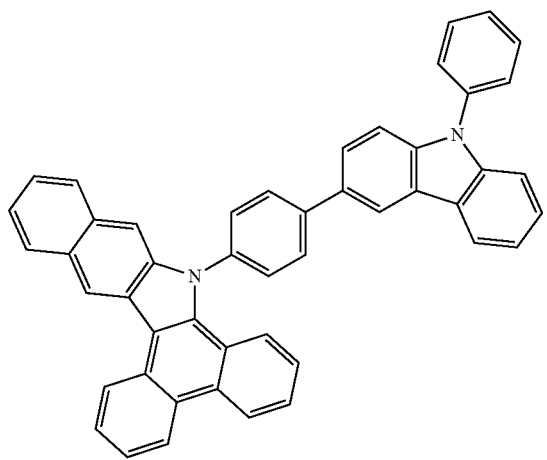

295
-continued
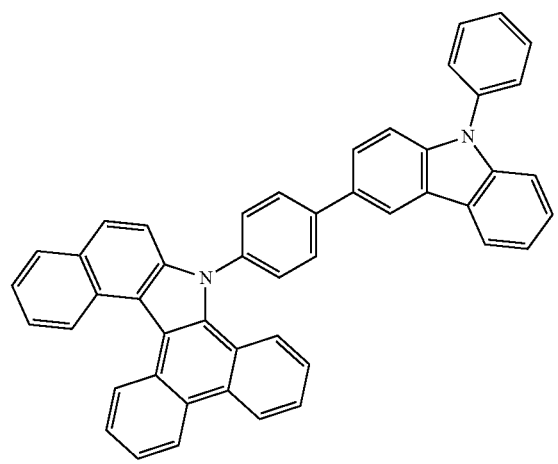
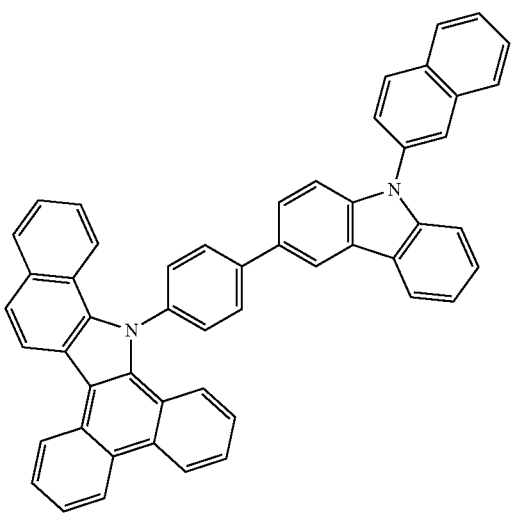
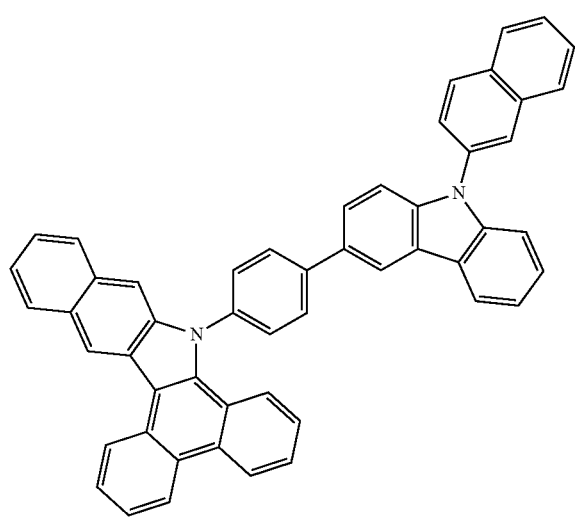
296
-continued
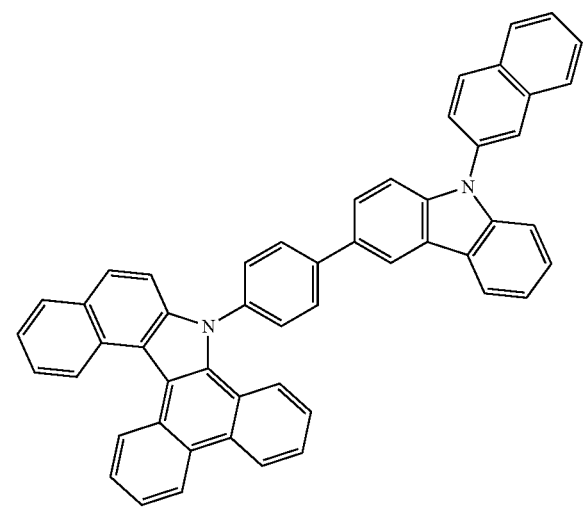
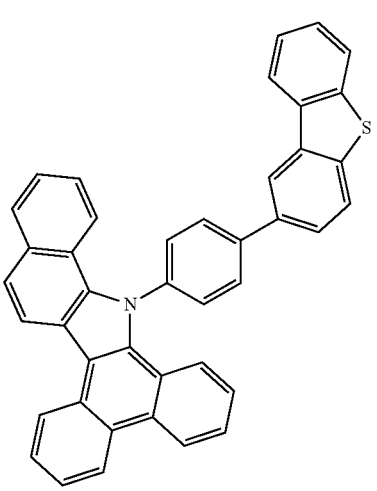
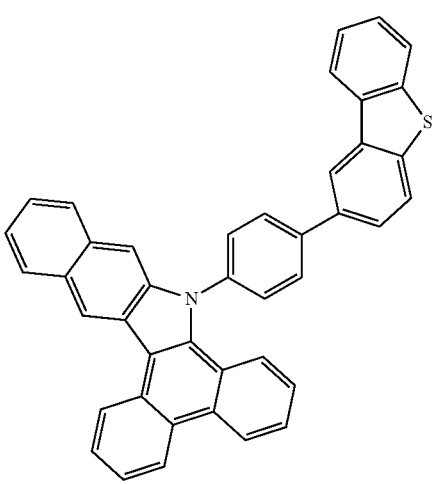

297
-continued
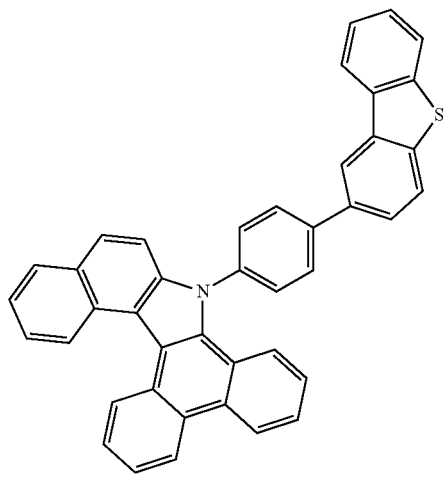
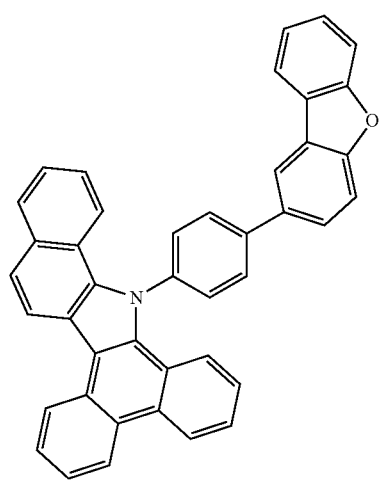
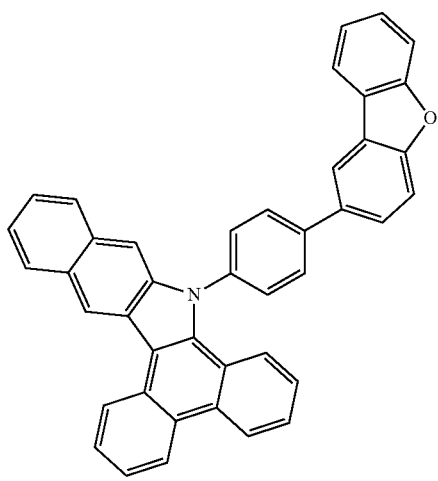
298
-continued
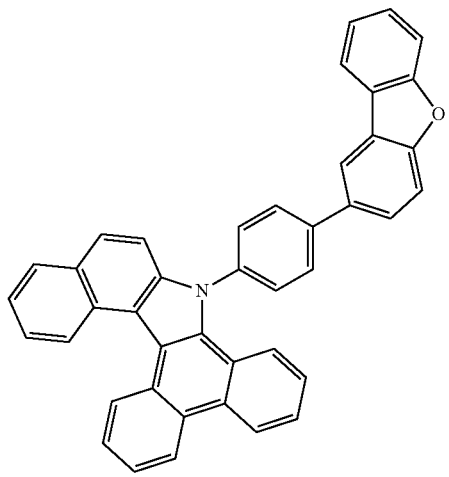
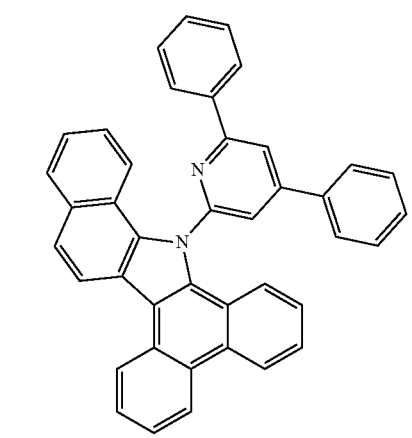
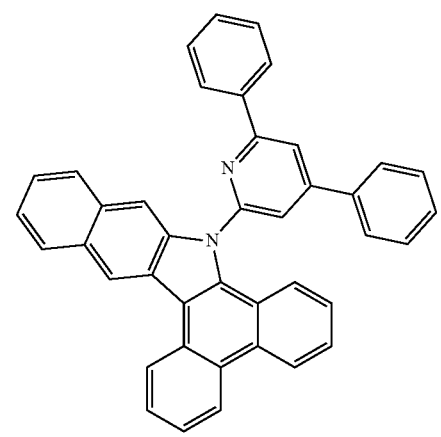

299
-continued
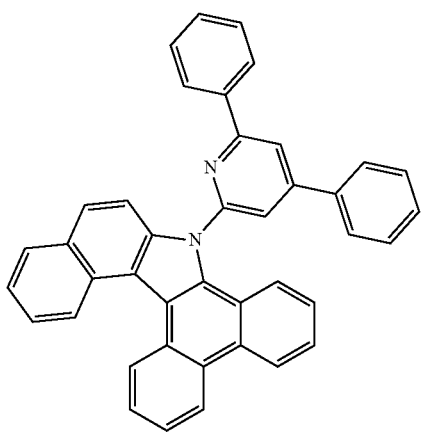
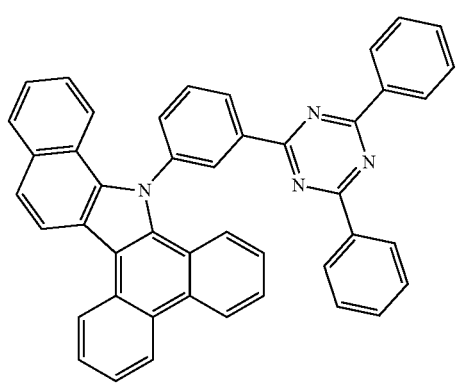
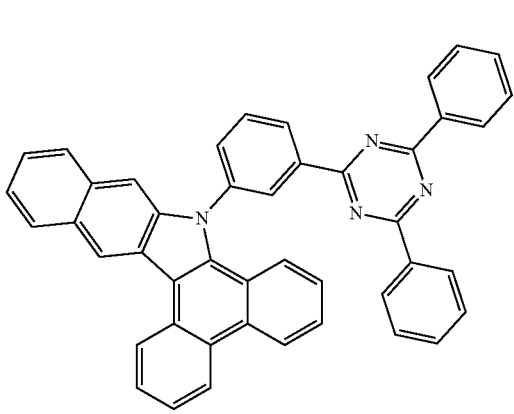
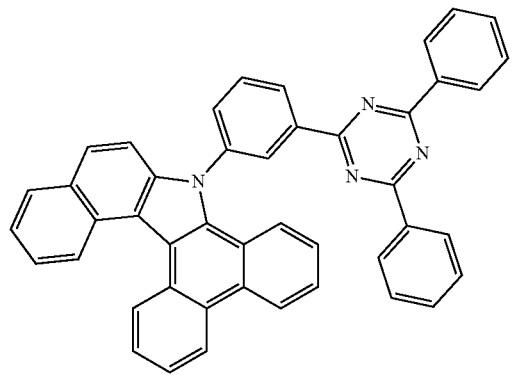
300
-continued
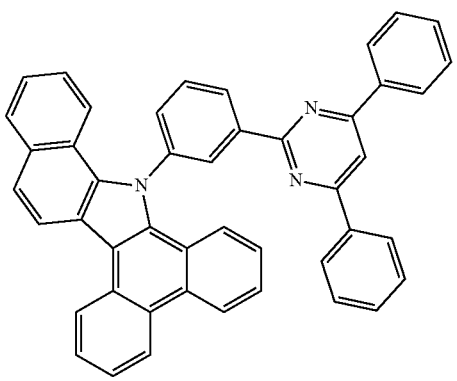
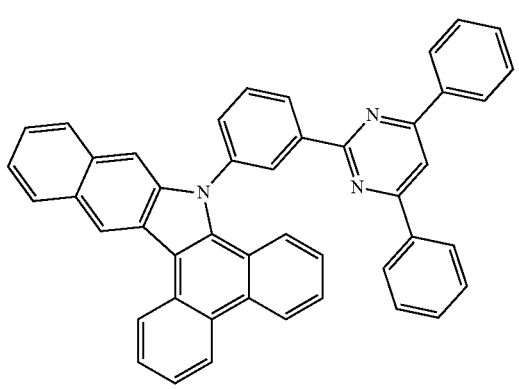
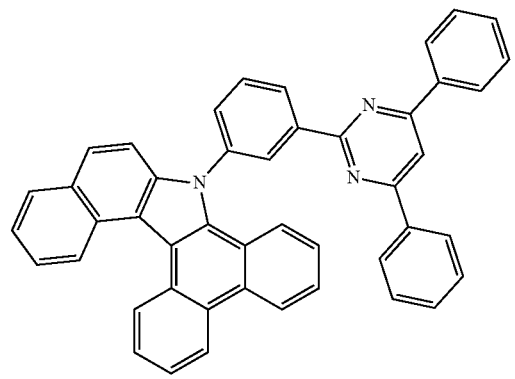
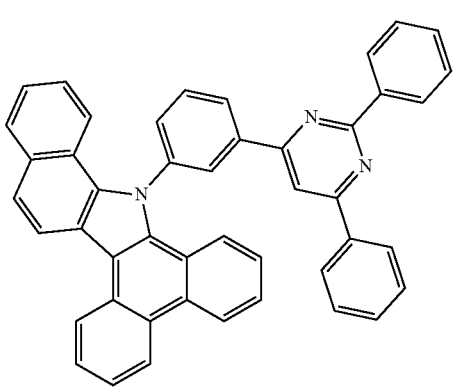

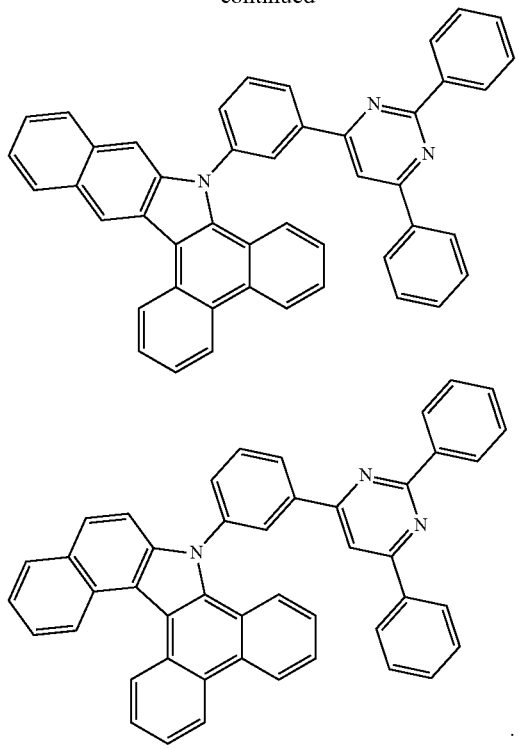

6. An organic light emitting device comprising:
a first electrode;
a second electrode provided to face the first electrode; and
one or more organic material layers provided between the first electrode and the second electrode,
wherein one or more layers of the organic material layers comprise the hetero-cyclic compound of claim 1.

7. The organic light emitting device of claim 6, wherein the organic material layer comprises a hole injection layer or a hole transport layer, and the hole injection layer or the hole transport layer comprises the hetero-cyclic compound.

8. The organic light emitting device of claim 6, wherein the organic material layer comprises an electron blocking layer, and the electron blocking layer comprises the hetero-cyclic compound.

9. The organic light emitting device of claim 6, wherein the organic material layer comprises a light emitting layer, and the light emitting layer comprises the hetero-cyclic compound.

10. The organic light emitting device of claim 6, wherein the organic material layer comprises a hole blocking layer, and the hole blocking layer comprises the hetero-cyclic compound.

11. The organic light emitting device of claim 6, wherein the organic material layer comprises an electron transport layer, an electron injection layer, or a layer which transports and injects electrons simultaneously, and the electron transport layer, the electron injection layer, or the layer which transports and injects electrons simultaneously comprise the hetero-cyclic compound.

12. The organic light emitting device of claim 6, wherein the organic material layer comprises a light emitting layer, and the light emitting layer comprises the compound as a phosphorescent host of the light emitting layer.

13. The organic light emitting device of claim 6, wherein the organic material layer comprises a light emitting layer, and the light emitting layer comprises a compound represented by the following Chemical Formula 1-A:

[Chemical Formula 1-A]

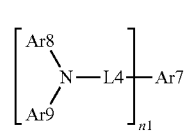

in Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group,
Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and
when n1 is 2 or more, two or more structures in the parenthesis are the same as or different from each other.

14. The organic light emitting device of claim 13, wherein L4 is a direct bond, Ar7 is a divalent pyrene group, Ar8 and Ar9 are the same as or different from each other, and are each independently an aryl group which is unsubstituted or substituted with a germanium group substituted with an alkyl group, and n1 is 2.

15. The organic light emitting device of claim 6, wherein the organic material layer comprises a light emitting layer, and the light emitting layer comprises a compound represented by the following Chemical Formula 2-A:

[Chemical Formula 2-A]

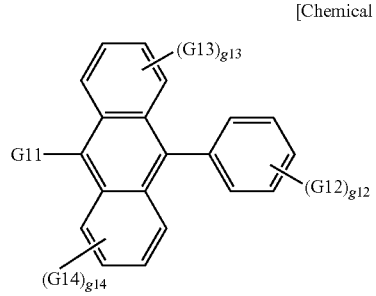

in Chemical Formula 2-A,
G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

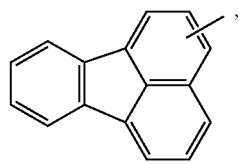

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

16. The organic light emitting device of claim 15, wherein G11 is a 1-naphthyl group, and G12 is a 2-naphthyl group.

17. The organic light emitting device of claim 13, wherein the light emitting layer comprises a compound represented by the following Chemical Formula 2-A:

[Chemical Formula 2-A]

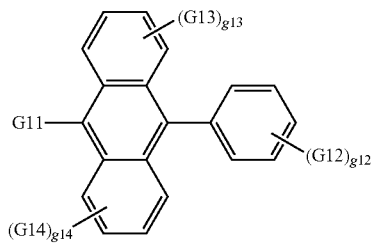

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

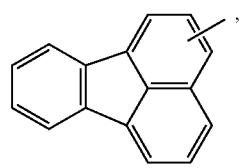

G12 is a phenyl group, a 1-naphtyl group, a 2-naphtyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

* * * * *